US012767707B2

(12) United States Patent
Volker Côrte-Real et al.

(10) Patent No.: US 12,767,707 B2
(45) Date of Patent: Oct. 20, 2026

(54) ANTIBODY MOLECULES AND PEPTIDE DELIVERY SYSTEMS FOR USE IN ALZHEIMER'S DISEASE AND RELATED DISORDERS

(71) Applicant: TECHNOPHAGE, INVESTIGAÇÃO E DESENVOLVIMENTO EM BIOTECNOLOGIA, S.A., Lisbon (PT)

(72) Inventors: Sofia Volker Côrte-Real, Cruz Quebrada-Dafundo (PT); Vera Luísa Santos Neves, Lisbon (PT); Pedro Manuel Correia Canhão, Vila Viçosa (PT); Tiago Fleming Outeiro, Lisbon (PT); Miguel Augusto Rico Botas Castanho, Santarém (PT); Frederico Nuno Castanheira Aires Da Silva, Lisbon (PT); Soraia Rafaela Santiago De Oliveira, Lisbon (PT)

(73) Assignee: TECHNOPHAGE, INVESTIGAÃO E DESENVOLVIMENTO EM BIOTECNOLOGIA, S.A., Lisbon (PT)

(*) Notice: Subject to any disclaimer, the term of this patent is extended or adjusted under 35 U.S.C. 154(b) by 1031 days.

(21) Appl. No.: 16/863,184

(22) Filed: Apr. 30, 2020

(65) Prior Publication Data

US 2021/0355200 A1 Nov. 18, 2021

Related U.S. Application Data

(63) Continuation of application No. 15/545,399, filed as application No. PCT/IB2016/050467 on Jan. 29, 2016, now Pat. No. 10,654,917.

(30) Foreign Application Priority Data

Jan. 29, 2015 (PT) ........................................ 108181
Jan. 29, 2015 (PT) ........................................ 108182

(51) Int. Cl.
*C07K 16/18* (2006.01)
*A61K 39/00* (2006.01)
(Continued)

(52) U.S. Cl.
CPC .......... *C07K 16/18* (2013.01); *A61K 39/3955* (2013.01); *A61K 51/10* (2013.01);
(Continued)

(58) Field of Classification Search
CPC combination set(s) only.
See application file for complete search history.

(56) References Cited

U.S. PATENT DOCUMENTS 6,017,535 A * 1/2000 Fu ........................ C07K 14/005 435/235.1
6,962,793 B2 11/2005 Diamandis
(Continued)

FOREIGN PATENT DOCUMENTS

WO WO 2004/031400 4/2004
WO WO 2006/040153 4/2006
(Continued)

OTHER PUBLICATIONS

Neves V, Aires-da-Silva F, Morais M, Gano L, Ribeiro E, Pinto A, Aguiar S, Gaspar D, Fernandes C, Correia JDG, Castanho MARB. ACS Chem Biol. May 19, 2017;12(5):1257-1268. doi: 10.1021/acschembio.7b00087. Epub Mar. 21, 2017. PMID: 28263555. (Year: 2017).*
(Continued)

*Primary Examiner* — Jeffrey Stucker
*Assistant Examiner* — Laura Ann Essex
(74) *Attorney, Agent, or Firm* — Ballard Spahr LLP

(57) ABSTRACT

The present invention relates to antibody molecules and peptide delivery systems for use in the treatment and man-
(Continued)

agement of Alzheimer's disease and related disorders. In particular, the antibody molecules preferentially bind oligomeric forms of beta-amyloid peptide, in single domain format, and the peptide delivery systems facilitate specific transport of such antibody molecules, as well as other cargo molecules, across the blood-brain barrier. The invention also relates to constructs of the antibody molecules and the delivery peptides, as well as pharmaceutical compositions comprising effective amounts of the antibody molecules, delivery peptides, and/or their constructs, including humanized versions of the antibody molecules and constructs. The invention further relates to methods of making these products and pharmaceutical compositions thereof; and methods of using the pharmaceutical compositions in treating or preventing Alzheimer's and related disorders, such as those involving accumulation of beta-amyloid peptide or other peptides that aggregate in the brain; as well as to methods and kits for diagnosing these disorders.

9 Claims, 22 Drawing Sheets
(19 of 22 Drawing Sheet(s) Filed in Color)

Specification includes a Sequence Listing.

(51) Int. Cl.

| | |
|---|---|
| ***A61K 39/395*** | (2006.01) |
| ***A61K 51/10*** | (2006.01) |
| ***C07K 14/005*** | (2006.01) |
| ***C07K 14/18*** | (2006.01) |
| ***G01N 33/68*** | (2006.01) |

(52) U.S. Cl.

CPC ........ *A61K 51/1018* (2013.01); *C07K 14/005* (2013.01); *C07K 14/18* (2013.01); *G01N 33/6896* (2013.01); *A61K 2039/505* (2013.01); *C07K 2317/20* (2013.01); *C07K 2317/21* (2013.01); *C07K 2317/24* (2013.01); *C07K 2317/33* (2013.01); *C07K 2317/35* (2013.01); *C07K 2317/52* (2013.01); *C07K 2317/56* (2013.01); *C07K 2317/569* (2013.01); *C07K 2317/622* (2013.01); *C07K 2317/76* (2013.01); *C07K 2317/92* (2013.01); *C07K 2317/94* (2013.01); *C07K 2319/01* (2013.01); *G01N 2333/4709* (2013.01); *G01N 2800/2821* (2013.01); *G01N 2800/56* (2013.01)

(56) References Cited

U.S. PATENT DOCUMENTS

| | | | | |
|---|---|---|---|---|
| 7,094,411 B2 * | 8/2006 | Kinney | ................ | C07K 14/005 435/235.1 |
| 7,682,795 B2 | 3/2010 | Huang | | |
| 8,263,558 B2 | 9/2012 | Holzman | | |
| 8,858,949 B2 | 10/2014 | Yokoseki | | |
| 2010/0297700 A1 | 11/2010 | Votsmeier | | |

FOREIGN PATENT DOCUMENTS

| | | | |
|---|---|---|---|
| WO | WO 2008/136694 | 11/2008 | |
| WO | WO 2010/119704 | 10/2010 | |
| WO | WO 2012/120035 | 9/2012 | |
| WO | WO 2013/167681 | 11/2013 | |
| WO | WO 2014/060444 | 4/2014 | |
| WO | WO-2014089209 A2 * | 6/2014 | ............. A61P 25/00 |

OTHER PUBLICATIONS

Uniprot, DENV2 (Year: 1990).*

Byk LA, Gamarnik AV. Properties and Functions of the Dengue Virus Capsid Protein. Annu Rev Virol. Sep. 29, 2016;3(1):263-281. doi: 10.1146/annurev-virology-110615-042334. Epub Aug. 3, 2016. PMID: 27501261; PMCID: PMC5417333. (Year: 2016).*

Francis DM, Page R. Strategies to optimize protein expression in *E. coli*. Curr Protoc Protein Sci. Aug. 2010;Chapter 5(1):5.24.1-5.24.29. doi: 10.1002/0471140864.ps0524s61. PMID: 20814932; PMCID: PMC7162232. (Year: 2010).*

Fusion Protein Definition (2024) https://www.sinobiological.com/resource/protein-review/fusion-protein (Year: 2024).*

Freire JM, Veiga AS, Conceição TM, Kowalczyk W, Mohana-Borges R, Andreu D, Santos NC, Da Poian AT, Castanho MA. PLoS One. Dec. 5, 2013;8(12):e81450. doi: 10.1371/journal.pone.0081450. PMID: 24339931; PMCID: PMC3855322. (Year: 2013).*

U.S. Appl. No. 15/545,399, filed Jul. 21, 2017, Sofia Volker Côrte-Real.

WO PCT/IB2016/050467, Jan. 29, 2016, Technophage, Investigacção E Desenvolvimento EM.

Kasturirangan,et al. "Nanobody specific for oligomeric beta-amyloid stabilizes nontoxic form". Neurobiology of Aging 33 (2012) 1320-1328.

Zameer et al. "Anti-oligomeric AP Single-chain Variable Domain Antibody Blocks AP-induced Toxicity Against Human Neuroblastoma Cells". J. Mol. Biol. (2008) 384, 917-928.

Ledford, Heidi. "Engineered antibodies cross blood-brain barrier". Published online May 25, 20111Natureldoi:10.1038/news.2011.319.

Neves et al. "Antibody Approaches to Treat Brain Diseases". CellPress. p. 1-13.; Trends in Biotechnology, Jan. 2016, vol. 34, No. 1.

Finke et al. "Antibody blood-brain barrier efflux is modulated by glycan modifica-tion". Biochim Biophys Acta. Sep. 2017; 1861(9): 2228-2239.

EP Appeal Decision; T 0511/14 for EP 08725133.6; Applicant Medimmune; Jun. 12, 2018.

Freire, et al., "Nucleic acid delivery by cell penetrating peptides derived from dengue virus capsid protein: design and mechanism of action," FEBS J, 281(1): p. 191-215, 2014.

Ribeiro et al., "Translocating the blood-brain barrier using electrostatics," Frontiers in Cell Neurosci., 6(44), pp. 1-7, 2012.

Brannstrom et al., "A Generic Method for Design of Oligomer-Specific Antibodies," PLOS One, 9(3), E90857, 13 pages 2014.

Cheng et al., "Inhibiting Toxic Aggregation of Amyloidgenic Proteins: A Therapeutic Strategy for Protein Misfolding Diseases," Biochimica et Biophysica Acta, 1830, pp. 4860-4871, 2013.

Gardberg et al., "Molecular Basis for Passive Immunotherapy of Alzheimer's Disease," PNAS, 104(40), pp. 15659-15664, 2007.

Goure et al., "Targeting the Proper Amyloid-Beta Neuronal Toxins: a Path Forward for Alzheimer's Disease Immunotherapeutics," Alzheimers Res. & Ther., 6(42), pp. 1-15, 2014.

Kayed et al., "Common Structure of Soluble Amyloid Oligomers Implies Common Mechanism of Pathogenesis," Science, 300, pp. 486-489, 2003.

Sha et al., "Active Immunotherapy Facilitates AR Plaque Removal Following Through Microglial Activation Without Obvious T Cells Infiltrating the CNS," Journal of Neuroimmunology, 274, pp. 62-70, 2014.

Suter et al., "Rabbit Single Domain Antibodies Specific to Protein C Expressed in Prokaryotes," Immunology Letters, 33, pp. 53-59, 1992.

Wu "Single-domain antibodies as therapeutics against human viral diseases" front immu 8:1802 (2017).

Chen "Enhancement and destruction of antibody function by somatic mutation: unequal occurrence is controlled by V gene combinatorial associations" EMBO 14(12):2784-2794 (Year: 1995).

Kussie "A Single Engineered Amino Acid Substitution Changes Antibody Fine Specificity" J immunol 152(1):146-52 (Year: 1994).

Reitz "Toward precision medicine in Alzheimer's disease" Ann Trend Med 4(6):107 (Year: 2016).

Stanford "Alzheimer's Prevention, Treatment and Research—A Q&A with Dr. Frank Longo" stanfordhealthcare.org accessed on May 3, 2016 (Year: 2016.

(56) References Cited

OTHER PUBLICATIONS

Sengupta "The Role of Annyloid-8 Oligomers in Toxicity, Propagation and Immunotherapy" ebiomed 6:42-49 (Year: 2016).
Uniprot "067420" accessed from uniprot.org on Jun. 30, 2018 (Year: 1996).
Neves-Coelho et al. "A New Noncanonical Anionic Peptide That Translocates a Cellular Blood-Brain Barrier Model", Molecules 2017, 22, 1753; doi:10.3390/molecules22101753.
Cavaco et al. "PepH3, an Improved Peptide Shuttle for Receptor-independent Transport Across the Blood-Brain Barrier", Current Pharmaceutical Design, 2020, 26, 1-12.
Neves et al. "Novel Peptides Derived from Dengue Virus Capsid Protein Translocate Reversibly the BloodBrain Barrier through a Receptor-Free Mechanisml", American Chemical Society, Mar. 2017.

* cited by examiner

SEQUENCE LISTING

```
<160> NUMBER OF SEQ ID NOS: 135

<210> SEQ ID NO 1
<211> LENGTH: 112
<212> TYPE: PRT
<213> ORGANISM: Unknown
<220> FEATURE:
<221> NAME/KEY: source
<223> OTHER INFORMATION: /note="Description of Unknown:
      rabbit immunoglobulin VL domain polypeptide"
<220> FEATURE:
<221> NAME/KEY: source
<223> OTHER INFORMATION: /note="#2"

<400> SEQUENCE: 1

Glu Leu Val Met Thr Gln Thr Pro Ser Pro Val Ser Ala Ala Val Gly
1               5                   10                  15

Gly Thr Val Ser Ile Ser Cys Gln Ser Ser Lys Ser Val Tyr Asn Asn
            20                  25                  30

Asn Trp Leu Ser Trp Phe Gln Gln Lys Pro Gly Gln Pro Pro Lys Leu
```

```
        35                  40                  45

Leu Ile Tyr Ser Ala Ser Thr Leu Ala Ser Gly Val Ser Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Gln Gly Glu Phe Asp Cys
                85                  90                  95

Ser Gly Asp Cys Asn Val Phe Gly Gly Gly Thr Glu Leu Glu Ile Leu
            100                 105                 110


<210> SEQ ID NO 2
<211> LENGTH: 112
<212> TYPE: PRT
<213> ORGANISM: Unknown
<220> FEATURE:
<221> NAME/KEY: source
<223> OTHER INFORMATION: /note="Description of Unknown:
      rabbit immunoglobulin VL domain polypeptide"
<220> FEATURE:
<221> NAME/KEY: source
<223> OTHER INFORMATION: /note="#20"

<400> SEQUENCE: 2

Glu Leu Asp Leu Thr Gln Thr Pro Ser Ser Lys Ser Val Pro Val Gly
1               5                   10                  15

Asp Thr Val Thr Ile Asn Cys Gln Ala Ser Glu Ser Val Tyr Ser Asn
            20                  25                  30

Asn Arg Leu Ala Trp Phe Gln Gln Lys Pro Gly Gln Pro Pro Lys Leu
        35                  40                  45

Leu Ile Tyr Tyr Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Val
65                  70                  75                  80

Val Cys Asp Asp Ala Ala Thr Tyr Tyr Cys Ala Gly Tyr Lys Ser Ser
                85                  90                  95

Thr Ser Asp Gly Ile Ala Phe Gly Gly Gly Thr Glu Val Val Val Lys
            100                 105                 110


<210> SEQ ID NO 3
<211> LENGTH: 109
<212> TYPE: PRT
<213> ORGANISM: Unknown
<220> FEATURE:
<221> NAME/KEY: source
<223> OTHER INFORMATION: /note="Description of Unknown:
      rabbit immunoglobulin VL domain polypeptide"
<220> FEATURE:
<221> NAME/KEY: source
<223> OTHER INFORMATION: /note="#6in"

<400> SEQUENCE: 3

Glu Leu Asp Leu Thr Gln Thr Pro Ser Ser Val Ser Glu Pro Val Gly
1               5                   10                  15

Gly Thr Val Thr Ile Lys Cys Gln Ala Ser Gln Ser Ile Asn Ser Tyr
            20                  25                  30

Leu Ala Trp Tyr Gln Gln Lys Pro Gly Gln Pro Pro Lys Leu Leu Ile
        35                  40                  45

Tyr Arg Thr Ser Thr Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80
```

```
Ala Asp Ala Ala Thr Tyr Tyr Cys Gln Ser Tyr Tyr Ser Ala Ser Ser
                85                  90                  95

Gly Trp Ala Phe Gly Gly Gly Thr Glu Val Val Val Lys
            100                 105


<210> SEQ ID NO 4
<211> LENGTH: 108
<212> TYPE: PRT
<213> ORGANISM: Unknown
<220> FEATURE:
<221> NAME/KEY: source
<223> OTHER INFORMATION: /note="Description of Unknown:
      rabbit immunoglobulin VL domain polypeptide"
<220> FEATURE:
<221> NAME/KEY: source
<223> OTHER INFORMATION: /note="#27in"

<400> SEQUENCE: 4

Glu Leu Val Leu Thr Gln Thr Pro Ser Ser Val Ser Ala Ala Val Gly
1               5                   10                  15

Gly Thr Val Thr Ile Asn Cys Gln Ala Ser Gln Ser Val Ser Asn Arg
            20                  25                  30

Leu Ala Trp Tyr Gln Gln Lys Pro Gly Gln Pro Pro Lys Leu Leu Ile
        35                  40                  45

Tyr Gly Ala Ser Arg Leu Glu Ser Gly Val Pro Ser Arg Phe Arg Gly
    50                  55                  60

Ser Gly Ser Gly Thr Glu Phe Thr Leu Thr Ile Ser Gly Met Lys Ala
65                  70                  75                  80

Glu Asp Ala Ala Thr Tyr Tyr Cys Gln Ser Cys Tyr Tyr Ser Val Gly
                85                  90                  95

Val Thr Phe Gly Ala Gly Thr Asn Val Glu Ile Lys
            100                 105


<210> SEQ ID NO 5
<211> LENGTH: 110
<212> TYPE: PRT
<213> ORGANISM: Unknown
<220> FEATURE:
<221> NAME/KEY: source
<223> OTHER INFORMATION: /note="Description of Unknown:
      rabbit immunoglobulin VL domain polypeptide"
<220> FEATURE:
<221> NAME/KEY: source
<223> OTHER INFORMATION: /note="#1"

<400> SEQUENCE: 5

Glu Leu Asp Leu Thr Gln Thr Pro Ala Ser Val Glu Ala Ala Val Gly
1               5                   10                  15

Gly Thr Val Thr Ile Asn Cys Gln Ala Ser Glu Ser Ile Ser Asn Tyr
            20                  25                  30

Leu Asn Trp Tyr Gln Gln Lys Pro Gly Gln Pro Pro Lys Arg Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Gly Val Glu Cys
65                  70                  75                  80

Ala Asp Ala Ala Thr Tyr Tyr Cys Gln Gln Ser Tyr Ser Tyr Ser Asn
                85                  90                  95

Val Asp Asn Thr Phe Gly Gly Gly Thr Glu Val Val Val Lys
            100                 105                 110
```

<210> SEQ ID NO 6
<211> LENGTH: 109
<212> TYPE: PRT
<213> ORGANISM: Unknown
<220> FEATURE:
<221> NAME/KEY: source
<223> OTHER INFORMATION: /note="Description of Unknown: rabbit immunoglobulin VL domain polypeptide"
<220> FEATURE:
<221> NAME/KEY: source
<223> OTHER INFORMATION: /note="#3"

<400> SEQUENCE: 6

```
Glu Leu Val Leu Thr Gln Thr Pro Ala Ser Val Ser Glu Pro Val Gly
1               5                   10                  15

Gly Thr Val Thr Ile Lys Cys Gln Ala Ser Gln Ser Ile Gly Ser Tyr
            20                  25                  30

Leu Ser Trp Tyr Gln Gln Lys Pro Gly Gln Arg Pro Lys Leu Leu Ile
        35                  40                  45

Tyr Asp Ala Ser Asn Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Cys Thr Tyr Tyr Gly Ser Ser
                85                  90                  95

Tyr Tyr Thr Phe Gly Gly Gly Thr Glu Val Val Val Lys
            100                 105
```

<210> SEQ ID NO 7
<211> LENGTH: 112
<212> TYPE: PRT
<213> ORGANISM: Unknown
<220> FEATURE:
<221> NAME/KEY: source
<223> OTHER INFORMATION: /note="Description of Unknown: rabbit immunoglobulin VL domain polypeptide"
<220> FEATURE:
<221> NAME/KEY: source
<223> OTHER INFORMATION: /note="#4"

<400> SEQUENCE: 7

```
Glu Leu Asp Leu Thr Gln Thr Pro Ser Ser Lys Ser Val Pro Val Gly
1               5                   10                  15

Asp Thr Val Thr Ile Asn Cys Gln Ala Ser Asp Ser Val Tyr Ser Asn
            20                  25                  30

Asn Arg Leu Ala Trp Phe Gln Gln Lys Pro Gly Gln Pro Pro Lys Leu
        35                  40                  45

Leu Ile Tyr Gln Ala Ser Lys Leu Ala Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Gln Gly Ala Tyr Tyr Ser
                85                  90                  95

Ser Gly Trp Ser Asn Gly Phe Gly Gly Gly Thr Glu Val Val Val Lys
            100                 105                 110
```

<210> SEQ ID NO 8
<211> LENGTH: 110
<212> TYPE: PRT
<213> ORGANISM: Unknown
<220> FEATURE:
<221> NAME/KEY: source

```
<223> OTHER INFORMATION: /note="Description of Unknown:
      rabbit immunoglobulin VL domain polypeptide"
<220> FEATURE:
<221> NAME/KEY: source
<223> OTHER INFORMATION: /note="#5"

<400> SEQUENCE: 8

Glu Leu Asp Leu Thr Gln Thr Pro Ala Ser Val Glu Val Ala Val Gly
1               5                   10                  15

Gly Thr Val Thr Ile Lys Cys Gln Ala Ser Gln Ser Ile Ser Thr Tyr
            20                  25                  30

Leu Ser Trp Tyr Gln Gln Lys Ala Gly Gln Arg Pro Lys Leu Leu Ile
        35                  40                  45

Tyr Gly Ala Ser Asn Leu Ala Ser Gly Val Pro Ser Arg Phe Lys Gly
    50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Gly Tyr Ser Ser Ser Asn
                85                  90                  95

Val Asp Asn Ala Phe Gly Gly Gly Thr Glu Leu Glu Ile Leu
            100                 105                 110


<210> SEQ ID NO 9
<211> LENGTH: 112
<212> TYPE: PRT
<213> ORGANISM: Unknown
<220> FEATURE:
<221> NAME/KEY: source
<223> OTHER INFORMATION: /note="Description of Unknown:
      rabbit immunoglobulin VL domain polypeptide"
<220> FEATURE:
<221> NAME/KEY: source
<223> OTHER INFORMATION: /note="#6"

<400> SEQUENCE: 9

Glu Leu Asp Met Thr Gln Thr Pro Ser Ser Lys Ser Val Pro Val Gly
1               5                   10                  15

Asp Thr Val Thr Ile Asn Cys Gln Ala Ser Glu Ser Val Tyr Ser Asn
            20                  25                  30

Asn Tyr Leu Ala Trp Tyr Gln Gln Lys Pro Gly Gln Pro Pro Lys Leu
        35                  40                  45

Leu Ile Tyr Lys Ala Ser Thr Leu Ala Ser Gly Val Ser Ser Arg Phe
    50                  55                  60

Ser Gly Ser Gly Ser Gly Thr Gln Phe Thr Leu Thr Ile Ser Asp Val
65                  70                  75                  80

Val Cys Asp Asp Ala Gly Thr Tyr Tyr Cys Ala Gly Phe Lys Gly Thr
                85                  90                  95

Gly Thr Asp Gly Asn Ala Phe Gly Gly Gly Thr Glu Leu Glu Ile Leu
            100                 105                 110


<210> SEQ ID NO 10
<211> LENGTH: 113
<212> TYPE: PRT
<213> ORGANISM: Unknown
<220> FEATURE:
<221> NAME/KEY: source
<223> OTHER INFORMATION: /note="Description of Unknown:
      rabbit immunoglobulin VL domain polypeptide"
<220> FEATURE:
<221> NAME/KEY: source
<223> OTHER INFORMATION: /note="#7"

<400> SEQUENCE: 10
```

```
Glu Leu Val Leu Thr Gln Thr Pro Ser Ser Lys Ser Val Pro Val Gly
1               5                   10                  15

Asp Thr Val Thr Ile Asn Cys Gln Ala Ser Asp Ser Val Tyr Ser Asn
            20                  25                  30

Asn Phe Leu Ser Trp Phe Gln Gln Lys Pro Gly Gln Pro Pro Lys Leu
        35                  40                  45

Leu Ile Tyr Ser Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Ala Asp Ala Ala Thr Tyr Tyr Cys Gln Asn Tyr Arg Asn Ile
                85                  90                  95

Gly Asp Tyr Gly Val Pro Phe Gly Gly Gly Thr Glu Val Val Val Lys
            100                 105                 110

Gly


<210> SEQ ID NO 11
<211> LENGTH: 111
<212> TYPE: PRT
<213> ORGANISM: Unknown
<220> FEATURE:
<221> NAME/KEY: source
<223> OTHER INFORMATION: /note="Description of Unknown:
      rabbit immunoglobulin VL domain polypeptide"
<220> FEATURE:
<221> NAME/KEY: source
<223> OTHER INFORMATION: /note="#8"

<400> SEQUENCE: 11

Glu Leu Val Met Thr Gln Thr Pro Ser Ser Val Ser Glu Pro Val Gly
1               5                   10                  15

Gly Thr Val Thr Ile Lys Cys Gln Ala Ser Gln Asn Ile Gly Gly Tyr
            20                  25                  30

Leu Ala Trp Tyr Gln Gln Lys Pro Gly Gln Pro Pro Lys Leu Leu Ile
        35                  40                  45

Tyr Asp Ala Ser Thr Leu Pro Ser Gly Val Pro Ser Arg Phe Ser Gly
    50                  55                  60

Ser Gly Tyr Gly Thr Glu Phe Thr Leu Thr Ile Ser Asp Leu Glu Cys
65                  70                  75                  80

Ala Asp Ala Ala Thr Tyr Tyr Cys Gln Cys Thr Asp Tyr Gly Ser Ser
                85                  90                  95

Tyr Ile Tyr Asn Thr Phe Gly Gly Gly Thr Glu Leu Glu Ile Leu
            100                 105                 110


<210> SEQ ID NO 12
<211> LENGTH: 111
<212> TYPE: PRT
<213> ORGANISM: Unknown
<220> FEATURE:
<221> NAME/KEY: source
<223> OTHER INFORMATION: /note="Description of Unknown:
      rabbit immunoglobulin VL domain polypeptide"
<220> FEATURE:
<221> NAME/KEY: source
<223> OTHER INFORMATION: /note="#9"

<400> SEQUENCE: 12

Glu Leu Asp Leu Thr Gln Thr Pro Ser Pro Val Ser Ala Ala Val Gly
1               5                   10                  15

Gly Thr Val Thr Ile Ser Cys Gln Ser Ser Glu Ser Val Tyr Ser Asn
```

```
            20                  25                  30

Asn Arg Leu Ala Trp Tyr Gln Gln Lys Pro Gly Gln Pro Pro Lys Leu
        35                  40                  45

Leu Ile Tyr Leu Ala Ser Ser Leu Ala Ser Gly Val Pro Ser Arg Phe
    50                  55                  60

Lys Gly Ser Gly Ser Gly Thr Gln Phe Thr Leu Thr Ile Arg Asp Leu
65                  70                  75                  80

Glu Cys Asp Asp Ala Ala Thr Tyr Tyr Cys Leu Gly Tyr Arg Ser Gly
                85                  90                  95

Ser Asp Gly Asp Ala Phe Gly Gly Gly Thr Glu Leu Glu Ile Leu
            100                 105                 110


<210> SEQ ID NO 13
<211> LENGTH: 110
<212> TYPE: PRT
<213> ORGANISM: Unknown
<220> FEATURE:
<221> NAME/KEY: source
<223> OTHER INFORMATION: /note="Description of Unknown:
      rabbit immunoglobulin VL domain polypeptide"
<220> FEATURE:
<221> NAME/KEY: source
<223> OTHER INFORMATION: /note="#10"

<400> SEQUENCE: 13

Glu Leu Asp Leu Thr Gln Thr Pro Ala Ser Val Glu Val Ala Val Gly
1               5                   10                  15

Gly Thr Val Thr Ile Lys Cys Gln Ala Ser Glu Ser Ile Gly Asn Trp
            20                  25                  30

Leu Ala Trp Tyr Gln Gln Lys Pro Gly Gln Pro Pro Lys Leu Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Val Gln Cys
65                  70                  75                  80

Asp Asp Ala Ala Thr Tyr Tyr Cys Ala Gly Gly Tyr Ser Ser Ser Ser
                85                  90                  95

Asp Lys Phe Pro Phe Gly Gly Gly Thr Glu Leu Glu Ile Leu
            100                 105                 110


<210> SEQ ID NO 14
<211> LENGTH: 110
<212> TYPE: PRT
<213> ORGANISM: Unknown
<220> FEATURE:
<221> NAME/KEY: source
<223> OTHER INFORMATION: /note="Description of Unknown:
      rabbit immunoglobulin VL domain polypeptide"
<220> FEATURE:
<221> NAME/KEY: source
<223> OTHER INFORMATION: /note="#11"

<400> SEQUENCE: 14

Glu Leu Asp Leu Thr Gln Thr Pro Ala Ser Val Glu Val Ala Val Gly
1               5                   10                  15

Gly Thr Val Thr Ile Asn Cys Gln Ala Ser Gln Asn Ile Tyr Asn Tyr
            20                  25                  30

Leu Ser Trp Tyr Gln Gln Lys Pro Gly Gln Arg Pro Lys Leu Leu Ile
        35                  40                  45

Tyr Arg Ala Ser Thr Leu Ala Ser Gly Val Ser Ser Arg Phe Lys Gly
    50                  55                  60
```

Ser Gly Ser Gly Thr Glu Tyr Thr Leu Thr Ile Ser Gly Val Gln Cys
65 70 75 80

Ala Asp Ala Ala Thr Tyr Tyr Cys Gln Gln Gly Tyr Asn Ile Gly His
85 90 95

Val Glu Asn Ala Phe Gly Gly Gly Thr Glu Leu Glu Ile Leu
100 105 110

<210> SEQ ID NO 15
<211> LENGTH: 112
<212> TYPE: PRT
<213> ORGANISM: Unknown
<220> FEATURE:
<221> NAME/KEY: source
<223> OTHER INFORMATION: /note="Description of Unknown: rabbit immunoglobulin VL domain polypeptide"
<220> FEATURE:
<221> NAME/KEY: source
<223> OTHER INFORMATION: /note="#14"

<400> SEQUENCE: 15

Glu Leu Val Met Thr Gln Thr Pro Ser Pro Val Ser Ala Ala Val Gly
1 5 10 15

Gly Thr Val Thr Ile Asn Cys Gln Ala Ser Gln Ser Val Tyr Ser Asn
20 25 30

Asn Trp Leu Ser Trp Tyr Gln Gln Lys Pro Gly Gln Pro Pro Lys Leu
35 40 45

Leu Ile Tyr Asp Ala Ser Lys Leu Ala Ser Gly Val Pro Ser Arg Phe
50 55 60

Ser Gly Ser Gly Ser Gly Thr Gln Phe Thr Leu Thr Ile Ser Gly Val
65 70 75 80

Gln Cys Asp Asp Ala Ala Thr Tyr Tyr Cys Leu Gly Gly Tyr Tyr Ser
85 90 95

Ser Gly Trp Tyr Ser Ala Phe Gly Gly Gly Thr Glu Leu Glu Ile Leu
100 105 110

<210> SEQ ID NO 16
<211> LENGTH: 109
<212> TYPE: PRT
<213> ORGANISM: Unknown
<220> FEATURE:
<221> NAME/KEY: source
<223> OTHER INFORMATION: /note="Description of Unknown: rabbit immunoglobulin VL domain polypeptide"
<220> FEATURE:
<221> NAME/KEY: source
<223> OTHER INFORMATION: /note="#17"

<400> SEQUENCE: 16

Glu Leu Val Met Thr Gln Thr Pro Ala Ser Val Ser Glu Pro Val Gly
1 5 10 15

Gly Thr Val Thr Ile Lys Cys Gln Ala Ser Gln Ser Ile Ser Ser Tyr
20 25 30

Leu Ala Trp Tyr Gln Gln Lys Pro Gly Gln Pro Pro Lys Leu Leu Ile
35 40 45

Tyr Ala Ala Ser Thr Leu Ala Ser Gly Val Pro Ser Arg Phe Lys Gly
50 55 60

Ser Gly Ser Gly Thr Gln Phe Thr Leu Thr Ile Ser Asp Leu Glu Cys
65 70 75 80

Ala Asp Ala Ala Thr Tyr Tyr Cys Gln Ser Tyr Tyr Asp Ser Ser Ser
85 90 95

```
Thr Asn Ala Phe Gly Gly Gly Thr Glu Val Val Val Lys
            100                 105


<210> SEQ ID NO 17
<211> LENGTH: 112
<212> TYPE: PRT
<213> ORGANISM: Unknown
<220> FEATURE:
<221> NAME/KEY: source
<223> OTHER INFORMATION: /note="Description of Unknown:
      rabbit immunoglobulin VL domain polypeptide"
<220> FEATURE:
<221> NAME/KEY: source
<223> OTHER INFORMATION: /note="#19"

<400> SEQUENCE: 17

Glu Leu Val Met Thr Gln Thr Pro Ser Pro Val Ser Ala Ala Val Gly
1               5                   10                  15

Gly Thr Val Thr Ile Ser Cys Gln Ala Ser Gln Ser Val Tyr Asn Asn
            20                  25                  30

Lys Asn Leu Ala Trp Tyr Gln Gln Lys Pro Gly Gln Pro Pro Lys Leu
        35                  40                  45

Leu Ile Tyr Asp Ala Ser Lys Leu Ala Ser Gly Val Ser Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Val Tyr Asn Ser
                85                  90                  95

Asn Asn Asp Ala Cys Ala Phe Gly Gly Gly Thr Glu Val Val Val Lys
            100                 105                 110


<210> SEQ ID NO 18
<211> LENGTH: 111
<212> TYPE: PRT
<213> ORGANISM: Unknown
<220> FEATURE:
<221> NAME/KEY: source
<223> OTHER INFORMATION: /note="Description of Unknown:
      rabbit immunoglobulin VL domain polypeptide"
<220> FEATURE:
<221> NAME/KEY: source
<223> OTHER INFORMATION: /note="#26"

<400> SEQUENCE: 18

Glu Leu Asp Leu Thr Gln Thr Pro Ser Pro Val Ser Ala Ala Val Gly
1               5                   10                  15

Gly Thr Val Thr Ile Ser Cys Gln Ser Ser Glu Ser Val Tyr Ser Asn
            20                  25                  30

Asn Arg Leu Ala Trp Tyr Gln Gln Lys Pro Gly Gln Pro Pro Lys Leu
        35                  40                  45

Leu Ile Tyr Leu Ala Ser Ser Leu Ala Ser Gly Val Pro Ser Arg Phe
    50                  55                  60

Lys Gly Ser Gly Ser Gly Thr Gln Phe Thr Leu Thr Ile Arg Asp Leu
65                  70                  75                  80

Glu Cys Asp Asp Ala Ala Thr Tyr Tyr Cys Leu Gly Tyr Arg Ser Gly
                85                  90                  95

Ser Asp Gly Asp Ala Phe Gly Gly Gly Thr Glu Leu Glu Ile Leu
            100                 105                 110


<210> SEQ ID NO 19
<211> LENGTH: 108
<212> TYPE: PRT
```

```
<213> ORGANISM: Unknown
<220> FEATURE:
<221> NAME/KEY: source
<223> OTHER INFORMATION: /note="Description of Unknown:
      rabbit immunoglobulin VL domain polypeptide"
<220> FEATURE:
<221> NAME/KEY: source
<223> OTHER INFORMATION: /note="#29"

<400> SEQUENCE: 19

Glu Leu Asp Leu Thr Gln Thr Pro Ser Ser Val Glu Ala Ala Val Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly Gln Pro Pro Lys Leu Leu Ile
        35                  40                  45

Tyr Arg Ala Ser Ile Leu Ala Ser Gly Val Pro Ser Arg Phe Lys Ala
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Asp His Tyr Gly Ile Ser Asp
                85                  90                  95

Val Ala Phe Gly Gly Gly Thr Glu Leu Glu Ile Leu
            100                 105


<210> SEQ ID NO 20
<211> LENGTH: 112
<212> TYPE: PRT
<213> ORGANISM: Unknown
<220> FEATURE:
<221> NAME/KEY: source
<223> OTHER INFORMATION: /note="Description of Unknown:
      rabbit immunoglobulin VL domain polypeptide"
<220> FEATURE:
<221> NAME/KEY: source
<223> OTHER INFORMATION: /note="#37"

<400> SEQUENCE: 20

Glu Leu Asp Leu Thr Gln Thr Pro Ser Ser Lys Ser Val Pro Val Gly
1               5                   10                  15

Asp Thr Val Thr Ile Asn Cys Gln Ala Ser Asp Ser Val Tyr Ser Asn
            20                  25                  30

Asn Arg Leu Ala Trp Phe Gln Gln Lys Pro Gly Gln Pro Pro Lys Leu
        35                  40                  45

Leu Ile Tyr Gln Ala Ser Lys Leu Ala Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Gln Gly Ala Tyr Tyr Ser
                85                  90                  95

Ser Gly Trp Ser Asn Gly Phe Gly Gly Gly Thr Glu Val Val Val Lys
            100                 105                 110


<210> SEQ ID NO 21
<211> LENGTH: 110
<212> TYPE: PRT
<213> ORGANISM: Unknown
<220> FEATURE:
<221> NAME/KEY: source
<223> OTHER INFORMATION: /note="Description of Unknown:
      rabbit immunoglobulin VL domain polypeptide"
<220> FEATURE:
<221> NAME/KEY: source
```

<223> OTHER INFORMATION: /note="#53"

<400> SEQUENCE: 21

Glu Leu Val Leu Thr Gln Thr Pro Ala Ser Val Ser Glu Pro Val Gly
1 5 10 15

Gly Thr Val Thr Ile Lys Cys Gln Ala Ser Gln Ser Val Ser Asp Tyr
20 25 30

Leu Ala Trp Tyr Gln Gln Lys Pro Gly Gln Pro Pro Lys Leu Leu Ile
35 40 45

Tyr Arg Ala Ser Thr Leu Ala Ser Gly Val Pro Ser Arg Phe Lys Gly
50 55 60

Ser Gly Ser Gly Thr Gln Phe Thr Leu Thr Ile Ser Asp Leu Glu Cys
65 70 75 80

Ala Asp Ala Ala Thr Tyr Tyr Cys Gln Gly Gly Tyr Ala Gly Ser Ser
85 90 95

Tyr Gly Asn Ala Phe Gly Gly Gly Thr Glu Leu Glu Ile Leu
100 105 110

<210> SEQ ID NO 22
<211> LENGTH: 10
<212> TYPE: PRT
<213> ORGANISM: Dengue virus 2
<220> FEATURE:
<221> NAME/KEY: source
<223> OTHER INFORMATION: /note="#PepH1"

<400> SEQUENCE: 22

Val Gln Gln Leu Thr Lys Arg Phe Ser Leu
1 5 10

<210> SEQ ID NO 23
<211> LENGTH: 14
<212> TYPE: PRT
<213> ORGANISM: Dengue virus 2
<220> FEATURE:
<221> NAME/KEY: source
<223> OTHER INFORMATION: /note="#PepH2"

<400> SEQUENCE: 23

Lys Leu Phe Met Ala Leu Val Ala Phe Leu Arg Phe Leu Thr
1 5 10

<210> SEQ ID NO 24
<211> LENGTH: 7
<212> TYPE: PRT
<213> ORGANISM: Dengue virus 2
<220> FEATURE:
<221> NAME/KEY: source
<223> OTHER INFORMATION: /note="#PepH3 (PEP+)"

<400> SEQUENCE: 24

Ala Gly Ile Leu Lys Arg Trp
1 5

<210> SEQ ID NO 25
<211> LENGTH: 23
<212> TYPE: PRT
<213> ORGANISM: Dengue virus 2
<220> FEATURE:
<221> NAME/KEY: source
<223> OTHER INFORMATION: /note="#PepH4"

<400> SEQUENCE: 25

Lys Ser Lys Ala Ile Asn Val Leu Arg Gly Phe Arg Lys Glu Ile Gly 1 5 10 15

Arg Met Leu Asn Ile Leu Asn
20

<210> SEQ ID NO 26
<211> LENGTH: 20
<212> TYPE: PRT
<213> ORGANISM: Dengue virus 2
<220> FEATURE:
<221> NAME/KEY: source
<223> OTHER INFORMATION: /note="#PepHM'"

<400> SEQUENCE: 26

Leu Val Ala Phe Leu Arg Phe Leu Thr Ile Pro Pro Thr Ala Gly Ile
1 5 10 15

Leu Lys Arg Trp
20

<210> SEQ ID NO 27
<211> LENGTH: 15
<212> TYPE: PRT
<213> ORGANISM: Dengue virus 2
<220> FEATURE:
<221> NAME/KEY: source
<223> OTHER INFORMATION: /note="#PepHR'"

<400> SEQUENCE: 27

Lys Glu Ile Gly Arg Met Leu Asn Ile Leu Asn Arg Arg Arg Arg
1 5 10 15

<210> SEQ ID NO 28
<211> LENGTH: 132
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#2-PEP+"

<400> SEQUENCE: 28

Glu Leu Val Met Thr Gln Thr Pro Ser Pro Val Ser Ala Ala Val Gly
1 5 10 15

Gly Thr Val Ser Ile Ser Cys Gln Ser Ser Lys Ser Val Tyr Asn Asn
20 25 30

Asn Trp Leu Ser Trp Phe Gln Gln Lys Pro Gly Gln Pro Pro Lys Leu
35 40 45

Leu Ile Tyr Ser Ala Ser Thr Leu Ala Ser Gly Val Ser Ser Arg Phe
50 55 60

Lys Gly Ser Gly Ser Gly Thr Gln Phe Thr Leu Thr Ile Ser Asp Val
65 70 75 80

Gln Cys Asp Asp Ala Ala Thr Tyr Tyr Cys Gln Gly Glu Phe Asp Cys
85 90 95

Ser Gly Asp Cys Asn Val Phe Gly Gly Gly Thr Glu Leu Glu Ile Leu
100 105 110

Gly Ser Gly Gly Gly Gly Ser Gly Gly Gly Gly Ser Ser Ala Gly Ile
115 120 125

Leu Lys Arg Trp
130

<210> SEQ ID NO 29
<211> LENGTH: 135
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#2-PepH1"

<400> SEQUENCE: 29

```
Glu Leu Val Met Thr Gln Thr Pro Ser Pro Val Ser Ala Ala Val Gly
1               5                   10                  15

Gly Thr Val Ser Ile Ser Cys Gln Ser Ser Lys Ser Val Tyr Asn Asn
            20                  25                  30

Asn Trp Leu Ser Trp Phe Gln Gln Lys Pro Gly Gln Pro Pro Lys Leu
        35                  40                  45

Leu Ile Tyr Ser Ala Ser Thr Leu Ala Ser Gly Val Ser Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Gln Gly Glu Phe Asp Cys
                85                  90                  95

Ser Gly Asp Cys Asn Val Phe Gly Gly Gly Thr Glu Leu Glu Ile Leu
            100                 105                 110

Gly Ser Gly Gly Gly Gly Ser Gly Gly Gly Gly Ser Ser Val Gln Gln
        115                 120                 125

Leu Thr Lys Arg Phe Ser Leu
    130                 135
```

<210> SEQ ID NO 30
<211> LENGTH: 139
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#2-PepH2"

<400> SEQUENCE: 30

```
Glu Leu Val Met Thr Gln Thr Pro Ser Pro Val Ser Ala Ala Val Gly
1               5                   10                  15

Gly Thr Val Ser Ile Ser Cys Gln Ser Ser Lys Ser Val Tyr Asn Asn
            20                  25                  30

Asn Trp Leu Ser Trp Phe Gln Gln Lys Pro Gly Gln Pro Pro Lys Leu
        35                  40                  45

Leu Ile Tyr Ser Ala Ser Thr Leu Ala Ser Gly Val Ser Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Gln Gly Glu Phe Asp Cys
                85                  90                  95

Ser Gly Asp Cys Asn Val Phe Gly Gly Gly Thr Glu Leu Glu Ile Leu
            100                 105                 110

Gly Ser Gly Gly Gly Gly Ser Gly Gly Gly Gly Ser Ser Lys Leu Phe
        115                 120                 125
```

```
Met Ala Leu Val Ala Phe Leu Arg Phe Leu Thr
    130                 135


<210> SEQ ID NO 31
<211> LENGTH: 148
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#2-PepH4"

<400> SEQUENCE: 31

Glu Leu Val Met Thr Gln Thr Pro Ser Pro Val Ser Ala Ala Val Gly
1               5                   10                  15

Gly Thr Val Ser Ile Ser Cys Gln Ser Ser Lys Ser Val Tyr Asn Asn
            20                  25                  30

Asn Trp Leu Ser Trp Phe Gln Gln Lys Pro Gly Gln Pro Pro Lys Leu
        35                  40                  45

Leu Ile Tyr Ser Ala Ser Thr Leu Ala Ser Gly Val Ser Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Gln Gly Glu Phe Asp Cys
                85                  90                  95

Ser Gly Asp Cys Asn Val Phe Gly Gly Gly Thr Glu Leu Glu Ile Leu
            100                 105                 110

Gly Ser Gly Gly Gly Gly Ser Gly Gly Gly Gly Ser Ser Lys Ser Lys
        115                 120                 125

Ala Ile Asn Val Leu Arg Gly Phe Arg Lys Glu Ile Gly Arg Met Leu
    130                 135                 140

Asn Ile Leu Asn
145


<210> SEQ ID NO 32
<211> LENGTH: 132
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#20-PEP+"

<400> SEQUENCE: 32

Glu Leu Asp Leu Thr Gln Thr Pro Ser Ser Lys Ser Val Pro Val Gly
1               5                   10                  15

Asp Thr Val Thr Ile Asn Cys Gln Ala Ser Glu Ser Val Tyr Ser Asn
            20                  25                  30

Asn Arg Leu Ala Trp Phe Gln Gln Lys Pro Gly Gln Pro Pro Lys Leu
        35                  40                  45

Leu Ile Tyr Tyr Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Val
65                  70                  75                  80
```

Val Cys Asp Asp Ala Ala Thr Tyr Tyr Cys Ala Gly Tyr Lys Ser Ser
85 90 95

Thr Ser Asp Gly Ile Ala Phe Gly Gly Gly Thr Glu Val Val Val Lys
100 105 110

Gly Ser Gly Gly Gly Gly Ser Gly Gly Gly Gly Ser Ser Ala Gly Ile
115 120 125

Leu Lys Arg Trp
130

<210> SEQ ID NO 33
<211> LENGTH: 135
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#20-PepH1"

<400> SEQUENCE: 33

Glu Leu Asp Leu Thr Gln Thr Pro Ser Ser Lys Ser Val Pro Val Gly
1 5 10 15

Asp Thr Val Thr Ile Asn Cys Gln Ala Ser Glu Ser Val Tyr Ser Asn
20 25 30

Asn Arg Leu Ala Trp Phe Gln Gln Lys Pro Gly Gln Pro Pro Lys Leu
35 40 45

Leu Ile Tyr Tyr Ala Ser Thr Leu Ala Ser Gly Val Pro Ser Arg Phe
50 55 60

Lys Gly Ser Gly Ser Gly Thr Gln Phe Thr Leu Thr Ile Ser Asp Val
65 70 75 80

Val Cys Asp Asp Ala Ala Thr Tyr Tyr Cys Ala Gly Tyr Lys Ser Ser
85 90 95

Thr Ser Asp Gly Ile Ala Phe Gly Gly Gly Thr Glu Val Val Val Lys
100 105 110

Gly Ser Gly Gly Gly Gly Ser Gly Gly Gly Gly Ser Ser Val Gln Gln
115 120 125

Leu Thr Lys Arg Phe Ser Leu
130 135

<210> SEQ ID NO 34
<211> LENGTH: 139
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#20-PepH2"

<400> SEQUENCE: 34

Glu Leu Asp Leu Thr Gln Thr Pro Ser Ser Lys Ser Val Pro Val Gly
1 5 10 15

Asp Thr Val Thr Ile Asn Cys Gln Ala Ser Glu Ser Val Tyr Ser Asn
20 25 30

Asn Arg Leu Ala Trp Phe Gln Gln Lys Pro Gly Gln Pro Pro Lys Leu
35 40 45

Leu Ile Tyr Tyr Ala Ser Thr Leu Ala Ser Gly Val Pro Ser Arg Phe 50 55 60

Lys Gly Ser Gly Ser Gly Thr Gln Phe Thr Leu Thr Ile Ser Asp Val
65 70 75 80

Val Cys Asp Asp Ala Ala Thr Tyr Tyr Cys Ala Gly Tyr Lys Ser Ser
85 90 95

Thr Ser Asp Gly Ile Ala Phe Gly Gly Gly Thr Glu Val Val Val Lys
100 105 110

Gly Ser Gly Gly Gly Gly Ser Gly Gly Gly Gly Ser Ser Lys Leu Phe
115 120 125

Met Ala Leu Val Ala Phe Leu Arg Phe Leu Thr
130 135

<210> SEQ ID NO 35
<211> LENGTH: 148
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#20-PepH4"

<400> SEQUENCE: 35

Glu Leu Asp Leu Thr Gln Thr Pro Ser Ser Lys Ser Val Pro Val Gly
1 5 10 15

Asp Thr Val Thr Ile Asn Cys Gln Ala Ser Glu Ser Val Tyr Ser Asn
20 25 30

Asn Arg Leu Ala Trp Phe Gln Gln Lys Pro Gly Gln Pro Pro Lys Leu
35 40 45

Leu Ile Tyr Tyr Ala Ser Thr Leu Ala Ser Gly Val Pro Ser Arg Phe
50 55 60

Lys Gly Ser Gly Ser Gly Thr Gln Phe Thr Leu Thr Ile Ser Asp Val
65 70 75 80

Val Cys Asp Asp Ala Ala Thr Tyr Tyr Cys Ala Gly Tyr Lys Ser Ser
85 90 95

Thr Ser Asp Gly Ile Ala Phe Gly Gly Gly Thr Glu Val Val Val Lys
100 105 110

Gly Ser Gly Gly Gly Gly Ser Gly Gly Gly Gly Ser Ser Lys Ser Lys
115 120 125

Ala Ile Asn Val Leu Arg Gly Phe Arg Lys Glu Ile Gly Arg Met Leu
130 135 140

Asn Ile Leu Asn
145

<210> SEQ ID NO 36
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#6in-PEP+"

<400> SEQUENCE: 36

Glu Leu Asp Leu Thr Gln Thr Pro Ser Ser Val Ser Glu Pro Val Gly
1 5 10 15

Gly Thr Val Thr Ile Lys Cys Gln Ala Ser Gln Ser Ile Asn Ser Tyr
20 25 30

Leu Ala Trp Tyr Gln Gln Lys Pro Gly Gln Pro Pro Lys Leu Leu Ile
35 40 45

Tyr Arg Thr Ser Thr Leu Ala Ser Gly Val Ser Ser Arg Phe Lys Gly
50 55 60

Ser Gly Ser Gly Thr Glu Phe Thr Leu Thr Ile Ser Asp Leu Glu Cys
65 70 75 80

Ala Asp Ala Ala Thr Tyr Tyr Cys Gln Ser Tyr Tyr Ser Ala Ser Ser
85 90 95

Gly Trp Ala Phe Gly Gly Gly Thr Glu Val Val Val Lys Ser Gly Gly
100 105 110

Gly Gly Ser Gly Gly Gly Gly Ser Ser Ala Gly Ile Leu Lys Arg Trp
115 120 125

<210> SEQ ID NO 37
<211> LENGTH: 131
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#6in-PepH1"

<400> SEQUENCE: 37

Glu Leu Asp Leu Thr Gln Thr Pro Ser Ser Val Ser Glu Pro Val Gly
1 5 10 15

Gly Thr Val Thr Ile Lys Cys Gln Ala Ser Gln Ser Ile Asn Ser Tyr
20 25 30

Leu Ala Trp Tyr Gln Gln Lys Pro Gly Gln Pro Pro Lys Leu Leu Ile
35 40 45

Tyr Arg Thr Ser Thr Leu Ala Ser Gly Val Ser Ser Arg Phe Lys Gly
50 55 60

Ser Gly Ser Gly Thr Glu Phe Thr Leu Thr Ile Ser Asp Leu Glu Cys
65 70 75 80

Ala Asp Ala Ala Thr Tyr Tyr Cys Gln Ser Tyr Tyr Ser Ala Ser Ser
85 90 95

Gly Trp Ala Phe Gly Gly Gly Thr Glu Val Val Val Lys Ser Gly Gly
100 105 110

Gly Gly Ser Gly Gly Gly Gly Ser Ser Val Gln Gln Leu Thr Lys Arg
115 120 125

Phe Ser Leu
130

<210> SEQ ID NO 38
<211> LENGTH: 135
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#6in-PepH2"

<400> SEQUENCE: 38

```
Glu Leu Asp Leu Thr Gln Thr Pro Ser Ser Val Ser Glu Pro Val Gly
1               5                   10                  15

Gly Thr Val Thr Ile Lys Cys Gln Ala Ser Gln Ser Ile Asn Ser Tyr
            20                  25                  30

Leu Ala Trp Tyr Gln Gln Lys Pro Gly Gln Pro Pro Lys Leu Leu Ile
        35                  40                  45

Tyr Arg Thr Ser Thr Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Tyr Tyr Ser Ala Ser Ser
                85                  90                  95

Gly Trp Ala Phe Gly Gly Gly Thr Glu Val Val Val Lys Ser Gly Gly
            100                 105                 110

Gly Gly Ser Gly Gly Gly Gly Ser Ser Lys Leu Phe Met Ala Leu Val
        115                 120                 125

Ala Phe Leu Arg Phe Leu Thr
    130                 135
```

<210> SEQ ID NO 39
<211> LENGTH: 144
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#6in-PepH4"

<400> SEQUENCE: 39

```
Glu Leu Asp Leu Thr Gln Thr Pro Ser Ser Val Ser Glu Pro Val Gly
1               5                   10                  15

Gly Thr Val Thr Ile Lys Cys Gln Ala Ser Gln Ser Ile Asn Ser Tyr
            20                  25                  30

Leu Ala Trp Tyr Gln Gln Lys Pro Gly Gln Pro Pro Lys Leu Leu Ile
        35                  40                  45

Tyr Arg Thr Ser Thr Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Tyr Tyr Ser Ala Ser Ser
                85                  90                  95

Gly Trp Ala Phe Gly Gly Gly Thr Glu Val Val Val Lys Ser Gly Gly
            100                 105                 110

Gly Gly Ser Gly Gly Gly Gly Ser Ser Lys Ser Lys Ala Ile Asn Val
        115                 120                 125

Leu Arg Gly Phe Arg Lys Glu Ile Gly Arg Met Leu Asn Ile Leu Asn
    130                 135                 140
```

<210> SEQ ID NO 40
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:

<221> NAME/KEY: source
<223> OTHER INFORMATION: /note="#27in-PEP+"

<400> SEQUENCE: 40

Glu Leu Val Leu Thr Gln Thr Pro Ser Ser Val Ser Ala Ala Val Gly
1               5                   10                  15

Gly Thr Val Thr Ile Asn Cys Gln Ala Ser Gln Ser Val Ser Asn Arg
            20                  25                  30

Leu Ala Trp Tyr Gln Gln Lys Pro Gly Gln Pro Pro Lys Leu Leu Ile
        35                  40                  45

Tyr Gly Ala Ser Arg Leu Glu Ser Gly Val Pro Ser Arg Phe Arg Gly
    50                  55                  60

Ser Gly Ser Gly Thr Glu Phe Thr Leu Thr Ile Ser Gly Met Lys Ala
65                  70                  75                  80

Glu Asp Ala Ala Thr Tyr Tyr Cys Gln Ser Cys Tyr Tyr Ser Val Gly
                85                  90                  95

Val Thr Phe Gly Ala Gly Thr Asn Val Glu Ile Lys Ser Gly Gly Gly
            100                 105                 110

Gly Ser Gly Gly Gly Gly Ser Ser Ala Gly Ile Leu Lys Arg Trp
        115                 120                 125

<210> SEQ ID NO 41
<211> LENGTH: 130
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#27in-PepH1"

<400> SEQUENCE: 41

Glu Leu Val Leu Thr Gln Thr Pro Ser Ser Val Ser Ala Ala Val Gly
1               5                   10                  15

Gly Thr Val Thr Ile Asn Cys Gln Ala Ser Gln Ser Val Ser Asn Arg
            20                  25                  30

Leu Ala Trp Tyr Gln Gln Lys Pro Gly Gln Pro Pro Lys Leu Leu Ile
        35                  40                  45

Tyr Gly Ala Ser Arg Leu Glu Ser Gly Val Pro Ser Arg Phe Arg Gly
    50                  55                  60

Ser Gly Ser Gly Thr Glu Phe Thr Leu Thr Ile Ser Gly Met Lys Ala
65                  70                  75                  80

Glu Asp Ala Ala Thr Tyr Tyr Cys Gln Ser Cys Tyr Tyr Ser Val Gly
                85                  90                  95

Val Thr Phe Gly Ala Gly Thr Asn Val Glu Ile Lys Ser Gly Gly Gly
            100                 105                 110

Gly Ser Gly Gly Gly Gly Ser Ser Val Gln Gln Leu Thr Lys Arg Phe
        115                 120                 125

Ser Leu
    130

<210> SEQ ID NO 42
<211> LENGTH: 134
<212> TYPE: PRT
<213> ORGANISM: Artificial Sequence
<220> FEATURE:
<221> NAME/KEY: source
<223> OTHER INFORMATION: /note="Description of Artificial Sequence:

```
      Synthetic polypeptide construct"
<220> FEATURE:
<221> NAME/KEY: source
<223> OTHER INFORMATION: /note="#27in-PepH2"

<400> SEQUENCE: 42

Glu Leu Val Leu Thr Gln Thr Pro Ser Ser Val Ser Ala Ala Val Gly
1               5                   10                  15

Gly Thr Val Thr Ile Asn Cys Gln Ala Ser Gln Ser Val Ser Asn Arg
            20                  25                  30

Leu Ala Trp Tyr Gln Gln Lys Pro Gly Gln Pro Pro Lys Leu Leu Ile
        35                  40                  45

Tyr Gly Ala Ser Arg Leu Glu Ser Gly Val Pro Ser Arg Phe Arg Gly
    50                  55                  60

Ser Gly Ser Gly Thr Glu Phe Thr Leu Thr Ile Ser Gly Met Lys Ala
65                  70                  75                  80

Glu Asp Ala Ala Thr Tyr Tyr Cys Gln Ser Cys Tyr Tyr Ser Val Gly
                85                  90                  95

Val Thr Phe Gly Ala Gly Thr Asn Val Glu Ile Lys Ser Gly Gly Gly
            100                 105                 110

Gly Ser Gly Gly Gly Gly Ser Ser Lys Leu Phe Met Ala Leu Val Ala
        115                 120                 125

Phe Leu Arg Phe Leu Thr
    130


<210> SEQ ID NO 43
<211> LENGTH: 143
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#27in-PepH4"

<400> SEQUENCE: 43

Glu Leu Val Leu Thr Gln Thr Pro Ser Ser Val Ser Ala Ala Val Gly
1               5                   10                  15

Gly Thr Val Thr Ile Asn Cys Gln Ala Ser Gln Ser Val Ser Asn Arg
            20                  25                  30

Leu Ala Trp Tyr Gln Gln Lys Pro Gly Gln Pro Pro Lys Leu Leu Ile
        35                  40                  45

Tyr Gly Ala Ser Arg Leu Glu Ser Gly Val Pro Ser Arg Phe Arg Gly
    50                  55                  60

Ser Gly Ser Gly Thr Glu Phe Thr Leu Thr Ile Ser Gly Met Lys Ala
65                  70                  75                  80

Glu Asp Ala Ala Thr Tyr Tyr Cys Gln Ser Cys Tyr Tyr Ser Val Gly
                85                  90                  95

Val Thr Phe Gly Ala Gly Thr Asn Val Glu Ile Lys Ser Gly Gly Gly
            100                 105                 110

Gly Ser Gly Gly Gly Gly Ser Ser Lys Ser Lys Ala Ile Asn Val Leu
        115                 120                 125

Arg Gly Phe Arg Lys Glu Ile Gly Arg Met Leu Asn Ile Leu Asn
    130                 135                 140


<210> SEQ ID NO 44
<211> LENGTH: 129
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#1-PEP+"

<400> SEQUENCE: 44

Glu Leu Asp Leu Thr Gln Thr Pro Ala Ser Val Glu Ala Ala Val Gly
1               5                   10                  15

Gly Thr Val Thr Ile Asn Cys Gln Ala Ser Glu Ser Ile Ser Asn Tyr
            20                  25                  30

Leu Asn Trp Tyr Gln Gln Lys Pro Gly Gln Pro Pro Lys Arg Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Gly Val Glu Cys
65                  70                  75                  80

Ala Asp Ala Ala Thr Tyr Tyr Cys Gln Gln Ser Tyr Ser Tyr Ser Asn
                85                  90                  95

Val Asp Asn Thr Phe Gly Gly Gly Thr Glu Val Val Val Lys Ser Gly
            100                 105                 110

Gly Gly Gly Ser Gly Gly Gly Gly Ser Ser Ala Gly Ile Leu Lys Arg
        115                 120                 125

Trp


<210> SEQ ID NO 45
<211> LENGTH: 132
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#1-PepH1"

<400> SEQUENCE: 45

Glu Leu Asp Leu Thr Gln Thr Pro Ala Ser Val Glu Ala Ala Val Gly
1               5                   10                  15

Gly Thr Val Thr Ile Asn Cys Gln Ala Ser Glu Ser Ile Ser Asn Tyr
            20                  25                  30

Leu Asn Trp Tyr Gln Gln Lys Pro Gly Gln Pro Pro Lys Arg Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Gly Val Glu Cys
65                  70                  75                  80

Ala Asp Ala Ala Thr Tyr Tyr Cys Gln Gln Ser Tyr Ser Tyr Ser Asn
                85                  90                  95

Val Asp Asn Thr Phe Gly Gly Gly Thr Glu Val Val Val Lys Ser Gly
            100                 105                 110

Gly Gly Gly Ser Gly Gly Gly Gly Ser Ser Val Gln Gln Leu Thr Lys
        115                 120                 125

Arg Phe Ser Leu
    130
```

<210> SEQ ID NO 46
<211> LENGTH: 136
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#1-PepH2"

<400> SEQUENCE: 46

```
Glu Leu Asp Leu Thr Gln Thr Pro Ala Ser Val Glu Ala Ala Val Gly
1               5                   10                  15

Gly Thr Val Thr Ile Asn Cys Gln Ala Ser Glu Ser Ile Ser Asn Tyr
            20                  25                  30

Leu Asn Trp Tyr Gln Gln Lys Pro Gly Gln Pro Pro Lys Arg Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Gly Val Glu Cys
65                  70                  75                  80

Ala Asp Ala Ala Thr Tyr Tyr Cys Gln Gln Ser Tyr Ser Tyr Ser Asn
                85                  90                  95

Val Asp Asn Thr Phe Gly Gly Gly Thr Glu Val Val Val Lys Ser Gly
            100                 105                 110

Gly Gly Gly Ser Gly Gly Gly Gly Ser Ser Lys Leu Phe Met Ala Leu
        115                 120                 125

Val Ala Phe Leu Arg Phe Leu Thr
    130                 135
```

<210> SEQ ID NO 47
<211> LENGTH: 145
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#1-PepH4"

<400> SEQUENCE: 47

```
Glu Leu Asp Leu Thr Gln Thr Pro Ala Ser Val Glu Ala Ala Val Gly
1               5                   10                  15

Gly Thr Val Thr Ile Asn Cys Gln Ala Ser Glu Ser Ile Ser Asn Tyr
            20                  25                  30

Leu Asn Trp Tyr Gln Gln Lys Pro Gly Gln Pro Pro Lys Arg Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Gly Val Glu Cys
65                  70                  75                  80

Ala Asp Ala Ala Thr Tyr Tyr Cys Gln Gln Ser Tyr Ser Tyr Ser Asn
                85                  90                  95

Val Asp Asn Thr Phe Gly Gly Gly Thr Glu Val Val Val Lys Ser Gly
            100                 105                 110
```

```
Gly Gly Gly Ser Gly Gly Gly Gly Ser Ser Lys Ser Lys Ala Ile Asn
        115                 120                 125

Val Leu Arg Gly Phe Arg Lys Glu Ile Gly Arg Met Leu Asn Ile Leu
    130                 135                 140

Asn
145


<210> SEQ ID NO 48
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#3-PEP+"

<400> SEQUENCE: 48

Glu Leu Val Leu Thr Gln Thr Pro Ala Ser Val Ser Glu Pro Val Gly
1               5                   10                  15

Gly Thr Val Thr Ile Lys Cys Gln Ala Ser Gln Ser Ile Gly Ser Tyr
            20                  25                  30

Leu Ser Trp Tyr Gln Gln Lys Pro Gly Gln Arg Pro Lys Leu Leu Ile
        35                  40                  45

Tyr Asp Ala Ser Asn Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Cys Thr Tyr Tyr Gly Ser Ser
                85                  90                  95

Tyr Tyr Thr Phe Gly Gly Gly Thr Glu Val Val Val Lys Ser Gly Gly
            100                 105                 110

Gly Gly Ser Gly Gly Gly Gly Ser Ser Ala Gly Ile Leu Lys Arg Trp
        115                 120                 125


<210> SEQ ID NO 49
<211> LENGTH: 131
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#3-PepH1"

<400> SEQUENCE: 49

Glu Leu Val Leu Thr Gln Thr Pro Ala Ser Val Ser Glu Pro Val Gly
1               5                   10                  15

Gly Thr Val Thr Ile Lys Cys Gln Ala Ser Gln Ser Ile Gly Ser Tyr
            20                  25                  30

Leu Ser Trp Tyr Gln Gln Lys Pro Gly Gln Arg Pro Lys Leu Leu Ile
        35                  40                  45

Tyr Asp Ala Ser Asn Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Cys Thr Tyr Tyr Gly Ser Ser
```

```
                85                  90                  95

Tyr Tyr Thr Phe Gly Gly Gly Thr Glu Val Val Val Lys Ser Gly Gly
            100                 105                 110

Gly Gly Ser Gly Gly Gly Gly Ser Ser Val Gln Gln Leu Thr Lys Arg
        115                 120                 125

Phe Ser Leu
    130


<210> SEQ ID NO 50
<211> LENGTH: 135
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#3-PepH2"

<400> SEQUENCE: 50

Glu Leu Val Leu Thr Gln Thr Pro Ala Ser Val Ser Glu Pro Val Gly
1               5                   10                  15

Gly Thr Val Thr Ile Lys Cys Gln Ala Ser Gln Ser Ile Gly Ser Tyr
            20                  25                  30

Leu Ser Trp Tyr Gln Gln Lys Pro Gly Gln Arg Pro Lys Leu Leu Ile
        35                  40                  45

Tyr Asp Ala Ser Asn Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Cys Thr Tyr Tyr Gly Ser Ser
                85                  90                  95

Tyr Tyr Thr Phe Gly Gly Gly Thr Glu Val Val Val Lys Ser Gly Gly
            100                 105                 110

Gly Gly Ser Gly Gly Gly Gly Ser Ser Lys Leu Phe Met Ala Leu Val
        115                 120                 125

Ala Phe Leu Arg Phe Leu Thr
    130                 135


<210> SEQ ID NO 51
<211> LENGTH: 144
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#3-PepH4"

<400> SEQUENCE: 51

Glu Leu Val Leu Thr Gln Thr Pro Ala Ser Val Ser Glu Pro Val Gly
1               5                   10                  15

Gly Thr Val Thr Ile Lys Cys Gln Ala Ser Gln Ser Ile Gly Ser Tyr
            20                  25                  30

Leu Ser Trp Tyr Gln Gln Lys Pro Gly Gln Arg Pro Lys Leu Leu Ile
        35                  40                  45

Tyr Asp Ala Ser Asn Leu Ala Ser Gly Val Pro Ser Arg Phe Lys Gly
    50                  55                  60
```

```
Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Cys Thr Tyr Tyr Gly Ser Ser
                85                  90                  95

Tyr Tyr Thr Phe Gly Gly Gly Thr Glu Val Val Val Lys Ser Gly Gly
            100                 105                 110

Gly Gly Ser Gly Gly Gly Gly Ser Ser Lys Ser Lys Ala Ile Asn Val
        115                 120                 125

Leu Arg Gly Phe Arg Lys Glu Ile Gly Arg Met Leu Asn Ile Leu Asn
    130                 135                 140


<210> SEQ ID NO 52
<211> LENGTH: 131
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#4-PEP+"

<400> SEQUENCE: 52

Glu Leu Asp Leu Thr Gln Thr Pro Ser Ser Lys Ser Val Pro Val Gly
1               5                   10                  15

Asp Thr Val Thr Ile Asn Cys Gln Ala Ser Asp Ser Val Tyr Ser Asn
            20                  25                  30

Asn Arg Leu Ala Trp Phe Gln Gln Lys Pro Gly Gln Pro Pro Lys Leu
        35                  40                  45

Leu Ile Tyr Gln Ala Ser Lys Leu Ala Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Gln Gly Ala Tyr Tyr Ser
                85                  90                  95

Ser Gly Trp Ser Asn Gly Phe Gly Gly Gly Thr Glu Val Val Val Lys
            100                 105                 110

Ser Gly Gly Gly Gly Ser Gly Gly Gly Gly Ser Ser Ala Gly Ile Leu
        115                 120                 125

Lys Arg Trp
    130


<210> SEQ ID NO 53
<211> LENGTH: 134
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#4-PepH1"

<400> SEQUENCE: 53

Glu Leu Asp Leu Thr Gln Thr Pro Ser Ser Lys Ser Val Pro Val Gly
1               5                   10                  15

Asp Thr Val Thr Ile Asn Cys Gln Ala Ser Asp Ser Val Tyr Ser Asn
            20                  25                  30
```

Asn Arg Leu Ala Trp Phe Gln Gln Lys Pro Gly Gln Pro Pro Lys Leu
        35                  40                  45

Leu Ile Tyr Gln Ala Ser Lys Leu Ala Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Gln Gly Ala Tyr Tyr Ser
                85                  90                  95

Ser Gly Trp Ser Asn Gly Phe Gly Gly Gly Thr Glu Val Val Val Lys
            100                 105                 110

Ser Gly Gly Gly Gly Ser Gly Gly Gly Gly Ser Ser Val Gln Gln Leu
        115                 120                 125

Thr Lys Arg Phe Ser Leu
    130

<210> SEQ ID NO 54
<211> LENGTH: 138
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#4-PepH2"

<400> SEQUENCE: 54

Glu Leu Asp Leu Thr Gln Thr Pro Ser Ser Lys Ser Val Pro Val Gly
1               5                   10                  15

Asp Thr Val Thr Ile Asn Cys Gln Ala Ser Asp Ser Val Tyr Ser Asn
            20                  25                  30

Asn Arg Leu Ala Trp Phe Gln Gln Lys Pro Gly Gln Pro Pro Lys Leu
        35                  40                  45

Leu Ile Tyr Gln Ala Ser Lys Leu Ala Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Gln Gly Ala Tyr Tyr Ser
                85                  90                  95

Ser Gly Trp Ser Asn Gly Phe Gly Gly Gly Thr Glu Val Val Val Lys
            100                 105                 110

Ser Gly Gly Gly Gly Ser Gly Gly Gly Gly Ser Ser Lys Leu Phe Met
        115                 120                 125

Ala Leu Val Ala Phe Leu Arg Phe Leu Thr
    130                 135

<210> SEQ ID NO 55
<211> LENGTH: 147
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#4-PepH4"

<400> SEQUENCE: 55

Glu Leu Asp Leu Thr Gln Thr Pro Ser Ser Lys Ser Val Pro Val Gly 1 5 10 15

Asp Thr Val Thr Ile Asn Cys Gln Ala Ser Asp Ser Val Tyr Ser Asn
20 25 30

Asn Arg Leu Ala Trp Phe Gln Gln Lys Pro Gly Gln Pro Pro Lys Leu
35 40 45

Leu Ile Tyr Gln Ala Ser Lys Leu Ala Ser Gly Val Pro Ser Arg Phe
50 55 60

Ser Gly Ser Gly Ser Gly Thr Gln Phe Thr Leu Thr Ile Ser Gly Val
65 70 75 80

Gln Cys Asp Asp Ala Ala Thr Tyr Tyr Cys Gln Gly Ala Tyr Tyr Ser
85 90 95

Ser Gly Trp Ser Asn Gly Phe Gly Gly Gly Thr Glu Val Val Val Lys
100 105 110

Ser Gly Gly Gly Gly Ser Gly Gly Gly Gly Ser Ser Lys Ser Lys Ala
115 120 125

Ile Asn Val Leu Arg Gly Phe Arg Lys Glu Ile Gly Arg Met Leu Asn
130 135 140

Ile Leu Asn
145

<210> SEQ ID NO 56
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#5-PEP+"

<400> SEQUENCE: 56

Glu Leu Asp Leu Thr Gln Thr Pro Ala Ser Val Glu Val Ala Val Gly
1 5 10 15

Gly Thr Val Thr Ile Lys Cys Gln Ala Ser Gln Ser Ile Ser Thr Tyr
20 25 30

Leu Ser Trp Tyr Gln Gln Lys Ala Gly Gln Arg Pro Lys Leu Leu Ile
35 40 45

Tyr Gly Ala Ser Asn Leu Ala Ser Gly Val Pro Ser Arg Phe Lys Gly
50 55 60

Ser Gly Ser Gly Thr Gln Phe Thr Leu Thr Ile Ser Gly Val Glu Cys
65 70 75 80

Ala Asp Ala Ala Thr Tyr Tyr Cys Gln Gln Gly Tyr Ser Ser Ser Asn
85 90 95

Val Asp Asn Ala Phe Gly Gly Gly Thr Glu Leu Glu Ile Leu Ser Gly
100 105 110

Gly Gly Gly Ser Gly Gly Gly Gly Ser Ser Ala Gly Ile Leu Lys Arg
115 120 125

Trp

<210> SEQ ID NO 57
<211> LENGTH: 132
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"

```
<220> FEATURE:
<221> NAME/KEY: source
<223> OTHER INFORMATION: /note="#5-PepH1"

<400> SEQUENCE: 57

Glu Leu Asp Leu Thr Gln Thr Pro Ala Ser Val Glu Val Ala Val Gly
1               5                   10                  15

Gly Thr Val Thr Ile Lys Cys Gln Ala Ser Gln Ser Ile Ser Thr Tyr
            20                  25                  30

Leu Ser Trp Tyr Gln Gln Lys Ala Gly Gln Arg Pro Lys Leu Leu Ile
        35                  40                  45

Tyr Gly Ala Ser Asn Leu Ala Ser Gly Val Pro Ser Arg Phe Lys Gly
    50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Gly Tyr Ser Ser Ser Asn
                85                  90                  95

Val Asp Asn Ala Phe Gly Gly Gly Thr Glu Leu Glu Ile Leu Ser Gly
            100                 105                 110

Gly Gly Gly Ser Gly Gly Gly Gly Ser Ser Val Gln Gln Leu Thr Lys
        115                 120                 125

Arg Phe Ser Leu
    130


<210> SEQ ID NO 58
<211> LENGTH: 136
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#5-PepH2"

<400> SEQUENCE: 58

Glu Leu Asp Leu Thr Gln Thr Pro Ala Ser Val Glu Val Ala Val Gly
1               5                   10                  15

Gly Thr Val Thr Ile Lys Cys Gln Ala Ser Gln Ser Ile Ser Thr Tyr
            20                  25                  30

Leu Ser Trp Tyr Gln Gln Lys Ala Gly Gln Arg Pro Lys Leu Leu Ile
        35                  40                  45

Tyr Gly Ala Ser Asn Leu Ala Ser Gly Val Pro Ser Arg Phe Lys Gly
    50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Gly Tyr Ser Ser Ser Asn
                85                  90                  95

Val Asp Asn Ala Phe Gly Gly Gly Thr Glu Leu Glu Ile Leu Ser Gly
            100                 105                 110

Gly Gly Gly Ser Gly Gly Gly Gly Ser Ser Lys Leu Phe Met Ala Leu
        115                 120                 125

Val Ala Phe Leu Arg Phe Leu Thr
    130                 135


<210> SEQ ID NO 59
<211> LENGTH: 145
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#5-PepH4"

<400> SEQUENCE: 59

```
Glu Leu Asp Leu Thr Gln Thr Pro Ala Ser Val Glu Val Ala Val Gly
1               5                   10                  15

Gly Thr Val Thr Ile Lys Cys Gln Ala Ser Gln Ser Ile Ser Thr Tyr
            20                  25                  30

Leu Ser Trp Tyr Gln Gln Lys Ala Gly Gln Arg Pro Lys Leu Leu Ile
        35                  40                  45

Tyr Gly Ala Ser Asn Leu Ala Ser Gly Val Pro Ser Arg Phe Lys Gly
    50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Gly Tyr Ser Ser Ser Asn
                85                  90                  95

Val Asp Asn Ala Phe Gly Gly Gly Thr Glu Leu Glu Ile Leu Ser Gly
            100                 105                 110

Gly Gly Gly Ser Gly Gly Gly Gly Ser Ser Lys Ser Lys Ala Ile Asn
        115                 120                 125

Val Leu Arg Gly Phe Arg Lys Glu Ile Gly Arg Met Leu Asn Ile Leu
    130                 135                 140

Asn
145
```

<210> SEQ ID NO 60
<211> LENGTH: 131
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#6-PEP+"

<400> SEQUENCE: 60

```
Glu Leu Asp Met Thr Gln Thr Pro Ser Ser Lys Ser Val Pro Val Gly
1               5                   10                  15

Asp Thr Val Thr Ile Asn Cys Gln Ala Ser Glu Ser Val Tyr Ser Asn
            20                  25                  30

Asn Tyr Leu Ala Trp Tyr Gln Gln Lys Pro Gly Gln Pro Pro Lys Leu
        35                  40                  45

Leu Ile Tyr Lys Ala Ser Thr Leu Ala Ser Gly Val Ser Ser Arg Phe
    50                  55                  60

Ser Gly Ser Gly Ser Gly Thr Gln Phe Thr Leu Thr Ile Ser Asp Val
65                  70                  75                  80

Val Cys Asp Asp Ala Gly Thr Tyr Tyr Cys Ala Gly Phe Lys Gly Thr
                85                  90                  95

Gly Thr Asp Gly Asn Ala Phe Gly Gly Gly Thr Glu Leu Glu Ile Leu
            100                 105                 110

Ser Gly Gly Gly Gly Ser Gly Gly Gly Gly Ser Ser Ala Gly Ile Leu
        115                 120                 125
```

```
Lys Arg Trp
    130


<210> SEQ ID NO 61
<211> LENGTH: 134
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#6-PepH1"

<400> SEQUENCE: 61

Glu Leu Asp Met Thr Gln Thr Pro Ser Ser Lys Ser Val Pro Val Gly
1               5                   10                  15

Asp Thr Val Thr Ile Asn Cys Gln Ala Ser Glu Ser Val Tyr Ser Asn
            20                  25                  30

Asn Tyr Leu Ala Trp Tyr Gln Gln Lys Pro Gly Gln Pro Pro Lys Leu
        35                  40                  45

Leu Ile Tyr Lys Ala Ser Thr Leu Ala Ser Gly Val Ser Ser Arg Phe
    50                  55                  60

Ser Gly Ser Gly Ser Gly Thr Gln Phe Thr Leu Thr Ile Ser Asp Val
65                  70                  75                  80

Val Cys Asp Asp Ala Gly Thr Tyr Tyr Cys Ala Gly Phe Lys Gly Thr
                85                  90                  95

Gly Thr Asp Gly Asn Ala Phe Gly Gly Gly Thr Glu Leu Glu Ile Leu
            100                 105                 110

Ser Gly Gly Gly Gly Ser Gly Gly Gly Gly Ser Ser Val Gln Gln Leu
        115                 120                 125

Thr Lys Arg Phe Ser Leu
    130


<210> SEQ ID NO 62
<211> LENGTH: 138
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#6-PepH2"

<400> SEQUENCE: 62

Glu Leu Asp Met Thr Gln Thr Pro Ser Ser Lys Ser Val Pro Val Gly
1               5                   10                  15

Asp Thr Val Thr Ile Asn Cys Gln Ala Ser Glu Ser Val Tyr Ser Asn
            20                  25                  30

Asn Tyr Leu Ala Trp Tyr Gln Gln Lys Pro Gly Gln Pro Pro Lys Leu
        35                  40                  45

Leu Ile Tyr Lys Ala Ser Thr Leu Ala Ser Gly Val Ser Ser Arg Phe
    50                  55                  60

Ser Gly Ser Gly Ser Gly Thr Gln Phe Thr Leu Thr Ile Ser Asp Val
65                  70                  75                  80

Val Cys Asp Asp Ala Gly Thr Tyr Tyr Cys Ala Gly Phe Lys Gly Thr
                85                  90                  95
```

```
Gly Thr Asp Gly Asn Ala Phe Gly Gly Gly Thr Glu Leu Glu Ile Leu
            100                 105                 110

Ser Gly Gly Gly Gly Ser Gly Gly Gly Gly Ser Ser Lys Leu Phe Met
        115                 120                 125

Ala Leu Val Ala Phe Leu Arg Phe Leu Thr
    130                 135


<210> SEQ ID NO 63
<211> LENGTH: 147
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#6-PepH4"

<400> SEQUENCE: 63

Glu Leu Asp Met Thr Gln Thr Pro Ser Ser Lys Ser Val Pro Val Gly
1               5                   10                  15

Asp Thr Val Thr Ile Asn Cys Gln Ala Ser Glu Ser Val Tyr Ser Asn
            20                  25                  30

Asn Tyr Leu Ala Trp Tyr Gln Gln Lys Pro Gly Gln Pro Pro Lys Leu
        35                  40                  45

Leu Ile Tyr Lys Ala Ser Thr Leu Ala Ser Gly Val Ser Ser Arg Phe
    50                  55                  60

Ser Gly Ser Gly Ser Gly Thr Gln Phe Thr Leu Thr Ile Ser Asp Val
65                  70                  75                  80

Val Cys Asp Asp Ala Gly Thr Tyr Tyr Cys Ala Gly Phe Lys Gly Thr
                85                  90                  95

Gly Thr Asp Gly Asn Ala Phe Gly Gly Gly Thr Glu Leu Glu Ile Leu
            100                 105                 110

Ser Gly Gly Gly Gly Ser Gly Gly Gly Gly Ser Ser Lys Ser Lys Ala
        115                 120                 125

Ile Asn Val Leu Arg Gly Phe Arg Lys Glu Ile Gly Arg Met Leu Asn
    130                 135                 140

Ile Leu Asn
145


<210> SEQ ID NO 64
<211> LENGTH: 132
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#7-PEP+"

<400> SEQUENCE: 64

Glu Leu Val Leu Thr Gln Thr Pro Ser Ser Lys Ser Val Pro Val Gly
1               5                   10                  15

Asp Thr Val Thr Ile Asn Cys Gln Ala Ser Asp Ser Val Tyr Ser Asn
            20                  25                  30

Asn Phe Leu Ser Trp Phe Gln Gln Lys Pro Gly Gln Pro Pro Lys Leu
        35                  40                  45

Leu Ile Tyr Ser Ala Ser Thr Leu Ala Ser Gly Val Pro Ser Arg Phe
```

```
    50                  55                  60

Lys Gly Ser Gly Ser Gly Thr Gln Phe Thr Leu Thr Ile Ser Asp Leu
65                  70                  75                  80

Glu Cys Ala Asp Ala Ala Thr Tyr Tyr Cys Gln Asn Tyr Arg Asn Ile
                85                  90                  95

Gly Asp Tyr Gly Val Pro Phe Gly Gly Gly Thr Glu Val Val Val Lys
            100                 105                 110

Gly Ser Gly Gly Gly Gly Ser Gly Gly Gly Gly Ser Ser Ala Gly Ile
        115                 120                 125

Leu Lys Arg Trp
    130


<210> SEQ ID NO 65
<211> LENGTH: 135
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#7-PepH1"

<400> SEQUENCE: 65

Glu Leu Val Leu Thr Gln Thr Pro Ser Ser Lys Ser Val Pro Val Gly
1               5                   10                  15

Asp Thr Val Thr Ile Asn Cys Gln Ala Ser Asp Ser Val Tyr Ser Asn
            20                  25                  30

Asn Phe Leu Ser Trp Phe Gln Gln Lys Pro Gly Gln Pro Pro Lys Leu
        35                  40                  45

Leu Ile Tyr Ser Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Ala Asp Ala Ala Thr Tyr Tyr Cys Gln Asn Tyr Arg Asn Ile
                85                  90                  95

Gly Asp Tyr Gly Val Pro Phe Gly Gly Gly Thr Glu Val Val Val Lys
            100                 105                 110

Gly Ser Gly Gly Gly Gly Ser Gly Gly Gly Gly Ser Ser Val Gln Gln
        115                 120                 125

Leu Thr Lys Arg Phe Ser Leu
    130                 135


<210> SEQ ID NO 66
<211> LENGTH: 139
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#7-PepH2"

<400> SEQUENCE: 66

Glu Leu Val Leu Thr Gln Thr Pro Ser Ser Lys Ser Val Pro Val Gly
1               5                   10                  15

Asp Thr Val Thr Ile Asn Cys Gln Ala Ser Asp Ser Val Tyr Ser Asn
            20                  25                  30
```

```
Asn Phe Leu Ser Trp Phe Gln Gln Lys Pro Gly Gln Pro Pro Lys Leu
        35                  40                  45

Leu Ile Tyr Ser Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Ala Asp Ala Ala Thr Tyr Tyr Cys Gln Asn Tyr Arg Asn Ile
                85                  90                  95

Gly Asp Tyr Gly Val Pro Phe Gly Gly Gly Thr Glu Val Val Val Lys
            100                 105                 110

Gly Ser Gly Gly Gly Gly Ser Gly Gly Gly Gly Ser Ser Lys Leu Phe
        115                 120                 125

Met Ala Leu Val Ala Phe Leu Arg Phe Leu Thr
    130                 135


<210> SEQ ID NO 67
<211> LENGTH: 148
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#7-PepH4"

<400> SEQUENCE: 67

Glu Leu Val Leu Thr Gln Thr Pro Ser Ser Lys Ser Val Pro Val Gly
1               5                   10                  15

Asp Thr Val Thr Ile Asn Cys Gln Ala Ser Asp Ser Val Tyr Ser Asn
            20                  25                  30

Asn Phe Leu Ser Trp Phe Gln Gln Lys Pro Gly Gln Pro Pro Lys Leu
        35                  40                  45

Leu Ile Tyr Ser Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Ala Asp Ala Ala Thr Tyr Tyr Cys Gln Asn Tyr Arg Asn Ile
                85                  90                  95

Gly Asp Tyr Gly Val Pro Phe Gly Gly Gly Thr Glu Val Val Val Lys
            100                 105                 110

Gly Ser Gly Gly Gly Gly Ser Gly Gly Gly Gly Ser Ser Lys Ser Lys
        115                 120                 125

Ala Ile Asn Val Leu Arg Gly Phe Arg Lys Glu Ile Gly Arg Met Leu
    130                 135                 140

Asn Ile Leu Asn
145


<210> SEQ ID NO 68
<211> LENGTH: 130
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#8-PEP+"
```

<400> SEQUENCE: 68

Glu Leu Val Met Thr Gln Thr Pro Ser Ser Val Ser Glu Pro Val Gly
1 5 10 15

Gly Thr Val Thr Ile Lys Cys Gln Ala Ser Gln Asn Ile Gly Gly Tyr
20 25 30

Leu Ala Trp Tyr Gln Gln Lys Pro Gly Gln Pro Pro Lys Leu Leu Ile
35 40 45

Tyr Asp Ala Ser Thr Leu Pro Ser Gly Val Pro Ser Arg Phe Ser Gly
50 55 60

Ser Gly Tyr Gly Thr Glu Phe Thr Leu Thr Ile Ser Asp Leu Glu Cys
65 70 75 80

Ala Asp Ala Ala Thr Tyr Tyr Cys Gln Cys Thr Asp Tyr Gly Ser Ser
85 90 95

Tyr Ile Tyr Asn Thr Phe Gly Gly Gly Thr Glu Leu Glu Ile Leu Ser
100 105 110

Gly Gly Gly Gly Ser Gly Gly Gly Gly Ser Ser Ala Gly Ile Leu Lys
115 120 125

Arg Trp
130

<210> SEQ ID NO 69
<211> LENGTH: 133
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#8-PepH1"

<400> SEQUENCE: 69

Glu Leu Val Met Thr Gln Thr Pro Ser Ser Val Ser Glu Pro Val Gly
1 5 10 15

Gly Thr Val Thr Ile Lys Cys Gln Ala Ser Gln Asn Ile Gly Gly Tyr
20 25 30

Leu Ala Trp Tyr Gln Gln Lys Pro Gly Gln Pro Pro Lys Leu Leu Ile
35 40 45

Tyr Asp Ala Ser Thr Leu Pro Ser Gly Val Pro Ser Arg Phe Ser Gly
50 55 60

Ser Gly Tyr Gly Thr Glu Phe Thr Leu Thr Ile Ser Asp Leu Glu Cys
65 70 75 80

Ala Asp Ala Ala Thr Tyr Tyr Cys Gln Cys Thr Asp Tyr Gly Ser Ser
85 90 95

Tyr Ile Tyr Asn Thr Phe Gly Gly Gly Thr Glu Leu Glu Ile Leu Ser
100 105 110

Gly Gly Gly Gly Ser Gly Gly Gly Gly Ser Ser Val Gln Gln Leu Thr
115 120 125

Lys Arg Phe Ser Leu
130

<210> SEQ ID NO 70
<211> LENGTH: 137
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic polypeptide construct"
<220> FEATURE:
<221> NAME/KEY: source
<223> OTHER INFORMATION: /note="#8-PepH2"

<400> SEQUENCE: 70

Glu Leu Val Met Thr Gln Thr Pro Ser Ser Val Ser Glu Pro Val Gly
1               5                   10                  15

Gly Thr Val Thr Ile Lys Cys Gln Ala Ser Gln Asn Ile Gly Gly Tyr
            20                  25                  30

Leu Ala Trp Tyr Gln Gln Lys Pro Gly Gln Pro Pro Lys Leu Leu Ile
        35                  40                  45

Tyr Asp Ala Ser Thr Leu Pro Ser Gly Val Pro Ser Arg Phe Ser Gly
    50                  55                  60

Ser Gly Tyr Gly Thr Glu Phe Thr Leu Thr Ile Ser Asp Leu Glu Cys
65                  70                  75                  80

Ala Asp Ala Ala Thr Tyr Tyr Cys Gln Cys Thr Asp Tyr Gly Ser Ser
                85                  90                  95

Tyr Ile Tyr Asn Thr Phe Gly Gly Gly Thr Glu Leu Glu Ile Leu Ser
            100                 105                 110

Gly Gly Gly Gly Ser Gly Gly Gly Gly Ser Ser Lys Leu Phe Met Ala
        115                 120                 125

Leu Val Ala Phe Leu Arg Phe Leu Thr
    130                 135


<210> SEQ ID NO 71
<211> LENGTH: 146
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#8-PepH4"

<400> SEQUENCE: 71

Glu Leu Val Met Thr Gln Thr Pro Ser Ser Val Ser Glu Pro Val Gly
1               5                   10                  15

Gly Thr Val Thr Ile Lys Cys Gln Ala Ser Gln Asn Ile Gly Gly Tyr
            20                  25                  30

Leu Ala Trp Tyr Gln Gln Lys Pro Gly Gln Pro Pro Lys Leu Leu Ile
        35                  40                  45

Tyr Asp Ala Ser Thr Leu Pro Ser Gly Val Pro Ser Arg Phe Ser Gly
    50                  55                  60

Ser Gly Tyr Gly Thr Glu Phe Thr Leu Thr Ile Ser Asp Leu Glu Cys
65                  70                  75                  80

Ala Asp Ala Ala Thr Tyr Tyr Cys Gln Cys Thr Asp Tyr Gly Ser Ser
                85                  90                  95

Tyr Ile Tyr Asn Thr Phe Gly Gly Gly Thr Glu Leu Glu Ile Leu Ser
            100                 105                 110

Gly Gly Gly Gly Ser Gly Gly Gly Gly Ser Ser Lys Ser Lys Ala Ile
        115                 120                 125

Asn Val Leu Arg Gly Phe Arg Lys Glu Ile Gly Arg Met Leu Asn Ile
    130                 135                 140

Leu Asn
145
```

<210> SEQ ID NO 72
<211> LENGTH: 130
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#9-PEP+"

<400> SEQUENCE: 72

```
Glu Leu Asp Leu Thr Gln Thr Pro Ser Pro Val Ser Ala Ala Val Gly
1               5                   10                  15

Gly Thr Val Thr Ile Ser Cys Gln Ser Ser Glu Ser Val Tyr Ser Asn
            20                  25                  30

Asn Arg Leu Ala Trp Tyr Gln Gln Lys Pro Gly Gln Pro Pro Lys Leu
        35                  40                  45

Leu Ile Tyr Leu Ala Ser Ser Leu Ala Ser Gly Val Pro Ser Arg Phe
    50                  55                  60

Lys Gly Ser Gly Ser Gly Thr Gln Phe Thr Leu Thr Ile Arg Asp Leu
65                  70                  75                  80

Glu Cys Asp Asp Ala Ala Thr Tyr Tyr Cys Leu Gly Tyr Arg Ser Gly
                85                  90                  95

Ser Asp Gly Asp Ala Phe Gly Gly Gly Thr Glu Leu Glu Ile Leu Ser
            100                 105                 110

Gly Gly Gly Gly Ser Gly Gly Gly Gly Ser Ser Ala Gly Ile Leu Lys
        115                 120                 125

Arg Trp
    130
```

<210> SEQ ID NO 73
<211> LENGTH: 133
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#9-PepH1"

<400> SEQUENCE: 73

```
Glu Leu Asp Leu Thr Gln Thr Pro Ser Pro Val Ser Ala Ala Val Gly
1               5                   10                  15

Gly Thr Val Thr Ile Ser Cys Gln Ser Ser Glu Ser Val Tyr Ser Asn
            20                  25                  30

Asn Arg Leu Ala Trp Tyr Gln Gln Lys Pro Gly Gln Pro Pro Lys Leu
        35                  40                  45

Leu Ile Tyr Leu Ala Ser Ser Leu Ala Ser Gly Val Pro Ser Arg Phe
    50                  55                  60

Lys Gly Ser Gly Ser Gly Thr Gln Phe Thr Leu Thr Ile Arg Asp Leu
65                  70                  75                  80

Glu Cys Asp Asp Ala Ala Thr Tyr Tyr Cys Leu Gly Tyr Arg Ser Gly
                85                  90                  95

Ser Asp Gly Asp Ala Phe Gly Gly Gly Thr Glu Leu Glu Ile Leu Ser
            100                 105                 110
```

Gly Gly Gly Gly Ser Gly Gly Gly Gly Ser Ser Val Gln Gln Leu Thr
        115                 120                 125

Lys Arg Phe Ser Leu
    130

<210> SEQ ID NO 74
<211> LENGTH: 137
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#9-PepH2"

<400> SEQUENCE: 74

Glu Leu Asp Leu Thr Gln Thr Pro Ser Pro Val Ser Ala Ala Val Gly
1               5                   10                  15

Gly Thr Val Thr Ile Ser Cys Gln Ser Ser Glu Ser Val Tyr Ser Asn
            20                  25                  30

Asn Arg Leu Ala Trp Tyr Gln Gln Lys Pro Gly Gln Pro Pro Lys Leu
        35                  40                  45

Leu Ile Tyr Leu Ala Ser Ser Leu Ala Ser Gly Val Pro Ser Arg Phe
    50                  55                  60

Lys Gly Ser Gly Ser Gly Thr Gln Phe Thr Leu Thr Ile Arg Asp Leu
65                  70                  75                  80

Glu Cys Asp Asp Ala Ala Thr Tyr Tyr Cys Leu Gly Tyr Arg Ser Gly
                85                  90                  95

Ser Asp Gly Asp Ala Phe Gly Gly Gly Thr Glu Leu Glu Ile Leu Ser
            100                 105                 110

Gly Gly Gly Gly Ser Gly Gly Gly Gly Ser Ser Lys Leu Phe Met Ala
        115                 120                 125

Leu Val Ala Phe Leu Arg Phe Leu Thr
    130                 135

<210> SEQ ID NO 75
<211> LENGTH: 146
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#9-PepH4"

<400> SEQUENCE: 75

Glu Leu Asp Leu Thr Gln Thr Pro Ser Pro Val Ser Ala Ala Val Gly
1               5                   10                  15

Gly Thr Val Thr Ile Ser Cys Gln Ser Ser Glu Ser Val Tyr Ser Asn
            20                  25                  30

Asn Arg Leu Ala Trp Tyr Gln Gln Lys Pro Gly Gln Pro Pro Lys Leu
        35                  40                  45

Leu Ile Tyr Leu Ala Ser Ser Leu Ala Ser Gly Val Pro Ser Arg Phe
    50                  55                  60

Lys Gly Ser Gly Ser Gly Thr Gln Phe Thr Leu Thr Ile Arg Asp Leu
65                  70                  75                  80

Glu Cys Asp Asp Ala Ala Thr Tyr Tyr Cys Leu Gly Tyr Arg Ser Gly

```
                85                  90                  95

Ser Asp Gly Asp Ala Phe Gly Gly Gly Thr Glu Leu Glu Ile Leu Ser
            100                 105                 110

Gly Gly Gly Gly Ser Gly Gly Gly Gly Ser Ser Lys Ser Lys Ala Ile
        115                 120                 125

Asn Val Leu Arg Gly Phe Arg Lys Glu Ile Gly Arg Met Leu Asn Ile
    130                 135                 140

Leu Asn
145
```

<210> SEQ ID NO 76
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#10-PEP+"

<400> SEQUENCE: 76

```
Glu Leu Asp Leu Thr Gln Thr Pro Ala Ser Val Glu Val Ala Val Gly
1               5                   10                  15

Gly Thr Val Thr Ile Lys Cys Gln Ala Ser Glu Ser Ile Gly Asn Trp
            20                  25                  30

Leu Ala Trp Tyr Gln Gln Lys Pro Gly Gln Pro Pro Lys Leu Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Val Gln Cys
65                  70                  75                  80

Asp Asp Ala Ala Thr Tyr Tyr Cys Ala Gly Gly Tyr Ser Ser Ser Ser
                85                  90                  95

Asp Lys Phe Pro Phe Gly Gly Gly Thr Glu Leu Glu Ile Leu Ser Gly
            100                 105                 110

Gly Gly Gly Ser Gly Gly Gly Gly Ser Ser Ala Gly Ile Leu Lys Arg
        115                 120                 125

Trp
```

<210> SEQ ID NO 77
<211> LENGTH: 132
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#10-PepH1"

<400> SEQUENCE: 77

```
Glu Leu Asp Leu Thr Gln Thr Pro Ala Ser Val Glu Val Ala Val Gly
1               5                   10                  15

Gly Thr Val Thr Ile Lys Cys Gln Ala Ser Glu Ser Ile Gly Asn Trp
            20                  25                  30

Leu Ala Trp Tyr Gln Gln Lys Pro Gly Gln Pro Pro Lys Leu Leu Ile
        35                  40                  45
```

```
Tyr Lys Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Val Gln Cys
65                  70                  75                  80

Asp Asp Ala Ala Thr Tyr Tyr Cys Ala Gly Gly Tyr Ser Ser Ser Ser
                85                  90                  95

Asp Lys Phe Pro Phe Gly Gly Gly Thr Glu Leu Glu Ile Leu Ser Gly
            100                 105                 110

Gly Gly Gly Ser Gly Gly Gly Gly Ser Ser Val Gln Gln Leu Thr Lys
        115                 120                 125

Arg Phe Ser Leu
    130
```

<210> SEQ ID NO 78
<211> LENGTH: 136
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#10-PepH2"

<400> SEQUENCE: 78

```
Glu Leu Asp Leu Thr Gln Thr Pro Ala Ser Val Glu Val Ala Val Gly
1               5                   10                  15

Gly Thr Val Thr Ile Lys Cys Gln Ala Ser Glu Ser Ile Gly Asn Trp
            20                  25                  30

Leu Ala Trp Tyr Gln Gln Lys Pro Gly Gln Pro Pro Lys Leu Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Val Gln Cys
65                  70                  75                  80

Asp Asp Ala Ala Thr Tyr Tyr Cys Ala Gly Gly Tyr Ser Ser Ser Ser
                85                  90                  95

Asp Lys Phe Pro Phe Gly Gly Gly Thr Glu Leu Glu Ile Leu Ser Gly
            100                 105                 110

Gly Gly Gly Ser Gly Gly Gly Gly Ser Ser Lys Leu Phe Met Ala Leu
        115                 120                 125

Val Ala Phe Leu Arg Phe Leu Thr
    130                 135
```

<210> SEQ ID NO 79
<211> LENGTH: 145
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#10-PepH4"

<400> SEQUENCE: 79

```
Glu Leu Asp Leu Thr Gln Thr Pro Ala Ser Val Glu Val Ala Val Gly
1               5                   10                  15

Gly Thr Val Thr Ile Lys Cys Gln Ala Ser Glu Ser Ile Gly Asn Trp
```

```
            20                  25                  30

Leu Ala Trp Tyr Gln Gln Lys Pro Gly Gln Pro Pro Lys Leu Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Val Gln Cys
65                  70                  75                  80

Asp Asp Ala Ala Thr Tyr Tyr Cys Ala Gly Gly Tyr Ser Ser Ser Ser
                85                  90                  95

Asp Lys Phe Pro Phe Gly Gly Gly Thr Glu Leu Glu Ile Leu Ser Gly
            100                 105                 110

Gly Gly Gly Ser Gly Gly Gly Gly Ser Ser Lys Ser Lys Ala Ile Asn
        115                 120                 125

Val Leu Arg Gly Phe Arg Lys Glu Ile Gly Arg Met Leu Asn Ile Leu
    130                 135                 140

Asn
145
```

<210> SEQ ID NO 80
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#11-PEP+"

<400> SEQUENCE: 80

```
Glu Leu Asp Leu Thr Gln Thr Pro Ala Ser Val Glu Val Ala Val Gly
1               5                   10                  15

Gly Thr Val Thr Ile Asn Cys Gln Ala Ser Gln Asn Ile Tyr Asn Tyr
            20                  25                  30

Leu Ser Trp Tyr Gln Gln Lys Pro Gly Gln Arg Pro Lys Leu Leu Ile
        35                  40                  45

Tyr Arg Ala Ser Thr Leu Ala Ser Gly Val Ser Ser Arg Phe Lys Gly
    50                  55                  60

Ser Gly Ser Gly Thr Glu Tyr Thr Leu Thr Ile Ser Gly Val Gln Cys
65                  70                  75                  80

Ala Asp Ala Ala Thr Tyr Tyr Cys Gln Gln Gly Tyr Asn Ile Gly His
                85                  90                  95

Val Glu Asn Ala Phe Gly Gly Gly Thr Glu Leu Glu Ile Leu Ser Gly
            100                 105                 110

Gly Gly Gly Ser Gly Gly Gly Gly Ser Ser Ala Gly Ile Leu Lys Arg
        115                 120                 125

Trp
```

<210> SEQ ID NO 81
<211> LENGTH: 132
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#11-PepH1"

<400> SEQUENCE: 81

```
Glu Leu Asp Leu Thr Gln Thr Pro Ala Ser Val Glu Val Ala Val Gly
1               5                   10                  15

Gly Thr Val Thr Ile Asn Cys Gln Ala Ser Gln Asn Ile Tyr Asn Tyr
            20                  25                  30

Leu Ser Trp Tyr Gln Gln Lys Pro Gly Gln Arg Pro Lys Leu Leu Ile
        35                  40                  45

Tyr Arg Ala Ser Thr Leu Ala Ser Gly Val Ser Ser Arg Phe Lys Gly
    50                  55                  60

Ser Gly Ser Gly Thr Glu Tyr Thr Leu Thr Ile Ser Gly Val Gln Cys
65                  70                  75                  80

Ala Asp Ala Ala Thr Tyr Tyr Cys Gln Gln Gly Tyr Asn Ile Gly His
                85                  90                  95

Val Glu Asn Ala Phe Gly Gly Gly Thr Glu Leu Glu Ile Leu Ser Gly
            100                 105                 110

Gly Gly Gly Ser Gly Gly Gly Gly Ser Ser Val Gln Gln Leu Thr Lys
        115                 120                 125

Arg Phe Ser Leu
    130
```

<210> SEQ ID NO 82
<211> LENGTH: 136
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#11-PepH2"

<400> SEQUENCE: 82

```
Glu Leu Asp Leu Thr Gln Thr Pro Ala Ser Val Glu Val Ala Val Gly
1               5                   10                  15

Gly Thr Val Thr Ile Asn Cys Gln Ala Ser Gln Asn Ile Tyr Asn Tyr
            20                  25                  30

Leu Ser Trp Tyr Gln Gln Lys Pro Gly Gln Arg Pro Lys Leu Leu Ile
        35                  40                  45

Tyr Arg Ala Ser Thr Leu Ala Ser Gly Val Ser Ser Arg Phe Lys Gly
    50                  55                  60

Ser Gly Ser Gly Thr Glu Tyr Thr Leu Thr Ile Ser Gly Val Gln Cys
65                  70                  75                  80

Ala Asp Ala Ala Thr Tyr Tyr Cys Gln Gln Gly Tyr Asn Ile Gly His
                85                  90                  95

Val Glu Asn Ala Phe Gly Gly Gly Thr Glu Leu Glu Ile Leu Ser Gly
            100                 105                 110

Gly Gly Gly Ser Gly Gly Gly Gly Ser Ser Lys Leu Phe Met Ala Leu
        115                 120                 125

Val Ala Phe Leu Arg Phe Leu Thr
    130                 135
```

<210> SEQ ID NO 83
<211> LENGTH: 145
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide construct"
<220> FEATURE:
<221> NAME/KEY: source
<223> OTHER INFORMATION: /note="#11-PepH4"

<400> SEQUENCE: 83

Glu Leu Asp Leu Thr Gln Thr Pro Ala Ser Val Glu Val Ala Val Gly
1 5 10 15

Gly Thr Val Thr Ile Asn Cys Gln Ala Ser Gln Asn Ile Tyr Asn Tyr
20 25 30

Leu Ser Trp Tyr Gln Gln Lys Pro Gly Gln Arg Pro Lys Leu Leu Ile
35 40 45

Tyr Arg Ala Ser Thr Leu Ala Ser Gly Val Ser Ser Arg Phe Lys Gly
50 55 60

Ser Gly Ser Gly Thr Glu Tyr Thr Leu Thr Ile Ser Gly Val Gln Cys
65 70 75 80

Ala Asp Ala Ala Thr Tyr Tyr Cys Gln Gln Gly Tyr Asn Ile Gly His
85 90 95

Val Glu Asn Ala Phe Gly Gly Gly Thr Glu Leu Glu Ile Leu Ser Gly
100 105 110

Gly Gly Gly Ser Gly Gly Gly Gly Ser Ser Lys Ser Lys Ala Ile Asn
115 120 125

Val Leu Arg Gly Phe Arg Lys Glu Ile Gly Arg Met Leu Asn Ile Leu
130 135 140

Asn
145

<210> SEQ ID NO 84
<211> LENGTH: 131
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide construct"
<220> FEATURE:
<221> NAME/KEY: source
<223> OTHER INFORMATION: /note="#14-PEP+"

<400> SEQUENCE: 84

Glu Leu Val Met Thr Gln Thr Pro Ser Pro Val Ser Ala Ala Val Gly
1 5 10 15

Gly Thr Val Thr Ile Asn Cys Gln Ala Ser Gln Ser Val Tyr Ser Asn
20 25 30

Asn Trp Leu Ser Trp Tyr Gln Gln Lys Pro Gly Gln Pro Pro Lys Leu
35 40 45

Leu Ile Tyr Asp Ala Ser Lys Leu Ala Ser Gly Val Pro Ser Arg Phe
50 55 60

Ser Gly Ser Gly Ser Gly Thr Gln Phe Thr Leu Thr Ile Ser Gly Val
65 70 75 80

Gln Cys Asp Asp Ala Ala Thr Tyr Tyr Cys Leu Gly Gly Tyr Tyr Ser
85 90 95

Ser Gly Trp Tyr Ser Ala Phe Gly Gly Gly Thr Glu Leu Glu Ile Leu
100 105 110

Ser Gly Gly Gly Gly Ser Gly Gly Gly Gly Ser Ser Ala Gly Ile Leu
115 120 125

Lys Arg Trp
130

<210> SEQ ID NO 85
<211> LENGTH: 134
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#14-PepH1"

<400> SEQUENCE: 85

```
Glu Leu Val Met Thr Gln Thr Pro Ser Pro Val Ser Ala Ala Val Gly
1               5                   10                  15

Gly Thr Val Thr Ile Asn Cys Gln Ala Ser Gln Ser Val Tyr Ser Asn
            20                  25                  30

Asn Trp Leu Ser Trp Tyr Gln Gln Lys Pro Gly Gln Pro Pro Lys Leu
        35                  40                  45

Leu Ile Tyr Asp Ala Ser Lys Leu Ala Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Gly Gly Tyr Tyr Ser
                85                  90                  95

Ser Gly Trp Tyr Ser Ala Phe Gly Gly Gly Thr Glu Leu Glu Ile Leu
            100                 105                 110

Ser Gly Gly Gly Gly Ser Gly Gly Gly Gly Ser Ser Val Gln Gln Leu
        115                 120                 125

Thr Lys Arg Phe Ser Leu
    130
```

<210> SEQ ID NO 86
<211> LENGTH: 138
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#14-PepH2"

<400> SEQUENCE: 86

```
Glu Leu Val Met Thr Gln Thr Pro Ser Pro Val Ser Ala Ala Val Gly
1               5                   10                  15

Gly Thr Val Thr Ile Asn Cys Gln Ala Ser Gln Ser Val Tyr Ser Asn
            20                  25                  30

Asn Trp Leu Ser Trp Tyr Gln Gln Lys Pro Gly Gln Pro Pro Lys Leu
        35                  40                  45

Leu Ile Tyr Asp Ala Ser Lys Leu Ala Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Gly Gly Tyr Tyr Ser
                85                  90                  95

Ser Gly Trp Tyr Ser Ala Phe Gly Gly Gly Thr Glu Leu Glu Ile Leu
            100                 105                 110
```

```
Ser Gly Gly Gly Gly Ser Gly Gly Gly Gly Ser Ser Lys Leu Phe Met
        115                 120                 125

Ala Leu Val Ala Phe Leu Arg Phe Leu Thr
    130                 135


<210> SEQ ID NO 87
<211> LENGTH: 147
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#14-PepH4"

<400> SEQUENCE: 87

Glu Leu Val Met Thr Gln Thr Pro Ser Pro Val Ser Ala Ala Val Gly
1               5                   10                  15

Gly Thr Val Thr Ile Asn Cys Gln Ala Ser Gln Ser Val Tyr Ser Asn
            20                  25                  30

Asn Trp Leu Ser Trp Tyr Gln Gln Lys Pro Gly Gln Pro Pro Lys Leu
        35                  40                  45

Leu Ile Tyr Asp Ala Ser Lys Leu Ala Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Gly Gly Tyr Tyr Ser
                85                  90                  95

Ser Gly Trp Tyr Ser Ala Phe Gly Gly Gly Thr Glu Leu Glu Ile Leu
            100                 105                 110

Ser Gly Gly Gly Gly Ser Gly Gly Gly Gly Ser Ser Lys Ser Lys Ala
        115                 120                 125

Ile Asn Val Leu Arg Gly Phe Arg Lys Glu Ile Gly Arg Met Leu Asn
    130                 135                 140

Ile Leu Asn
145


<210> SEQ ID NO 88
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#17-PEP+"

<400> SEQUENCE: 88

Glu Leu Val Met Thr Gln Thr Pro Ala Ser Val Ser Glu Pro Val Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly Gln Pro Pro Lys Leu Leu Ile
        35                  40                  45

Tyr Ala Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
```

```
65                  70                  75                  80

Ala Asp Ala Ala Thr Tyr Tyr Cys Gln Ser Tyr Tyr Asp Ser Ser Ser
                85                  90                  95

Thr Asn Ala Phe Gly Gly Gly Thr Glu Val Val Val Lys Ser Gly Gly
            100                 105                 110

Gly Gly Ser Gly Gly Gly Gly Ser Ser Ala Gly Ile Leu Lys Arg Trp
        115                 120                 125


<210> SEQ ID NO 89
<211> LENGTH: 131
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#17-PepH1"

<400> SEQUENCE: 89

Glu Leu Val Met Thr Gln Thr Pro Ala Ser Val Ser Glu Pro Val Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly Gln Pro Pro Lys Leu Leu Ile
        35                  40                  45

Tyr Ala Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Ser Tyr Tyr Asp Ser Ser Ser
                85                  90                  95

Thr Asn Ala Phe Gly Gly Gly Thr Glu Val Val Val Lys Ser Gly Gly
            100                 105                 110

Gly Gly Ser Gly Gly Gly Gly Ser Ser Val Gln Gln Leu Thr Lys Arg
        115                 120                 125

Phe Ser Leu
    130


<210> SEQ ID NO 90
<211> LENGTH: 135
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#17-PepH2"

<400> SEQUENCE: 90

Glu Leu Val Met Thr Gln Thr Pro Ala Ser Val Ser Glu Pro Val Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly Gln Pro Pro Lys Leu Leu Ile
        35                  40                  45

Tyr Ala Ala Ser Thr Leu Ala Ser Gly Val Pro Ser Arg Phe Lys Gly
    50                  55                  60
```

Ser Gly Ser Gly Thr Gln Phe Thr Leu Thr Ile Ser Asp Leu Glu Cys
65 70 75 80

Ala Asp Ala Ala Thr Tyr Tyr Cys Gln Ser Tyr Tyr Asp Ser Ser Ser
85 90 95

Thr Asn Ala Phe Gly Gly Gly Thr Glu Val Val Val Lys Ser Gly Gly
100 105 110

Gly Gly Ser Gly Gly Gly Gly Ser Ser Lys Leu Phe Met Ala Leu Val
115 120 125

Ala Phe Leu Arg Phe Leu Thr
130 135

<210> SEQ ID NO 91
<211> LENGTH: 144
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#17-PepH4"

<400> SEQUENCE: 91

Glu Leu Val Met Thr Gln Thr Pro Ala Ser Val Ser Glu Pro Val Gly
1 5 10 15

Gly Thr Val Thr Ile Lys Cys Gln Ala Ser Gln Ser Ile Ser Ser Tyr
20 25 30

Leu Ala Trp Tyr Gln Gln Lys Pro Gly Gln Pro Pro Lys Leu Leu Ile
35 40 45

Tyr Ala Ala Ser Thr Leu Ala Ser Gly Val Pro Ser Arg Phe Lys Gly
50 55 60

Ser Gly Ser Gly Thr Gln Phe Thr Leu Thr Ile Ser Asp Leu Glu Cys
65 70 75 80

Ala Asp Ala Ala Thr Tyr Tyr Cys Gln Ser Tyr Tyr Asp Ser Ser Ser
85 90 95

Thr Asn Ala Phe Gly Gly Gly Thr Glu Val Val Val Lys Ser Gly Gly
100 105 110

Gly Gly Ser Gly Gly Gly Gly Ser Ser Lys Ser Lys Ala Ile Asn Val
115 120 125

Leu Arg Gly Phe Arg Lys Glu Ile Gly Arg Met Leu Asn Ile Leu Asn
130 135 140

<210> SEQ ID NO 92
<211> LENGTH: 131
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#19-PEP+"

<400> SEQUENCE: 92

Glu Leu Val Met Thr Gln Thr Pro Ser Pro Val Ser Ala Ala Val Gly
1 5 10 15

Gly Thr Val Thr Ile Ser Cys Gln Ala Ser Gln Ser Val Tyr Asn Asn
20 25 30

Lys Asn Leu Ala Trp Tyr Gln Gln Lys Pro Gly Gln Pro Pro Lys Leu
35 40 45

Leu Ile Tyr Asp Ala Ser Lys Leu Ala Ser Gly Val Ser Ser Arg Phe
50 55 60

Lys Gly Ser Gly Ser Gly Thr Gln Phe Thr Leu Thr Ile Ser Asp Leu
65 70 75 80

Glu Cys Asp Asp Ala Ala Thr Tyr Tyr Cys Ala Gly Val Tyr Asn Ser
85 90 95

Asn Asn Asp Ala Cys Ala Phe Gly Gly Gly Thr Glu Val Val Val Lys
100 105 110

Ser Gly Gly Gly Gly Ser Gly Gly Gly Gly Ser Ser Ala Gly Ile Leu
115 120 125

Lys Arg Trp
130

<210> SEQ ID NO 93
<211> LENGTH: 134
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#19-PepH1"

<400> SEQUENCE: 93

Glu Leu Val Met Thr Gln Thr Pro Ser Pro Val Ser Ala Ala Val Gly
1 5 10 15

Gly Thr Val Thr Ile Ser Cys Gln Ala Ser Gln Ser Val Tyr Asn Asn
20 25 30

Lys Asn Leu Ala Trp Tyr Gln Gln Lys Pro Gly Gln Pro Pro Lys Leu
35 40 45

Leu Ile Tyr Asp Ala Ser Lys Leu Ala Ser Gly Val Ser Ser Arg Phe
50 55 60

Lys Gly Ser Gly Ser Gly Thr Gln Phe Thr Leu Thr Ile Ser Asp Leu
65 70 75 80

Glu Cys Asp Asp Ala Ala Thr Tyr Tyr Cys Ala Gly Val Tyr Asn Ser
85 90 95

Asn Asn Asp Ala Cys Ala Phe Gly Gly Gly Thr Glu Val Val Val Lys
100 105 110

Ser Gly Gly Gly Gly Ser Gly Gly Gly Gly Ser Ser Val Gln Gln Leu
115 120 125

Thr Lys Arg Phe Ser Leu
130

<210> SEQ ID NO 94
<211> LENGTH: 138
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#19-PepH2"

<400> SEQUENCE: 94

Glu Leu Val Met Thr Gln Thr Pro Ser Pro Val Ser Ala Ala Val Gly 1 5 10 15

Gly Thr Val Thr Ile Ser Cys Gln Ala Ser Gln Ser Val Tyr Asn Asn
20 25 30

Lys Asn Leu Ala Trp Tyr Gln Gln Lys Pro Gly Gln Pro Pro Lys Leu
35 40 45

Leu Ile Tyr Asp Ala Ser Lys Leu Ala Ser Gly Val Ser Ser Arg Phe
50 55 60

Lys Gly Ser Gly Ser Gly Thr Gln Phe Thr Leu Thr Ile Ser Asp Leu
65 70 75 80

Glu Cys Asp Asp Ala Ala Thr Tyr Tyr Cys Ala Gly Val Tyr Asn Ser
85 90 95

Asn Asn Asp Ala Cys Ala Phe Gly Gly Gly Thr Glu Val Val Val Lys
100 105 110

Ser Gly Gly Gly Gly Ser Gly Gly Gly Gly Ser Ser Lys Leu Phe Met
115 120 125

Ala Leu Val Ala Phe Leu Arg Phe Leu Thr
130 135

<210> SEQ ID NO 95
<211> LENGTH: 147
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#19-PepH4"

<400> SEQUENCE: 95

Glu Leu Val Met Thr Gln Thr Pro Ser Pro Val Ser Ala Ala Val Gly
1 5 10 15

Gly Thr Val Thr Ile Ser Cys Gln Ala Ser Gln Ser Val Tyr Asn Asn
20 25 30

Lys Asn Leu Ala Trp Tyr Gln Gln Lys Pro Gly Gln Pro Pro Lys Leu
35 40 45

Leu Ile Tyr Asp Ala Ser Lys Leu Ala Ser Gly Val Ser Ser Arg Phe
50 55 60

Lys Gly Ser Gly Ser Gly Thr Gln Phe Thr Leu Thr Ile Ser Asp Leu
65 70 75 80

Glu Cys Asp Asp Ala Ala Thr Tyr Tyr Cys Ala Gly Val Tyr Asn Ser
85 90 95

Asn Asn Asp Ala Cys Ala Phe Gly Gly Gly Thr Glu Val Val Val Lys
100 105 110

Ser Gly Gly Gly Gly Ser Gly Gly Gly Gly Ser Ser Lys Ser Lys Ala
115 120 125

Ile Asn Val Leu Arg Gly Phe Arg Lys Glu Ile Gly Arg Met Leu Asn
130 135 140

Ile Leu Asn
145

<210> SEQ ID NO 96
<211> LENGTH: 130
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide construct"
<220> FEATURE:
<221> NAME/KEY: source
<223> OTHER INFORMATION: /note="#26-PEP+"

<400> SEQUENCE: 96

Glu Leu Asp Leu Thr Gln Thr Pro Ser Pro Val Ser Ala Ala Val Gly
1 5 10 15

Gly Thr Val Thr Ile Ser Cys Gln Ser Ser Glu Ser Val Tyr Ser Asn
20 25 30

Asn Arg Leu Ala Trp Tyr Gln Gln Lys Pro Gly Gln Pro Pro Lys Leu
35 40 45

Leu Ile Tyr Leu Ala Ser Ser Leu Ala Ser Gly Val Pro Ser Arg Phe
50 55 60

Lys Gly Ser Gly Ser Gly Thr Gln Phe Thr Leu Thr Ile Arg Asp Leu
65 70 75 80

Glu Cys Asp Asp Ala Ala Thr Tyr Tyr Cys Leu Gly Tyr Arg Ser Gly
85 90 95

Ser Asp Gly Asp Ala Phe Gly Gly Gly Thr Glu Leu Glu Ile Leu Ser
100 105 110

Gly Gly Gly Gly Ser Gly Gly Gly Gly Ser Ser Ala Gly Ile Leu Lys
115 120 125

Arg Trp
130

<210> SEQ ID NO 97
<211> LENGTH: 133
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide construct"
<220> FEATURE:
<221> NAME/KEY: source
<223> OTHER INFORMATION: /note="#26-PepH1"

<400> SEQUENCE: 97

Glu Leu Asp Leu Thr Gln Thr Pro Ser Pro Val Ser Ala Ala Val Gly
1 5 10 15

Gly Thr Val Thr Ile Ser Cys Gln Ser Ser Glu Ser Val Tyr Ser Asn
20 25 30

Asn Arg Leu Ala Trp Tyr Gln Gln Lys Pro Gly Gln Pro Pro Lys Leu
35 40 45

Leu Ile Tyr Leu Ala Ser Ser Leu Ala Ser Gly Val Pro Ser Arg Phe
50 55 60

Lys Gly Ser Gly Ser Gly Thr Gln Phe Thr Leu Thr Ile Arg Asp Leu
65 70 75 80

Glu Cys Asp Asp Ala Ala Thr Tyr Tyr Cys Leu Gly Tyr Arg Ser Gly
85 90 95

Ser Asp Gly Asp Ala Phe Gly Gly Gly Thr Glu Leu Glu Ile Leu Ser
100 105 110

Gly Gly Gly Gly Ser Gly Gly Gly Gly Ser Ser Val Gln Gln Leu Thr
115 120 125

Lys Arg Phe Ser Leu
130

<210> SEQ ID NO 98
<211> LENGTH: 137

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#26-PepH2"

<400> SEQUENCE: 98

```
Glu Leu Asp Leu Thr Gln Thr Pro Ser Pro Val Ser Ala Ala Val Gly
1               5                   10                  15

Gly Thr Val Thr Ile Ser Cys Gln Ser Ser Glu Ser Val Tyr Ser Asn
            20                  25                  30

Asn Arg Leu Ala Trp Tyr Gln Gln Lys Pro Gly Gln Pro Pro Lys Leu
        35                  40                  45

Leu Ile Tyr Leu Ala Ser Ser Leu Ala Ser Gly Val Pro Ser Arg Phe
    50                  55                  60

Lys Gly Ser Gly Ser Gly Thr Gln Phe Thr Leu Thr Ile Arg Asp Leu
65                  70                  75                  80

Glu Cys Asp Asp Ala Ala Thr Tyr Tyr Cys Leu Gly Tyr Arg Ser Gly
                85                  90                  95

Ser Asp Gly Asp Ala Phe Gly Gly Gly Thr Glu Leu Glu Ile Leu Ser
            100                 105                 110

Gly Gly Gly Gly Ser Gly Gly Gly Gly Ser Ser Lys Leu Phe Met Ala
        115                 120                 125

Leu Val Ala Phe Leu Arg Phe Leu Thr
    130                 135
```

<210> SEQ ID NO 99
<211> LENGTH: 146
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#26-PepH4"

<400> SEQUENCE: 99

```
Glu Leu Asp Leu Thr Gln Thr Pro Ser Pro Val Ser Ala Ala Val Gly
1               5                   10                  15

Gly Thr Val Thr Ile Ser Cys Gln Ser Ser Glu Ser Val Tyr Ser Asn
            20                  25                  30

Asn Arg Leu Ala Trp Tyr Gln Gln Lys Pro Gly Gln Pro Pro Lys Leu
        35                  40                  45

Leu Ile Tyr Leu Ala Ser Ser Leu Ala Ser Gly Val Pro Ser Arg Phe
    50                  55                  60

Lys Gly Ser Gly Ser Gly Thr Gln Phe Thr Leu Thr Ile Arg Asp Leu
65                  70                  75                  80

Glu Cys Asp Asp Ala Ala Thr Tyr Tyr Cys Leu Gly Tyr Arg Ser Gly
                85                  90                  95

Ser Asp Gly Asp Ala Phe Gly Gly Gly Thr Glu Leu Glu Ile Leu Ser
            100                 105                 110

Gly Gly Gly Gly Ser Gly Gly Gly Gly Ser Ser Lys Ser Lys Ala Ile
        115                 120                 125

Asn Val Leu Arg Gly Phe Arg Lys Glu Ile Gly Arg Met Leu Asn Ile
```

130 135 140

Leu Asn
145

<210> SEQ ID NO 100
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#29-PEP+"

<400> SEQUENCE: 100

Glu Leu Asp Leu Thr Gln Thr Pro Ser Ser Val Glu Ala Ala Val Gly
1 5 10 15

Gly Thr Val Thr Ile Lys Cys Gln Ala Ser Gln Ser Ile Ser Ser Tyr
20 25 30

Leu Ala Trp Tyr Gln Gln Lys Pro Gly Gln Pro Pro Lys Leu Leu Ile
35 40 45

Tyr Arg Ala Ser Ile Leu Ala Ser Gly Val Pro Ser Arg Phe Lys Ala
50 55 60

Ser Gly Ser Gly Thr Gln Phe Thr Leu Thr Ile Ser Asp Leu Glu Cys
65 70 75 80

Ala Asp Ala Ala Thr Tyr Tyr Cys Gln Asp His Tyr Gly Ile Ser Asp
85 90 95

Val Ala Phe Gly Gly Gly Thr Glu Leu Glu Ile Leu Ser Gly Gly Gly
100 105 110

Gly Ser Gly Gly Gly Gly Ser Ser Ala Gly Ile Leu Lys Arg Trp
115 120 125

<210> SEQ ID NO 101
<211> LENGTH: 130
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#29-PepH1"

<400> SEQUENCE: 101

Glu Leu Asp Leu Thr Gln Thr Pro Ser Ser Val Glu Ala Ala Val Gly
1 5 10 15

Gly Thr Val Thr Ile Lys Cys Gln Ala Ser Gln Ser Ile Ser Ser Tyr
20 25 30

Leu Ala Trp Tyr Gln Gln Lys Pro Gly Gln Pro Pro Lys Leu Leu Ile
35 40 45

Tyr Arg Ala Ser Ile Leu Ala Ser Gly Val Pro Ser Arg Phe Lys Ala
50 55 60

Ser Gly Ser Gly Thr Gln Phe Thr Leu Thr Ile Ser Asp Leu Glu Cys
65 70 75 80

Ala Asp Ala Ala Thr Tyr Tyr Cys Gln Asp His Tyr Gly Ile Ser Asp
85 90 95

Val Ala Phe Gly Gly Gly Thr Glu Leu Glu Ile Leu Ser Gly Gly Gly
100 105 110

Gly Ser Gly Gly Gly Gly Ser Ser Val Gln Gln Leu Thr Lys Arg Phe
115 120 125

Ser Leu
130

<210> SEQ ID NO 102
<211> LENGTH: 134
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#29-PepH2"

<400> SEQUENCE: 102

Glu Leu Asp Leu Thr Gln Thr Pro Ser Ser Val Glu Ala Ala Val Gly
1 5 10 15

Gly Thr Val Thr Ile Lys Cys Gln Ala Ser Gln Ser Ile Ser Ser Tyr
20 25 30

Leu Ala Trp Tyr Gln Gln Lys Pro Gly Gln Pro Pro Lys Leu Leu Ile
35 40 45

Tyr Arg Ala Ser Ile Leu Ala Ser Gly Val Pro Ser Arg Phe Lys Ala
50 55 60

Ser Gly Ser Gly Thr Gln Phe Thr Leu Thr Ile Ser Asp Leu Glu Cys
65 70 75 80

Ala Asp Ala Ala Thr Tyr Tyr Cys Gln Asp His Tyr Gly Ile Ser Asp
85 90 95

Val Ala Phe Gly Gly Gly Thr Glu Leu Glu Ile Leu Ser Gly Gly Gly
100 105 110

Gly Ser Gly Gly Gly Gly Ser Ser Lys Leu Phe Met Ala Leu Val Ala
115 120 125

Phe Leu Arg Phe Leu Thr
130

<210> SEQ ID NO 103
<211> LENGTH: 143
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#29-PepH4"

<400> SEQUENCE: 103

Glu Leu Asp Leu Thr Gln Thr Pro Ser Ser Val Glu Ala Ala Val Gly
1 5 10 15

Gly Thr Val Thr Ile Lys Cys Gln Ala Ser Gln Ser Ile Ser Ser Tyr
20 25 30

Leu Ala Trp Tyr Gln Gln Lys Pro Gly Gln Pro Pro Lys Leu Leu Ile
35 40 45

Tyr Arg Ala Ser Ile Leu Ala Ser Gly Val Pro Ser Arg Phe Lys Ala
50 55 60

Ser Gly Ser Gly Thr Gln Phe Thr Leu Thr Ile Ser Asp Leu Glu Cys
65 70 75 80

```
Ala Asp Ala Ala Thr Tyr Tyr Cys Gln Asp His Tyr Gly Ile Ser Asp
                85                  90                  95

Val Ala Phe Gly Gly Gly Thr Glu Leu Glu Ile Leu Ser Gly Gly Gly
            100                 105                 110

Gly Ser Gly Gly Gly Gly Ser Ser Lys Ser Lys Ala Ile Asn Val Leu
        115                 120                 125

Arg Gly Phe Arg Lys Glu Ile Gly Arg Met Leu Asn Ile Leu Asn
    130                 135                 140
```

<210> SEQ ID NO 104
<211> LENGTH: 131
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#37-PEP+"

<400> SEQUENCE: 104

```
Glu Leu Asp Leu Thr Gln Thr Pro Ser Ser Lys Ser Val Pro Val Gly
1               5                   10                  15

Asp Thr Val Thr Ile Asn Cys Gln Ala Ser Asp Ser Val Tyr Ser Asn
            20                  25                  30

Asn Arg Leu Ala Trp Phe Gln Gln Lys Pro Gly Gln Pro Pro Lys Leu
        35                  40                  45

Leu Ile Tyr Gln Ala Ser Lys Leu Ala Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Gln Gly Ala Tyr Tyr Ser
                85                  90                  95

Ser Gly Trp Ser Asn Gly Phe Gly Gly Gly Thr Glu Val Val Val Lys
            100                 105                 110

Ser Gly Gly Gly Gly Ser Gly Gly Gly Gly Ser Ser Ala Gly Ile Leu
        115                 120                 125

Lys Arg Trp
    130
```

<210> SEQ ID NO 105
<211> LENGTH: 134
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#37-PepH1"

<400> SEQUENCE: 105

```
Glu Leu Asp Leu Thr Gln Thr Pro Ser Ser Lys Ser Val Pro Val Gly
1               5                   10                  15

Asp Thr Val Thr Ile Asn Cys Gln Ala Ser Asp Ser Val Tyr Ser Asn
            20                  25                  30

Asn Arg Leu Ala Trp Phe Gln Gln Lys Pro Gly Gln Pro Pro Lys Leu
        35                  40                  45

Leu Ile Tyr Gln Ala Ser Lys Leu Ala Ser Gly Val Pro Ser Arg Phe
```

```
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Gln Gly Ala Tyr Tyr Ser
                85                  90                  95

Ser Gly Trp Ser Asn Gly Phe Gly Gly Gly Thr Glu Val Val Val Lys
            100                 105                 110

Ser Gly Gly Gly Gly Ser Gly Gly Gly Gly Ser Ser Val Gln Gln Leu
        115                 120                 125

Thr Lys Arg Phe Ser Leu
    130


<210> SEQ ID NO 106
<211> LENGTH: 138
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#37-PepH2"

<400> SEQUENCE: 106

Glu Leu Asp Leu Thr Gln Thr Pro Ser Ser Lys Ser Val Pro Val Gly
1               5                   10                  15

Asp Thr Val Thr Ile Asn Cys Gln Ala Ser Asp Ser Val Tyr Ser Asn
            20                  25                  30

Asn Arg Leu Ala Trp Phe Gln Gln Lys Pro Gly Gln Pro Pro Lys Leu
        35                  40                  45

Leu Ile Tyr Gln Ala Ser Lys Leu Ala Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Gln Gly Ala Tyr Tyr Ser
                85                  90                  95

Ser Gly Trp Ser Asn Gly Phe Gly Gly Gly Thr Glu Val Val Val Lys
            100                 105                 110

Ser Gly Gly Gly Gly Ser Gly Gly Gly Gly Ser Ser Lys Leu Phe Met
        115                 120                 125

Ala Leu Val Ala Phe Leu Arg Phe Leu Thr
    130                 135


<210> SEQ ID NO 107
<211> LENGTH: 147
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#37-PepH4"

<400> SEQUENCE: 107

Glu Leu Asp Leu Thr Gln Thr Pro Ser Ser Lys Ser Val Pro Val Gly
1               5                   10                  15

Asp Thr Val Thr Ile Asn Cys Gln Ala Ser Asp Ser Val Tyr Ser Asn
            20                  25                  30
```

```
Asn Arg Leu Ala Trp Phe Gln Gln Lys Pro Gly Gln Pro Pro Lys Leu
        35                  40                  45

Leu Ile Tyr Gln Ala Ser Lys Leu Ala Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Gln Gly Ala Tyr Tyr Ser
                85                  90                  95

Ser Gly Trp Ser Asn Gly Phe Gly Gly Gly Thr Glu Val Val Val Lys
            100                 105                 110

Ser Gly Gly Gly Gly Ser Gly Gly Gly Gly Ser Ser Lys Ser Lys Ala
        115                 120                 125

Ile Asn Val Leu Arg Gly Phe Arg Lys Glu Ile Gly Arg Met Leu Asn
    130                 135                 140

Ile Leu Asn
145


<210> SEQ ID NO 108
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#53-PEP+"

<400> SEQUENCE: 108

Glu Leu Val Leu Thr Gln Thr Pro Ala Ser Val Ser Glu Pro Val Gly
1               5                   10                  15

Gly Thr Val Thr Ile Lys Cys Gln Ala Ser Gln Ser Val Ser Asp Tyr
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Gly Gly Tyr Ala Gly Ser Ser
                85                  90                  95

Tyr Gly Asn Ala Phe Gly Gly Gly Thr Glu Leu Glu Ile Leu Ser Gly
            100                 105                 110

Gly Gly Gly Ser Gly Gly Gly Gly Ser Ser Ala Gly Ile Leu Lys Arg
        115                 120                 125

Trp


<210> SEQ ID NO 109
<211> LENGTH: 132
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#53-PepH1"
```

<400> SEQUENCE: 109

```
Glu Leu Val Leu Thr Gln Thr Pro Ala Ser Val Ser Glu Pro Val Gly
1               5                   10                  15

Gly Thr Val Thr Ile Lys Cys Gln Ala Ser Gln Ser Val Ser Asp Tyr
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Gly Gly Tyr Ala Gly Ser Ser
                85                  90                  95

Tyr Gly Asn Ala Phe Gly Gly Gly Thr Glu Leu Glu Ile Leu Ser Gly
            100                 105                 110

Gly Gly Gly Ser Gly Gly Gly Gly Ser Ser Val Gln Gln Leu Thr Lys
        115                 120                 125

Arg Phe Ser Leu
    130
```

<210> SEQ ID NO 110
<211> LENGTH: 136
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#53-PepH2"

<400> SEQUENCE: 110

```
Glu Leu Val Leu Thr Gln Thr Pro Ala Ser Val Ser Glu Pro Val Gly
1               5                   10                  15

Gly Thr Val Thr Ile Lys Cys Gln Ala Ser Gln Ser Val Ser Asp Tyr
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Gly Gly Tyr Ala Gly Ser Ser
                85                  90                  95

Tyr Gly Asn Ala Phe Gly Gly Gly Thr Glu Leu Glu Ile Leu Ser Gly
            100                 105                 110

Gly Gly Gly Ser Gly Gly Gly Gly Ser Ser Lys Leu Phe Met Ala Leu
        115                 120                 125

Val Ala Phe Leu Arg Phe Leu Thr
    130                 135
```

<210> SEQ ID NO 111
<211> LENGTH: 145
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide construct"
<220> FEATURE:
<221> NAME/KEY: source
<223> OTHER INFORMATION: /note="#53-PepH4"

<400> SEQUENCE: 111

Glu Leu Val Leu Thr Gln Thr Pro Ala Ser Val Ser Glu Pro Val Gly
1 5 10 15

Gly Thr Val Thr Ile Lys Cys Gln Ala Ser Gln Ser Val Ser Asp Tyr
20 25 30

Leu Ala Trp Tyr Gln Gln Lys Pro Gly Gln Pro Pro Lys Leu Leu Ile
35 40 45

Tyr Arg Ala Ser Thr Leu Ala Ser Gly Val Pro Ser Arg Phe Lys Gly
50 55 60

Ser Gly Ser Gly Thr Gln Phe Thr Leu Thr Ile Ser Asp Leu Glu Cys
65 70 75 80

Ala Asp Ala Ala Thr Tyr Tyr Cys Gln Gly Gly Tyr Ala Gly Ser Ser
85 90 95

Tyr Gly Asn Ala Phe Gly Gly Gly Thr Glu Leu Glu Ile Leu Ser Gly
100 105 110

Gly Gly Gly Ser Gly Gly Gly Gly Ser Ser Lys Ser Lys Ala Ile Asn
115 120 125

Val Leu Arg Gly Phe Arg Lys Glu Ile Gly Arg Met Leu Asn Ile Leu
130 135 140

Asn
145

<210> SEQ ID NO 112
<211> LENGTH: 126
<212> TYPE: PRT
<213> ORGANISM: Lama glama
<220> FEATURE:
<221> NAME/KEY: source
<223> OTHER INFORMATION: /note="#FC5"

<400> SEQUENCE: 112

Ala Ser Glu Val Gln Leu Gln Ala Ser Gly Gly Gly Leu Val Gln Ala
1 5 10 15

Gly Gly Ser Leu Arg Leu Ser Cys Ala Ala Ser Gly Phe Lys Ile Thr
20 25 30

His Tyr Thr Met Gly Trp Phe Arg Gln Ala Pro Gly Lys Glu Arg Glu
35 40 45

Phe Val Ser Arg Ile Thr Trp Gly Gly Asp Asn Thr Phe Tyr Ser Asn
50 55 60

Ser Val Lys Gly Arg Phe Thr Ile Ser Arg Asp Asn Ala Lys Asn Thr
65 70 75 80

Val Tyr Leu Gln Met Asn Ser Leu Lys Pro Glu Asp Thr Ala Asp Tyr
85 90 95

Tyr Cys Ala Ala Gly Ser Thr Ser Thr Ala Thr Pro Leu Arg Val Asp
100 105 110

Tyr Trp Gly Lys Gly Thr Gln Val Thr Val Ser Ser Leu Glu
115 120 125

<210> SEQ ID NO 113
<211> LENGTH: 145
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#FC5-PEP+"

<400> SEQUENCE: 113

Ala Ser Glu Val Gln Leu Gln Ala Ser Gly Gly Gly Leu Val Gln Ala
1               5                   10                  15

Gly Gly Ser Leu Arg Leu Ser Cys Ala Ala Ser Gly Phe Lys Ile Thr
            20                  25                  30

His Tyr Thr Met Gly Trp Phe Arg Gln Ala Pro Gly Lys Glu Arg Glu
        35                  40                  45

Phe Val Ser Arg Ile Thr Trp Gly Gly Asp Asn Thr Phe Tyr Ser Asn
    50                  55                  60

Ser Val Lys Gly Arg Phe Thr Ile Ser Arg Asp Asn Ala Lys Asn Thr
65                  70                  75                  80

Val Tyr Leu Gln Met Asn Ser Leu Lys Pro Glu Asp Thr Ala Asp Tyr
                85                  90                  95

Tyr Cys Ala Ala Gly Ser Thr Ser Thr Ala Thr Pro Leu Arg Val Asp
            100                 105                 110

Tyr Trp Gly Lys Gly Thr Gln Val Thr Val Ser Ser Leu Glu Ser Gly
        115                 120                 125

Gly Gly Gly Ser Gly Gly Gly Gly Ser Ser Ala Gly Ile Leu Lys Arg
    130                 135                 140

Trp
145

<210> SEQ ID NO 114
<211> LENGTH: 148
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#FC5-PepH1"

<400> SEQUENCE: 114

Ala Ser Glu Val Gln Leu Gln Ala Ser Gly Gly Gly Leu Val Gln Ala
1               5                   10                  15

Gly Gly Ser Leu Arg Leu Ser Cys Ala Ala Ser Gly Phe Lys Ile Thr
            20                  25                  30

His Tyr Thr Met Gly Trp Phe Arg Gln Ala Pro Gly Lys Glu Arg Glu
        35                  40                  45

Phe Val Ser Arg Ile Thr Trp Gly Gly Asp Asn Thr Phe Tyr Ser Asn
    50                  55                  60

Ser Val Lys Gly Arg Phe Thr Ile Ser Arg Asp Asn Ala Lys Asn Thr
65                  70                  75                  80

Val Tyr Leu Gln Met Asn Ser Leu Lys Pro Glu Asp Thr Ala Asp Tyr
                85                  90                  95

Tyr Cys Ala Ala Gly Ser Thr Ser Thr Ala Thr Pro Leu Arg Val Asp
            100                 105                 110

Tyr Trp Gly Lys Gly Thr Gln Val Thr Val Ser Ser Leu Glu Ser Gly
        115                 120                 125

Gly Gly Gly Ser Gly Gly Gly Gly Ser Ser Val Gln Gln Leu Thr Lys
    130                 135                 140

Arg Phe Ser Leu
145

<210> SEQ ID NO 115
<211> LENGTH: 152
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#FC5-PepH2"

<400> SEQUENCE: 115

Ala Ser Glu Val Gln Leu Gln Ala Ser Gly Gly Gly Leu Val Gln Ala
1 5 10 15

Gly Gly Ser Leu Arg Leu Ser Cys Ala Ala Ser Gly Phe Lys Ile Thr
20 25 30

His Tyr Thr Met Gly Trp Phe Arg Gln Ala Pro Gly Lys Glu Arg Glu
35 40 45

Phe Val Ser Arg Ile Thr Trp Gly Gly Asp Asn Thr Phe Tyr Ser Asn
50 55 60

Ser Val Lys Gly Arg Phe Thr Ile Ser Arg Asp Asn Ala Lys Asn Thr
65 70 75 80

Val Tyr Leu Gln Met Asn Ser Leu Lys Pro Glu Asp Thr Ala Asp Tyr
85 90 95

Tyr Cys Ala Ala Gly Ser Thr Ser Thr Ala Thr Pro Leu Arg Val Asp
100 105 110

Tyr Trp Gly Lys Gly Thr Gln Val Thr Val Ser Ser Leu Glu Ser Gly
115 120 125

Gly Gly Gly Ser Gly Gly Gly Gly Ser Ser Lys Leu Phe Met Ala Leu
130 135 140

Val Ala Phe Leu Arg Phe Leu Thr
145 150

<210> SEQ ID NO 116
<211> LENGTH: 161
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#FC5-PepH4"

<400> SEQUENCE: 116

Ala Ser Glu Val Gln Leu Gln Ala Ser Gly Gly Gly Leu Val Gln Ala
1 5 10 15

Gly Gly Ser Leu Arg Leu Ser Cys Ala Ala Ser Gly Phe Lys Ile Thr
20 25 30

His Tyr Thr Met Gly Trp Phe Arg Gln Ala Pro Gly Lys Glu Arg Glu
35 40 45

Phe Val Ser Arg Ile Thr Trp Gly Gly Asp Asn Thr Phe Tyr Ser Asn
50 55 60

Ser Val Lys Gly Arg Phe Thr Ile Ser Arg Asp Asn Ala Lys Asn Thr
65 70 75 80

```
Val Tyr Leu Gln Met Asn Ser Leu Lys Pro Glu Asp Thr Ala Asp Tyr
                85                  90                  95

Tyr Cys Ala Ala Gly Ser Thr Ser Thr Ala Thr Pro Leu Arg Val Asp
            100                 105                 110

Tyr Trp Gly Lys Gly Thr Gln Val Thr Val Ser Ser Leu Glu Ser Gly
        115                 120                 125

Gly Gly Gly Ser Gly Gly Gly Gly Ser Ser Lys Ser Lys Ala Ile Asn
    130                 135                 140

Val Leu Arg Gly Phe Arg Lys Glu Ile Gly Arg Met Leu Asn Ile Leu
145                 150                 155                 160

Asn
```

```
<210> SEQ ID NO 117
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="#Abx"

<400> SEQUENCE: 117

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Tyr Trp Val Arg Gln Ala Pro Gly Lys Gly Leu Glu Trp Val
        35                  40                  45

Ser Thr Ile Ser Pro Arg Ala Ala Val Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Glu Pro Asp Asp Thr Ala Leu Tyr Tyr Cys
                85                  90                  95

Ala Arg Ser Leu Lys Tyr Trp His Arg Pro Gln Ser Ser Asp Phe Ala
            100                 105                 110

Ser Trp Arg Arg Gly Thr Gln Val Thr Val Ser Ser
        115                 120
```

```
<210> SEQ ID NO 118
<211> LENGTH: 143
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#Abx-PEP+"

<400> SEQUENCE: 118

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Tyr Trp Val Arg Gln Ala Pro Gly Lys Gly Leu Glu Trp Val
        35                  40                  45
```

Ser Thr Ile Ser Pro Arg Ala Ala Val Thr Tyr Tyr Ala Asp Ser Val
50 55 60

Lys Gly Arg Phe Thr Ile Ser Arg Asp Asn Ala Lys Asn Thr Leu Tyr
65 70 75 80

Leu Gln Met Asn Ser Leu Glu Pro Asp Asp Thr Ala Leu Tyr Tyr Cys
85 90 95

Ala Arg Ser Leu Lys Tyr Trp His Arg Pro Gln Ser Ser Asp Phe Ala
100 105 110

Ser Trp Arg Arg Gly Thr Gln Val Thr Val Ser Ser Ser Gly Gly Gly
115 120 125

Gly Ser Gly Gly Gly Gly Ser Ser Ala Gly Ile Leu Lys Arg Trp
130 135 140

<210> SEQ ID NO 119
<211> LENGTH: 146
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#Abx-PepH1"

<400> SEQUENCE: 119

Asp Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Trp Met Tyr Trp Val Arg Gln Ala Pro Gly Lys Gly Leu Glu Trp Val
35 40 45

Ser Thr Ile Ser Pro Arg Ala Ala Val Thr Tyr Tyr Ala Asp Ser Val
50 55 60

Lys Gly Arg Phe Thr Ile Ser Arg Asp Asn Ala Lys Asn Thr Leu Tyr
65 70 75 80

Leu Gln Met Asn Ser Leu Glu Pro Asp Asp Thr Ala Leu Tyr Tyr Cys
85 90 95

Ala Arg Ser Leu Lys Tyr Trp His Arg Pro Gln Ser Ser Asp Phe Ala
100 105 110

Ser Trp Arg Arg Gly Thr Gln Val Thr Val Ser Ser Ser Gly Gly Gly
115 120 125

Gly Ser Gly Gly Gly Gly Ser Ser Val Gln Gln Leu Thr Lys Arg Phe
130 135 140

Ser Leu
145

<210> SEQ ID NO 120
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#Abx-PepH2"

<400> SEQUENCE: 120

```
Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Tyr Trp Val Arg Gln Ala Pro Gly Lys Gly Leu Glu Trp Val
        35                  40                  45

Ser Thr Ile Ser Pro Arg Ala Ala Val Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Glu Pro Asp Asp Thr Ala Leu Tyr Tyr Cys
                85                  90                  95

Ala Arg Ser Leu Lys Tyr Trp His Arg Pro Gln Ser Ser Asp Phe Ala
            100                 105                 110

Ser Trp Arg Arg Gly Thr Gln Val Thr Val Ser Ser Ser Gly Gly Gly
        115                 120                 125

Gly Ser Gly Gly Gly Gly Ser Ser Lys Leu Phe Met Ala Leu Val Ala
    130                 135                 140

Phe Leu Arg Phe Leu Thr
145                 150
```

<210> SEQ ID NO 121
<211> LENGTH: 159
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide construct"
<220> FEATURE:
<221> NAME/KEY: source
<223> OTHER INFORMATION: /note="#Abx-PepH4"

<400> SEQUENCE: 121

```
Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Tyr Trp Val Arg Gln Ala Pro Gly Lys Gly Leu Glu Trp Val
        35                  40                  45

Ser Thr Ile Ser Pro Arg Ala Ala Val Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Glu Pro Asp Asp Thr Ala Leu Tyr Tyr Cys
                85                  90                  95

Ala Arg Ser Leu Lys Tyr Trp His Arg Pro Gln Ser Ser Asp Phe Ala
            100                 105                 110

Ser Trp Arg Arg Gly Thr Gln Val Thr Val Ser Ser Ser Gly Gly Gly
        115                 120                 125

Gly Ser Gly Gly Gly Gly Ser Ser Lys Ser Lys Ala Ile Asn Val Leu
    130                 135                 140

Arg Gly Phe Arg Lys Glu Ile Gly Arg Met Leu Asn Ile Leu Asn
145                 150                 155
```

<210> SEQ ID NO 122
<211> LENGTH: 119
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="#PMP6A6"

<400> SEQUENCE: 122

Ala Ser Ala Val Gln Leu Val Glu Ser Gly Gly Gly Leu Val Gln Pro
1               5                   10                  15

Gly Asn Ser Leu Arg Leu Ser Cys Ala Ala Ser Gly Phe Thr Phe Arg
            20                  25                  30

Ser Phe Gly Met Ser Trp Val Arg Gln Ala Pro Gly Lys Glu Pro Glu
        35                  40                  45

Trp Val Ser Ser Ile Ser Gly Ser Gly Ser Asp Thr Leu Tyr Ala Asp
    50                  55                  60

Ser Val Lys Gly Arg Phe Thr Ile Ser Arg Asp Asn Ala Lys Thr Thr
65                  70                  75                  80

Leu Tyr Leu Gln Met Asn Ser Leu Lys Pro Glu Asp Thr Ala Val Tyr
                85                  90                  95

Tyr Cys Thr Ile Gly Gly Ser Leu Ser Arg Ser Ser Gln Gly Thr Gln
            100                 105                 110

Val Thr Val Ser Ser Leu Glu
        115


<210> SEQ ID NO 123
<211> LENGTH: 138
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#PMP6A6-PEP+"

<400> SEQUENCE: 123

Ala Ser Ala Val Gln Leu Val Glu Ser Gly Gly Gly Leu Val Gln Pro
1               5                   10                  15

Gly Asn Ser Leu Arg Leu Ser Cys Ala Ala Ser Gly Phe Thr Phe Arg
            20                  25                  30

Ser Phe Gly Met Ser Trp Val Arg Gln Ala Pro Gly Lys Glu Pro Glu
        35                  40                  45

Trp Val Ser Ser Ile Ser Gly Ser Gly Ser Asp Thr Leu Tyr Ala Asp
    50                  55                  60

Ser Val Lys Gly Arg Phe Thr Ile Ser Arg Asp Asn Ala Lys Thr Thr
65                  70                  75                  80

Leu Tyr Leu Gln Met Asn Ser Leu Lys Pro Glu Asp Thr Ala Val Tyr
                85                  90                  95

Tyr Cys Thr Ile Gly Gly Ser Leu Ser Arg Ser Ser Gln Gly Thr Gln
            100                 105                 110

Val Thr Val Ser Ser Leu Glu Ser Gly Gly Gly Gly Ser Gly Gly Gly
        115                 120                 125

Gly Ser Ser Ala Gly Ile Leu Lys Arg Trp
    130                 135


<210> SEQ ID NO 124
```

<211> LENGTH: 141
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#PMP6A6-PepH1"

<400> SEQUENCE: 124

Ala Ser Ala Val Gln Leu Val Glu Ser Gly Gly Gly Leu Val Gln Pro
1 5 10 15

Gly Asn Ser Leu Arg Leu Ser Cys Ala Ala Ser Gly Phe Thr Phe Arg
20 25 30

Ser Phe Gly Met Ser Trp Val Arg Gln Ala Pro Gly Lys Glu Pro Glu
35 40 45

Trp Val Ser Ser Ile Ser Gly Ser Gly Ser Asp Thr Leu Tyr Ala Asp
50 55 60

Ser Val Lys Gly Arg Phe Thr Ile Ser Arg Asp Asn Ala Lys Thr Thr
65 70 75 80

Leu Tyr Leu Gln Met Asn Ser Leu Lys Pro Glu Asp Thr Ala Val Tyr
85 90 95

Tyr Cys Thr Ile Gly Gly Ser Leu Ser Arg Ser Ser Gln Gly Thr Gln
100 105 110

Val Thr Val Ser Ser Leu Glu Ser Gly Gly Gly Gly Ser Gly Gly Gly
115 120 125

Gly Ser Ser Val Gln Gln Leu Thr Lys Arg Phe Ser Leu
130 135 140

<210> SEQ ID NO 125
<211> LENGTH: 145
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide construct"
<220> FEATURE:
<221> NAME/KEY: source
<223> OTHER INFORMATION: /note="#PMP6A6-PepH2"

<400> SEQUENCE: 125

Ala Ser Ala Val Gln Leu Val Glu Ser Gly Gly Gly Leu Val Gln Pro
1 5 10 15

Gly Asn Ser Leu Arg Leu Ser Cys Ala Ala Ser Gly Phe Thr Phe Arg
20 25 30

Ser Phe Gly Met Ser Trp Val Arg Gln Ala Pro Gly Lys Glu Pro Glu
35 40 45

Trp Val Ser Ser Ile Ser Gly Ser Gly Ser Asp Thr Leu Tyr Ala Asp
50 55 60

Ser Val Lys Gly Arg Phe Thr Ile Ser Arg Asp Asn Ala Lys Thr Thr
65 70 75 80

Leu Tyr Leu Gln Met Asn Ser Leu Lys Pro Glu Asp Thr Ala Val Tyr
85 90 95

Tyr Cys Thr Ile Gly Gly Ser Leu Ser Arg Ser Ser Gln Gly Thr Gln
100 105 110

Val Thr Val Ser Ser Leu Glu Ser Gly Gly Gly Gly Ser Gly Gly Gly
115 120 125

```
Gly Ser Ser Lys Leu Phe Met Ala Leu Val Ala Phe Leu Arg Phe Leu
    130                 135                 140

Thr
145


<210> SEQ ID NO 126
<211> LENGTH: 154
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide construct"
<220> FEATURE:
<221> NAME/KEY: source
<223> OTHER INFORMATION: /note="#PMP6A6-PepH4"

<400> SEQUENCE: 126

Ala Ser Ala Val Gln Leu Val Glu Ser Gly Gly Gly Leu Val Gln Pro
1               5                   10                  15

Gly Asn Ser Leu Arg Leu Ser Cys Ala Ala Ser Gly Phe Thr Phe Arg
            20                  25                  30

Ser Phe Gly Met Ser Trp Val Arg Gln Ala Pro Gly Lys Glu Pro Glu
        35                  40                  45

Trp Val Ser Ser Ile Ser Gly Ser Gly Ser Asp Thr Leu Tyr Ala Asp
    50                  55                  60

Ser Val Lys Gly Arg Phe Thr Ile Ser Arg Asp Asn Ala Lys Thr Thr
65                  70                  75                  80

Leu Tyr Leu Gln Met Asn Ser Leu Lys Pro Glu Asp Thr Ala Val Tyr
                85                  90                  95

Tyr Cys Thr Ile Gly Gly Ser Leu Ser Arg Ser Ser Gln Gly Thr Gln
            100                 105                 110

Val Thr Val Ser Ser Leu Glu Ser Gly Gly Gly Gly Ser Gly Gly Gly
        115                 120                 125

Gly Ser Ser Lys Ser Lys Ala Ile Asn Val Leu Arg Gly Phe Arg Lys
    130                 135                 140

Glu Ile Gly Arg Met Leu Asn Ile Leu Asn
145                 150


<210> SEQ ID NO 127
<211> LENGTH: 100
<212> TYPE: PRT
<213> ORGANISM: Dengue virus 2
<220> FEATURE:
<221> NAME/KEY: source
<223> OTHER INFORMATION: /note="DEN2C"

<400> SEQUENCE: 127

Met Asn Asn Gln Arg Lys Asn Ala Arg Lys Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Phe Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95
```

Arg Arg Arg Arg
100

<210> SEQ ID NO 128
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic sense primer for rabbit VL domain"
<220> FEATURE:
<221> NAME/KEY: source
<223> OTHER INFORMATION: /note="SDV-kappa-1-F"

<400> SEQUENCE: 128
gggcccaggc ggccgagctc gtgmtgaccc agactcca 38

<210> SEQ ID NO 129
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic sense primer for rabbit VL domain"
<220> FEATURE:
<221> NAME/KEY: source
<223> OTHER INFORMATION: /note="SDV-kappa-2-F"

<400> SEQUENCE: 129
gggcccaggc ggccgagctc gatmtgaccc agactcca 38

<210> SEQ ID NO 130
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic sense primer for rabbit VL domain"
<220> FEATURE:
<221> NAME/KEY: source
<223> OTHER INFORMATION: /note="SDV-kappa-3-F"

<400> SEQUENCE: 130
gggcccaggc ggccgagctc gtgatgaccc agactgaa 38

<210> SEQ ID NO 131
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic sense primer for rabbit VL domain"
<220> FEATURE:
<221> NAME/KEY: source
<223> OTHER INFORMATION: /note="SDV-lambda-F"

<400> SEQUENCE: 131
gggcccaggc ggccgagctc gtgctgactc agtcgccctc 40

<210> SEQ ID NO 132
<211> LENGTH: 37
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic antisense primer for rabbit VL domain"
<220> FEATURE:
<221> NAME/KEY: source
<223> OTHER INFORMATION: /note="SDV-kappa-j10-R"

<400> SEQUENCE: 132

cctggccggc ctggcctttg atttccacat tggtgcc                              37


<210> SEQ ID NO 133
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic antisense primer for rabbit VL domain"
<220> FEATURE:
<221> NAME/KEY: source
<223> OTHER INFORMATION: /note="SDV-kappa-j0-R"

<400> SEQUENCE: 133

cctggccggc ctggcctagg atctccagct cggtccc                              37


<210> SEQ ID NO 134
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic antisense primer for rabbit VL domain"
<220> FEATURE:
<221> NAME/KEY: source
<223> OTHER INFORMATION: /note="SDV-kappa-j42-R"

<400> SEQUENCE: 134

cctggccggc ctggcctttg acsaccacct cggtccc                              37


<210> SEQ ID NO 135
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic antisense primer for rabbit VL domain"
<220> FEATURE:
<221> NAME/KEY: source
<223> OTHER INFORMATION: /note="SDV-lambda-R"

<400> SEQUENCE: 135

cctggccggc ctggccgcct gtgacggtca gctgggtccc                           40
```

ANTIBODY MOLECULES AND PEPTIDE DELIVERY SYSTEMS FOR USE IN ALZHEIMER'S DISEASE AND RELATED DISORDERS

FIELD OF THE INVENTION

The present invention relates to antibody molecules and peptide delivery systems for use in the treatment and management of Alzheimer's disease and related disorders. In particular, the antibody molecules preferentially bind oligomeric forms of beta-amyloid peptide, in single domain format, and the peptide delivery systems facilitate specific transport of such antibody molecules, as well as other cargo molecules, across the blood-brain barrier. The invention also relates to constructs of the antibody molecules and the delivery peptides, as well as pharmaceutical compositions comprising effective amounts of the antibody molecules, delivery peptides, and/or their constructs, including humanized versions of the antibody molecules and constructs. The invention further relates to methods of making these products and pharmaceutical compositions thereof; and methods of using the pharmaceutical compositions in treating or preventing Alzheimer's and related disorders, such as those involving accumulation of beta-amyloid peptide or other peptides that aggregate in the brain; as well as to methods and kits for diagnosing these disorders.

CROSS REFERENCE TO RELATED APPLICATIONS

This application claims foreign priority to Portuguese Patent Application No. 108182D, filed Jan. 29, 2015 and Portuguese Patent Application No. 108181C, filed Jan. 29, 2015, the entire disclosure of each of which are hereby incorporated by reference herein.

SEQUENCE LISTING

The instant application contains a Sequence Listing which has been submitted electronically in ASCII format and is hereby incorporated by reference in its entirety. Said ASCII copy, created on Jan. 28, 2016, is named 14116-105015PC_SL.txt and is 168,632 bytes in size.

BACKGROUND

Neurodegenerative diseases such as Alzheimer's, Parkinson's, and Huntington's disease are increasingly common due to aging of the human population. These diseases are known as "proteinopathies", as they are characterized by the dysfunction of specific proteins, leading to extracellular and intracellular accumulation of protein aggregates.

Alzheimer's disease (AD) is the most common form of dementia worldwide. Recent data show an exponential increase in the number of cases of Alzheimer's patients, emphasizing the need to develop effective treatments. Today about 35.6 million people worldwide live with this disease; by 2050 it is expected that the numbers reach close to 115 million. Indeed, the sector with highest growth potential in the pharmaceutical industry concerns developing drugs for neurological disease.

AD is characterized neuropathologically by accumulation of beta-amyloid peptide (BAP), which results from the processing of amyloid precursor protein (APP). BAP forms the main component of senile plaques, which are the starting point of AD pathogenesis.

Although, in recent years, there have been advances in understanding and treating brain pathologies, many disorders of the central nervous system (CNS), including AD, continue to be devastating and poorly treatable. One problem in treating these disorders is that many drug are unable to cross the blood-brain barrier (BBB) to reach the CNS, a problem especially seen with large molecule drugs. The BBB is formed by specialized endothelial cells (brain endothelial cells) that line capillaries supplying the brain and which prevent, or hinder, the passage of substances from the blood into the CNS.

Various approaches have been attempted to overcome this difficulty. For example, controlled release systems have been used, but these systems sometimes interfere with the operation of the BBB. Another approach involves developing lipophilic drugs, but these have the disadvantage of being rapidly excreted into the bloodstream. Surgical procedures to temporarily open the barrier also have been tested, for example using mannitol injections to decrease cell size and leave voids between the cells, but such procedures may be unsafe, potentially causing swelling, convulsion, and increased susceptibility to infection. Still another approach to deliver drugs across the BBB involves linking the drug to an antibody specific for receptors on the BBB, such as the insulin, leptin, or transferrin receptor, and taking advantage of existing "portals" across the BBB using receptor mediated cytosis. Nonetheless, delivery using this approach is limited by receptor saturation and poor penetration into the extravascular tissue. Moreover, these receptors are expressed in other tissues and are implicated in metabolically critical cellular functions, creating safety risks.

An alternative approach involves using cell-penetrating peptides (CPPs), having translocation capacity. Following the discovery that the third helix of Antennapedia homeodomain crosses biological membranes, investigators have studied different CPPs capable of carrying various cargo loads to the interior of cells, including low molecular weight drugs, liposomes, plasmids, antibodies, and nanoparticles. Nonetheless, use of CPPs as delivery systems is limited by a lack of cell specificity in CPP-mediated cargo delivery.

Further, having crossed the BBB, it is advantageous for a therapeutic to exert its therapeutic effect, and then be efficiently cleared from the brain and CNS and returned to the general circulation for elimination from a patient's body.

Accordingly, there remains a need in the art for therapeutics for treating and managing AD, and related disorders, in particular, a need for therapeutics capable of crossing the BBB specifically and then being cleared therefrom efficiently, as well as delivery systems that safely deliver therapeutics across the barrier to the CNS. There also remains a need for effective diagnosis of initial and late stages of AD. The instant invention addresses these and other needs.

SUMMARY OF THE INVENTION

One aspect of the invention relates to antibody molecules that selectively target non-fibrillar forms of beta-amyloid peptide, such as monomeric and oligomeric forms, over fibrillar forms of the peptide. In a particular embodiment, the antibody molecule is a single domain antibody having immunospecificity to oligomers of the beta-amyloid peptide known as beta-amyloid peptide 42, such as a single domain antibody comprising an amino acid sequence selected from the group consisting of SEQ ID NOS: 1-21, as well as dimeric forms thereof and humanized form thereof, where one or more CDRs of the sequences are combined with framework regions of corresponding human antibody domains. In particular embodiments, the antibody molecule is used in conjunction with a delivery system to facilitate passage across the blood-brain barrier.

Another aspect of the invention relates to peptides that cross the blood-brain barrier, in particular, fragments of the amino acid sequence corresponding to SEQ ID NO: 127 that specifically cross this barrier. The peptides provide delivery systems, facilitating transfer of cargo molecules across the blood-brain barrier for delivery to the brain and central nervous system. In particular embodiments, an antibody molecule of the invention is linked to the delivery peptide to form an antibody-peptide construct with greater ability to cross the blood-brain barrier, and to do so more specifically, than the antibody molecule without the linked peptide. In particular embodiments, the antibody-peptide construct then is cleared more efficiently from the brain than the antibody molecule without the linked peptide.

Another aspect of the invention relates to methods of making the antibody molecules, delivery peptides, and antibody-peptide constructs, described above. The invention also provides polynucleotides encoding polypeptides comprising the antibody molecules, delivery peptides, and/or antibody-peptide constructs described herein, as well as vectors and host cells containing same, in particular, expression vectors and host cells that allow expression of the polypeptides.

Another aspect of the invention relates to pharmaceutical compositions comprising effective amounts of the antibody molecules, delivery peptides, and/or antibody-peptide constructs, described above, as well as to methods of making the pharmaceutical compositions, e.g., mixing with a pharmaceutically acceptable carrier. In a particular embodiment, the pharmaceutical compositions are formulated for parenteral administration.

Still another aspect of the invention relates to use of the pharmaceutical compositions for treating or preventing a neurological disorder, such as Alzheimer's disease, a related disorder, or a symptom thereof. In particular embodiments, a pharmaceutical composition of the invention, comprising an effective amount of an antibody molecule, with or without linkage to a delivery peptide, is administered to a patient with Alzheimer's to prevent or reduce formation of plaques in the brain, by crossing the blood-brain barrier and specifically binding oligomeric and/or monomeric forms of beta-amyloid peptide 42, but preferably not fibrillar forms, thus preventing or reducing plaque formation. In particular embodiments, the antibody molecule, with or without linkage to a delivery peptide, then is cleared from the brain, quickly and efficiently returning to the circulation for excretion.

Yet another aspect of the invention relates to diagnostic use of the antibody molecules, delivery peptides, and antibody-peptide constructs, such as in diagnosing Alzheimer's disease or a related disorder. The invention also provides kits comprising the antibody molecules, delivery peptides, and/or antibody-peptide constructs of the present invention, such as kits for use in diagnosing Alzheimer's disease or a related disorder.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6A shows profiles of size distribution of individual particles present in monomer (gray), oligomer (red), and fiber (green) samples; FIG. 6B shows profiles of class size distribution, that is, the distribution profile of the percentage of signal intensity as a function of particle diameter for ranges of differently-sized particles.

DETAILED DESCRIPTION

1. Definitions

Figure 1:
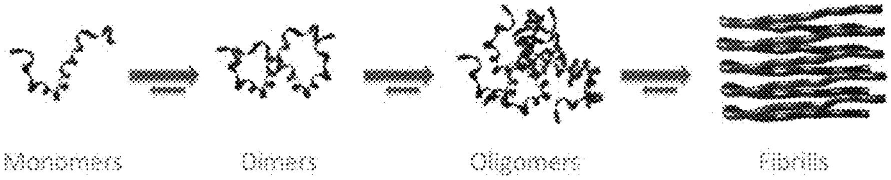
FIG. 1 depicts a BAP42 aggregation scheme, progressing from monomers of the peptide to dimers, oligomers, and then fibrils, capable of forming plaques.

By "neurological disease or disorder" is meant a disease or disorder of the nervous system including, but not limited to, epilepsy, global and focal ischemic and hemorrhagic stroke, head trauma, spinal cord injury, hypoxia-induced nerve cell damage as in cardiac arrest or neonatal distress, as well as neurological conditions associated with cancer, and neurodegenerative disease.

By "neurodegenerative disease" is meant diseases including, but not limited to, Alzheimer's Disease, Parkinson's Disease, Huntington's Disease, and amyotrophic lateral sclerosis (ALS). Alzheimer's disease (AD), also referred to as Alzheimer disease or just Alzheimer's, is a chronic neurodegenerative disorder characterized by progressive cognitive deterioration, involving increasing memory loss, as well as problems with language, judgment, and problem solving, that leads to inability to perform daily tasks, and eventually dementia.

"Beta-amyloid peptide" (BAP) refers to peptides formed in the brain that play a crucial role in the disease process of AD. The disease process is associated with plaque formation due to accumulation of abnormally-folded beta-amyloid peptides (BAPs), ranging from 37-42 amino acids in length, which are fragments of a larger amyloid precursor protein (APP). APP is a transmembrane protein that penetrates neuron membranes and plays a role in neuron growth, survival, and repair. One BAP in particular, a C-terminal fragment composed of the first 42 amino acids of APP, is referred to herein as "BAP42", "Aβ42", "βA42", "beta-amyloid peptide 42", or "beta-amyloid peptide 1-42". This fragment has high aggregation propensity, contributing to fibrils that clump together in deposits outside neurons, and thus plays an important role in the formation of "senile plaques" characteristic of AD.

A "non-fibrillar form" of BAP42 refers to monomers, dimers, trimers, and low-order oligomers of the peptide molecules, that are not clumped together densely enough to form a plaque. "Oligomeric forms" or "BAP42 oligomers" refer to oligomers of the peptide with molecular weights ranging from 10-200 kDa, corresponding to dimers of two associated monomers, or associations of more than two monomers, such as 3, 4, 6, 8, or 10 monomers; as well as associations of 15, 20, 25, 30, 35, and 40 monomers of BAP42.

A "fibrillar form" of BAP42, or "BAP42 fibrils" refer to higher-order clumps of BAP42 molecules, that make up senile plaques characteristic of AD. "Particles" or "species" within a sample refer to the individual monomer, dimer, oligomer, etc., complexes within the sample. A distribution of the different species present in a sample can be described by giving percentages of the individual species in the sample.

By "antibody molecule" is meant an immunospecific polypeptide, or binding fragment thereof, that contains at least one domain of an immunoglobulin, such as a heavy chain domain or light chain domain of a naturally-occurring immunoglobulin or the corresponding domains of synthetic (e.g., recombinant) binding proteins (e.g., humanized antibodies, single chain antibodies, chimeric antibodies, etc.). The basic structural unit of naturally occurring immunoglobulins (e.g., IgG) is a tetramer having two light chains (L) and two heavy chains (H), usually expressed as a glycoprotein of about 150,000 Da. Each light chain is made up generally of a variable domain (VL) and a constant domain (CL); while each heavy chain generally involves a variable domain (VH) and three constant domains ($CH_1$, $CH_2$, and $CH_3$), as well as a hinge region (H). The variable regions of the antibodies or antibody fragments include the complementarity determining regions (CDRs), which contain the residues in contact with antigen, and non-CDR segments, referred to as framework segments or framework regions (FRs or FwRs), which in general maintain the structure and determine the positioning of the CDR loops (although certain framework residues may also contact the antigen).

Antibody fragments can be generated from an intact conventional IgG and include antigen-binding fragments, Fc domains, Fab fragments (F(ab)), F(ab') fragments, single-chain Fv fragments (scFv), VH-VL dimer, heavy chain domains only, light chain domains only, as well as individual (single) domains, e.g., VH domain, VL domain, $CH_1$ domain, $CH_2$ domain, $CH_1$ domain, CL domain, etc.

The terms “antibody single domain”, “single domain antibody”, “small domain antibody” or “sdAb” refer to antibody fragments that comprise or consist of a single monomeric fragment of an antibody, having only a light chain variable domain (VL) or a heavy chain variable domain (VH). Like an intact antibody, a single domain antibody can immunospecifically bind a specific antigen. Unlike whole antibodies, however, single domain antibodies do not exhibit complement system triggered cytotoxicity, as they lack an Fc region. Two or more single domain antibodies may combine to give dimers and higher order structures thereof.

As used herein, the term “humanized antibody molecule” refers to a polypeptide comprising at least one immunoglobulin variable comprising a human framework region and one or more CDRs of the antibody molecules of the invention. In some embodiments, the antibody molecule of the invention does not comprise an entire immunoglobulin, e.g., it may comprise a single immunoglobulin variable domain (e.g., a VH or VL domain) but not any other immunoglobulin domain or region (e.g., not an Fc, $CH_1$, $CH_2$, $CH_3$, CL, etc.). The antibody molecule (e.g., VL domain) providing the CDRs is called the “donor” and the human immunoglobulin, or fragment thereof (e.g., human variable domain) providing the framework is called the “acceptor”. Constant regions need not be present, but if they are, they preferably are substantially identical to human immunoglobulin constant regions, i.e., at least about 85-90%, preferably about 95% or more identical. Hence, in accordance with embodiments wherein the antibody molecule of the invention is humanized, all parts of the antibody molecule, except possibly the CDRs, are substantially identical to corresponding parts of natural human immunoglobulin sequences. One says that the donor molecule has been “humanized”, as the resultant humanized molecule is expected to bind to the same antigen as the donor antibody that provides the CDRs. Generally, humanized immunospecific molecules are human immunoglobulins (or variable domains and/or fragments thereof) in which hypervariable region residues are replaced by hypervariable region residues from a non-human species (e.g., donor CDRs from a rabbit VL domain) having the desired specificity, affinity, and capacity.

Furthermore, humanized molecules may comprise residues which are not found in the recipient antibody nor in the donor antibody. These modifications are made to further refine functionality, e.g., immunospecificity or to reduce immunogenicity. In general, the humanized antibody molecule will comprise substantially all of at least one variable domain in which all or substantially all of the hypervariable regions correspond to those of a rabbit variable domain and all or substantially all of the FRs are those of a human immunoglobulin sequence. In some embodiments, a humanized antibody molecule of the invention is a variant. Such a humanized molecule may comprise amino acid residue substitutions, deletions or additions in one or more of the non-human, e.g., rabbit CDRs. The variant of the humanized molecule may have substantially the same binding, better binding, or worse binding when compared to the parent humanized antibody molecule.

As used herein, the term “immunospecificity” refers to the ability of a molecule to specifically bind to an antigen (e.g., epitope or immune complex) but not to specifically bind to another molecule under physiological conditions. An antibody molecule can be said to “immunospecifically bind” or “immunospecifically recognize” its target antigen, binding preferentially to this antigen over other moieties. A molecule with immunospecificity for a given antigen may be described as “antigen-binding” or “antigen-specific”, with regard to that particular antigen. Molecules that immunospecifically bind an antigen can be identified, e.g., by immunoassays, BIAcore, or other techniques known to those of skill in the art. Immunospecific binding may be defined quantitatively in terms of minimal binding parameters, e.g., about 0.001 nM to about 1,000 pM. A molecule that immunospecifically binds an antigen may bind (or “cross react” with) other moieties, but does so with lower affinity, preferably much lower affinity, as determined by, e.g., immunoassays, BIAcore, or other assays known in the art.

“Blood-brain barrier” or “BBB” refers to the barrier that separates circulating blood from the brain extracellular fluid in the CNS. The BBB has high selective permeability and is formed by brain endothelial cells (“BEC” or “bEnd3 cells”), at the level of the cerebral capillaries, connected by tight junctions. The BBB restricts passage of substances from the bloodstream to a much greater extent than the endothelial cells in capillaries elsewhere in the body. For example, the BBB restricts diffusion of microscopic bacteria and large or hydrophilic molecules, allowing only diffusion of small, hydrophobic molecules, e.g., oxygen, carbon dioxide, and certain hormones. Cells of the BBB also actively transport metabolic products, such as glucose and amino acids, across the barrier utilizing specific proteins. Conversely, a “non-brain endothelial cell layer” refers to an endothelial cell layer made up of cells other than brain endothelial cells, e.g., endothelial cell layers other than the blood-brain barrier.

By a “peptide delivery system” is meant an approach for delivering cargo molecules using a “delivery peptide”, also referred to herein as a “transposon peptide” or “cell-penetrating peptide” (CPP). CPPs are short peptides with the ability to cross cell membranes and thus can translocate various cargo loads to the interior of cells, including translocating low molecular weight drugs, liposomes, plasmids, antibodies, and nanoparticles. The cargo molecules associate with the peptides either by covalent or non-covalent interactions. CPPs commonly deliver their cargo molecules within cells through a process of endocytosis, specifically absorptive-mediated transcytosis.

CPPs typically have an amino acid composition containing an abundance of positively charged amino acids, such as lysine or arginine residues; or show an alternating pattern of polar/charged amino acids and non-polar/hydrophobic amino acids. These two types of CPP are referred to as polycationic and amphipathic, respectively. A third type of CPP is the hydrophobic peptides, containing an abundance of apolar residues, with low net charge, or an abundance of hydrophobic amino acid groups that facilitate cellular uptake. Various examples of CPPs include the trans-activating transcriptional activator (TAT) from the human immunodeficiency virus 1 (HIV-1); the third helix of Antennapedia homeodomain, pAntp (4358); and a capsid protein of Dengue type 2 virus (“DEN2C”). DEN2C is a 12 kDa protein that forms a symmetrical dimer, with basic residues for interacting with RNA, and an apolar region for interacting with membranes. The protein is formed from 4 domains: α1, α2, α3, and α4 (Ma, et al., *Proc Natl Acad Sci USA* (2004) 101(10): 3414-3419).

"Blood-brain barrier-specific" or "BBB-specific" refers to the ability of a delivery peptide to cross the blood-brain barrier, and thus penetrate the brain and deliver cargo molecules to the CNS, to a greater extent than it crosses other membranes or barriers in the body.

As used herein, the term "derivative" or "variant" in the context of polypeptides refers to a polypeptide that comprises an amino acid sequence which has been altered by the introduction of amino acid residue substitutions, deletions, or additions. The term "derivative" or "variant" also refers to a polypeptide that has been modified, i.e., by the covalent attachment of any type of molecule to the polypeptide. For example, but not by way of limitation, a polypeptide may be modified by glycosylation, acetylation, pegylation, phosphorylation, amidation, derivatization by known protecting/blocking groups, proteolytic cleavage, linkage to a cellular ligand or other protein, etc. A derivative polypeptide may be produced by chemical modifications using techniques known to those of skill in the art, including, but not limited to, specific chemical cleavage, acetylation, formylation, metabolic synthesis of tunicamycin, etc. Further, a derivative polypeptide may contain one or more non-classical amino acids. A polypeptide derivative or variant possesses a similar or identical function as the polypeptide from which it was derived. The term "derived" as used in reference to a polypeptide "derived" from an organism may also refer to isolation of a polypeptide directly from said organism (e.g. bacterial cells or phage).

The terms "subject", "host", and "patient" are used interchangeably. As used herein, a subject is preferably a mammal, such as a non-primate (e.g., cows, pigs, horses, cats, dogs, rats, etc.) or a primate (e.g., monkeys and humans), most preferably a human.

As used herein, the term "therapeutic agent" refers to any agent that can be used in treating, managing, or ameliorating symptoms associated with Alzheimer's disease or a related disorder, including a condition associated with accumulation of oligomeric beta-amyloid peptides to form fibrils, or with the accumulation of other aggregation-prone peptides, in the brain. As used herein, a "therapeutically effective amount" refers to the amount of agent (e.g., an amount of a single domain antibody, or a construct of the antibody with a delivery peptide, in a pharmaceutical composition of the invention) that provides at least one therapeutic benefit in the treatment or management of the target disease or disorder, when administered to a subject suffering therefrom. Further, a therapeutically effective amount with respect to an agent of the invention means that amount of agent alone, or when in combination with other therapies, that provides at least one therapeutic benefit in the treatment or management of the disease or disorder.

In the case of Alzheimer's, the therapeutically effective amount of the antibody molecule, or construct thereof, may reduce one or more cognitive or emotional symptoms of the disease, such as reducing short term memory loss; reducing disorientation, mood swings, or loss of motivation; and increasing independence from caregivers otherwise typical of later stages of the disease.

As used herein, the term "prophylactic agent" refers to any agent which can be used in the prevention, delay, or slowing down of the progression of Alzheimer's disease, or a related disorder, or a symptom thereof. As used herein, a "prophylactically effective amount" refers to the amount of the prophylactic agent (e.g., an amount of a single domain antibody, or a construct of the antibody with a delivery peptide, in a pharmaceutical composition of the invention) that provides at least one prophylactic benefit in the prevention or delay of the target disease or disorder, when administered to a subject predisposed thereto. A prophylactically effective amount also may refer to the amount of agent sufficient to prevent, delay, or reduce the occurrence of the target disease or disorder; or to slow the progression of the target disease or disorder; or to delay or minimize the onset of the target disease or disorder; or to prevent or delay recurrence or relapse of the target disease or disorder. A prophylactically effective amount also may refer to the amount of agent sufficient to prevent or delay exacerbation of symptoms of the target disease or disorder. Further, a prophylactically effective amount refers to the amount of a prophylactic agent alone, or when in combination with other agents, that provides at least one prophylactic benefit in the prevention or delay of the disease or disorder.

A prophylactic agent of the invention can be administered to a subject "pre-disposed" to the target disease or disorder, that is, pre-disposed to Alzheimer's or a related disorder, including a condition associated with accumulation of non-fibrillar beta-amyloid peptides or other aggregation-prone oligomers. A subject that is "pre-disposed" to a disease or disorder is one that shows symptoms associated with the development of the disease or disorder, or that has a genetic makeup, environmental exposure, or other risk factor for such a disease or disorder, but where the symptoms are not yet at the level to be diagnosed as the disease or disorder. For example, a patient with a family history of Alzheimer's may qualify as one predisposed thereto.

As used herein, the term "in combination" refers to the use of more than one prophylactic and/or therapeutic agents or active agents. The use of the term "in combination" does not restrict the order in which prophylactic and/or therapeutic agents are administered to a subject. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent (different from the first prophylactic or therapeutic agent) to a subject in need thereof.

2. Antibody Molecules Targeting Non-Fibrillar Forms of Beta-Amyloid Peptide

One aspect of the instant invention relates to antibody molecules that preferentially bind non-fibrillar forms of beta-amyloid peptide 42 (BAP42), such as monomeric and oligomeric forms, over fibrillar forms of the peptide. For example, the antibody molecule may show at least about 10, at least about 100, at least about 1,000, at least about 2,000, at least about 4,000, at least about 6,000, at least about 8,000, or at least about 10,000 times higher binding to oligomeric forms compared to fibrillar forms of the peptide. In particular, antibody molecules are provided that have immunospecificity to one or more oligomeric forms of BAP42, but do not show immunospecificity to BAP42 fibrils (or show very low immunospecificity to the fibrils).

In some embodiments, the antibody molecules comprise variable domains, or amino acid sequences or residues, derived from and/or identified in rabbit immunoglobulins, which molecules immunospecifically bind BAP42 monomers and/or oligomers, or epitopes of either. Immunospecific binding may be determined by any standard method known in the art for assessing antigen/protein-binding specificities. Assays to determine the binding specificity of an antibody, or antigen-binding fragment thereof, for an antigen or epitope include, but are not limited to, ELISA, western blot, surface plasmon resonance (e.g., BIAcore), and radioimmunoassay. Any method known in the art for assessing binding specificity may be used to identify antibody molecules of the invention. In preferred embodiments, an isolated single domain antibody molecule of the invention exhibits a Kd of greater than 0.001 nM, greater than 0.005 nM, greater than 0.01 nM, greater than 0.05 nM, greater than 0.1 nM, greater than 0.5 nM, greater than 1 nM, greater than 2 nM; but not greater than 5 nM, not greater than 10 nM, not greater than 20 nM, not greater than 30 nM, not greater than 40 nM, not greater than 50 nM, not greater than 60 nM, not greater than 70 nM, not greater than 80 nM, not greater than 90 nM, or not greater than 100 nM. In certain embodiments, the isolated single domain antibody molecules of the invention exhibit a Kd of approximately 10 nM, approximately 15 nM, approximately 20 nM, approximately 25 nM, approximately 30 nM, approximately 35 nM, approximately 40 nM, approximately 45 nM, approximately 50 nM, approximately 55 nM, approximately 60 nM, approximately 65 nM, approximately 70 nM, approximately 75 nM, approximately 80 nM, approximately 85 nM, or approximately 90 nM. See also FIGS. 16A-16D.

In preferred embodiments, the antibody molecules preferentially bind an oligomer form of BAP42 over fibrillar forms of BAP42. For example, the antibody molecules may bind BAP42 oligomers more strongly than fibrils, such as by a factor of at least about 2-fold, at least about 3-fold, at least about 5-fold, at least about 10-fold, at least about 20-fold, or at least about 50-fold. In some embodiments, the antibody molecule shows no, or substantially no, immunospecific binding for BAP42 fibrils, e.g., binding that cannot be detected by standard methods known in the art for assessing binding specificity.

The antibody molecules of the invention may be multivalent or monovalent. Multivalent antibody molecules, include bivalent (e.g., as a dimer of single domain antibody molecules of the invention), tri-valent, and higher orders of valency, such as a bivalent IgG complex with two antigen-binding sites, each recognizing the same epitope. In preferred embodiments, the antibody molecules are monovalent, presenting a single antigen-binding site per molecule. In particular embodiments, the antibody molecule is a single domain antibody, or antigen binding fragment thereof, such as a single light chain variable domain (VL) or a single heavy chain variable domain (VH), still more preferably, a VL of VH of a rabbit, or antigen-binding domain of the VH or VL.

The nucleotide sequences encoding immunoglobulin VH or VL domains may be obtained from naïve rabbits or rabbits that have been previously immunized with an antigen, e.g., with BAP42 monomers or oligomers. Immunization of rabbits and isolation of nucleotide sequences (e.g., cDNA) encoding rabbit VH or VL domains may be done by any method known in the art or described herein. In certain embodiments, nucleotide sequences encoding VH or VL domains may be obtained from any tissue of the naïve or immunized rabbit, but is preferably obtained from a tissue source rich in plasma cells, e.g., B cells. In certain embodiments, the rabbit tissue comprising nucleotide sequences encoding VH or VL domains is bone marrow. In other embodiments, the rabbit tissue comprising nucleotide sequences encoding VH or VL domains is appendix tissue and/or lymphoid tissue, such as spleen or lymph node tissue (see, e.g., WO 2008/136694 to Goncalves et al, incorporated by reference in its entirety).

In certain embodiments, the antibody molecules of the invention are monoclonal antibodies, multispecific antibodies, humanized antibodies, synthetic antibodies, chimeric antibodies, polyclonal antibodies, single-chain Fvs (scFv), VH-VL dimers, single chain antibodies, anti-idiotypic (anti-Id) antibodies (including, e.g., anti-Id and anti-anti-Id antibodies to antibodies of the invention), diabodies, minibodies, nobodies, or antigen binding fragments of any of the above, including, but not limited to, Fab fragments, F(ab') fragments, disulfide-linked bispecific Fvs (sdFv), and intrabodies.

The antibody molecules of the invention may be bi- or multi-specific, such as a bispecific molecule with two antigen-binding sites exhibiting affinity for different antigens or different epitopes. Bi- or multi-specific molecules of the invention may be formed using methods well known in the art, e.g., chemical conjugation of one or more single domain antibody molecules of the invention to each other and/or to differing epitope-binding polypeptides. For example, the antibody molecule of the invention may comprise a first and a second VL domain, or a first and second VH domain, wherein said first and second domain have different binding specificities (i.e., bind to different antigens).

In certain embodiments, the antibody molecules of the invention, or antigen-binding fragments thereof, do not comprise a $CH_1$ domain. In other embodiments, the antibody molecules of the invention, or antigen-binding fragments thereof, do not comprise one or more of a $CH_1$ domain, $CH_2$ domain, CL domain, $CH_3$ domain, or H domain, or do not comprise any of a $CH_1$ domain, $CH_2$ domain, CL domain, $CH_3$ domain, or H domain. In still other embodiments, the antibody molecules of the invention, or antigen-binding fragments thereof, comprise one of a $CH_1$ domain, H domain, $CH_2$ domain, CL domain, or $CH_3$ domain, and do not comprise any other constant domain or hinge region derived from an immunoglobulin.

In certain embodiments, the antibody molecule of the invention comprises one or more of a VH CDR1 domain, a VH CDR2 domain, a VH CDR3 domain, a VL CDR1 domain, a VL CDR2 domain, and/or a VL CDR3 domain. In certain embodiments, the antibody molecule comprises each of a VH CDR1 domain, a VH CDR2 domain, and a VH CDR3 domain; or each of a VL CDR1 domain, a VL CDR2 domain, and a VL CDR3 domain. In preferred embodiments, the antibody molecule comprises each of a VL CDR1 domain, a VL CDR2 domain, and a VL CDR3 domain.

The antibody molecule of the invention may include immunoglobulin molecules derived from any species (e.g., rabbit, mouse, rat), but are preferably human or humanized immunoglobulin molecules that can be of any type (e.g., IgG, IgE, IgM, IgD, IgA and IgY), or class (e.g., $IgG_1$, $IgG_2$, $IgG_3$, $IgG_4$, $IgA_1$, and $IgA_2$) or subclass. The antibody molecules of the invention, or antigen binding fragments thereof, can be produced by any method known in the art, for example, chemical synthesis or recombinant techniques.

In certain embodiments, the antibody molecules of the invention are de-immunized. That is, the antibody molecule may be modified to reduce its immunogenicity, e.g., where at least one $T_H$ epitope is eliminated and/or reduced. In some embodiments, the antibody molecule is mutated to provide improved solubility and/or immunospecificity, as well as (or separately from) reduced immunogenicity. An antibody molecule having reduced immunogenicity is referred to as a "de-immunized" antibody molecule. Generally, the antibody molecule comprises substitutions at one or more amino acid positions to reduce or eliminate epitopes that bind one or more HLA class II receptors. De-immunized antibody molecules of the invention result in reduced immunogenicity in the intended host, e.g., in a human patient.

De-immunization may be achieved by any process known in the art and/or described herein. In one approach, a model of the 3-D structure of the antibody molecule is built. A list of substitutions then is proposed to minimize the number of $T_H$ epitopes, preferably eliminating the most important epitopes, without affecting the stability of the antibody molecule or its binding affinity to a target, e.g., BAP42 oligomers. In some embodiments, the de-immunized antibody molecule comprises substitutions that eliminate at least about 10 $T_H$ epitopes, at least about 15 $T_H$ epitopes, at least about 20 $T_H$ epitopes, at least about 25 $T_H$ epitopes, at least about 30 $T_H$ epitopes, at least about 40 $T_H$ epitopes, or at least about 50 $T_H$ epitopes. In preferred embodiments, the substitutions do not affect, or at least do not substantially affect, immunospecific binding of the antibody molecule as compared with the antibody molecule before de-immunization.

In certain embodiments, the antibody molecules of the invention are associated with an Fc domain, preferably a human Fc domain, e.g., to increase half-life of the antibody molecule. The antibody molecule may be linked directly to the Fc domain, or indirectly via a linker such as an intervening amino acid sequence comprising or consisting of a peptide linker. In preferred embodiments, the antibody molecule is linked to the N-terminus of a human Fc domain as a fusion product, to give a divalent construct (see also WO 2013/106577 (Biogen) to Farrington et al). In some embodiments, two antibody molecules of the invention each are linked to the N-terminus of each of two Fc domains, of a complete Fc region, preferably via peptide linkers, wherein the two antibody molecules may be the same or different. In some embodiments, the antibody molecule is linked to the N-terminus of an scFv molecule.

Without wishing to be bound to theory, the antibody molecules of the invention may work by interfering with aggregation of BAP42 or other aggregation-prone peptide in the brain, to produce beneficial therapeutic/prophylactic effects in Alzheimer's or related disorders. BAP42 occurs in different forms of association in the brain of Alzheimer's patients. BAP42 is one of a set of molecules with high oligomerization capacity with the ability to form fibers, a process involving the peptide passing through different stages of maturation, depicted schematically in FIG. 1.

As FIG. 1 shows, BAP42 aggregates according to an aggregation scheme, progressing from monomers of the peptide to fibers, capable of forming plaques. The peptide has high oligomerization capacity, and starts by autoassociating to give small oligomers, which then associate with other molecules of this peptide. The structure of the peptides change to provide a secondary structure rich in beta-sheets—characteristic of fibers. Toxicity of BAP42 and other amyloidogenic proteins may lie not in the insoluble fibrils that accumulate, but rather in the soluble oligomeric intermediates (Rakez et al (2003) *Science* 300: 486-489; Selkoe (1991) *Neuron* 6: 487-498; and Hardy (1992) *Science* 256: 184-185). According to this hypothesis, an imbalance between the production and clearance or degradation of BAP42 in the brain is an initiating event in Alzheimer's, ultimately leading to synaptic and neuronal dysfunction and degeneration, with subsequent cognitive disturbances.

Antibody molecules that preferentially target non-fibrillar BAP42 may be obtained by recombinant means, starting with the sequence information disclosed herein, or developed by raising and isolating immunoglobulins to select BAP42 forms, in accordance with procedures disclosed herein. Example 1 exemplifies such procedures. Briefly, different BAP42 forms were prepared and characterized; and then monomeric or oligomeric forms were used to immunize rabbits. Isolated rabbit antibodies were used to build VL antibody libraries, and anti-BAP42 antibodies selected by phage display.

In a particular embodiment, the phage display process is optimized using "phage display membranes", comprising panning phage-displayed antibody repertoires against proteins separated by sodium dodecyl sulphate-polyacrylamide gel electrophoresis (SDS-PAGE) and electroblotted on polyvinylidene fluoride (PVDF) membranes. These membranes offer the advantage of significantly lower levels of background phage binding than other membranes (Marks et al. (2001) "Towards Proteome-wide Production of Monoclonal Antibody by Phage Display" *J. Mol. Biol.* 315:1063-1073). Accordingly, monomeric and oligomeric BAP42 forms are immobilized on PVDF membranes to pan for single domain antibody molecules specific to these forms. Another aspect of the invention relates to membrane assemblies of different BAP42 forms, for use in panning antibody libraries.

Antibody molecules of the invention generally provide therapeutic and prophylactic approaches concerning Alzheimer's disease and related disorders, with advantages over previous approaches. For example, antibody molecules in single domain format combine small size and stability, along with high immunospecificity for non-fibrillar BAP42 forms, to provide advantageous agents for use in Alzheimer's immunotherapy.

In some embodiments, the antibody molecules are small in size, e.g., less than about 30 kDa, less than about 20 kDa, less than about 15 kDa, or less than about 10 kDa; and/or greater than about 5 kDa, greater than about 10 kDa, or greater than 15 kDa. In a particularly preferred embodiment, the antibody molecule is a single domain antibody about 12 to 15 kDa in size. This small size is about an order of magnitude less than the size of an $IgG_1$ molecule (about 150 kDa). Small size can increase penetration into tissues, with the ability to bind in cavities or active sites of protein targets that may not be accessible to full-size antibodies. Small size also may allow for higher molar quantities per gram of product, increasing potency per dose and reducing overall manufacturing costs. Small size also facilitates crossing the BBB, either alone or fused to a delivery peptide, as described in more detail below.

In certain embodiments, the antibody molecule of the invention comprises a VL domain, and does not comprise a VH domain. In a particular embodiment, the antibody molecule consists of a single domain antibody, preferably a rabbit VL domain or a humanized VL domain derived therefrom. The single domain antibody generally is about 100 amino acids in length, e.g., about 90, about 100, about 110, or about 115 amino acids in length.

In some embodiments, the antibody molecules are monomeric and soluble, preferably not forming aggregates or not forming aggregates to a significant extent (or can be engineered to reduce aggregation). Single domain antibody molecules of the invention provide further advantages in production, e.g., as they generally are well-expressed in bacterial, yeast, and/or mammalian cell systems. In some embodiments, the antibody molecules are stable, e.g., single domain antibodies generally are more stable than full-size antibodies in the circulation and can be engineered to further increase their stability. In some embodiments, serum half-life of the antibody molecule is increased from minutes or hours to weeks using, e.g., approaches for increasing half-life, such as, but not limited to, PEGylation, fusion to human serum albumin (HAS), and fusion to HAS-binding peptides (see, also, e.g., approaches described in WO 2013/043071 to da Silva, et al., incorporated by reference in its entirety). Antibody molecules of the invention having increased stability may provide the option of oral administration or delivery via the pulmonary route and/or may be able to penetrate the BBB. Antibody molecules having increased stability may be able to better retain activity, e.g., during purification, storage, and/or transport. For example, in some embodiments, the antibody molecule retains activity after being subjected to harsh conditions, such as freeze-drying or heat denaturation.

In particular embodiments, the antibody molecules are selected for stability using a modified CAT-fusion assay (see, e.g., WO 2008/136694 to Goncalves et al, incorporated by reference in its entirety). See also Example 1, part (c), subpart (iv), provided below, describing selection of stable sdAb libraries using the CAT-fusion assay. Briefly, stable domains may be selected by fusion of a putative domain to chloramphenicol acetyl transferase, where bacteria expressing a fusion containing a stable domain are more resistant to chloramphenicol. Stability may be defined in terms of this assay, for example, a stable antibody molecule of the invention may be defined as one that, when fused to CAT and expressed in a given bacteria, allows growth of a certain number of colonies of the bacteria, within a certain amount of time, in the presence of a defined amount of chloramphenicol.

In a particular embodiment, stability of an antibody molecule is defined as allowing growth, within 24 hours, of 400-600 colonies of transformed *E. coli*, at 37° C. and in the presence of 1.86 mM chloramphenicol, due to transformation with 1 colony forming unit of a vector encoding said antibody molecule in fusion with chloramphenicol acetyl transferase and expression of the fusion by the transformed *E. coli*. See Example 1, Table 6, below. Stability may be defined in terms of other parameters, e.g., parameters provided in Table 6 and accompanying text.

In preferred embodiments, the antibody molecule interferes with aggregation of monomeric or oligomeric species of BAP42, reducing, reversing, preventing, slowing, or delaying fibrillization and/or aggregation of the oligomers to form fibrils in the brain; or brings about disaggregation of plaques in the brain. In a particular embodiment, the antibody molecule hinders fibrillization of BAP42 in the brain by at least about 20%, at least about 30%, at least about 40%, at least about 50%, at least about 60%, at least about 70%, or at least about 80%. The extent that fibrillization is hindered can be assessed, e.g., by in vitro assays using candidate anti-oligomer BAP42 antibody molecules. See, Example 1, part (c), subpart (v) for an example of such an in vitro.

In some embodiments, the antibody molecules cross an endothelial cell layer comprising brain endothelial cells, e.g., the BBB of a human. The antibody molecule may cross the BBB to reach the brain and CNS after administration, e.g., after parenteral administration to a subject. In preferred embodiments, the antibody molecules cross the BBB without use of a delivery peptide. In more preferred embodiments, the antibody molecule crosses the BBB to a greater extent than other endothelial cell layers, such as barriers comprising no brain endothelial cells.

In preferred embodiments, the antibody molecule shows effective translocation across a model BBB, without being fused to a delivery peptide. For example, antibody molecules of the invention preferably show at least about 40%, at least about 50%, at least about 60%, at least about 70%, or at least about 80% translocation within 24 hours of incubation in a BBB model, e.g., as measured by radioactivity of the labeled antibody molecule. In particularly preferred embodiments, translocation occurs without or substantially without interacting with the cells of the BBB, such as without or substantially without becoming internalized and accumulating within the BBB cells. Accordingly, in highly preferred embodiments, the antibody molecules of the invention surprisingly combine high solubility in aqueous medium with efficient translocation across the BBB, as well as low entrapment within brain endothelial cells.

In preferred embodiments, the antibody molecule has a favorable biodistribution profile for reaching the brain of the subject and/or for subsequently being cleared from the brain and eventually being eliminated from the body of the subject. Biodistribution profiles may be determined by techniques known in the art or described herein. For example, antibody molecules may be labelled with one or more radioisotopes, and injected into test animals. Following sacrifice at different times following injection, different organs/tissues, including brain tissues, are removed, weighed, and tested for radioactivity. Crossing or translocation across the BBB also may be measured in vivo by techniques known in the art or described herein. For example, healthy or 5xFAD transgenic mice may be used, where the animals are injected with antibody molecules, with or without fusion to a delivery peptide, followed by imaging the brain to determine translocation of the antibody molecule. Example 4 provides further details regarding this approach, using Thiazin Red to identify plaques under 2-photon microscopy, after administration of exemplary antibody molecules of the invention.

In specific embodiments, the antibody molecule of the invention comprises one or more of single domain antibodies comprising or consisting of one amino acid sequence selected from the group consisting of SEQ ID NOs: 1-21, or a BAP42 oligomer-binding fragment of any one of SEQ ID NOs: 1-21. In particular embodiments, the antibody molecule of the invention is a single domain antibody comprising or consisting of one amino acid sequence selected from the group consisting of SEQ ID NOS: 1-21, or a BAP42 oligomer-binding fragment thereof. A BAP42 oligomer-binding fragment refers to a truncated form of the identified antibody molecule, which retains immunospecificity of the parent molecule, or substantially retains parental immunospecificity. For example, the fragment may retain preferential immunospecific binding to a BAP42 oligomer, while not immunospecifically binding to fibers of BAP42. Fragments retaining this activity can be selected by generating fragments of varying length, of a given amino acid sequence, and testing for binding to BAP42 oligomers over BAP42 fibers, as described herein and set forth in detail in Example 1, below.

In certain embodiments, the antibody molecules of the invention are humanized. For example, a humanized antibody molecule of the invention may comprise human variable domains, and/or fragments thereof, in which hypervariable region residues are replaced by hypervariable region residues from a rabbit VL domain having preferential and immunospecific binding to BAP42 oligomers and/or monomers. In preferred embodiments, the humanized antibody molecule comprises substantially all of a human VL domain in which all or substantially all of the hypervariable regions correspond to those of a rabbit VL domain and all or substantially all of the FRs are those of a human immunoglobulin sequence.

In some embodiments, a humanized antibody molecule of the invention is a variant. Such a humanized molecule comprises amino acid residue substitutions, deletions or additions in one or more of the non-human, e.g., rabbit, CDRs. The variant of the humanized antibody molecule may have substantially the same binding or better binding compared to the parent humanized antibody molecule, e.g., with respect to one or more BAP42 oligomers or the BAP42 monomer; and/or may have substantially the same binding or worse binding when compared to the parent humanized antibody molecule of the invention with respect to BAP42 fibrils. In some embodiments, the humanized antibody molecule of the invention comprises one or more of a VL CDR1 domain, a VL CDR2 domain, and a VL CDR3 domain from a rabbit single domain antibody grafted into human framework regions, based on methods known in the art. In further embodiment, additional changes to the framework regions can be made, based on methods known in the art, to further modify binding when compared to the parent, e.g., increasing immunospecific binding with respect to one or more BAP42 oligomers or the BAP42 monomer; and/or reducing binding with respect to BAP42 fibrils.

In certain embodiments, the invention encompasses a humanized variant or derivative of the amino acid sequence of SEQ ID NOs: 1-21, e.g., comprising one or more CDRs from any of SEQ ID NOs: 1-21, where the CDR(s) are grafted into human framework regions, and where the humanized variant or derivative retains at least one activity of the parent sequence. For example, the humanized variant, or fragment thereof, may preferentially and immunospecifically bind BAP42 oligomers and/or monomers. Humanized variants (and fragments thereof) retaining this activity can be selected by retaining one or more VL CDRs of the parent sequence, replacing other regions or amino acid residues with corresponding regions or amino acid residues of a human antibody domain, and testing for binding to BAP42 oligomers or monomer over fibers of BAP42, as described herein and set forth in detail in Example 1, below.

In certain embodiments, the invention encompasses a variant or derivative of the amino acid sequence of SEQ ID NOs: 1-21, which retains at least one activity of the parent sequence, or a fragment of said variant or derivative, which also retains at least one activity of the parent. For example, the variant or fragment may preferentially and immunospecifically bind BAP42 oligomers and/or monomers. Variants (and fragments thereof) retaining this activity can be selected by generating variants of a given amino acid sequence, and testing for binding to BAP42 oligomers or monomer over fibers of BAP42, as described herein and set forth in detail in Example 1, below.

In certain embodiments, the antibody molecule of the invention is a variant that comprises or consists of an amino acid sequence having at least 60%, 65%, 70%, 75%, 80%, 85%, 86%, 87%, 88%, 89%, 90%, 91%, 92%, 93%, 94%, 95%, 96%, 97%, 98%, 99%, or greater sequence identity to a second amino acid sequence of the same length (i.e., consisting of the same number of residues), which second amino acid sequence is selected from SEQ ID NOs: 1-21, and/or a fragment thereof, and wherein the variant exhibits at least one activity of the parent sequence from which it was derived (e.g., preferentially and immunospecifically binding BAP42 oligomers and/or monomers).

Amino acid sequence variants of the antibody molecules of the invention can be generated by techniques known in the art, based on disclosures provided herein regarding candidate sequences. In some embodiments, a variant may be a substitutional, insertional and/or deletion variant. Deletion variants lack one or more residues of the parent amino acid sequence which typically are not essential for function (e.g., BAP42 oligomer binding). Insertional mutants typically involve the addition of material at a non-terminal point in the polypeptide.

Substitutional variants typically involve the exchange of one amino acid for another at one or more sites within the amino acid sequence, and may be designed to modulate one or more properties of the antibody molecule, such as stability against proteolytic cleavage, preferably without the loss (or substantial loss) of other functions or properties. Substitutions of this kind preferably are conservative, that is, one amino acid is replaced with another of similar shape and charge. Conservative substitutions are well known in the art and include, e.g., the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

One of skill in the art can generate, e.g., single amino acid changes, preferably in non-conserved positions amongst SEQ ID NOs: 1-21, to identify with greater particularity which amino acid residues are important in immunospecific binding. Preferably, mutation of the amino acids creates an equivalent, or even an improved, second-generation antibody molecule. For example, certain amino acids may be substituted for other amino acids without detectable or substantial loss of function (e.g., preferential binding to BAP42 oligomers). In making such changes, the hydropathic index of amino acids may be considered. The importance of the hydropathic amino acid index in conferring immunospecificity is generally understood in the art. It is accepted that the relative hydropathic character of the amino acid contributes to secondary structure of the resultant protein, which in turn defines the interaction of the protein with other molecules, for example, immunospecific binding to BAP42 oligomers or monomers over fibrils. Each amino acid has been assigned a hydropathic index on the basis of their hydrophobicity and charge characteristics; for example: isoleucine(+4.5); valine(+4.2); leucine(+3.8); phenylalanine(+2.8); cysteine/cystine(+2.5); methionine(+1.9); alanine(+1.8); glycine(−0.4); threonine(−0.7); serine(−0.8); tryptophan 0.9); tyrosine(−1.3); proline(−1.6); histidine(−3.2); glutamate(−3.5); glutamine(−3.5); aspartate (−3.5); asparagine (−3.5); lysine (−3.9); and arginine (−4.5). It is also understood in the art that the substitution of like amino acids can be made effectively on the basis of hydrophilicity. Like hydrophobicity, values of hydrophilicity have been assigned to each amino acid: arginine (+3.0); lysine (+3.0); aspartate (+3.0+1); glutamate (+3.0+1); serine (+0.3); asparagine (+0.2); glutamine (+0.2); glycine (0); threonine (−0.4); proline (−0.5+1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). Equivalent molecules may be obtained by substitution of one amino acid for another where their hydropathic and/or their hydrophilicity indices are within +2, preferably +1, or most preferably +5 of each other.

In certain embodiments, the invention encompasses antibody molecules that comprise 1, 2, 3, 4, 5, 6, 7, 8, 9, or 10 or more amino acid modifications (e.g., insertion, substitution, deletion, etc.) relative to an amino acid sequence disclosed herein. In preferred embodiments, the mutation(s) are made such that immunospecificity is retained or substantially retained.

3. Peptides that Cross the Blood-Brain Barrier

Another aspect of the invention relates to peptides that cross the blood-brain barrier, in particular, fragments of the polypeptide having amino acid sequence of SEQ ID NO: 127, where the fragment specifically crosses the BBB. The peptides provide delivery systems, facilitating transfer of cargo molecules, such as therapeutic and prophylactic agents, across the BBB for delivery to the brain and CNS. In particular embodiments, the delivery peptide comprises a fragment of about 10 to about 30 amino acids, preferably a fragment of about 15 to about 25 amino acids, or about 10 to about 20 amino acids in length.

Delivery peptides of the present invention exhibit the ability to cross an endothelial cell layer comprising brain endothelial cells, e.g., the BBB of mammals, preferably the BBB of a human. In certain embodiments, the delivery peptide crosses a brain endothelial cell layer to a greater extent than an endothelial cell layer comprising other cells, such as endothelial layers other than the blood-brain barrier. In particular embodiments, the delivery peptide selectively or preferentially crosses the BBB, crossing this barrier to a greater extent than it crosses other endothelial layers, even though the BBB generally is more difficult to cross.

Selective or preferential delivery to the BBB is termed "BBB-specific delivery" and a peptide achieving such delivery is termed a "BBB-specific delivery peptide" or a "BBB-specific peptide". For example, the delivery peptide may cross a BBB to a greater extent than an endothelial cell layer comprising no brain endothelial cells, by a factor of at least about 2-fold, at least about 3-fold, at least about 5-fold, at least about 10-fold, at least about 20-fold, or at least about 50-fold, at least about 60-fold, at least about 70-fold, or at least about 80-fold. In some embodiments, the peptide molecules do not cross, or substantially do not cross, endothelial cell layers other than the BBB.

Crossing or translocation across a blood-brain barrier may be measured by techniques known in the art or described herein. Example 2 provides a number of exemplary approaches for measuring BBB crossing. For example, an in vitro BBB model can used, made up of brain endothelial cells (BECs, e.g., bEnd3 cells) growing in a tissue culture insert in a transwell system. The BECs can be grown on a microporous membrane, forming an in vitro endothelial barrier between the upper compartment (apex) and lower compartment (base) of the system. Delivery peptides, either isolated and labelled, or presented by phage display techniques, may be introduced in the apex and incubated for various periods of time. Detecting label or phage in the base, after a given incubation period, and comparing these measurements to amounts of label or phage in the apex, will determine the extent the peptides cross the model BBB. Example 2, part (a), provides further details of this approach (see also FIG. 17); as well as Example 2, part (c) (see also FIGS. 22A-22F).

In certain embodiments, the delivery peptide preferentially interacts with negatively-charged membranes, combining hydrophobicity with hydrophilicity due to positive charges. Hydrophobicity and hydrophilicity of amino acids are described above and can be calculated for a given peptide based on its amino acid composition. Interaction with different membranes can be tested in in vitro and in vivo models. In vitro assays include measuring uptake by cells of a model BBB, to determine internalizing ability of the peptide. Example 2, part (c), for example, provides further details of this approach (see also FIGS. 23A-23E and Table 9).

In vitro assays also include measuring membrane potential, partition coefficient, or affinity constant for a delivery peptide for various membranes, such as membrane models designed to have different lipidic compositions, with different amounts of negative charges on their surfaces. Example 2, part (e), for example, provides further details of this approach (see also FIGS. 26A-26C, FIG. 27, and Table 10). Whereas the majority of eukaryotic cells have negatively charged lipids in the inner parts of their membranes, endothelial cells from the BBB have higher negatively-charged surfaces compared to cells from other endothelia. This negative charge is due not only to the negatively-charged lipids, but also to higher levels of glycosylation. Membrane models that mimic the negatively-charged BBB allows for analysis of their electrostatics interactions with delivery peptides of the invention. In preferred embodiments, the delivery peptide only shows interaction with membranes rich in negative charges, e.g., a membrane rich in negatively-charged phospholipids, e.g., a model membrane made of phospholipids where at least about 50% of the phospholipids are negatively-charged. In more preferred embodiments, the delivery peptide shows interaction only with membranes where at least about 60%, at least about 70%, at least about 80%, or at least about 90% of the phospholipids are negatively-charged. Negatively-charged lipids include, without limitation, 1-palmitoyl-2-oleoyl-phosphatidylserine (POPS) and 1-palmitoyl-2-oleoyl-phosphatidylglycerol (POPG).

In preferred embodiments, the delivery peptide shows effective translocation across a model BBB. For example, delivery peptides of the invention preferably show at least about 40%, at least about 50%, at least about 60%, at least about 70%, or at least about 80% translocation or transmigration, within 24 hours of incubation in a BBB model, e.g., as measured by radioactivity of the labeled delivery peptide. In particularly preferred embodiments, translocation occurs without or substantially without interacting with the cells of the BBB, such as without or substantially without becoming internalized and accumulating within the BBB cells. Accordingly, in highly preferred embodiments, the delivery peptides of the invention combine high solubility in aqueous medium with efficient translocation across the BBB, as well as low entrapment within brain endothelial cells.

The delivery peptides of the invention provide advantages in delivering cargo across the BBB, including, e.g., not disrupting the integrity of the BBB and/or lacking toxicity towards endothelial cells, in particular, lacking toxicity to brain endothelial cells.

In preferred embodiments, delivery peptides of the invention lack toxicity towards endothelial cells, in particular, lacking toxicity to brain endothelial cells. Toxicity may be measured by techniques known in the art or described herein. For example, toxicity to BBB cells can be measured in vitro using a colorimetric assay, such as a MTT assay, to assess cell metabolism in the presence of varying concentrations of a delivery peptide. Example 2, part (d) provides additional details regarding this approach (see also FIGS. 24A-24E). A delivery peptide that lacks toxicity towards brain endothelial cells may be defined as one that does not decrease viability of the cells, in a layer, upon incubation with a certain concentration of the peptide for a given incubation period. For example, a delivery peptide lacking toxicity towards endothelial cells of a blood-brain barrier may be defined as a peptide that causes no more than a 20% decrease, or no more than a 10% decrease, in viability of the endothelial cells following a 24-hour incubation with 100 μM of the peptide. Lack of toxicity may be defined in terms of other parameters, e.g., parameters provided in FIGS. 24A-24E and accompanying text.

In preferred embodiments, the delivery peptide has a favorable biodistribution profile for reaching the brain of the subject and/or for subsequently being cleared from the brain and eventually being eliminated from the body of the subject. Biodistribution profiles may be determined by techniques known in the art or described herein. For example, delivery peptides may be labelled with one or more radioisotopes, and injected into test animals. Following sacrifice, different organs/tissues, including brain tissues, are removed, weighed, and tested for radioactivity. Example 2, part (f) provides further details regarding this approach, identifying delivery peptides that show rapid brain uptake (see also Table 11). A delivery peptide showing rapid brain uptake may be defined as one that reaches the brain of a test animal within a certain period of time following injection of a certain amount of the peptide. For example, a delivery peptide that reaches the brain of a mouse within about 2 minutes of injecting the mouse with 104 μg peptide may be identified as showing desired biodistribution, in terms of rapid brain uptake. Rapid brain uptake may be defined in terms of other parameters, e.g., parameters provided in Table 11 and accompanying text.

Biodistribution concerns not only how quickly a delivery peptide crosses the BBB and reaches the brain, but also how quickly it then is cleared from the brain, returning to circulation for excretion. Clearance from the brain may be referred to as "brain washout", where a desired delivery peptide is one that shows rapid penetration to the brain, followed by rapid brain washout. Brain clearance may be determined by techniques known in the art or described herein, e.g., measuring the brain of scarified animals for radioactivity following injection of radiolabelled candidate peptides. Example 2, part (f) provides further details regarding this approach, identifying delivery peptides that show rapid brain clearance (see also Table 11). Desired clearance of a delivery peptide from the brain may be defined in terms of the percentage of peptide remaining in the brain, or conversely the percentage cleared from the brain, of a test animal within a certain period of time following injection of a certain amount of the peptide. For example, in a preferred embodiment, at least about 90% of a delivery peptide that had reached the brain of a mouse may be cleared therefrom within 60 minutes of injecting the mouse with 104 μg peptide. Rapid clearance may be defined in terms of other parameters, e.g., parameters provided in Table 11 and accompanying text.

Biodistribution also concerns whether a delivery peptide accumulates in other organs, besides the excretory organs. Methods of generating biodistribution profiles, as described above and/or known in the art may be used to further assay for this feature. See again, e.g., Example 2, part (0, and Table 11.

Accordingly, delivery peptides of the present invention include fragments of SEQ ID NO: 127 that combine hydrophobicity and hydrophilicity due to positively-charged amino acid residues, to interact only or substantially only with negatively-charged membranes mimicking the BBB; preferably without accumulating or without substantially accumulating in BECs and/or without disrupting or without substantially disrupting BBB membranes and/or without decreasing or without substantially decreases BECs viability; more preferably showing rapid brain uptake and/or rapid brain clearance in animal models. The present approach provides BBB-specific delivery peptides that preferentially and efficiently cross the BBB and surprisingly effect delivery to the brain greater than or comparable with other molecules described in the literature (Muruganandam, et al. (2002) *FASEB* J, 16(2): 240-241; and Abulrob, et al. (2005) *J Neurochem* 95(4):1201-1214). For example, percentages of brain uptake of other radiolabelled peptides, such as TAT, penetratin, synB1, and others range from only 0.2-0.9% ID/g of tissue (Sarko, et al., *Mol Pharm* (2010) 7(6):2224-2231).

In specific embodiments, the delivery peptide of the invention comprises or consists of at least one amino acid sequence selected from the group consisting of SEQ ID NOs: 22-25, or a BBB-specific fragment of any one of SEQ ID NOs: 22-25. In particular embodiments, the delivery peptide comprises or consists of one amino acid sequence selected from the group consisting of SEQ ID NOS: 22-25, or a BBB-specific fragment thereof. A BBB-specific fragment refers to a truncated form of the identified delivery peptide, which retains the ability of the parent molecule, or substantially retains parental ability to selectively cross the BBB. For example, the fragment may retain the ability to cross the BBB to a greater extent than a non-brain endothelial cell layer. Fragments retaining this activity can be selected by generating fragments of varying length, of a given amino acid sequence, and testing for preferential BBB crossing, as described herein and set forth in detail in Example 2, below.

In certain embodiments, the invention encompasses a variant or derivative of the amino acid sequence of SEQ ID NOs: 22-25, which retains at least one activity of the parent sequence, or a fragment of said variant or derivative, which also retains at least one activity of the parent. For example, the variant or fragment thereof may preferentially cross the BBB. Variants (and fragments thereof) retaining this activity can be selected by generating variants of a given amino acid sequence, and testing for preferential BBB crossing, as described herein and set forth in detail in Example 2, below.

In certain embodiments, the delivery peptide of the invention is a variant that comprises or consists of an amino acid sequence having at least 60%, 65%, 70%, 75%, 80%, 85%, 86%, 87%, 88%, 89%, 90%, 91%, 92%, 93%, 94%, 95%, 96%, 97%, 98%, 99%, or greater sequence identity to a second amino acid sequence of the same length (i.e., consisting of the same number of residues), which second amino acid sequence is selected from SEQ ID NOs: 22-25, and/or a fragment thereof, and wherein the variant exhibits at least one activity of the parent sequence from which it was derived (e.g., crossing the BBB to a greater extend that other endothelial cell layers).

Amino acid sequence variants of the delivery peptides of the invention can be generated by techniques known in the art, based on disclosures provided herein regarding candidate sequences. In some embodiments, a variant may be a substitutional, insertional and/or deletion variant, including conservative substitutions as described above. In making such changes, the hydropathic index of amino acids may be considered, as described above; and/or hydrophobicity scales, also as described above. For example, a variant may be created by making conservative substitutions that do not change the hydrophobicity score of the delivery peptide or create a variant with greater overall hydrophobicity. In certain embodiments, the invention encompasses delivery peptides that comprise 1, 2, 3, 4, 5, 6, 7, 8, 9, or 10 or more amino acid modifications (e.g., insertion, substitution, deletion, etc.) relative to an amino acid sequence disclosed herein. In preferred embodiments, the mutation(s) are made such that BBB-specific delivery of the parent peptide is retained or substantially retained.

Without being bound by theory, the delivery peptides, e.g., the peptide of SEQ ID NO: 24 (pepH3), crosses brain epithelial cell membranes in a receptor-independent manner. Crossing without relying on a receptor provides additional advantages, because transport is not limited by receptor expression nor saturation.

In particular embodiments, the delivery peptide is associated with a cargo molecule. Association of a cargo molecule with a delivery peptide generally increases translocation of the cargo molecule across a brain endothelial cell layer, such as the BBB. The cargo molecule may be any molecule where it is desirable to enhance the molecule's transport across the BBB, e.g., for therapeutic, prophylactic, or diagnostic uses, or for furthering basis research, such as analysis of the cargo molecule's interaction with structures in the brain or CNS. The cargo molecule may comprise, for example, a nucleic acid, a polypeptide, an antibody molecule, a polysaccharide, a small molecule compound, a nanoparticle, a synthetic polymer, a virus, a plasmid, a metal, a lipid, a liposome, a macromolecule, a macromolecular complex, a toxin, or a label.

Examples of nucleic acids that may be suitable cargo molecules include any nucleic acid known to the person skilled in the art, e.g., DNA, RNA, single stranded DNA, cDNA, or derivatives thereof, including oligonucleotides, polynucleotides, antisense sequences for single- or double-stranded targets, ribosomes, and antisense RNA. Analogs include charged and uncharged backbone analogs, such as phosphonates, methyl phosphonates, phosphoramidates, such as N-3' or N-5', thiophosphates, uncharged morpholino-based polymers, and protein nucleic acids (PNAs). The nucleic acid may also comprise a plasmid. A plasmid may comprise any extrachromosomal generic material separate from the chromosomal DNA and capable of autonomous replication. For example, a plasmid may comprise a DNA molecule capable of autonomous replication in eukaryotic cells and which encodes a polypeptide of interest, e.g. a therapeutic protein.

Examples of polypeptides that may be suitable cargo molecules include any polypeptide known to the person skilled in the art, including proteins having known therapeutic or prophylactic effects, like certain enzymes or hormones, or proteins that can serve as labels, like EGFP or luciferin. Therapeutic polypeptides can include, without limitation, tumor suppressor proteins, transcription factors, kinase inhibitors, kinases, cytokines, regulatory proteins, apoptotic proteins, anti-apoptotic proteins, microbial antigens, viral antigens, bacterial antigens, parasitic antigens, or cellular antigens; as well as certain antibacterial agents, antifungal agents, antiviral agents, antiproliferative agents, immunosuppressive agents, histamine receptor antagonists, adhesion molecules, and receptor molecules. Polypeptides also includes glycoproteins.

Examples of hormones for use with the delivery peptides include, without limitation, prostaglandin, serotonin, histamine, bradykinin, kallikrein, and gastrointestinal hormones, releasing hormones, pituitary hormones, insulin, vasopressin (ADH), glucagon, and encephalin. Examples of adhesion molecules for use with the delivery peptides include, without limitation, IgSF CAMs like NCAM, ICAM-1, VCAM-1, PECAM-1, L1, CHL1, MAG, integrins, or selectins, as well as other molecules known to bind cells or the extracellular matrix (ECM) in a cell adhesion process. Examples of receptor molecules for use with the delivery peptides include, without limitation, metabotropic receptors, G protein-coupled receptors, muscarinic acetylcholine receptors, adenosine receptors, adrenoceptors, GABA receptors, angiotensin receptors, cannabinoid receptors, cholecystokinin receptors, dopamine receptors, glucagon receptors, metabotropic glutamate receptors, histamine receptors, olfactory receptors, opioid receptors, chemokine receptors, calcium-sensing receptor, somatostatin receptors, serotonin receptors or secretin receptors, and other protein, on the cell membrane, within the cytoplasm, or within the nucleus, known to bind to a ligand, e.g., to transduce a signal.

Examples of antibody molecules that may be suitable cargo molecules for use with the delivery peptides include any antibodies known to the person skilled in the art or any described herein. Antibody molecules may include immunosuppressive agents comprising an antibody molecule that inhibit, reduces, or delays of an activity of a mammalian immune system. Known immunosuppressive agents include, without limitation, anti IL-2 receptor antibodies, anti-OKT3 antibodies, anti-CD3 antibodies, and TNF-alpha binding antibodies.

Examples of polysaccharides that may be suitable cargo molecules include any polysaccharide known to the person skilled in the art or any described herein.

Examples of small molecule compounds that may be suitable cargo molecules include any organic molecules, e.g., traditional drug molecules with therapeutic activity, as well as certain chemotherapeutic agents, vitamins, analgesic agents, anti-inflammatory agents, and the like. Small molecule compounds may also include antiviral agents and antibacterial agents, comprising a compound that inhibits growth of a viral or bacterial species, respectively. Small molecule compounds may also include antifungal agents comprising a compound that inhibits growth of a fungal species.

Examples of anti-fungal agents for use with the delivery peptides include, without limitation, amphotericin, itraconazole, ketoconazole, miconazole, nystatin, clotrimazole, fluconazole, ciclopirox, econazole, naftifine, terbinafine, and griseofulvin. Examples of anti-viral agents for use with the delivery peptides include, without limitation, acyclovir, famciclovir, ganciclovir, foscarnet, idoxuridine, sorivudine, trifluridine (trifluoropyridine), valacyclovir, cidofovir, didanosine, stavudine, zalcitabine, zidovudine, ribavirin, and rimantatine. Examples of anti-bacterial agents for use with the delivery peptides include, without limitation, beta-lactam antibiotics or quinolone antibiotics, nafcillin, oxacillin, penicillin, amoxacillin, ampicillin, cephalosporin, cefotaxime, ceftriaxone, rifampin, minocycline, ciprofloxacin, norfloxacin, erythromycin, tetracycline, gentamicin, a macrolide, a quinolone, a β-lactone, a P-lactamase inhibitor, salicylamide, vancomycin, sulfanilamide, sulfamethoxazole, sulfacetamide, sulfisoxazole, sulfadiazine, penicillins such as penicillins G and V, methicillin, oxacillin, naficillin, ampicillin, amoxacillin, carbenicillin, ticarcillin, mezlocillin and piperacillin, cephalosporins such as cephalothin, cefaxolin, cephalexin, cefadroxil, cefamandole, cefoxitin, cefaclor, cefuroxine, loracarbef, cefonicid, cefotetan, ceforanide, cefotaxime, cefpodoxime, proxetil, ceftizoxime, cefoperazone, ceftazidime and cefepime, aminoglycosides such as gentamycin, tobramycin, amikacin, netilmicin, neomycin, kanamycin, streptomycin, and the like, tetracyclines such as chlortetracycline, oxytetracycline, demeclocycline, methacycline, doxycycline and minocycline, and macrolides such as erythromycin, clarithromycin, and azithromycin or analogs thereof.

Small molecule compounds may also include antiproliferative agents, comprising a compound that inhibits or restricts cell proliferation. Examples of antiproliferative agents for use with the delivery peptides include, without limitation, methotrexate, azathioprine, fluorouracil, hydroxyurea, 6-thioguanine, cyclophosphamide, mechloroethamine hydrochloride, carmustine, cyclosporine, taxol, tacrolimus, vinblastine, dapsone, nedocromil, cromolyn (cromoglycic acid), and sulfasalazine. Small molecule compounds may also include antineoplastic agents, comprising a compound that inhibits, reduces, or delays tumors. Examples of antineoplastic agents for use with the delivery peptides include, without limitation, pentostatin, 6-mercaptopurine, 6-thioguanine, methotrexate, bleomycins, etoposide, teniposide, dactinomycin, daunorubicin, doxorubicin, mitoxantrone, hydroxyurea, 5-fluorouracil, cytarabine, fludarabine, mitomycin, cisplatin, procarbazine, dacarbazine, paclitaxel, colchicine, and vinca alkaloids.

Examples of nanoparticles that may be suitable cargo molecules for use with the delivery peptides include any small particle with at least one dimension less than 400 nm, or any other suitable form and size known to the person skilled in the art, such as gold particles, quantum dot loaded polymeric micelles, or certain liposomes. More preferably the nanoparticle has at least one dimension less than about 300 nm, less than about 200 nm, less than about 100 nm, less than about 50 nm, less than about 20, less than about 10 nm, or less than 3 nm.

Examples of synthetic polymers that may be suitable cargo molecules for use with the delivery peptides include any man-made polymers known to the person skilled in the art or any described herein.

Examples of viruses that may be suitable cargo molecules for use with the delivery peptides include any type of virus or viral particles known to the person skilled in the art, for example, but without limitation, an adenovirus, adeno-associated virus, herpes virus, simplex virus, lentivirus, and retrovirus. The virus also may be modified, e.g., a virus that has been altered to increase or decrease infectivity. Viral particles includes viral vectors comprising genetic elements derived from viruses. Typically, in viral vectors a part of the viral genome necessary for viral replication has been deleted, so that a helper virus must be provided to allow for production of new virions.

Examples of metals that may be suitable cargo molecules for use with the delivery peptides include any metal known to the person skilled in the art, such has gold, platinum, lanthanide metals, actinides metals, and the like, as well as radioactive metals, where the cargo molecule facilitates detection and/or imaging.

Examples of toxins that may be suitable cargo molecules for use with the delivery peptides include any molecule capable of causing cell death on contact or absorption with body tissues. Examples include, without limitation, botulinum toxins, tetanus toxin, pertussis toxin, heat stable and heat labile *E. coli* entertoxin, Cholera toxin, Shiga toxin, cytolethal distending toxin, tracheal cytotoxin, diphtheria toxin, clostridial toxins, tetrodotoxin, batrachotoxin, maurotoxin, agitoxin, charybdotoxin, margatoxin, slotoxin, scyllatoxin, calciseptine, taicatoxin, and calcicludine.

Examples of lipids that may be suitable cargo molecules for use with the delivery peptides include any lipids known to the person skilled in the art including, without limitation, fatty acids (e.g., saturated, unsaturated, greater than four carbon chain length, prostanoids, leukotienes, ecosanoids, etc.), neutral lipids (e.g., cholesterol and esters thereof, triglycerides, steroids, spermaceti (cetyl palmitate), waxes, fatty alcohols, etc.), phospholipids (e.g., phosphatidyl choline, phosphatidyl serine, ethanolamine, phosphatidyl inositol, platelet activating factor, fatty acid glycerol ethers, cardiolipids, etc.), and complex lipids (e.g., sphingolipids, ceramides, glycolipids, gangliosides, sulfolipids, etc.).

In certain embodiments, the cargo molecule is a therapeutic or prophylactic agent that provides a therapeutic and/or prophylactic benefit upon crossing the BBB. In particular embodiments, the delivery peptide is linked not only to a cargo molecule, as described herein, but additionally linked to a targeting agent, e.g., for directing the cargo molecule to a specific structure or receptor within the CNS/brain. Such a linkage may be any linkage as described herein, and preferably is a peptide linkage. Examples of targeting agents include, without limitation, ligands for cell receptors (e.g., NGF, EGF, and others) and antibodies against receptors.

In certain embodiments, the cargo comprises a label, for imaging or detecting the location of the delivery peptide and any molecules that also may be associated therewith. A "label" within the context of the invention includes any diagnostic imaging or contrast agent that allows a visualization of molecular and/or cellular processes on either a macroscopic or microscopic level. Examples of labels include, without limitation, $^{m}$Tc glucoheptonate; substances used in magnetic resonance imaging (MRI) procedures such as gadolinium doped chelation agents, e.g. Gd-DTPA; marker genes that encode detectable proteins when expressed, such as beta-galactosidase, green fluorescent protein, horse-radish peroxidase (HRP), luciferase, or other enzyme suitable for marking a cell; heavy metals; halogens; enzymes; enzyme substrates; enzyme cofactors; enzyme inhibitors; ligands; and haptens; as well as a fluorescent moiety such as a fluor; a fluorescence-quenching moiety, a radioactive moiety such as a radionuclide; a radiopaque moiety; a paramagnetic moiety; a nanoparticle; a vesicle; a molecular beacon; an isotope; a marker, a dye, a radiation-sensitizer (e.g., for radiation therapy), or other diagnostic imaging or contrast agent.

Exemplary fluorescent labels include, without limitation, fluorescent dyes, fluorescein, semiconductor quantum dots, lanthanide atom-containing complexes, and fluorescent proteins. Exemplary fluorescent proteins include, without limitation, both naturally occurring and modified (i.e., mutant) green fluorescent proteins (Prasher et al., *Gene* 111:229-233 (1992); PCT Application WO 95/07463, which are hereby incorporated by reference in their entirety); both naturally occurring and modified blue fluorescent proteins (Karatani et al., *Photochem. Photobiol.* 55(2):293-299 (1992); Lee et al., *Methods Enzymol.* (Biolumin. Chemilumin.) 57:226-234 (1978); Gast et al., *Biochem. Biophys. Res. Commun.* 80(1):14-21 (1978), which are hereby incorporated by reference in their entirety); and phycobiliproteins of the type derived from cyanobacteria and eukaryotic algae (Apt et al., *J. Mol. Biol.* 238:79-96 (1995); Glazer, *Ann. Rev. Microbiol.* 36:173-198 (1982); Fairchild et al., *J. Biol. Chem.* 269:8686-8694 (1994); Pilot et al., *Proc. Natl. Acad. Sci. USA* 81:6983-6987 (1984); Lui et al., *Plant Physiol.* 103:293-294

(1993); Houmard et al., *J. Bacteriol.* 170:5512-5521 (1988), which are hereby incorporated by reference in their entirety), several of which are commercially available from ProZyme, Inc. (San Leandro, Calif.).

Examples of isotopes that may be suitable cargo molecules for labeling delivery peptides include any radioactive isotopes. Examples of radioactive isotopes include, without limitation, $N^{15}$, $C^{13}$, $P^{31}$, $F^{19}$, or $I^{131}$. Preferred radioisotopes include technetium (e.g., $^{99m}$Tc) and gallium (e.g., $GaCl_3$). Example 2, part (b) provides additional details regarding use of these radioisotopes to label delivery peptides of the invention for use in in vitro assays with BBB models; Example 2, part (f) provides details for use in in vivo biodistribution studies in mice.

Examples of dyes that may be suitable cargo molecules for labeling delivery peptides include any colored substance for molecular use. Exemplary dyes include, without limitation, Cy2, Cy3, Cy5, Cy7, Texas Red, Calcein, FITC, FluorX™, Alexa 405, 430, 488, 546, 559, 594, 633, 660, 674, 680, 700, rhodamine dyes, Cascade Blue, Pacific Blue, 5-FAM, Oregon Green™ 500, Oregon Green™ 488, RiboGreen™, Magnesium Green™ Calcium Green™, 564/570, Magnesium Orange™, Phycoerythrin, Calcium Orange™, Pyronin Y, Cy3.5™, Calcium Crimson™, Alexa™ 594, Nile Red, R-phycocyanin, C-Phycocyanin, DiD DilC(5), CyS™, Thiadicarbocyanine, and Cy5.5™. Exemplary lanthanide atoms include, without limitation, Ce, Pr, Nd, Pm, Sm, Eu, Gd, Tb, Dy, Ho, Er, Tm, Yb, and Lv. Of these, Nd, Er, and Tb are preferred because they are commonly used in imaging applications.

The delivery peptide may associate with its cargo molecule by covalent and/or non-covalent interactions, preferably to form a stable construct or complex for delivery across the BBB. For example, the delivery peptide and its cargo molecule may associate non-covalently by electrostatic interactions, van der Waals forces, and/or hydrogen bonding. Preferably, the association is by covalent means, such as formation of a chemical linkage between a group on the delivery peptide and a group on the cargo molecule. Linkage may be direct or indirect, e.g., using a linker. In particular embodiments, the linker is a peptide linker. The cargo molecule may be linked to either the N-terminal or C-terminal end of the delivery peptide, or to a site within its amino acid sequence.

In some embodiments where the cargo molecule comprises a polypeptide, the cargo molecule may be linked as a fusion to the delivery peptide. For example, the cargo molecule and the delivery peptide may be expressed from a single nucleic acid (or polynucleotide) as a single continuous region. Polynucleotides encoding these fusion proteins, vectors or host cells comprising these nucleic acids, and pharmaceutical compositions comprising these host cells, vectors, and/or polynucleotides are contemplated by the invention.

The delivery systems described herein may be used in conjunction with one or more other delivery approaches (see, e.g., approaches discussed in in Neuwelt et al. "Strategies to advance translational research into brain barriers" *Lancet Neurol.* 2008 (7):8496; Pardridge, *Pharmaceutical research* (2007) 24:1733-1744; Pardridge, *Drug Discov Today* (2007) 12(1-2): 54-61; Pardridge, *Nat Rev Drug Discov* (2002) 1(2):131-139; Strazielle, et al. *Mol Pharm* (2013) 10(5):1473-1491; Abbott, et al. *Neurobiol Dis.* (2010) 37:13-25; Patel, et al., *CNS Drugs* (2009) 23(1): 35-58; Neuwelt, et al. *Nature reviews Neuroscience* (2011) 12:169-182; Interlandi, *Scientific American* (2013) 308:52-57; Niewoehner, et al. *Neuron.* (2014) 81:49-60; Yu, et al. *Science translational medicine* (2014) 6:261ra154; Sharma, et al. *Journal of pharmaceutical sciences* (2012) 101:2468-2478; Derossi, et al. *The Journal of biological chemistry* (1994) 269:10444-10450; Zou, et al. *Curr Neuropharmacol* (2013) 11(2): 197-208; and Gupta, et al. *Advanced drug delivery reviews* (2005) 57:637-651; each of which is incorporated by reference in its entirety).

In particular embodiments, the cargo molecule comprises an active agent used in the art, or being tested, to treat Alzheimer's or a related disorder. For example, the cargo molecule may be one of more of: ELN 0005, an inhibitor of oligomer formation; CAD 106 (Novartis), providing a BAP1-6 peptide derived from the N-terminal B cell epitope of BAP; ACC-001 (Affitope AD02) providing BAP1-6 amino terminal fragment; and V950, providing the amino-terminal BAP conjugated to ISCO-MATRIX. One or more of any of these active agents may be associated with one or more delivery peptides of the invention, e.g., as a fusion, to improve delivery to the CNS and brain.

In particular embodiments, the cargo molecule comprises an antibody used in the art, or being tested, to treat Alzheimer's or a related disorder. In preferred embodiments, the cargo molecule comprises an antibody molecule that immunospecifically binds BAP or a fragment thereof, e.g., as described herein or known in the art. Examples of anti-BAP antibodies in the art include the humanized monoclonal anti-BAP antibody Bapineuzumab (Wyeth and Elan), that binds to both soluble and fibrillar forms of BAP (Bard et al. (2000) *Nature Medicine* 6: 916-919, incorporated herein in its entirety); BAN2401, a humanized monoclonal antibody targeting protofibrils; Crenezumab, a humanized antibody to BAP1-40 and BAP42; Gantenerumab, a humanized monoclonal antibody to BAP1-11; GSK933776, a humanized $IgG_1$ monoclonal antibody against the N-terminal of BAP; and Solanezumab (Eli Lilly), a humanized monoclonal antibody to BAP16-24 that preferentially binds soluble BAP (Teich (2012) *Biochem. J.* 446: 165-177, incorporated herein in its entirety), as well as the antibody described in Sumbria, et al. "Disaggregation of amyloid plaque in brain of Alzheimer's disease transgenic mice with daily subcutaneous administration of a tetravalent bispecific antibody that targets the transferrin receptor and the beta amyloid peptide" *Molecular pharmaceutics* (2013) 10: 3507-3513 (incorporated herein in its entirety). One or more of any of these antibodies may be associated with one or more delivery peptides of the invention, e.g., as a fusion, to improve delivery to the CNS and brain.

In more preferred embodiments, the cargo molecule comprises an antibody molecule of the present invention, e.g., fused to a delivery peptide of the invention, such as described in more detail below.

4. Antibody-Peptide Constructs

In a particular embodiment, an antibody molecule of the invention is linked to a delivery peptide of the invention to form an antibody-peptide construct. Generally, the antibody-peptide construct shows greater ability to cross the blood-brain barrier, and to do so specifically, than the antibody molecule without the linked peptide. Delivery of the antibody molecule can provide therapeutic and/or prophylactic benefit in Alzheimer's or disorders related thereto, including conditions associated with accumulation of aggregation-prone peptides in the brain. As noted above, the delivery peptides may provide advantages for therapeutic and prophylactic use, such as, in preferred embodiments, being broken down into non-toxic compounds and/or providing low potential for drug-drug interactions in vivo. They also generally have low probability to cause immunological reactions, compared with large proteins, providing low immunogenicity as carrier molecules.

Increased blood-brain barrier passage facilitates delivery of the antibody molecule of the invention to the brain, where the antibody molecule acts to reduce, prevent, slow, delay, or reverse fibrillization of BAP42 oligomers in the brain. In preferred embodiments, the antibody-peptide construct increases BBB crossing by a factor of at least about 2-fold, at least about 2.5-fold, at least about 3-fold, at least about 3.5-fold, at least about 4-fold, at least about 4.5-fold, at least about 5-fold, at least about 5.5-fold, or at least about 6-fold compared to the antibody molecule without the linked peptide.

In particularly preferred embodiments, the antibody-peptide construct preferentially crosses the BBB, crossing this barrier to a greater extent than it crosses other endothelial layers, even though the BBB generally is more difficult to cross. For example, the antibody-peptide construct may cross the BBB to a greater extent than an endothelial cell layer comprising no brain endothelial cells, by a factor of at least about 2-fold, at least about 3-fold, at least about 5-fold, at least about 10-fold, at least about 20-fold, at least about 50-fold, at least about 60-fold, at least about 70-fold, or at least about 80-fold. In some embodiments, the antibody-peptide construct does not cross, or substantially does not cross, endothelial cell layers other than the blood-brain barrier.

In particular embodiments, the antibody molecule is linked to the delivery peptide covalently, preferably as a fusion. The antibody molecule and the delivery peptide may be arranged in any order, relative to each other, e.g., the delivery peptide may be fused upstream of the N-terminal of the antibody molecule, or the delivery peptide may be fused downstream of the C-terminal of the antibody molecule. In some embodiments, the antibody molecule is linked to the delivery peptide by a linker, preferably a peptide linker. For example, the linker may be attached upstream of the N-terminal of the antibody molecule, or downstream of the C-terminal of the antibody molecule, and the delivery peptide linked to the free end of the linker.

In some embodiments, more than one antibody molecule may be linked to a given delivery peptide, where the multiple antibody molecules may be same or different antibody molecules. For example, two VL antibody molecules may be linked to give a dimer, which itself is linked to a delivery peptide, or to two or more delivery peptides, as discussed in more detail below.

That is, in some embodiments, more than one delivery peptide may be linked to a given antibody molecule, where the multiple delivery peptides may be the same or different delivery peptides. In a particular embodiment, two or three or four delivery peptides are linked to a given antibody molecule, e.g., in a row attached to the C-terminal or N-terminal of the antibody molecule, or one may be attached at the C-terminal and two in a row at the N-terminal of the antibody molecule, or two may be attached in a row at the C-terminal and one at the N-terminal of the antibody molecule. The multiple delivery peptides used in a given construct may each be the same, or two or three or more different delivery peptides may be used. The use of more than one delivery peptide per antibody molecule increases avidity and, preferably, the ability of the construct to cross the BBB.

The antibody-peptide constructs preferably combine one or more preferred characteristics of the antibody molecules of the invention, as discussed above; and/or one or more preferred characteristics of the delivery peptides of the invention, also as discussed above.

Further, the antibody-peptide constructs preferably show the characteristics of stability, solubility, and/or high expression in host cells. Suitable delivery peptides that link to antibody molecules, e.g., single domain antibody molecules, to give constructs with these characteristics may be selected by cloning with test single domain antibodies and determining their stability, solubility, and/or expression. Example 3, parts (a)-(b), provide details of test cloning exemplary embodiments of the delivery peptides, and measuring the expression of the test antibody-peptide constructs. For example, a test construct may be selected as having at least as high expression as a test antibody known to be well expressed from a given expression vector in a given host cell under suitable conditions. A test construct also may be selected as having at least as high stability and/or at least as high solubility as a test antibody known to be expressed stably, and in soluble form, from a given expression vector in a given host cell under suitable conditions. See, e.g., Example 3, part (b), where results are compared to the control pT7-sdAb, which shows high expression levels.

Preferred antibody-peptide constructs of the invention generally interfere with aggregation of oligomeric species of BAP42, reducing, reversing, preventing, slowing, or delaying fibrillization of the oligomers in the brain. In preferred embodiments, the construct does so to the same or substantially the same extent as the antibody molecule without the linked delivery peptide. For example, the antibody-peptide construct may hinder fibrillization by at least about 20%, at least about 30%, at least about 40%, at least about 50%, at least about 60%, at least about 70%, or at least about 80%, compared to fibrillization in the absence of a candidate antibody molecule or antibody-peptide construct. The extent that fibrillization is hindered in in vitro assays can indicate the extent fibrillization is hindered in the brain by a given antibody-peptide construct of the invention. Example 3, part (c), provides details of testing exemplary constructs of the invention for their ability to hinder BAP42 aggregation (see also FIGS. 29A-29B).

Preferred antibody-peptide constructs of the invention generally have favorable biodistribution profiles for reaching the brain of the subject and/or for subsequently being cleared from the brain and eventually being eliminated from the body of the subject. Biodistribution profiles may be determined by techniques known in the art and/or described herein. For example, antibody-peptide constructs may be labelled with one or more radioisotopes, and injected into test animals, followed by measuring the brain of scarified animals for radioactivity, after given intervals of time, as described above. Example 3, part (e) provides further details regarding this approach, identifying antibody-delivery constructs that show rapid brain uptake and/or rapid brain washout (see also Tables 14-16). An antibody-peptide construct showing rapid brain uptake may be defined as one that reaches the brain of a test animal within a certain period of time following injection of a certain amount of the peptide. For example, an antibody-peptide construct that reaches the brain of a mouse within about 2 minutes of injecting the mouse with about 0.1 mM to about 0.2 mM antibody-peptide construct may be identified as showing desired biodistribution in term of rapid brain uptake. Desired clearance of an antibody-peptide construct from the brain may be defined in terms of the percentage of peptide remaining in the brain, or conversely the percentage cleared from the brain, of a test animal within a certain period of time following injection of a certain amount of the antibody-peptide construct. For example, in a preferred embodiment, at least about 90% of antibody-peptide construct that had reached the brain of a mouse may be cleared therefrom within 60 minutes of injecting the mouse with about 0.1 mM to about 0.2 mM antibody-peptide construct. (0.1 mM to about 0.2 mM is equivalent to about 150 μg to about 250 μg of antibody or antibody-peptide construct). Desired biodistribution, including rapid brain uptake and rapid brain clearance, may be defined in terms of other parameters, e.g., parameters provided in Tables 14-16 and accompanying text.

In preferred embodiments, the constructs show surprisingly improved biodistribution profiles compared to the corresponding antibody molecule without a linked delivery peptide. For example, compared to the unlinked antibody molecule, an antibody-peptide construct may show increased brain uptake by a factor of at least about 1.5, at least about 2, at least about 4, at least about 6, at least about 8, or at least about 10. Compared to the unlinked antibody molecule, an antibody-peptide construct my show increased brain washout, or may show a decrease in brain washout to a lesser degree than the improvement in brain uptake. Table 14, for example, surprisingly shows that linking "#2" sdAb to the delivery peptide "pepH3" increased its presence in the brain, within 2 minutes, by a factor of about 3, and only slowed washout from the brain, after an hour, by a factor of about 2. That is, about three times as much antibody reached the brain, in 2 minutes, while only about twice as much of the antibody remained (i.e., was not washed out), after an hour. Even more surprisingly, Table 16 shows that linking "#27in" sdAb to the delivery peptide "pepH3" increased its presence in the brain, within 2 minutes, by a factor of about 6, and only slowed washout from the brain, after an hour, by a factor of about 2. That is, about six times as much antibody reached the brain, in 2 minutes, while only about twice as much of the antibody remained, after an hour.

Preferred antibody-peptide constructs of the invention generally show in vivo efficacy, e.g., in animal models. Suitable animal models for Alzheimer's or related disorders include those known in the art or described herein. For example, 5xFAD transgenic mice may be used (Jawhar, et al. (2012) *Neurobiology of Aging* 33(1): 96. e29-196. e40), where the animals are injected with antibody molecules, or peptide constructs thereof, followed by imaging to determine the presence and extent of beta amyloid plaques in the brains of the animals. Example 4 provides further details regarding this approach, using Thiazin Red to identify plaques under 2-photon microscopy, after administration of exemplary antibody-peptide constructs of the invention.

In specific embodiments, the antibody-peptide construct of the invention comprises or consists of at least one amino acid sequence selected from the group consisting of SEQ ID NOs: 28-111, or a fragment of any one of SEQ ID NOs: 28-111, which fragment retains BAP42 oligomer-immunospecificity and/or BBB-specificity of the parent sequence, or substantially retains BAP42 oligomer-immunospecificity and/or BBB-specificity of the parent. In particular embodiments, the antibody-peptide construct comprises or consists of one amino acid sequence selected from the group consisting of SEQ ID NOs: 28-111, or a BAP42 oligomer-immunospecific, BBB-specific fragment thereof. Fragments retaining these activities can be selected by generating fragments of varying length, of a given amino acid sequence, and testing for preferential binding to BAP42 oligomers and preferential crossing of the BBB, as described herein.

In certain embodiments, the invention encompasses a variant or derivative of the amino acid sequence of SEQ ID NOs: 28-111, which retains at least one activity of the parent sequence, or a fragment of said variant or derivative, which also retains at least one activity of the parent. For example, the variant or fragment thereof may preferentially cross the BBB and immunospecifically and preferentially bind BAP42 oligomers and/or monomers. Variants (and fragments thereof) retaining these activities can be selected by generating variants of a given amino acid sequence, and testing for immunospecific binding to BAP42 oligomers and/or monomers; and preferential BBB crossing, as described herein.

In certain embodiments, the antibody-peptide construct of the invention is a variant that comprises or consists of an amino acid sequence having at least 60%, 65%, 70%, 75%, 80%, 85%, 86%, 87%, 88%, 89%, 90%, 91%, 92%, 93%, 94%, 95%, 96%, 97%, 98%, 99%, or greater sequence identity to a second amino acid sequence of the same length (i.e., consisting of the same number of residues), which second amino acid sequence is selected from SEQ ID NOs: 26-109, and/or a fragment thereof, and wherein the variant exhibits at least one activity of the parent sequence from which it was derived (e.g., preferentially and immunospecifically binding BAP42 oligomers and/or crossing the BBB to a greater extend that other endothelial cell layers).

Amino acid sequence variants of the antibody-peptide constructs of the invention can be generated by techniques known in the art, based on disclosures provided herein regarding candidate sequences. In some embodiments, a variant may be a substitutional, insertional and/or deletion variant, including conservative substitutions as described above. In making such changes, the hydropathic index of amino acids may be considered, as described above; and/or hydrophobicity scales, also as described above.

In certain embodiments, the invention encompasses antibody-peptide constructs that comprise 1, 2, 3, 4, 5, 6, 7, 8, 9, or 10 or more amino acid modifications (e.g., insertion, substitution, deletion, etc.) relative to an amino acid sequence disclosed herein. In preferred embodiments, the mutation(s) are made such that BAP42 oligomer-binding and BBB-specific delivery are retained or substantially retained.

In certain embodiments, the antibody-peptide constructs of the invention are de-immunized. That is, the antibody-peptide construct may be modified to reduce its immunogenicity, e.g., where at least one $T_H$ epitope is eliminated and/or reduced. Specifically, antibody molecules, with or without fusion to a delivery peptide, can be modified, where the modification reduces immunogenicity. In some embodiments, delivery peptide of the fusion may be de-immunized separately. In particular, the present invention encompasses antibody molecules that comprise one or more antibody single domains fused to one or more delivery peptides, where either or both of which have been modified by any method known in the art and/or described herein to reduce immunogenicity of the antibody-peptide construct.

De-immunization may be achieved by any process known in the art and/or described herein, as noted above. Accordingly, in some embodiments, antibody molecule, and fusions thereof with delivery peptide(s), are provided that are de-immunized. The "de-immunized" polypeptide has been mutated to reduce $T_H$ epitope content and comprises one or more substations that reduce immunogenicity. Generally, the antibody-peptide construct comprises substitutions at one or more amino acid positions to reduce or eliminate epitopes that bind one or more HLA class II receptors.

Substitutions may occur, e.g., in an antibody single domain, such as in a light chain variable domain; and/or in the fused delivery peptide. In some embodiments, the de-immunized antibody molecule comprises substitutions that eliminate at least 10 $T_H$ epitopes, at least 15 $T_H$ epitopes, at least 20 $T_H$ epitopes, at least 25 $T_H$ epitopes, at least 30 $T_H$ epitopes, at least 40 $T_H$ epitopes, or at least 50 $T_H$ epitopes. In preferred embodiments, the substitutions do not affect, or at least do not substantially affect, immunospecific binding of the antibody molecule and/or do not affect, or at least do not substantially affect, BBB-specificity of the delivery peptide, as compared with the antibody molecule and/or delivery peptide before de-immunization.

The antibody-peptide constructs of the present invention find use in methods and pharmaceutical compositions for treating or preventing Alzheimer's and related disorders, as well as use in methods and kits for diagnosing these disorders, as discussed in more detail below.

5. Pharmaceutical Compositions and Methods of Making Same

Another aspect of the present invention involves pharmaceutical compositions and methods of making the pharmaceutical compositions of the invention. The pharmaceutical composition may be formulated by using at least one antibody molecule, delivery peptide, or antibody-peptide construct of the invention, and mixing with a pharmaceutically acceptable carrier. Antibody molecules, delivery peptides, and antibody-peptide constructs are considered "active agents" of the present invention, and may be therapeutic or prophylactic active agents, referred to also as "therapeutic or prophylactic agents". The pharmaceutical compositions may be termed "neuropharmaceuticals", due to their action on the CNS or brain. In some embodiments, the pharmaceutical composition comprises a polynucleotide encoding at least one antibody molecule, delivery peptide, or antibody-peptide construct of the invention, formulated with a pharmaceutically acceptable carrier, for expression after administration to a subject in need thereof.

The pharmaceutically acceptable carrier generally is selected based on the intended mode of administration, as well as the active agents to be delivered. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term also may refer to formulations used with the active agent, e.g., in Examples herein.

The term "carrier" refers to a diluent, adjuvant (e.g., Freund's complete and incomplete adjuvant), excipient, or vehicle with which the agent is administered. Such pharmaceutical carriers can be sterile liquids, such as water and oils, including those of petroleum, animal, vegetable, or synthetic origin, including, e.g., peanut oil, soybean oil, mineral oil, sesame oil and the like. Water is a common carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Additional examples of pharmaceutically acceptable carriers, excipients, and stabilizers include, but are not limited to, buffers such as phosphate, citrate, and other organic acids; antioxidants including ascorbic acid; low molecular weight polypeptides; proteins, such as serum albumin and gelatin; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™ as known in the art. These compositions can take the form of solutions, suspensions, emulsions, powders, sustained-release formulations, and the like.

In certain embodiments, pharmaceutical compositions are provided for use in accordance with the methods of the invention, said pharmaceutical compositions comprising a therapeutically and/or prophylactically effective amount of an active agent of the invention, along with a pharmaceutically acceptable carrier. The pharmaceutical compositions of the invention can be made by any technique known in the art and/or described herein.

In some embodiments, the pharmaceutical composition comprises one or more antibody molecules, one or more delivery peptides, and/or one or more antibody-peptide constructs of the invention for parenteral administration. Parenteral administration includes, e.g., intravenous, intradermal, subcutaneous, intraperitoneal, and intramuscular administration. Other routes of administration for delivery of the active agents include, e.g., oral, inhalation, transdermal (topical), and transmucosal administration, as well as intranasal and intrathecal administration.

Solutions or suspensions used for parenteral administration can include the following components: a sterile diluent such as water for injection, saline solution, polyethylene glycols, glycerine, propylene glycol or other synthetic solvents; buffers such as acetates, citrates or phosphates; agents for the adjustment of tonicity such as sodium chloride or dextrose; antibacterial agents such as benzyl alcohol or methyl parabens; antioxidants such as ascorbic acid or sodium bisulfite; chelating agents such as ethylenediaminetetraacetic acid. The parenteral preparation can be enclosed in ampoules, disposable syringes, or multiple dose vials made of glass or plastic.

Pharmaceutical compositions suitable for injectable use include sterile aqueous solutions or dispersions and sterile powders for the extemporaneous preparation of sterile injectable solutions or dispersions. For intravenous administration, suitable carriers include physiological saline, bacteriostatic water, Cremophor EL. (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. Suitable fluidity can be maintained, e.g., using surfactants. Prevention of the action of microorganisms can be achieved by various antibacterial and antifungal agents, for example, parabens, chlorobutanol, phenol, ascorbic acid, thimerosal, and the like. Prolonged absorption of the injectable compositions can be brought about by including in the composition an agent which delays absorption, for example, aluminum monostearate and gelatin.

Sterile injectable solutions can be prepared by incorporating the antibody molecule, delivery peptide, or antibody-peptide construct in the required amount in an appropriate solvent with one or more of the ingredients listed above, followed by filtered sterilization. Generally, dispersions are prepared by using a sterile vehicle that contains a basic dispersion medium. In the case of sterile powders for the preparation of sterile injectable solutions, vacuum drying or freeze-drying may be used.

In some embodiments, the pharmaceutical compositions comprise an antibody molecule, delivery peptide, or antibody-peptide construct of the invention in association with a label, e.g., for imaging and/or diagnostic purposes. The label may be any label known in the art or described herein. In preferred embodiments, the label facilitates imaging of the brain or CSF of the patient, following administration. Particular labels include, without limitation, a radiolabel, such as a radioactive isotope like technetium or gallium; fluorescent label, or any label suitable for use in SPECT or PET imaging, or CT or MRI scans. In preferred embodiments, the label used is not harmful to the patient. Example 2, part (b), provides details regarding labelling an agent of the invention with technetium or gallium; Example 5, part (b), provides details regarding use of radiolabelled agents of the invention in imaging.

The compositions of the invention include bulk drug compositions useful in the manufacture of pharmaceutical compositions (e.g., impure or non-sterile compositions) as well as pharmaceutical compositions (i.e., compositions that are suitable for administration to a subject or patient). Bulk drug compositions can be used in the preparation of unit dosage forms, e.g., comprising a prophylactically or therapeutically effective amount of an active agent disclosed herein or a combination of those agents and a pharmaceutically acceptable carrier. In preferred embodiments, the antibody molecule, delivery peptide, or antibody-peptide construct of the invention is substantially purified (i.e., substantially free from substances that limit its effect or produce undesired side-effects).

The invention further provides kits that can be used in the disclosed methods. In one embodiment, a kit comprises one or more active agents of the invention, e.g., in one or more containers. In another embodiment, the kit further comprises one or more other prophylactic or therapeutic agents useful for Alzheimer's disease or a disorder related thereto, in one or more containers. For example, in some embodiments, the invention provides a pharmaceutical pack or kit comprising one or more containers filled with one or more of the active agents of the pharmaceutical compositions of the invention. Optionally associated with such container(s) can be a notice in the form prescribed by a governmental agency regulating the manufacture, use, or sale of pharmaceuticals or biological products, which notice reflects approval by the agency of manufacture, use, or sale for human administration; and/or instructions for use.

Generally, the ingredients of pharmaceutical compositions of the invention are supplied either separately or mixed together in unit dosage form, for example, as a dry powder or water-free concentrate in a hermetically sealed container such as an ampoule or sachette indicating the quantity of active agent. Where the composition is to be administered orally, it can be provided in one or more tablets or capsules, e.g., providing unit doses of each of the one or more active agents for administration. Alternatively, where the composition is administered orally, it may be provided as a powder for adding to water or other beverage, to prepare a solution for drinking. Where the composition is to be administered by infusion, it can be dispensed with an infusion bottle containing sterile pharmaceutical grade water or saline. Where the composition is administered by injection, an ampoule of sterile water for injection or saline can be provided so that the active agents and other ingredients may be mixed prior to administration.

In pharmaceutical compositions comprising the antibody molecules or antibody-peptide constructs of the invention, or constructs comprising a delivery peptide of the invention with a different active agent used in the art to treat Alzheimer's or a related disorder, the antibody molecule or construct may be provided as the sole active ingredient. Alternatively, the antibody molecule, antibody-peptide construct, or construct comprising a delivery peptide of the invention with an antibody used in the art to treat Alzheimer's or a related disorder, may be provided in combination with one or more other therapeutic or prophylactic agents or approaches for use in Alzheimer's disease or a related disorder. For example, pharmaceutical compositions comprising antibody molecules, or antibody-peptide constructs of the invention, further may comprise one or more of the five drugs approved by the US Food and Drug Administration (FDA) for treatment of Alzheimer's, namely, the non-competitive antagonist of NMDA receptors, memantine, and the cholinesterase inhibitors, donepezil, galantamine, rivastigmine, and tacrine.

Pharmaceutical compositions comprising antibody molecules or antibody-peptide constructs of the invention may be used in combination with one or more of the following approaches for treating Alzheimer's: a tau-based therapy (such as tau phosphorylation inhibition, microtubule stabilization, blocking tau oligomerization, enhancing tau degradation, and tau-based immunotherapy); other amyloid-based strategies (such as secretase enzymes modulation, amyloid transport, preventing amyloid aggregation, and promoting amyloid clearance); modulating intracellular signaling cascades; oxidative stress reduction (such as exogenous antioxidant supplementation and augmenting endogenous defenses); mitochondria targeted therapy; modulation of cellular calcium homeostasis, and anti-inflammatory therapies, as well as gonadotropin supplementation, lipid modifiers like statins, growth factor supplementation, metal chelation, epigenetic modifiers, caspase inhibitors, nitric oxide synthase modulation, nucleic acid drugs, and multi-target directed ligands.

Pharmaceutical compositions comprising antibody molecules, or antibody-peptide constructs of the invention, further may comprise one or more active agents for treating Alzheimer's or a related disorder. For example, pharmaceutical compositions of the invention may be used in combination with one or more of ELN 0005, an inhibitor of oligomer formation; CAD 106 (Novartis), a vaccine providing multiple copies of BAP1-6 peptide derived from the N-terminal B cell epitope of BAP, itself coupled to a carrier containing 180 copies of bacteriophage Qβ coat protein; ACC-001 (Affitope AD02) another vaccine providing BAP1-6 amino terminal fragment; and V950, comprising the amino-terminal BAP conjugated to ISCO-MATRIX. For example, one or more of any of these active agents may be combined in a pharmaceutical composition comprising an antibody molecule or antibody-peptide construct of the invention. Further, one or more of any of these active agents may be associated with one or more delivery peptides of the invention, e.g., as a fusion, to improve delivery to the CNS and brain, and provided in a pharmaceutical composition of the invention.

Pharmaceutical compositions comprising antibody molecules, or antibody-peptide constructs of the invention, further may comprise one or more other antibodies for treating Alzheimer's or a related disorder. For example, pharmaceutical compositions of the invention may be used in combination with one or more of the antibodies disclosed in Ohshima-Hosoyama, S., et al., *PLoS One* (2012) 7(6): e39036; and Couch, et al., *Sci Transl Med* (2013) 5(183): 183ra57, 1-12. The antibody molecules of the invention also may be used in combination with passive immunization of one or more other anti-BAP antibodies, e.g., avoiding a pro-inflammatory T-cell reaction. Examples of other anti-BAP antibodies include the humanized monoclonal anti-BAP antibody Bapineuzumab (Wyeth and Elan), that binds to both soluble and fibrillar forms of BAP; BAN2401, a humanized monoclonal antibody targeting protofibrils; Crenezumab, a humanized antibody to BAP1-40 and BAP42; Gantenerumab, humanized monoclonal antibody to BAP1-11; GSK933776, a humanised $IgG_1$ monoclonal antibody against the N-terminal of BAP; and Solanezumab (Eli Lilly), a humanized monoclonal antibody to BAP16-24 that preferentially binds soluble BAP (Solanezumab on its own, however, has failed to demonstrate significant functional improvement nor changes in brain amyloid accumulation (Williams (2013) *Pharmacology* 85: 289-305; incorporated by reference)). For example, one or more of any of these other anti-BAP antibodies may be combined in a pharmaceutical composition comprising an antibody molecule or antibody-peptide construct of the invention. Further, one or more of any of these anti-BAP antibodies may be associated with one or more delivery peptides of the invention, e.g., as a fusion, to improve delivery to the CNS and brain, and provided in a pharmaceutical composition of the invention.

Pharmaceutical compositions of the invention find use in therapeutic and/or prophylactic strategies against Alzheimer's disease or related disorders, as described in more detail below.

6. Therapeutic and Prophylactic Uses

Another aspect of the present invention relates to strategies that involve administering a pharmaceutical composition according to the invention to a subject in need thereof, for delaying, slowing, preventing, treating, reversing, reducing the incidence of, and/or managing a neurological disease or disorder, and/or ameliorating one or more symptoms associated therewith. A subject in need thereof includes a subject suffering from the disease or disorder, or a subject pre-disposed thereto, e.g., a subject at risk of developing or having a recurrence of the disease or disorder.

Neurological disorders include neurodegenerative diseases, including, but not limited to, Alzheimer's Disease (AD), Parkinson's Disease, Huntington's Disease, and amyotrophic lateral sclerosis (ALS). Neurological disorders also include conditions associated with accumulation of other aggregation-prone oligomeric peptides in the brain.

At the histopathological level, Alzheimer's is a complex progressive condition with sequentially interacting pathological cascades combined with downstream processes such as inflammation and oxidative stress, all of which contribute to loss of synaptic integrity, effective neural network connectivity, and progressive regional neurodegeneration. The two major neuropathologic hallmarks of Alzheimer's are extracellular beta-amyloid plaques and intracellular neurofibrillary tangles derived from tau ($\tau$) protein hyperphosphorylation. Alzheimer's brains show deposition of the beta amyloid protein in senile plaques. This protein is produced by cleavage of amyloid precursor protein (APP), which has important developmental functions in cell differentiation and possibly in the establishment of synapses by the enzymes beta-secretase and gamma-secretase.

In addition to beta amyloid accumulation during the development of Alzheimer's, tau protein also accumulates in neurofibrillary tangles. This protein is an integral component of microtubules, which are the internal support structures that transport nutrients, vesicles, mitochondria, and chromosomes from the cell body to the ends of axon and backwards. In Alzheimer's, tau protein becomes hyperphosphorylated. This phosphorylation causes the proteins to bind together and form tangled threads, leading to the transport disruption and eventually contributing to neuron death.

It is believed that tau and beta-amyloid lead to the formation of episodic memory that requires neuronal connections of small areas of the entorhinal cortex and the hippocampus in the medial temporal lobe (hippocampus and the parahippocampal gyms). The huge amount of information acquired by seeing, hearing, and feeling is processed in the neocortex and funneled by projections from almost all neocortical areas to the entorhinal region. It is believed that abnormalities in tau and beta-amyloid, e.g., as described above, interfere with these processes, leading to the clinical manifestations of Alzheimer's.

The present invention provides methods for delaying, slowing, preventing, reducing the incidence of, treating, reversing, and/or managing Alzheimer's, or a related disorder, or ameliorating one or more symptoms thereof, in a subject in need thereof. The methods generally comprise administration to said subject a therapeutically or prophylactically effective amount of a pharmaceutical composition of the invention, such as a composition comprising an antibody molecule or antibody-peptide construct of the invention, or a construct comprising a delivery peptide of the invention with a different active agent. In a particular embodiment, the invention provides for slowing or retarding the progression of the disease itself, as well as preventing or delaying the onset of the disease in a subject at risk for Alzheimer's or a related disorder.

The pharmaceutical compositions of the invention provide therapeutic and/or prophylactic benefit with respect to Alzheimer's and/or related disorders. Related disorders include other conditions associated with the CNS, such as other neuropathological conditions involving accumulation of BAP, in particular BAP42, in oligomeric or higher order forms, as well as other dementia. Related disorders also include conditions involving different aggregation-prone oligomers that also may be targeted by the antibody molecules of the invention, that is, other aggregation-prone peptides that characterize other neurodegenerative diseases or prion disorders. Examples of other aggregation-prone peptides include, e.g., soluble oligomers derived from the following recombinant disease proteins: $\alpha$-synuclein (involved in Parkinson's disease), islet amyloid polypeptide (IAPP, involved in type II diabetes), huntington with extended polyglutamine stretches (involved in Huntington's disease); and the prion protein (PrP; involved in transmissible and inherited spongiform encephalopathies).

Without wishing to be bound by theory, these different aggregation-prone oligomers may have some common structural features, such that soluble peptides of entirely different sequences can fold into beta-sheet-rich structures that contain one or more shared conformational epitopes. It follows that assemblies produced by different disease-causing proteins might initiate similar cytotoxic mechanisms and, moreover, may be targeted by their common structures using the antibody molecules of the present invention for therapeutic and/or prophylactic intervention.

Symptoms of Alzheimer's and some disorders related thereto include, e.g., memory loss, disorientation, dementia, cognitive impairment, mild cognitive impairment, as well as problems with language, judgment, and problem solving. These problems generally lead to an inability to perform daily tasks, and eventually dementia. The most common early symptom is difficulty in remembering recent events (short term memory loss), often followed by problems speaking, getting lost easily, mood swings, loss of motivation, and not managing self-care. Alzheimer's is divided into four stages: pre-dementia that resemble the effects of aging on memory loss; an early stage, with increased forgetfulness and confusion in unfamiliar situations; a middle stage, accompanied by difficulty remembering recently-learned information and loss of independence; and a late stage, characterized by complete dependence on caregivers, possible loss of speech, and becoming bedridden. Gradually, even bodily functions are lost, eventually leading to death.

In preferred embodiments, a pharmaceutical composition comprising an antibody molecule or antibody-peptide construct of the invention, or a construct comprising a delivery peptide of the invention with a different active agent, is administered at the early stages of Alzheimer's, more preferably during pre-dementia or to patients pre-disposed to Alzheimer's who do not yet show pre-dementia signs. Subjects pre-disposed, or at risk, of Alzheimer's can be identified by biomarkers for the disease, such as biomarkers known in the art and/or disclosed herein. Subjects pre-disposed to or at risk of Alzheimer's can be identified by family history, or a combination of family history and biomarker information. Without wishing to be bound by theory, intervention at the early or pre-dementia stage, or even before these stages, allows for preventing formation of senile plaques before they build up, or before they build up to signification amounts, preserving normal brain architecture and functioning.

A pharmaceutical composition of the invention generally will be administered for a time and in an amount effective for obtaining a desired therapeutic and/or prophylactic benefit. In preferred embodiments, the effective amounts formulated and/or administered do not cause substantial toxicity, even with chronic use. The data obtained from the cell culture assays and animal studies can be used in formulating a range and/or schedule for dosage of the active agents of the invention for use in humans. The amount of an active agent of the invention to provide a therapeutically and/or prophylactically effective dose can be determined by clinical techniques, in view of the disclosures presented herein. For example, effective doses may be extrapolated from biodistribution studies in CD1 mice (see, Example 3, part (e)) and efficacy studies in 5xFAD mice (see, Example 4), which provide information regarding suitable dosage and administration routes for exemplary antibody molecules and antibody-peptide constructs of the invention. Such information can be used to more accurately determine useful doses in humans.

The dosage and frequency may vary according to factors specific for each patient depending on the particular therapeutic or prophylactic agents administered, the severity and type of disease, the route of administration, as well as age, body weight, response, and the past medical history of the patient, and is decided, in some embodiments, according to the judgment of the practitioner and each patient's circumstances. Suitable doses and regimens can be selected by one skilled in the art by considering such factors and by following, e.g., dosages reported in the literature and recommended in the Physician's Desk Reference ($56^{th}$ ed., 2002). The therapeutic or prophylactic agents can be administered repeatedly. Several aspects of the procedure may vary such as the temporal regimen of administering the therapeutic or prophylactic agents, and whether such agents are administered separately or in combination with other agents.

Prophylactic and/or therapeutic agents, as well as combinations thereof, can be tested in suitable animal model systems prior to use in humans. Such animal model systems include, but are not limited to, mice, rats, cows, monkeys, pigs, dogs, rabbits, etc. Any animal system well-known in the art may be used. Such model systems are widely used and well known to the skilled artisan, e.g., 5xFAD mice models. In some preferred embodiments, animal model systems for Alzheimer's or a related disorder are used that are based on rats, mice, or other small mammal. For example, in a specific embodiment, putative prophylactic and/or therapeutic compositions of BBB-specific, BAP42 oligomer-immunospecific antibody-peptide constructs are tested in a 5xFAD mice model.

Once the prophylactic and/or therapeutic agents of the invention have been tested in an animal model, they can be tested in clinical trials to establish efficacy. Establishing clinical trials will be done in accordance with common methodologies known to one skilled in the art, and the optimal dosages and routes of administration, as well as toxicity profiles of agents of the invention, can be established. For example, a clinical trial can be designed to test a pharmaceutical composition comprising a humanized antibody-peptide construct comprising one or more CDRs of an amino acid sequence selected from SEQ ID NOs: 1-21, for efficacy and toxicity in human patients with Alzheimer's disease. In some embodiments, the humanized antibody-peptide construct is administered in a dose of about 0.1 ng to about 1 g to treat Alzheimer's. The dose of about 0.1 ng to about 1 g may be administered as a single dose, or multiple doses over a course of treatment.

Toxicity and efficacy of the prophylactic and/or therapeutic agents of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, e.g., expressed as the ratio $LD_{50}/ED_{50}$. Prophylactic and/or therapeutic agents that exhibit large therapeutic indices are preferred. Further, the specificity of the agents of the invention, e.g., in preferred embodiments showing immunospecific binding to BAP42 oligomers and preferential translocation across the BBB, facilitate achieving efficacy well outside the toxic range.

Further, effective doses and dosage regimens can be selected by one skilled in the art, considering the present disclosures regarding various characteristics of BAP42 oligomer-immunospecific and BBB-specific agents in the context of Alzheimer's or a related disorder. For example, in preferred embodiments, as discussed above, the antibody molecule, or antibody molecule component of a construct of the invention, provides high immunospecificity for BAP42 oligomers and/or monomers over BAP42 fibrils. In preferred embodiments, as discussed above, the antibody molecule, or antibody molecule component of a construct of the invention, is small, monovalent, and/or stable. In preferred embodiments, as discussed above, the delivery peptide, or delivery peptide component of a construct of the invention, provides preferential BBB translocation, low toxicity to brain endothelial cells, rapid brain uptake, and/or rapid brain clearance. In preferred embodiments, as discussed above, the antibody-peptide constructs of the invention combine the above characteristics, more preferably further showing high expression in stable and/or soluble forms.

The active agents of the invention may be administered alone or in combination with different active agents of the invention, or still other prophylactic and/or therapeutic agents. Each prophylactic or therapeutic agent may be administered at the same time, either in the same or separate formulation; or sequentially, in separate formulations, in any order at different points in time; however, if not administered at the same time, they should be administered sufficiently close in time so as to provide the desired therapeutic or prophylactic effect, including any synergistic effect. Each therapeutic/prophylactic agent can be administered separately, in any appropriate form and by any suitable route.

In various embodiments, the different prophylactic and/or therapeutic agents are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart, or no more than 48 hours apart.

Treatment of a subject with a therapeutically or prophylactically effective amount of the active agents of the invention can include a single administration or can include a series of administrations over a course of treatment. For example, pharmaceutical compositions comprising an antibody molecule of the invention, specific for BAP42 oligomers, may be administered once a day, twice a day, or three times a day. In some embodiments, the active agent may be administered once a day, every other day, once a week, twice a week, once every two weeks, once a month, every other month, once every six weeks, twice a year, or once per year. In preferred embodiments, a once weekly dose is used and, more preferably, is continued over the course of the disease. It will also be appreciated that the effective dosage of certain active agents may increase or decrease over the course of treatment, e.g., depending on improvements in the subject over the course of treatment.

In some embodiments, ongoing treatment is indicated, e.g., on a long-term basis, such as in the ongoing treatment and/or management of chronic diseases like Alzheimer's. For example, in particular embodiments, an active agent of the invention is administered over a period of time, e.g., for at least 6 months, at least one year, at least two years, at least five years, at least ten years, at least fifteen years, at least twenty years, or for the rest of the lifetime of a subject in need thereof.

Various delivery systems are known and can be used to administer the active agents of the invention. Methods of administering active agents of the invention include, but are not limited to, parenteral administration (e.g., intradermal, intramuscular, intraperitoneal, intravenous, and subcutaneous, including infusion or bolus injection); epidural; oral administration (e.g., in capsules, tables, or solutions for consumption); intrathecal administration, and by absorption through epithelial or mucocutaneous or mucosal linings (e.g., intranasal, oral mucosa, rectal, and intestinal mucosa, etc.).

For intranasal or administration by inhalation, an active agent of the invention may be delivered in the form of a dry powder inhaler or an aerosol spray presentation. The aerosol may be delivered from a pressurized container, pump, spray or nebulizer, preferably with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A™) or 1,1,1,2,3,3,3-heptafluoropropane (HFA 227EA™), carbon dioxide, or other suitable gas. In the case of a pressurized aerosol, the dosage unit may be determined by providing a valve to deliver a metered amount. The pressurized container, pump, spray, or nebulizer may contain a solution or suspension of the active agent, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain, e.g., a powder mix of an antibody molecule and a suitable powder base such as lactose or starch.

In another specific embodiment, active agents of the invention may be delivered by intrathecal (IT) injection, that is, the administration of proteins to the cerebrospinal fluid (CSF). Intrathecal injection offers an advantage over other standard administration routes, in that the CSF provides superior access to the brain and meninges. The CSF covers the brain and provides large surface area contact with cortical neurons up to 6 mm below the surface, allowing for more efficient penetration into the brain tissue of an antibody molecule or antibody-peptide construct of the invention, or a construct comprising a delivery peptide of the invention with a different active agent.

In another specific embodiment, active agents of the invention may be delivered in a sustained release formulation, e.g., where the formulations provide extended release and thus extended half-life of the administered agent. Common reservoir devices include, e.g., membranes, capsules, film-coated capsules, microcapsules, liposomes, and hollow fibers. Monolithic (matrix) device are a second type of diffusion controlled system, wherein the pharmaceutical compositions are dispersed or dissolved in an rate-controlling matrix (e.g., a polymer matrix). Active agents of the invention can be homogeneously dispersed throughout a rate-controlling matrix and the rate of release is controlled by diffusion through the matrix. Polymers suitable for use in the monolithic matrix device include naturally occurring polymers, synthetic polymers and synthetically modified natural polymers, as well as polymer derivatives.

7. Diagnostic Uses

The antibody molecules or antibody-peptide constructs of the invention, or constructs comprising delivery peptides of the invention with different active agents, can identify biomarkers for Alzheimer's and related disorders, preferably providing antigen recognition patterns useful in diagnostic applications. In particular embodiments, antibody molecules and antibody-peptide constructs, as disclosed herein, provide compositions, kits, and methods for the diagnosis of brain/neurological disease involving abnormalities in BAP42 or other aggregation-prone peptides in the brain. In particular embodiments, the compositions, kits, and methods facilitate early clinical diagnosis of pre-dementia or early stages of Alzheimer's, or predict a subject's risk for developing Alzheimer's. In more preferred embodiments, the invention facilitates diagnosis of progression of mild cognitive impairment (MCI) in Alzheimer's patients.

Alzheimer's generally is diagnosed clinically on the basis of exclusion of other forms of dementia. The diagnosis can be confirmed neuropathologically by the demonstration of large amounts of neuritic (senile) plaques and neurofibrillary tangles (NFT) in particular brain regions.

The antibody molecules and antibody-peptide constructs of the invention immunospecifically bind BAP42 monomers and oligomers, and/or other aggregation-prone peptides, present at altered levels in the brain, CSF, or blood (serum) of a patient with Alzheimer's or a related disorder, or a patient predisposed thereto, where the altered levels correlate with increased fibrillization. That is, for patients with, or at risk for, Alzheimer's or a related disorder, the levels of BAP42 monomers and oligomers, and/or other aggregation-prone peptides, generally will be outside normal ranges for healthy, control subjects. Detection of immunospecific binding, to form immunological complexes, can provide a diagnosis, either in an in vitro context, or by in vivo imaging, as well as other information for monitoring the progression of the disease or disorder, or determining efficacy of a therapeutic or prophylactic agent over a course of treatment.

In particular embodiments, a test sample is obtained from the subject, e.g., to perform in vitro diagnosis. The test sample may be a sample of serum, brain tissue, or CSF. In preferred embodiments, the test sample comprises CSF. A CSF sample may be obtained by methods known in the art, such as lumbar puncture or a spinal tap. Generally, with the patient lying on his/her side, with knees pulled toward the chest, a health care provider injects a local numbing medicine (anesthetic) into the lower spine and then inserts a spinal needle, usually into the lower back area, to collect the test sample. In some instances, fluoroscopy is used to help guide the needle. Alternate approaches include cisternal puncture, which uses a needle placed below the occipital bone (back of the skull); and ventricular puncture, which involves drilling a hole in the skull and inserting a needle directly into one of brain's ventricles.

The patient or subject may have any stage of Alzheimer's or related disorder, or may be suspected of being at risk for Alzheimer's or related disorder, e.g., based on family history and/or other early markers. In preferred embodiments, the patient is at an early stage, characterized by mild cognitive impairment (MCI). For example, test samples may be obtained from patients with cognitive complaints, memory problems, and/or identified dementia, or patients identified as being in early-stage Alzheimer's by brain imaging (CT scan, MRI, PET, SPECT).

A control sample also may be collected, e.g., from a subject without Alzheimer's or any related disorder and/or who is not at risk for Alzheimer's nor any related disorder. A control sample is expected to have normal amounts of aggregation-prone oligomeric peptides associated with Alzheimer's and related disorders (referred to as the "relevant brain peptide" in the context of the present invention). For example, a control sample generally has amounts within a healthy range for BAP42 oligomers, peptides of a-synuclein (indicated in Parkinson's disease), peptides of islet amyloid polypeptide (indicated in type II diabetes), peptides of huntington (indicated in Huntington's disease); and/or peptides of prion protein (indicated in spongiform encephalopathies). In some embodiments, a control sample is not collected, e.g., where information already is available regarding the amount of relevant brain peptide in normal, healthy subjects, e.g., the concentration of the relevant brain peptide in the CSF, brain, or serum of a subject not having and not at risk for Alzheimer's or a related disorder.

Contacting an antibody molecule of the invention with a test sample from a subject having or pre-disposed to Alzheimer's, or related disorder, generally results in immunospecific binding at levels outside the range for that obtained upon contact with a control sample. Specifically, to determine the amount of BAP42 oligomer, or other relevant brain peptide, in a test sample, the test sample is brought into contact with one or more antibody molecules of the invention, or peptide constructs thereof, to allow immunospecific binding. The antibody molecule and/or antibody-peptide construct is brought into contact with the test sample under conditions that allow formation of immunocomplexes between the antibody molecule, or antibody component of the construct, and antigens it immunospecifically recognizes and binds. In a particular embodiment, that antibody molecule or construct shows modestly elevated, or a statistically significant elevation in, immunospecific binding when contacted with CSF of a patient in an early stage of Alzheimer's.

In some embodiments, the antibody molecules or antibody-peptide constructs are immobilized when contacted with the test sample. For example, a plurality of the antibody molecules or constructs may be immobilized on a suitable support. The support may be any solid or semi-solid material, such as a resin, chip (e.g., a microfluidic chip), microarray, bead, glass, vial, chromatography column, plate, ceramic, engineered thermal plastic, clay, polyester fiber, Teflon, polyethylene, polypropylene, or biological or artificial membrane, or in accordance with any immunoassay format known to the person skilled in the art.

Immobilization may be achieved by attaching the antibody molecules or constructs thereof to the support by covalent or non-covalent interactions, as described herein or known in the art. Non-covalent interactions include electrostatic attraction, van der Waals forces, and/or hydrogen bonding. Preferably, immobilization is by covalent interactions, such as formation of a chemical linkage between a group on the antibody molecule, or construct thereof, and a group on the support. Immobilization may occur directly to the support, or indirectly, such as via a linker or bound antibody that itself recognizes and binds the antibody molecule or antibody-peptide construct of the invention. Further, one of skill in the art will recognize that immobilization occurs in such a way as to retain a functionality of the antibody molecule, or antibody component of a construct thereof, e.g., to retain or substantially retain preferential and immunospecific binding to BAP42 oligomers or other relevant brain peptides.

The samples may be subjected to one or more steps before contact with the immobilized antibody molecules or antibody-peptide constructs. For example, BAP42 oligomers, or other relevant brain peptide, may be concentrated in the sample, or partially purified by removing certain impurities, such as materials that may interfere with immunospecific binding to antibody molecules of the invention. Alternatively, the relevant brain peptide in the sample may be immobilized, e.g., on a suitable support as described above, before being contacted with an antibody molecule or antibody-peptide construct of the invention.

Immunospecific binding to a relevant brain peptide, e.g., a BAP42 oligomer, in the test sample can be detected. Detection may be carried out by any means known in the art for detecting, measuring, or quantifying formation of immunocomplexes of an antibody molecule with its target antigen, that is, for detecting immunospecific binding using an immunoassay. Immunoassays that can be used include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays, and the like, as well as BIAcore analysis. Such assays are described in the art (see, e.g., Ausubel et al, eds, 1994, Current Protocols in Molecular Biology, Vol. 1, John Wiley & Sons, Inc., New York, which is incorporated by reference in its entirety). Immunospecific binding also may be detected, measured, or quantitated using, e.g., flow cytometry or a scintillation assay. For example, the antibody molecule or antibody-peptide construct of the invention can be labelled using, e.g., a radiolabel (such as $^{99}$Tc, $^{67}$Ga, $^{68}$Ga, $^{32}$P, $^{35}$S, and $^{125}$I), a fluorescent label (such as fluorescein isothiocyanate, rhodamine, phycoerythrin, phycocyanin, allophycocyanin, o-phthaldehyde and fluorescamine), or label described herein or known in the art, to allow detection of immunospecific binding.

Detection of immunospecific binding will indicate the amount of relevant brain peptide present in a sample, which may correspond to normal amounts, or more or less than normal amounts, where a normal amount corresponds to that detected in control samples obtained from subjects not having, nor pre-disposed to, Alzheimer's or related disorders.

Immunospecific binding outside the range obtained with a control sample, or towards the very low or very high end of the range, can provide a diagnosis of Alzheimer's or a related disorder. For example, an antibody molecule of the invention that immunospecifically binds BAP42 oligomers can indicate modestly elevated amounts (statistically significant elevation) of BAP42 oligomers in a CSF sample from a subject, thereby diagnosing said subject as having Alzheimer's, in particular when combined with other diagnostic measures. The extent of immunospecific binding may indicate different stages of Alzheimer's, e.g., where amounts of BAP42 oligomers slightly outside normal ranges indicate pre-dementia or early stage Alzheimer's and more pronounced alterations indicate more advanced stages. Example 5, part (a), provides additional details of in vitro diagnosis using exemplary antibody molecules and antibody-peptide constructs of the invention.

Different antibody molecules of the invention may also indicate different stages of Alzheimer's, e.g., where abnormal levels of immunospecific binding by a first antibody molecule indicates an earlier stage and abnormal levels of immunospecific binding by a second antibody molecule indicates a later stage. Accordingly, the present invention identifies biomarkers for specific stages of Alzheimer's, in particular, early stages and stages associated with MCI.

The present invention also provides in vivo diagnostic or imaging methods. Specifically, antibody molecules and antibody-peptide constructs of the invention immunospecifically bind BAP42 monomers and oligomers, and/or other aggregation-prone peptides, present in altered amounts and/or altered distribution patterns in the brain or CSF of a patient with Alzheimer's or a related disorder, or a patient predisposed thereto, compared to healthy, control subjects. Detection of the immunospecific binding by in vivo imaging can provide a diagnosis of the disease or disorder.

In particular embodiments, the invention provides a method for imaging an aggregation-prone peptide in a patient's body. For example, an antibody molecule or antibody-peptide construct of the invention may be associated with a label and administered to the patient. The label may be any label known in the art or described herein. In preferred embodiments, the label facilitates imaging of the brain or CSF of the patient, following administration. Particular labels include, without limitation, a radiolabel or fluorescent label. In preferred embodiments, the label used is not harmful to the patient.

Administration generally involves parenteral administration, preferably in a manner to facilitate delivery of the antibody molecule or antibody-peptide construct across the BBB to the brain or CNS of the subject. In preferred embodiments, the antibody molecule or antibody-peptide construct used for in vivo imaging is humanized and shows BBB-specific translocation and/or BAP42 oligomer-immunospecific binding, as described herein. In more preferred embodiments, the antibody molecule or antibody-peptide construct used does not cause disruption of the BBB in the patient, again as described herein.

The aggregation-prone peptide may be a BAP42 oligomer or other relevant brain peptide, as described herein. Detection of immunospecific binding will indicate the amount of relevant brain peptide present in the patient's brain, which may correspond to normal amounts, or greater or less than normal amounts, where a normal amount corresponds to that detected in subjects not having, nor pre-disposed to, Alzheimer's or related disorders.

In a particular embodiment, an image showing modestly elevated (statistically significant elevation in) immunospecific binding of BAP42 oligomers provides a diagnosis of Alzheimer's. Further, the extent and/or pattern of immunospecific binding may indicate different stages of Alzheimer's, as discussed herein. Example 5, part (b), provides additional details of in vivo imaging and diagnosis using exemplary antibody molecules and constructs thereof of the invention.

Different antibody molecules or antibody-peptide constructs of the invention may also indicate different stages of Alzheimer's, e.g., where a first antibody molecule indicates an earlier stage and a second antibody molecule indicates a later stage. Accordingly, the present invention identifies biomarkers and binding patterns for specific stages of Alzheimer's, in particular, early stages and stages associated with MCI.

The diagnostic methods described herein may be used alone or in combination with each other, or in combination with one or more other measures for diagnosing Alzheimer's. In some embodiments, the assays for total amount of tau protein (T-tau) and phosphorylated tau protein (P-tau181) may be used in combination with approaches in accordance with the present invention. In a particular example, analysis of T-tau combined with BAP42 oligomer measurements provides 83% specificity and 95% sensitivity with respect to the progression of slight cognitive defects in Alzheimer's. In another particular embodiment, analysis of T-tau combined with a ratio of BAP42 oligomers/P-tau provides 95% sensitivity and 87% specificity. The combination of these proteins in the CSF constitutes a predictive biomarker for the progression of slight cognitive impairment in Alzheimer's and may be included in criteria for Alzheimer's diagnosis.

Diagnosis using antibody molecules or antibody-peptide constructs of the invention can provide information regarding neurochemical abnormalities in a patient, allowing specific therapeutic intervention and/or selection of potential patients for clinical trials with new neuroprotective therapies. For example, in some embodiments, in vitro or in vivo diagnosis, as described herein, is followed by therapeutic intervention, such as administration to the diagnosed patient of an effective amount of a pharmaceutical composition described herein and/or administration of any other Alzheimer's therapies known in the art and/or described herein. In particular embodiments, the antibody molecule or antibody-peptide construct of the invention administered to the patient is the same antibody molecule or antibody-peptide construct that was used to provide the in vitro or in vivo diagnosis, or a humanized version thereof.

One of skill in the art will recognize that, since the antibody molecule or construct showed immunospecificity for a brain peptide identified as present in abnormal amounts, or in an abnormal pattern, in a particular patient, it follows that administration of the same antibody molecule, or construct thereof, provides a promising therapeutic agent to neutralize the brain peptide relevant to treating that particular patient. In specific embodiments, the step of treating the patient comprises administering a suitable therapeutic agent, e.g., a pharmaceutical composition comprising an antibody molecule of the invention. In specific embodiments, the step of treating the patient comprises making information regarding diagnosis available to a health care provider who then administers the treatment.

The present approaches also can be used to monitor Alzheimer's disease or a related disorder over a period of time, by repeating the in vivo imaging and/or in vitro assays for a given subject or population of subjects. Where the subject is being treated with a course of treatment, e.g., in a clinical or research setting, repeated tests can be used to assess efficacy throughout the course of treatment. For example, a patient may be tested before beginning treatment, e.g., before administration of an antibody molecule of the present invention, and then tested again after some administrations, or every administration, of the active agent. Determining changes in amounts of BAP42 oligomers, or other aggregation-prone peptides, e.g., in CFS samples or in brain images, over time, can provide information regarding efficacy of the agent being administered.

Specifically, a second test sample may be obtained from the same subject at a later time. The second test sample can be contacted with an antibody molecule or antibody-peptide construct of the invention, followed by detection of immunospecific binding. Comparing the amounts of immunospecific binding, at different time points, allows for monitoring the amount of aggregation-prone peptide in the subject. For example, increasing/decreasing levels of BAP42 oligomers in CSF samples from a subject can indicate improvements in Alzheimer's over time, where the levels approach the normal range, thereby demonstrating efficacy of a treatment being administered. Similarly, repeated in vivo imaging of a patient's brain over time can provide a series of images showing changes in amounts and/or patterns of an aggregation-prone peptide, such as changes in BAP42 oligomers in an Alzheimer's patient. Images showing trends towards normal amounts and/or normal patterns of BAP42 oligomers in the patient's brain can indicate improvements in Alzheimer's over time, thereby demonstrating efficacy of a treatment being administered

8. Diagnostic Kits

Another aspect of the invention relates to kits comprising the antibody molecules, delivery peptides, and/or antibody-peptide constructs of the present invention, such as kits for use in diagnosing Alzheimer's disease or a related disorder. The present invention provides kits for use the in vitro or in vivo diagnostic methods described above.

In some embodiments, the invention provides a kit comprising a plurality of an antibody molecule or an antibody-peptide construct of the invention. A plurality of antibody molecules, or antibody-peptide constructs, refers to more than one molecule of the same type of antibody, or construct thereof, provided as a collection for use together. In particular embodiments, the plurality of antibody molecules, or antibody-peptide constructs, provides a sufficient amount of the molecules to allow detection of immunospecific binding to target antigens in vitro, such as binding to BAP42 oligomers in a CSF sample. In particular embodiments, the plurality of antibody molecules, or antibody-peptide constructs, provides a sufficient amount of the molecules to allow detection of immunospecific binding to target antigens in vivo, such as providing an image of immunocomplexes formed with BAP42 oligomers in a patient's brain. One of skill in the art will recognize that the amount needed will depend on the detection approach, or immunoassay, used to determine, measure, or quantify immunospecific binding.

In some embodiments, the kit comprises a humanized version of the antibody molecule or antibody-peptide construct, e.g., where the agent is intended for administration to a patient (such as in in vivo imaging or diagnosis methods). In some embodiments, the kit also comprises a label to facilitate detection of immunospecific binding. The label may be included in a separate compartment of the kit or may be associated with the antibody molecules or antibody-peptide constructs. Suitable labels include any labels disclosed herein and/or known in the art for use in immunoassays.

In a particularly preferred embodiment, the plurality of antibody molecules or antibody-peptide construct is immobilized on a suitable support. The support may be any solid or semi-solid material, as disclosed above, and immobilization may be achieved by any covalent or non-covalent interactions, again as set forth above.

In some embodiments, the kit comprises one type of antibody molecule or antibody-peptide construct of the invention. In some embodiments, the kit comprises two or more different antibody molecules or antibody-peptide constructs. As discussed above, different antibody molecules of the invention may show different immunospecific binding patterns, allowing diagnosis of different stages of Alzheimer's and/or related disorders. Accordingly, in some embodiments, the kit provides a first plurality of a first antibody molecule or antibody-peptide construct of the invention and a second plurality of a second antibody molecule or antibody-peptide construct of the invention.

In a particular embodiment regarding in vitro detection, the first antibody molecule or construct shows abnormal levels of immunospecific binding when contacted with a test sample from an patient in an early stage of Alzheimer's; and the second antibody molecule or construct shows abnormal levels of immunospecific binding when contacted with a test sample from an patient in a later stage of Alzheimer's. In a particular embodiment regarding in vivo imaging, the first antibody molecule or construct shows modestly elevated (statistically significant elevation in) immunospecific binding in the brain of a patient in an early stage of Alzheimer's; and the second antibody molecule or construct shows modestly elevated (statistically significant elevation in) immunospecific binding in the brain of a patient in a later stage of Alzheimer's. One of skill in the art will appreciate that kits can be provided with multiple different antibody molecules, or antibody-peptide constructs, directed to different stages of Alzheimer's, to facilitate diagnosis of different stages of the subject's disease.

In a particularly preferred embodiment regarding in vitro diagnosis, different pluralities of different antibody molecules or antibody-peptide constructs are immobilized on distinguishable locations on a suitable support or on different supports or in different compartments within a kit. A distinguishable location refers to a separate site within the kit, capable of being differentiated from a first site during detection of immunospecific binding of each of the two pluralities. In some embodiments, the different pluralities of different antibody molecules or antibody-peptide constructs are distinguishably labelled, such that immunospecific binding of each of the two pluralities can be differentiated, e.g., even if the antibodies molecules or antibody-peptide constructs are immobilized in overlapping locations, or even if they are not immobilized.

9. Methods of Making Antibody Molecules, Delivery Peptides, and Constructs Thereof Another aspect of the invention involves methods of making the antibody molecules, delivery peptides, and antibody-peptide constructs of the invention, as well as BBB-specific and/or BAP42 oligomer-binding fragments or derivatives thereof, including de-immunized and/or humanized variants. In some embodiments, the antibody molecules, delivery peptides, antibody-peptide constructs, and fragments and variants thereof, are produced by recombinant DNA techniques, or other protein synthetic techniques, e.g., by use of a peptide synthesizer.

In some embodiments, the antibody molecule, or antibody-peptide construct thereof, includes more than one antibody single domains that are linked, e.g., to form a dimer, trimer, tetramer, etc., such as VL-VL dimers. Methods for producing dimeric polypeptides, as well as higher order polypeptide constructs, are known in the art. For example, a nucleic acid encoding a first antibody single domain can be cloned into an expression vector containing a second antibody single domain, such that the two domains are linked in-frame, with or without and intervening linker. See e.g., Morrison, 1985, *Science* 229:1202; Oi et al., 1986, *BioTechniques* 4:214; Gillies et al., 1989, J. *Immunol. Methods* 125:191-202; and U.S. Pat. Nos. 6,311,415; 5,807,715; 4,816,567; and 4,816,397, which are incorporated by reference in their entirety.

In some embodiments, an antibody molecule of the invention is fused to a delivery peptide. Fusion proteins also can be produced by standard recombinant DNA techniques or by protein synthetic techniques, e.g., by use of a peptide synthesizer, or by PCR amplification. In addition to recombinant fusion, linkage to a delivery peptide may involve, e.g., chemical conjugation, including both covalent and non-covalent conjugations.

Linkage does not necessarily need to be direct, but may occur through linker sequences or through chemical conjugation. Protein linkers between antibody molecules and delivery peptides of interest can be selected in order to maintain flexibility and proper folding, preferably such that the linked product shows BBB-specificity, as well as BAP42 oligomer immunospecificity. A linker can be selected, e.g., that allows good simultaneous binding to a BAP42 oligomer, as well as selectively crossing the BBB. Such binding can be assayed by techniques known to those of skill in the art and/or described herein.

Polynucleotides of the invention also encompass vectors, such as vectors for the expression of the antibody molecules of the invention. Expression vectors containing the coding sequences of the anti-BAP42 oligomer antibodies, in accordance with the invention, along with appropriate transcriptional and translational control signals, can be constructed using methods well known to those skilled in the art. These methods include, for example, in vitro recombinant DNA techniques, synthetic techniques, and in vivo genetic recombination. (See, for example, the techniques described in Sambrook et al., 1990, Molecular Cloning, A Laboratory Manual, 2d Ed., Cold Spring Harbor Laboratory, Cold Spring Harbor, N.Y. and Ausubel et al. eds., 1998, Current Protocols in Molecular Biology, John Wiley & Sons, NY).

An expression vector comprising the nucleotide sequence of an antibody molecule of the invention, e.g., a fusion protein with a delivery peptide as described herein, can be transferred to a host cell by conventional techniques (e.g., electroporation, liposomal transfection, and calcium phosphate precipitation) and the transfected cells then can be cultured by conventional techniques to produce a construct of the invention. In a specific embodiment, the expression of an antibody molecule or antibody-peptide fusion is regulated by a constitutive promoter. In another embodiment, expression is regulated by an inducible promoter. In accordance with these embodiments, the promoter may be a tissue-specific promoter.

In a specific embodiment, a vector is used that comprises a promoter operably linked to a protein-encoding nucleic acid, one or more origins of replication, and, optionally, one or more selectable markers (e.g., an antibiotic resistance gene). A variety of host-expression vector systems may be utilized to express the antibody molecules and delivery peptides of the invention, and/or fusions thereof. The host cells used to express the recombinant antibody molecules, delivery peptides, or fusions thereof may be, e.g., either bacterial cells such as *Escherichia coli*, or eukaryotic cells. Examples of suitable bacterial cells include the bacteria *E. coli* or *B. subtilis*, transformed with recombinant bacteriophage DNA, plasmid DNA, or cosmid DNA expression vectors.

In a particular embodiment, *E. coli* Tuner™ (DE3) cells are used for large-scale expression of antibody molecules, delivery peptides, and antibody-peptide constructs of the invention. "Tuner™ strains" are lacZY deletion mutants of *E. coli* BL21 that facilitate controlled adjustment of the level of protein expression in cell culture. Expression levels are controlled by the lac permease (lacY) mutation, which allows uniform entry of IPTG into cells in a population, producing a concentration-dependent, homogeneous induction in response to varying IPTG concentration. "DE3" indicates that the host is a lysogen of λϋE3, carrying a chromosomal copy of the T7 RNA polymerase gene under control of the lacUV5 promoter.

The expression levels of an antibody molecule, delivery peptide, or antibody-peptide construct of the invention can be increased, e.g., by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing a polypeptide described herein is amplifiable, changes in the culture medium can increase the number of copies of the marker gene. Since the amplified region can be associated with the nucleotide sequence encoding an antibody molecule, delivery peptide, or antibody-peptide construct of the invention, production of the agent also can increase (Crouse et al., 1983, Mol. Cell. Biol. 3:257).

For long-term, high-yield production of recombinant proteins, stable expression is preferred. For example, cell lines which stably express an antibody molecule, delivery peptide, or antibody-peptide construct of the invention, may be engineered. Rather than using expression vectors which contain viral origins of replication, host cells can be transformed with DNA controlled by appropriate expression control elements (e.g., promoter, enhancer sequences, transcription terminators, polyadenylation sites, etc.) and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci, which in turn can be cloned and expanded into cell lines. This method may advantageously be used to engineer cell lines which express antibody molecules, delivery peptides, or antibody-peptide constructs of the invention for long-term, high-yield production. Such engineered cell lines also may be particularly useful in screening and evaluation of compounds that interact directly or indirectly with the antibody molecules, delivery peptides, and/or fusions thereof.

Once an antibody molecule, delivery peptide, or antibody-peptide construct of the invention, has been recombinantly expressed, it may be purified by any method known in the art for purification of an agent, for example, by chromatography (e.g., ion exchange, affinity, particularly by affinity for the specific antigen after Protein A, and sizing column chromatography), centrifugation, differential solubility, or by any other standard technique for the purification of proteins. Polypeptides of the invention can be fused to marker sequences, such as a peptide, to facilitate purification. In some embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA,* 86:821 824, 1989 (hereby incorporated by reference in its entirety), for instance, a hexa-histidine tag provides for convenient purification of an antibody molecule, delivery peptide, or fusion thereof. Other peptide tags useful for purification include, but are not limited to, the hemagglutinin "HA" tag, which corresponds to an epitope derived from the influenza hemagglutinin protein (Wilson et al., Cell, 37:767 1984, hereby incorporated by reference in its entirety) and the "flag" tag (Knappik et al., *Biotechniques,* 17(4):754-761, 1994), each of which are hereby incorporated by reference in its entirety. Another technique involves nickel affinity chromatography for endotoxin removal, following expression in *E. coli.*

De-immunized antibody molecules, delivery peptides, or antibody-peptide constructs of the invention, may be generated using techniques to reduce or eliminate one or more Tx epitopes in the polypeptides, as described in detail above. Substitutions at the amino acid level inform the construction of the corresponding nucleic acids encoding same, also as described in more detail below.

Humanized antibody molecules or antibody-peptide constructs of the invention, may be generated using techniques to replace regions or amino acid residues of a non-human antibody with corresponding regions or amino acid residues from a human antibody, as described in detail above. Generally, humanized antibody molecules are human immunoglobulins (or variable domains and/or fragments thereof) in which hypervariable region residues are replaced by hypervariable region residues from a non-human species (e.g., donor CDRs from a rabbit VL domain) having the desired immunospecificity.

10. Polynucleotides Encoding Agents of the Invention

The invention provides polynucleotides comprising a nucleotide sequence encoding a polypeptide of the invention, such as an antibody molecule, delivery peptide, antibody-peptide construct, or fragments or variants thereof. In specific embodiments, the polynucleotide of the invention comprises or consists of a nucleic acid encoding an antibody molecule disclosed herein, such as one or more of SEQ ID NOs: 1-21, or a BAP42 oligomer-binding fragment thereof, or a humanized variant thereof, e.g., comprising one or more CDRs of SEQ ID NOs: 1-21 grafted into framework regions of a human antibody domain. In specific embodiments, the polynucleotide of the invention comprises or consists of a nucleic acid encoding a delivery peptide disclosed herein, such as one or more of SEQ ID NOs: 22-25. In specific embodiments, the polynucleotide of the invention comprises or consists of a nucleic acid encoding an antibody-peptide construct disclosed herein, such as one or more of SEQ ID NOs: 28-111, or a BAP42 oligomer-binding and/or BBB-specific fragment thereof, or a humanized variant thereof. The invention also encompasses polynucleotides that hybridize under high stringency, intermediate or lower stringency hybridization conditions, to polynucleotides that encode a polypeptide of the invention, as described above.

The polynucleotides may be obtained, and the nucleotide sequence of the polynucleotides determined, by any method known in the art. For example, a polynucleotide encoding an agent of the invention may be generated from nucleic acid from a suitable source (e.g., a BAP42 oligomer immunized rabbit). If a source containing a nucleic acid encoding a particular polypeptide is not available, but the amino acid sequence of the agent of the invention is known, a nucleic acid encoding the agent may be chemically synthesized, and cloned into replicable cloning vectors using methods well known in the art.

Once the nucleotide sequence of the polynucleotide of the invention is determined, the nucleotide sequence may be manipulated using methods well known in the art for the manipulation of nucleotide sequences, e.g., recombinant DNA techniques, site directed mutagenesis, PCR, etc. (see, for example, the techniques described in Sambrook et pal., 1990, Molecular Cloning, A Laboratory Manual, 2d Ed., Cold Spring Harbor Laboratory, Cold Spring Harbor, NY and Ausubel et al., eds., 1998, Current Protocols in Molecular Biology, John Wiley & Sons, NY, which are incorporated by reference in their entireties), to generate polypeptides having a different amino acid sequence, for example to create amino acid substitutions, deletions, and/or insertions. As described above, such mutated sequences can provide agents of the invention with enhanced pharmaceutical properties, e.g., improved immunospecificity, BBB-specificity, and/or reduced immunogenicity.

Polynucleotides encoding fusion products may be obtained by recombinant techniques, as are well known and routinely practiced in the art. Such polynucleotides may be referred to as "chimeric polynucleotides." Recombinant chimeric polynucleotides typically are created by joining two or more genes, or portions thereof, which originally coded for separate proteins. The individual sequences typically correspond to coding sequences for a functional domain of each of the respective proteins, such that the fusion polypeptide encodes a fusion protein having dual functionality (e.g., binding to BAP42 oligomers and specifically crossing the BBB). For example, a first coding sequence, or portion thereof, may be joined in frame to a second coding sequence, or portion thereof, which typically is achieved through ligation or overlap extension PCR. Ligation is used with the conventional method of creating chimeric genes, called the "cassette mutagenesis method." In this method, DNA can be cut into specific fragments by restriction endonucleases acting at restriction endonuclease recognition sites, and the specific fragments can be then ligated. A particular fragment can be substituted with a heterologous one having compatible ends in order to ligate it into the parental DNA. See, e.g., Wells et al., Gene 34:315-23 (1985), hereby incorporated by reference in its entirety.

Alternatively, various approaches involving PCR may be used, such as the overlap extension PCR method. See, e.g., Ho, S. N., et al (1989). Site-directed mutagenesis by overlap extension using the polymerase chain reaction. *Gene.* 77: 51-59, hereby incorporated by reference in its entirely. Several variations of this PCR approach are known and have been used to generate fusion products. One such approach, for example, involves modified overlap extension PCR to create chimeric genes in the absence of restriction enzymes in three steps: (i) a conventional PCR step, using primers partially complementary at their 5' ends to the adjacent fragments that are to be fused to create the chimeric molecule; (ii) a second PCR step where the PCR fragments generated in the first step are fused using the complementary extremities of the primers; and (iii) a third step involving PCR amplification of the fusion product. The final PCR product is a chimeric gene built up with the different amplified PCR fragments. See, e.g., Wurch, T. et al (1998) A modified overlap extension PCR method to create chimeric genes in the absence of restriction enzymes. *Biotechnology Techniques.* 12(9):653-657, hereby incorporated by reference in its entirety. Any ligation and/or PCR-based recombinant approaches may be used to create the chimeric (fusion) polynucleotides of the present invention.

Alternatively a nucleic acid encoding the fusion product may be chemically synthesized. For example, using the desired amino acid sequence of an antibody-peptide construct of the invention, the corresponding nucleotide sequence may be devised, chemically synthesized, and cloned into replicable cloning vectors using, e.g., well known methods in the art.

The invention further provides a vector comprising at least one polynucleotide encoding an agent of the invention. In some embodiments, the vector is an expression vector. The invention further provides host cells comprising one or more vectors of the invention, e.g., a host cell allowing expression of the encoded polypeptide. The vectors, expression vectors, and host cells can include any of polynucleotides those discussed above.

EXAMPLES

The following examples evidence development of antibody molecules that specifically target non-fibrillar forms of beta-amyloid peptide, in single domain format, and the development of peptides that specifically cross the blood-brain barrier, as well as constructs of the peptides and the single domain antibodies. The following examples further evidence unexpected results that the antibody molecules and constructs effectively reduce and prevent formation of senile plaques in animal models of Alzheimer's, as well as providing biomarkers for in vitro diagnosis and in vivo imaging to identify early stages of the disease.

Example 1—Production of sdAbs Targeting Non-Fibrillar BAP42

Single domain antibodies (sdAbs) were developed that specifically recognize monomeric and oligomeric forms of BAP42, but do not recognize fibrillar forms. Development of the sdAbs involved a three-part process, outlined below as (a)-(c). Briefly, (a) different BAP42 forms were prepared and (b) characterized; and then (c) sdAbs specifically targeting non-fibrillar forms were developed, by immunizing rabbits with the monomeric or oligomeric forms and using rabbit antibodies to build single domain antibody libraries, of VL domains, against each of these two forms. This selection process was optimized using "phage display membranes" with different forms of antigen immobilized, to provide a panel of sdAbs specific to the BAP42 monomeric and oligomeric forms.

a. Production of Different Forms of BAP42

As noted above, BAP42 occurs in different forms of association in the brain of Alzheimer's patients. BAP42 has high oligomerization capacity and the ability to form fibers, a process thought to involve the peptide passing through different stages of maturation, depicted schematically in FIG. 1.

As FIG. 1 shows, BAP42 aggregates according to an aggregation scheme, progressing from monomers of the peptide to fibers, capable of forming plaques. The peptide has high oligomerization capacity, and starts by autoassociating to give small oligomers, which then associate with other molecules of the peptide. The structures of the peptides change to provide a secondary structure rich in beta-sheets—characteristic of fibers.

Thus, as a first step, a peptide reconstitution protocol was established to produce different species (monomers, oligomers, fibrils) of BAP42. The starting material used was lyophilized synthetic BAP42, which was ressuspended in PBS buffer, pH 7.4, to a final concentration of 10 mg/mL. At this concentration and pH, the peptide was not soluble. The solubilization pH was optimized by titration with ammonia. At pH 10, the peptide became soluble. Then, the peptide was diluted to a working concentration of 1 mg/mL in PBS and the pH returned to 7.4. To quantitate the peptide concentration spectrophotometrically, the coefficient molar absorptivity at λ=280 nm was determined, as shown in FIG. 2.

Figure 2:
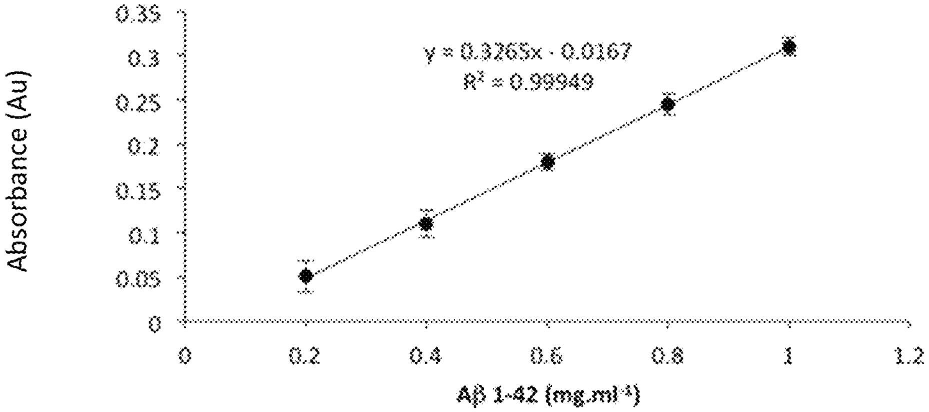
FIG. 2 shows a determination of molar absorption coefficient for BAP42, using different solutions of known concentration of the peptide to measure absorbance and correlate it in order to calculate the coefficient ε280 nm=0.3265±0.0043 $(mg/mL)^{-1}cm^{-1}$ or ±1474.041 ε280 nm=19,287 $M^{-1}cm^{-1}$.

FIG. 2 shows the determination of molar absorption coefficient for BAP42. Briefly, using different solutions of known concentration of the peptide, absorbance was measured and correlated in order to calculate the coefficient ε280 nm=0.3265±0.0043 $(mg/mL)^{-1}cm^{-1}$ or ±1474.041 ε280 nm=19,287 $M^{-1}cm^{-1}$.

To obtain different species of BAP42, after protein reconstitution, the protein was filtered through filters with a 5 kDa pore, which retains possible oligomeric/fibrillar species of the peptide, whereas monomeric species having lower molecular weights were eluted for immediate use. A representative method for preparing different species of BAP42 optimized to give oligomers or fibers, as shown in FIGS. 3A-3B.

Figure 3A:
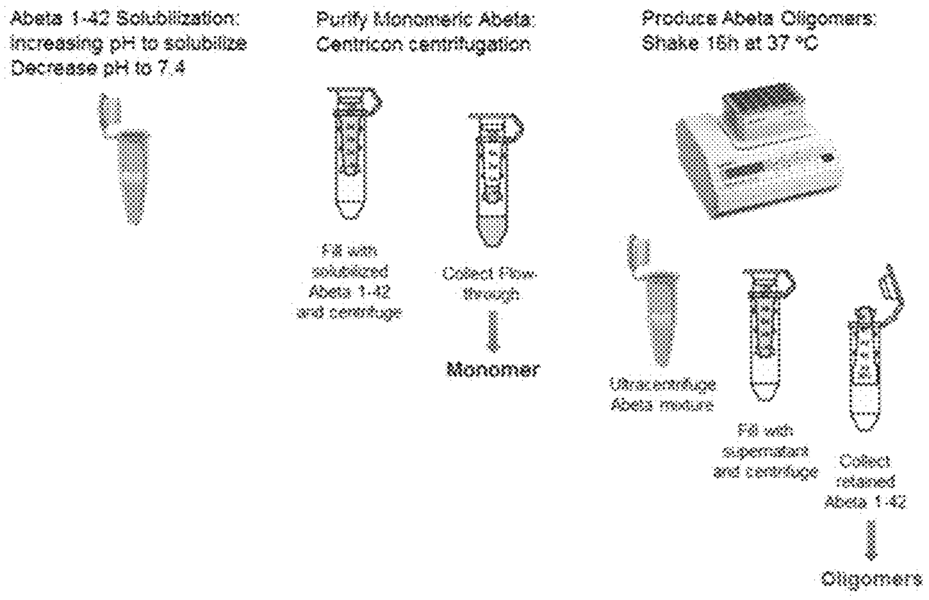
FIGS. 3A-3B depict representative schemes for preparing different species of BAP42, to give oligomers (FIG. 3A) or fibrils (FIG. 3B).

As shown in FIG. 3A, and noted above, a first step involved solubilization of lyophilized synthetic BAP42, by increasing pH and then returning to 7.4; followed by centricon centrifugation using solubilized BAP42, and collection of the flow through to provide monomers. The monomeric species were used to produce oligomers in an oligomerization reaction promoted by constant agitation (stirring) of 1 mg/mL BAP42 for a period of 16 hours at 37° C. After this period, resulting fibers are separated by ultracentrifugation, and the monomers were separated by centrifuging the supernatant, as described above. The fraction retained on the filters corresponds to the oligomeric BAP42 fraction, which is assayed spectrophotometrically using the previously-calculated coefficient. The oligomer concentration was determined to be 1 mg/mL.

Figure 3B:
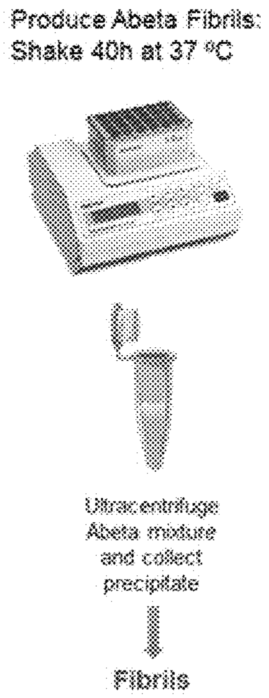

As shown in FIG. 3B, in a different reaction, monomeric species were used to produce fibrils, based on constantly agitating 1 mg/mL BAP42 for a period of 40 hours at 37° C. Resulting fibrils again were separated by ultracentrifugation, and the precipitate collected. The amount of fibrils was determined by calculating the difference between the initial amount of mononers present in the sample and the final amount present in the supernatant, from the ultracentrifugation, containing monomers and oligomers.

b. Characterization of Different Forms of BAP42

After the different forms of BAP42 had been isolated, as described above, they were characterized by three methods: (i) Thioflavin T-binding; (ii) Dynamic Light Scattering (DLS); and (iii) molecular exclusion chromatography.

i. Characterization by Thioflavin T-Binding

Figure 4:
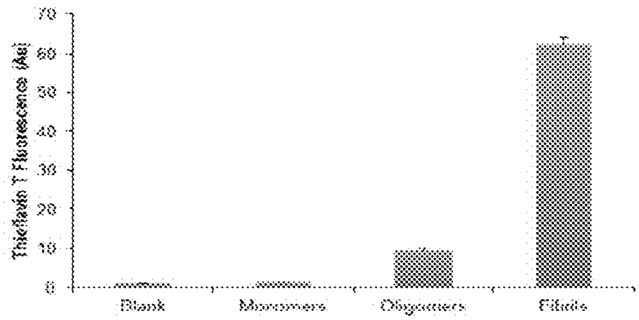
FIG. 4 depicts a characterization of BAP42 species, isolated in an optimized process, using a thioflavin T assay.

Isolated BAP42 species first were characterized using thioflavin T fluorescence. Thioflavin T compound is a fluorescent probe that specifically associates with protein mixtures rich in beta-sheet secondary structure, which then emit a higher wavelength accompanied by an increase in fluorescence yield. This technique thus relates fluorescent signal intensity with concentration of fibers present in a protein sample. Specifically, monomers do not exhibit reactivity with thioflavin T, oligomer fractions show low levels of reactivity, while fibrillar fractions show a high level of reactivity. FIG. 4 shows the results of a thioflavin T assay to characterize the BAP42 species isolated in the optimized process, described above.

Figure 5:
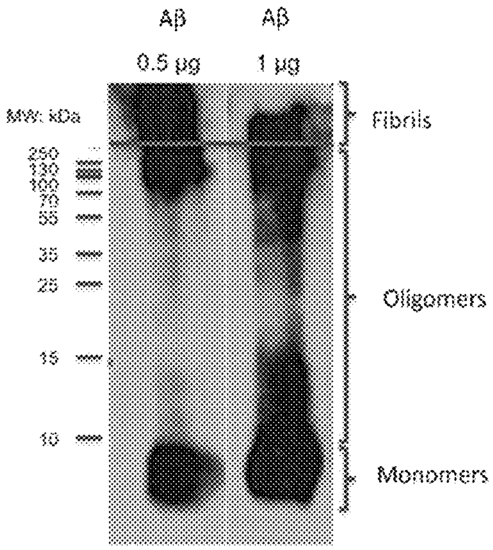
FIG. 5 shows the results of Western blotting a mixture of BAP42 species, separated by SDS-PAGE electrophoresis.

The monomer, oligomer, and fiber samples further were analyzed by Western blotting, using polyacrylamide gel electrophoresis under denaturing conditions (SDS-PAGE) to resolve the peptide species according to their molecular weight. Western blot detection was performed using rabbit-derived polyclonal serum, as described in more detail below with respect to various rabbit immunizations. FIG. 5 shows the results of Western blotting a mixture of BAP42 species, separated by SDS-PAGE electrophoresis.

Referring to FIG. 5, BAP42 monomers had a mass of about 5 kDa (found in the membrane region resolving less than 10 kDa molecular mass); oligomers were resolved along 10-200 kDa (which indicates that the population is heterogeneous in different oligomeric combinations with varying numbers of monomeric units); and fibrillar species were retained in the staining part of the gel (which indicates they have a molecular weight higher than 300 kDa). The morphology of the samples also was evaluated by atomic force microscopy to complete the characterization of the different species.

ii. Characterization by Dynamic Light Scattering (DLS)

Isolated BAP42 species also were characterized by dynamic light scattering (DLS). This technique determines the distribution of particle sizes as a suspension profile.

After dilution to a concentration of 0.1 mg/mL of different forms of isolated BAP42, 8 measurements were obtained for each independent experiment using a Zetasizer Nano ZS (Malvern, UK). Percent signal intensity of the different particles was expressed as a function of the diameter of the particles to give profiles of the distribution of sizes of individual particles present in samples of monomers, oligomers, and fibers; as well as to give profiles of the distribution of class sizes, each having particles with a range of diameters. All analyses were performed in triplicate with samples from independent isolations. Results are shown in FIGS. 6A-6B.

Figure 6A:
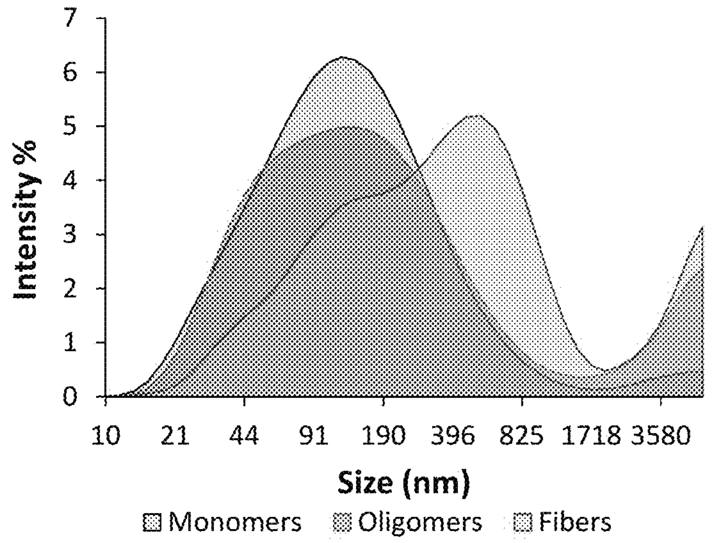
FIGS. 6A-B show Dynamic Light Scattering analysis of isolated BAP42 species, where percent signal intensity of the different particles was expressed as a function of the diameter of the particles.

FIG. 6A shows profiles of size distribution in monomer (gray), oligomer (red), and fiber (green) samples. The monomeric species showed a size distribution with a maximum peak intensity corresponding to a 122 nm diameter, and a small population with intensity greater than 2,500 nm. The oligomeric species showed an identical profile within the population having a maximum intensity corresponding to a 164 nm diameter but, beyond this, showed a more significant population of particles greater than 2,500 nm in diameter. The fibrillar species showed 3 distinct populations, with maximum intensity corresponding to sizes of 142 nm, 531 nm, and greater than 2,500 nm in diameter.

Figure 6B:
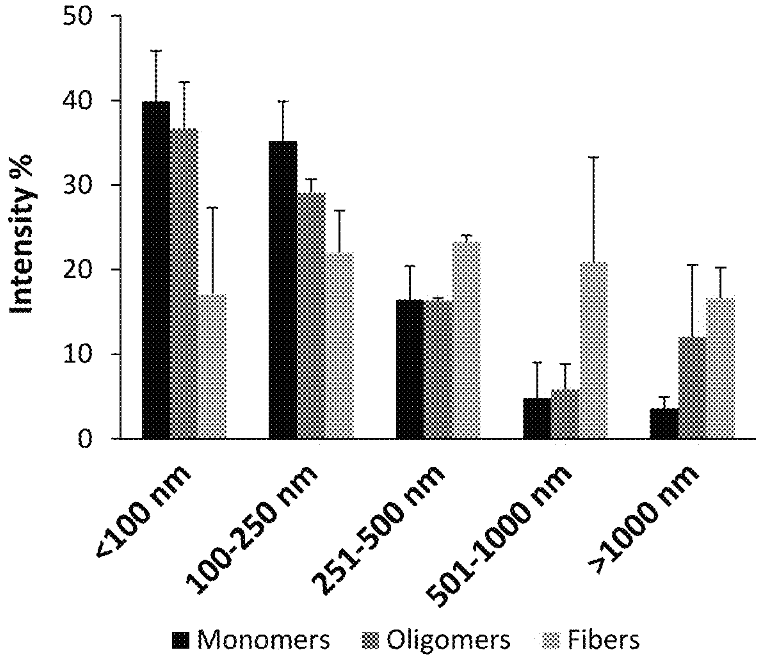

FIG. 6B shows profiles of class size distribution, that is, the distribution profile of the percentage of signal intensity as a function of hydrodynamic particle diameter for ranges of differently-sized particles, were analyzed. Compared to monomer samples, oligomer samples showed an expected shift to larger diameters. For oligomer samples, the proportion of signal intensity attributed to species less than 100 nm was 36.7%, while proportion of signal intensity attributed to species having diameters of 100-250 nm was 29.1%; thus showing a decrease of 8% and 17%, respectively, when compared to similarly-sized monomers (which showed an intensity of 39.9% for species less than 100 nm in diameter; and 35.2% for species 100-250 nm in diameter). Nonetheless, the percentage of species ranging from 251-500 nm was identical. For species in the 501-1,000 nm diameter range, and the over 1 mm in diameter range, monomer samples showed percent signal intensities of 4.9% and 3.6%, respectively; for the same ranges or classes, oligomer samples showed intensities of 5.8% and 12.1%, respectively. In these ranges, the oligomer samples clearly showed higher percent intensities compared to monomer samples, the oligomer samples showing a 20% increase relative to the monomer samples for particles in the 501-1,000 nm diameter range; and a 234% increase for particles in the over 1 mm in diameter range.

With regard to fiber samples, the differences from the monomers were further highlighted. In fiber samples, there was a large increase in percent intensity for larger particles, with percent intensities of 23.3%, 20.9%, and 16.6% for particles in the 251-500 nm diameter range, 501-1,000 nm diameter range, and over 1 mm diameter range, respectively. Thus, comparing fibers with monomers, there was an increase of 42% for species in the 251-500 nm diameter range; an increase of 330% for species in the 501-1,000 nm diameter range; and an increase of 361% for species in the over 1,000 nm diameter range.

In conclusion, samples of the monomeric form of BAP42 indeed mainly had a population of small size, corresponding to a population of monomeric species. Samples of the oligomeric form had, in addition to a similar population as a monomer sample, a population of larger species, greater than 1,000 nm in diameter, indeed corresponding to oligomerized BAP42. Samples of the fibers had, in addition to populations of low diameter, a larger population of species ranging in size from 501-1,000 nm in diameter; and another population of species with sizes exceeding 1,000 nm in diameter, indeed showing the later stages of oligomerization and fibrillization.

iii. Characterization by Size Exclusion Chromatography (SEC)

Formation of BAP42 species in the oligomerization mixture was assessed by molecular size exclusion chromatography. This technique separates species according to each particle's molecular mass and hydrodynamic radius. Higher associations (with higher molecular weights) do not interact with the solid matrix of the column and elute first, while monomeric species (with lower molecular weight) interact with the solid matrix and elute after longer retention times.

As described above, 1 mg/mL BAP42 preparations were subjected to constant stirring for a period of 16 hours at 37° C. After this period, resulting fibers were separated by ultracentrifugation, and the supernatant collected was applied to a size exclusion column. Results are shown in FIG. 7.

Figure 7:
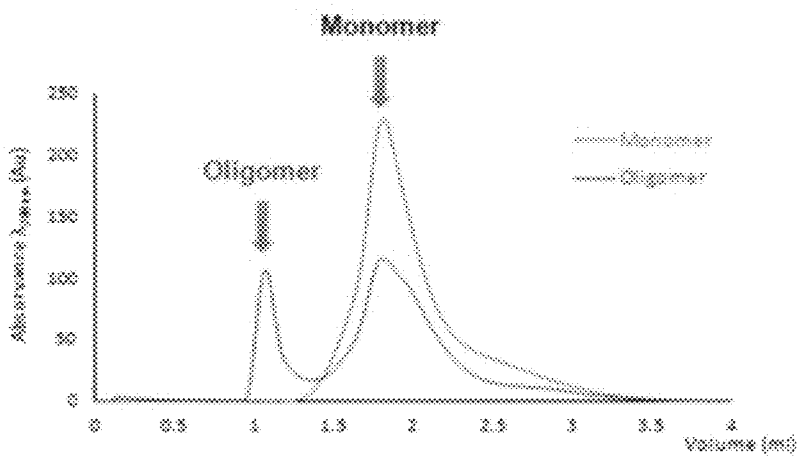
FIG. 7 depicts a representative chromatogram for separating monomeric and oligomeric BAP42 species.

Referring to FIG. 7, both monomers and oligomeric species of BAP42 were present in this mixture. The representative chromatogram for separating monomeric and oligomeric BAP42 species shows that the monomeric fraction (blue curve) eluted with a retention time corresponding to only the peptide monomer. Chromatographic injection of the mixture resulting from constant stirring for 16 hour at 37° C. (green curve) showed elution of not only monomers but also oligomeric species with shorter retention times.

c. Development of sdAbs Targeting Non-Fibrillar BAP42

To develop sdAbs specifically targeting non-fibrillar forms, a five-stage process was followed. Briefly, (i) rabbits were immunized with monomeric or oligomeric forms; then (ii) rabbit antibodies were obtained and used to construct single domain antibody libraries (VL) against each of these two forms; (iii) single domain antibodies that specifically target monomeric and oligomeric BAP42 forms were selected, using membrane phage display; and (iv) further selected by their binding and expression in ELISA, after which selected clones are still further selected for stability using a CAT-fusion assay; and (v) finally top candidates were sequenced and analyzed.

i. Rabbit Immunization with Different BAP42 Forms

Each of two New Zealand White rabbits were immunized with monomeric and oligomeric forms of BAP42 as described above, in the section regarding production of different forms of BAP42. Immunizations continued for 74 days, with about 100-150 μg of each purified antigen, monomers or oligomers, according to a protocol where rabbits were administered four subcutaneous injections, at 2-3 week intervals, in 1 mL adjuvant according to the manufacturer's directions (Ribi Immunochem Research, Hamilton, Mont.). Throughout the immunization process, serum was collected and samples evaluated by ELISA, to determine the evolution of the immune response to each antigen. Results are shown in FIGS. 8A-8B and FIGS. 9A-9B.

Figure 8A:
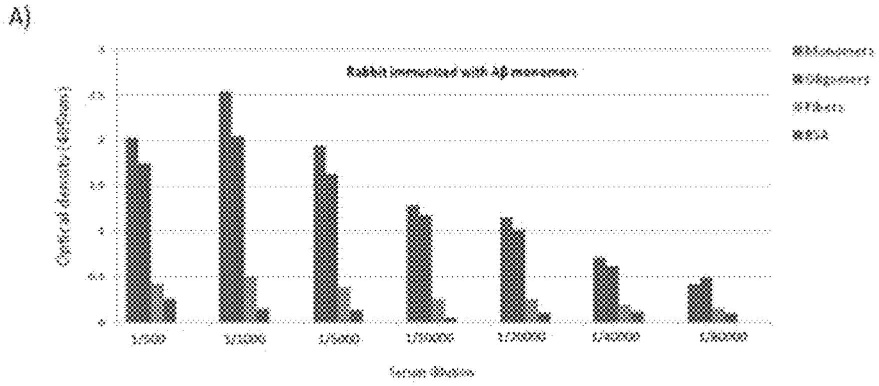
FIGS. 8A-8B show the immunologic response by ELISA of the rabbits immunized with BAP42 monomers (FIG. 8A) or BAP42 oligomers (FIG. 8B) on day 26 following immunization.
Figure 8B:
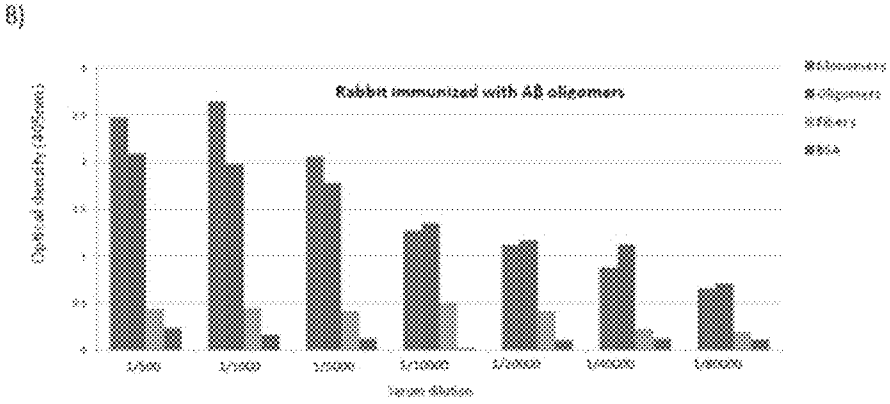
Figure 9A:
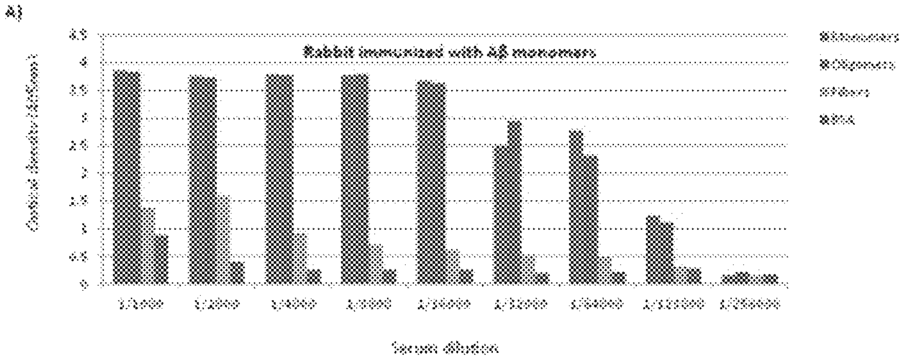
FIGS. 9A-9B show the immunologic response by ELISA of the rabbits immunized with BAP42 monomers (FIG. 9A) or BAP42 oligomers (FIG. 9B) on day 74 (final bleed) following immunization.
Figure 9B:
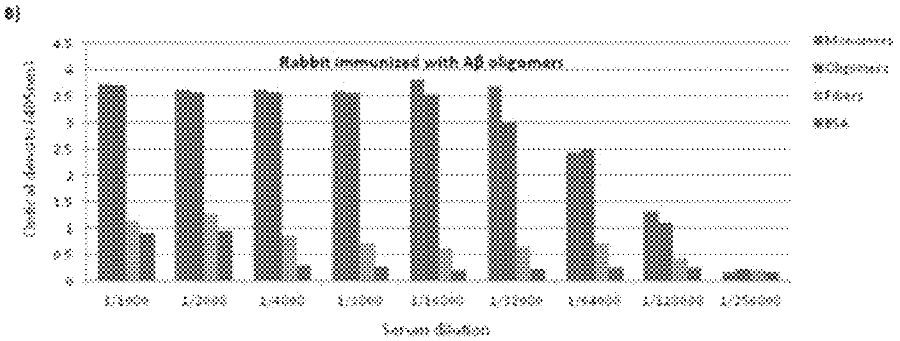

As shown in FIGS. 8A-8B and FIGS. 9A-9B, the sera titer increased over the immunization, demonstrating enrichment and specificity for each of the monomer and oligomer forms. Further, sera from both rabbits demonstrated lower titers of antibody to fibrillar BAP42. Sera titers and antibody specificity were evaluated on day 26 (FIGS. 8A-8B) and on day 74 (final bleed) (FIGS. 9A-9B).

Specifically, FIGS. 8A-8B show the immunologic response by ELISA of the rabbit immunized with BAP42 monomers (FIG. 8A) or the rabbit immunized with BAP42 oligomers (FIG. 8B). Results correspond to titration of serum antibodies corresponding to the second bleed (day 26), where antisera from the immunized animals was analyzed for binding 200 ng of monomers, oligomers, and fibrils of BAP42 by ELISA using HRP-conjugated goat anti-rabbit Fc polyclonal antibody as secondary antibody (PIERCE).

FIGS. 9A-9B show the later immunologic response by ELISA of the rabbit immunized with BAP42 monomers (FIG. 9A) or the rabbit immunized with BAP42 oligomers (FIG. 9B), when sera titers and antibody specificity were evaluated on day 74 (final bleed), as described above. Results obtained were very promising, showing that the immunization protocol produced more antibodies specific for each of the monomeric and oligomeric forms of BAP42.

ii. Construction of sdAb Libraries

The animals were sacrificed on day 74 and then organs of primary antibody production and maturation, that is, the bone marrow and spleen, were removed. RNA then was extracted from the organs, and cDNA synthesized to construct libraries of single domain antibodies (amplification of PCR products and cloning in phagemid).

Specifically, tissue samples were harvested and prepared for total RNA isolation using TRI reagent (Molecular Research Centre) according to the manufacturer's protocol. Isolated total RNA was dissolved in 500 μl of RNase-free water and concentration and purity were determined by spectrophotometry. First strand cDNA was synthesized from total RNA using an oligo (dT) primer and reverse transcriptase (Superscript; Invitrogen) using the manufacturer's protocol.

Primary amplification of the genes coding for variable regions of light chains was performed using the sense primers presented in Table 1 (5' part of the variable region) and the antisense primers presented in Table 2 (3' part of the constant region of the light chains).

TABLE 1

Sense Primers for Isolation of Rabbit VL domains From cDNA Preparation

| Domain | Primer | Sequence |
|---|---|---|
| VL | SDVκ1-F | 5' GGG CCC AGG CGG CC GAGC TCG TGM TGA CCC AGA CTC CA 3' (SEQ ID NO: 128) |
| | SDVκ2-F | 5' GGG CCC AGG CGG CC GAGC TCG ATM TGA CCC AGA CTC CA 3' (SEQ ID NO: 129) |
| | SDVκ3-F | 5' GGG CCC AGG CGG CC GAGC TCG TGA TGA CCC AGA CTG AA 3' (SEQ ID NO: 130) |
| | SDVλ-F | 5' GGG CCC AGG CGG CC GAGC TCG TGC TGA CTC AGT CGC CCT C 3' (SEQ ID NO: 131) |

TABLE 2

Antisense Primers for Isolation of Rabbit VL domains from cDNA Preparation

| Domain | Primer | Sequence |
|---|---|---|
| VL | SDVκj10-R | 5' CCT GGC CGG CCT GGCC TTT GAT TTC CAC ATT GGT GCC 3' (SEQ ID NO: 132) |
| | SDVκj0-R | 5' CCT GGC CGG CCT GGCC TAG GAT CTC CAG CTC GGT CCC 3' (SEQ ID NO: 133) |
| | SDVκj42-R | 5' CCT GGC CGG CCT GGCC TTT GAC SAC CAC CTC GGT CCC 3' (SEQ ID NO: 134) |
| | SDVλ-R | 5' CCT GGC CGG CCT GGC C GCCTGTGACGGTCAGCTGGGTCCC 3' (SEQ ID NO: 135) |

Primary PCR was performed in a 50 μl reaction volume using 25 pmol of each primer. 2.5 μl random primed or oligo-dT cDNA was used as template (equivalent of 5 μg mRNA). The reaction conditions for the primary PCR were 11 min at 94° C., followed by 30/60/120 sec at 54/55/72° C.

for 30 cycles, and 5 min at 72° C. All reactions were performed with 2.5 mM $MgCl_2$, 200 μM dNTP (Roche Diagnostics, Brussels, Belgium) and 1.25 U AmpliTaq Gold DNA polymerase (Roche). Accordingly, the cDNAs from each rabbit were subjected to separate 30-cycle polymerase chain reactions and 10 specific oligonucleotide primer combinations for the amplification of rabbit VL sdAbs (9×Vκ and 1×Vλ) coding sequences.

PCR products were separated on a 2% agarose gel and the DNA eluted using the QIAquick gel extraction kit or QIAEXII (Qiagen). After the RNA extraction and cDNA synthesis, purity and concentration were determined.

All primers have the SfiI site. The final PCR products were SfiI-cut, purified, and cloned into an appropriately-cut phagemid vector. The phagemid contained a suppressor stop codon and sequences encoding peptide tags for purification ($His_6$) and detection (HA).

The vectors were used to form a library and transform *E. coli*. Specifically, about 1.4 μg of linearized vector DNA (as determined by gel electrophoresis against known amounts) was ligated with approximately a 1-3 fold excess of insert in 20 μL reactions containing 1× ligase buffer (50 mM Tris pH 7.5, 5 mM $MgCl_2$, 1 mM dithioerythritol, 1 mM ATP, pH 7.5) and 1U T4 DNA ligase (Roche), for ligation of cohesive-end ligations. Ligations were incubated 16-18 hours at 12-14° C.

Results of the ligations and a corresponding number of cuvettes were incubated on ice for 10 min. Simultaneously, electrocompetent *E. coli* were thawed on ice. 2 μL of each ligation reaction were added to the electrocompetent bacteria, transferred to a cuvette and stored on ice for 1 min. Electroporation was performed at 2.5 kV, 25 μF, and 200Ω. Cuvettes were immediately flushed with 1 ml of SOC medium at room temperature and the cultures shaken at 250 rpm for 1 h at 37° C. or 30° C. Cultures were then spread on LB agar plates containing 100 μg/mL ampicillin, and 10 μg/mL tetracycline, and incubated overnight at 37° C. or 30° C.

Phagemid vector was isolated and electroporated into host cells according to manufacturer's protocols. After electroporation, 5 mL of SOC was added and cultures were shaken for 1 h at 37° C. 10 mL of SB medium was then added for 1 h at 37° C. 4.5 μL of 100 mg/mL carbenicillin was next added and cultures were shaken for another 1 h at 37° C. before adding 1 mL of VSCM13 (helper phage; $10^{13}$ pfu/mL) to each 15 mL culture. A total of 170 mL SB medium/carb was added to the cultures, which were shaken for 2 h at 37° C. 280 μL of 50 mg/mL kanamycin was added and the cultures continued shaking overnight at 37° C. The following morning, the cultures were centrifuged and the phage supernatants precipitated by adding 25 mL of PEG-8000 (polyethylene glycol)/NaCl and incubated on ice for 30 min. Phage was centrifuged from the supernatant and pellets were resuspended in 2 mL of TBS/BSA 1%, spun down and filtered through a 0.2 μm filter into a sterile tube.

After construction of the different libraries, sdAbs of interest were selected, as described below.

iii. Selection of sdAbs Against Non-Fibrillar BAP42—Membrane Phage Display

Figure 10:
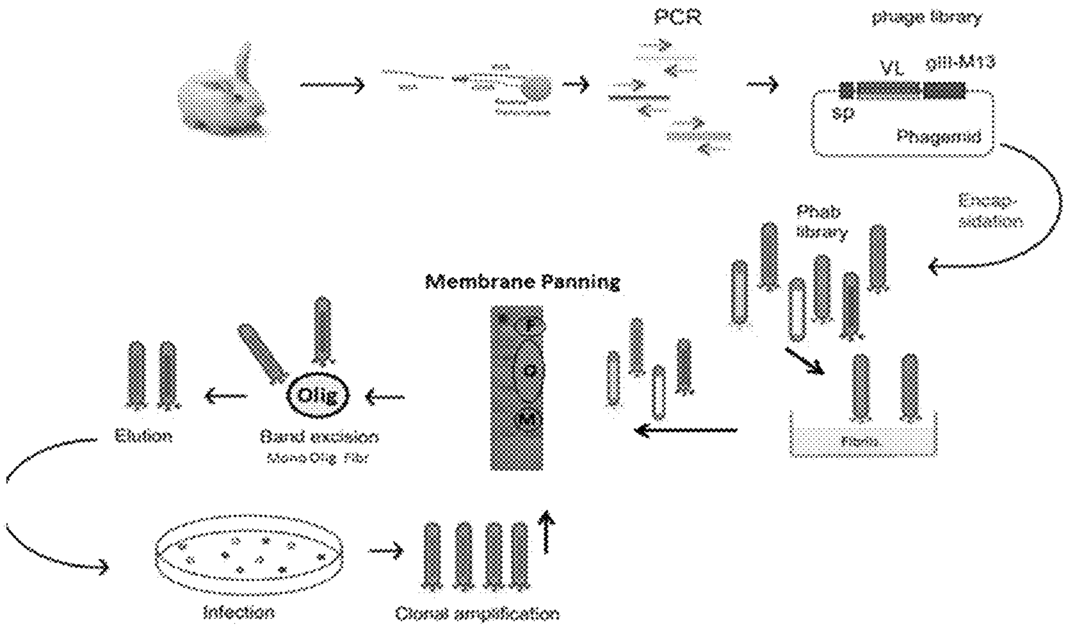
FIG. 10 depicts a schematic illustration for selection of sdAbs specific to BAP42 oligomers in a round of biopanning using membrane phage display (Western panning).

Instead of the traditional phage display with antigen immobilized in 96-well polystyrene microtiter plates (see Barbas, et al. (1991). Assembly of combinatorial antibody libraries on phage surfaces: The gene III site. *Proc. Natl. Acad. Sci.* 88:7978-7982), a phage display by membrane was performed, which is illustrated schematically in FIG. 10. This method was developed as a selection technique to select antibodies against different forms of BAP42, ensuring that they meet the desired shape and do not undergo aggregation. The methodology involved separating different forms of BAP42 by SDS-PAGE, which then were transferred by Western blotting to a PVDF membrane, and all rounds of selection then were performed on the membrane, serving to immobilize the target antigens. This process is also known as "Western panning" (Ravn et al. (2000) "Identification of phage antibodies toward the Werner protein by selection on Western blots" *Electrophoresis* 21:509-516).

To optimize conditions for phage display in blotted membrane, several tests were performed in order to design a protocol for use in the selection of small domains antibodies against monomers or oligomers of BAP42. These tests included: blocking conditions; wash conditions; and elution. These conditions were tested separately, following the same protocol, to identify optimal conditions. This protocol was performed using VCSM13 helper phages and a PVDF membrane (BioRad) without blotted antigen, to analyze the background, i.e., nonspecific binding to the membrane, as well as to the solutions used. Before each test, the first step was activating the membrane with methanol (Applichem) treatment, which makes the membrane more resistant to non-specific phage binding.

The optimization started with a standard protocol: membrane, after activation with methanol, was blocked with 5% milk in PBST, for 1 hour 30 minutes, and washed 3× with PBST 0.2%. Then, $1.0\times10^{11}$ CFU/mL of helper phages in 1% milk in PBST 0.2% were added, for 1 hour at room temperature, and were washed 5× with PBST 0.2. Then the phages were eluted with glycine pH 3.0 and Tris HCL pH 10.5, and the titer of bound phage was determined by infection of log phase *E. coli*, specifically ER2738 or SS320 electrocompetent cells The first condition evaluated was the blocking solution. Six blocking solutions were evaluated: Milk 5% in PBST 0.2%; BSA 3% in PBST 0.2%; Blocking Pierce; Gelatin 5% in PBST 0.2%, Casein 0.5% in PBST 0.2%; and VCSM13 helper phages as the blocking solution. All of them were evaluated at 4° C., overnight. For the evaluation of the wash conditions, three different solutions were tested: PBST 0.5%; 1M NaCl in PBST 0.2%; and 0.5M NaCl in PBST 0.2%. These tests also followed the same standard protocol, with the exception of the wash step.

In order to evaluate the elution step, a test was performed with the conditions previously chosen, for each of two different types of elution: elution with glycine and elution with trypsin. The results were compared through titration of bound phages, determined by infection of log phase *E. coli*, specifically ER2738 electrocompetent cells.

Membrane panning proceeded as follows: the PVDF membrane, with blotted BAP at 1 μg/well, was activated with methanol 100% and then was blocked with Pierce blocking or BSA 3%, overnight at 4° C. Meanwhile, 1 μg of fibrils was immobilized in four wells of an ELISA plate, which was incubated overnight at 4° C. This step was performed to remove the phages/antibodies with higher specificity for fibers. Next day, the membrane and wells were washed with PBS 1× and were blocked. The ELISA plate was blocked with the same blocking solution that was used in membrane, for 1 h at 37° C. After blocking, 1.1 mL of the freshly prepared phage in a 1% binding solution was added, e.g., PBS-Pierce, to fibrils ELISA plate, for 15 min at room temperature (RT). The membrane was incubated with helper phages ($1\times10^{12}$ phages/mL) during 30 min at RT, and then washed with PBS 1×.

After wash, the membrane was incubated with the freshly prepared phages provided from the fibrils ELISA plate, for 2 h at 20-25° C., with gentle rocking. Then the phage solution was discarded and the membrane was washed 5× with PBS/Tween 0.2% or 0.5%, in a rocking platform, in order to eliminate phages not specific for the antigen. The membrane was cut with a scissor in the region corresponding to monomers, oligomers, and fibrils, and then 1 mL of freshly prepared trypsin at 10 mg/mL was added for 30 min at 37° C., in order to recover the antibodies that are specific for the antigens in the membrane.

After phage elution, phages reamplification was performed, by infecting an *E. coli* SS320 culture (O.D. approximately equal to 0.6) with the phage eluate corresponding to the antigen of interest, for 30 min at 37° C. After incubation, 3 μL of 100 mg/mL ampicillin was added to the culture, incubated 1 hour, 37° C., 250 rpm. Then 4.5 μL of 100 mg/mL ampicillin was added and shaken for an additional hour at 250 rpm, 37° C. Finally, 85 mL of pre-warmed SB medium containing 46 μL of 100 μg/mL ampicillin and 184 μL of 5 mg/mL tetracycline were added. The culture was incubated overnight on 210 rpm, at 37° C. The following day, the culture was diluted by adding 5-95 mL of SB medium containing 100 mg/mL ampicillin and 10 mg/mL of tetracycline, until O.D. reached about 0.6. Then the culture was infected with 1 mL of VCSM13 helper phage and incubated 2 h, 210 rpm at 37° C. 140 μL of 50 mg/mL kanamycin was added and continued shaking overnight, 37° C., 210 rpm. The phages produced were recovered by precipitation with PEG 8000 and NaCl, as previously described, and a new round of selection was performed.

After the 4$^{th}$ membrane panning (round of selection) using membrane phage display, the following were obtained: 7.5×10$^5$ phage/mL specific for the oligomeric form of BAP42; and 1.8×10$^5$ phage/mL specific for the monomeric form of BAP42. Table 3 shows results obtained after the 4$^{th}$ pannings (selection rounds) using a standard phage display protocol with the oligomeric form immobilized in ELISA wells. Results using membrane phage display are shown in Tables 4-5 below, along with conditions used for each round.

TABLE 3

| | 1$^{st}$ Panning | 2$^{nd}$ Panning | 3$^{rd}$ Panning | 4$^{th}$ Panning |
|---|---|---|---|---|
| Input (phages/mL) | 2 × 10$^{12}$ | 3 × 10$^{12}$ | 3.9 × 10$^{11}$ | 3 × 10$^{12}$ |
| Output (phages/mL) | 7.5 × 10$^5$ | 9.8 × 10$^4$ | 1.6 × 10$^4$ | 1.3 × 10$^5$ |
| Conditions | Washes: 5× Detergent: 0.2% | Washes: 10× Detergent: 0.5% | Washes: 15× Detergent: 0.5% | Washes: 15× Detergent: 0.5% |

TABLE 4

| | 1$^{st}$ Panning | 2$^{nd}$ Panning | 3$^{rd}$ Panning | 4$^{th}$ Panning |
|---|---|---|---|---|
| Input (phages/mL) | 2.2 × 10$^{12}$ | 2 × 10$^{12}$ | 3 × 10$^{11}$ | 4 × 10$^{12}$ |
| Output (phages/mL) | 2.4 × 10$^6$ | 7.5 × 10$^4$ | 7.5 × 10$^3$ | 7.5 × 10$^5$ |
| Conditions | Washes: 5× Detergent: 0.2% | Washes: 10× Detergent: 0.5% | Washes: 15× Detergent: 0.5% | Washes: 15× Detergent: 0.5% |

TABLE 5

| | 1$^{st}$ Panning | 2$^{nd}$ Panning | 3$^{rd}$ Panning | 4$^{th}$ Panning |
|---|---|---|---|---|
| Input (phages/mL) | 2.3 × 10$^{12}$ | 1 × 10$^{12}$ | 8.2 × 10$^{11}$ | 4 × 10$^{12}$ |
| Output (phages/mL) | 6 × 10$^6$ | 1 × 10$^5$ | 1.5 × 10$^6$ | 1.8 × 10$^5$ |
| Conditions | Block: Pierce Washes: 5× with PBST 0.2% | Block: Pierce Washes: 10× with PBST 0.5% | Block: BSA 3% Washes: 15× with PBST 0.5% | Block: Pierce Washes: 15× with PBST 0.5% |

iv. Selection of Stable Single-Domain Antibody Libraries Using CAT-Fusion Assay

After pooling stable antibodies specific for the target species, monomers and oligomers, the next goal was to select candidates showing high immunospecificity toward the corresponding antigen. Accordingly, screening was carried out and then evaluated for anti-oligomer and anti-monomer activity, by ELISA, to determine binding profiles to the respective antigen. Results are shown in FIGS. 11-12.

Figure 11:
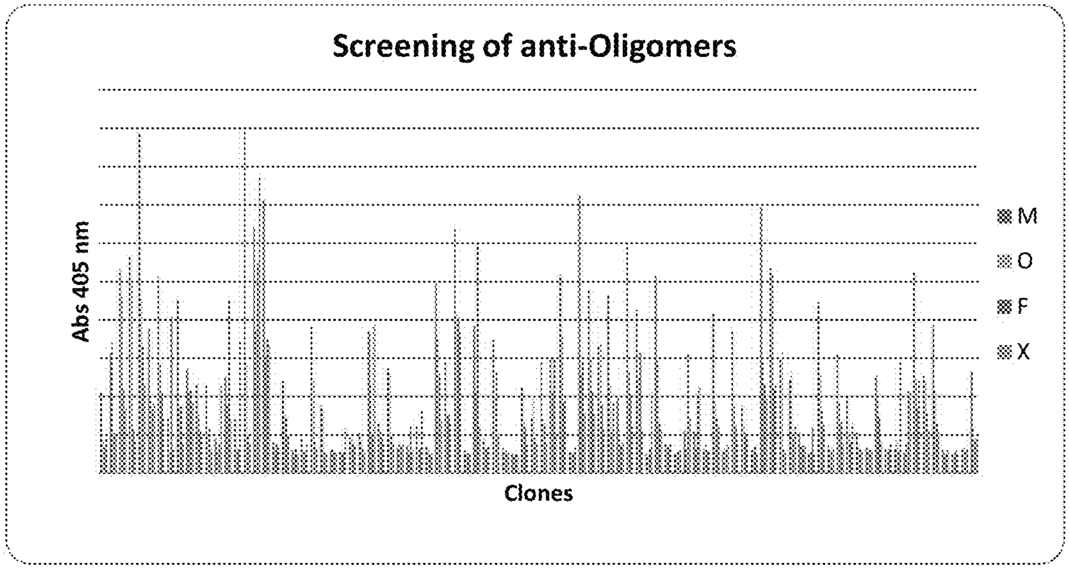
FIG. 11 shows binding profile and ligation values of 94 clones analyzed by ELISA for the oligomeric form of BAP42 (M—Monomers; O—Oligomers; F—Fibers; X-BSA 3%).
Figure 12:
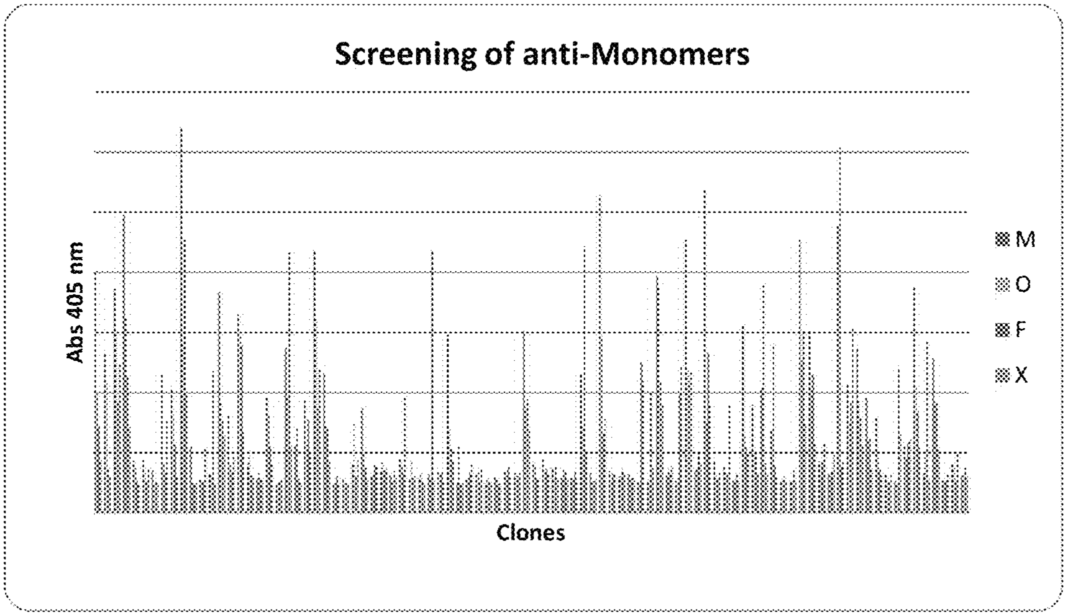
FIG. 12 show binding profile and ligation values of 94 clones analyzed by ELISA for the monomeric form of BAP42 (M—Monomers; O—Oligomers; F—Fibers; X-BSA 3%), respectively.

Specifically, FIG. 11 shows binding profile and ligation values of 94 clones analyzed by ELISA and derived from the membrane phage display with the oligomeric form of BAP42 (M—Monomers; O—Oligomers; F—Fibers; X-BSA 3%); and FIG. 12 shows binding profile ligation values of 94 clones analyzed by ELISA and derived from the membrane phage display with the monomeric form of BAP42 (M—Monomers; O—Oligomers; F—Fibers; X-BSA 3%).

Clones were further selected for stability using a modified CAT-fusion assay, as previously described (see, e.g., WO 2008/136694 to Goncalves et al). Specifically, the CAT gene was amplified from pCAT (Stratagene) by PCR and inserted into pET-derived plasmid using EcoRI and SphI restriction sites to create the pE-CAT. The 5'PCR primer originally used to clone the variable domains was also designed to contain two sequential and different SfiI cloning sites, and an amber codon (TAG) just before the beginning of the CAT gene.

To clone single-domain antibody libraries fused into the CAT gene, SDVL fragments were generated by PCR from phagemid vectors selected by panning. The resulting SDVL PCR fragments were gel-purified, digested with the restriction endonuclease SfiI, and cloned independently into the appropriately SfiI-cut vector pE-CAT. The pSDVL-CAT constructs were under the control of the strong Lac promoter that also included an N-terminal His$_6$ affinity tag and the ampicillin resistance gene. Alternatively, SDVL fragments may be cloned into readily available vectors designed to express cloned sequences as fusion proteins with CAT, e.g., the PCFN1 vector (see Maxwell, et al (1999) *J Prot Sci* 8:1908-1911, incorporated by reference in its entirety).

Chloramphenicol resistance assays were performed by transforming ER2783 cells (New England Biolabs, Inc) with each single domain CAT-fusion library. The transformation mixtures were inoculated into 5 mL of SOC and incubated at 37° C. for 1 hour. Next, 10 mL of SB medium with 3 μL of 100 mg/ml ampicillin was added to each library. A total of 15 mL of each culture was shaken for 1 hour at 37° C. Subsequently, 4.5 μL of 100 mg/ml ampicillin was added and cultures shaken for one hour at 37° C. Then 85 mL of SB medium with 85 μL of 100 mg/ml ampicillin was added and cultures grown overnight at 37° C. The following day, 600 μL of each culture was used to inoculate 20 mL of SB medium containing 100 μg/mL of ampicillin.

Expression of CAT-fusion single domain proteins was induced by addition of 0.5 mM IPTG when the optical density of cultures reached 0.9 (at 600 nM). After 2 hours of incubation at 37° C., 100 μL aliquots of each library were plated on agar plates with IPTG (200 μg/mL) and various concentrations of chloramphenicol. Plates were incubated at 37° C. for 16-20 hours. The level of resistance was quantified as the highest level of chloramphenicol at which colonies appeared after the 37° C. incubation period. Colonies detected at chloramphenicol concentrations of 1.86 mM or greater were selected as being stable. Results are shown in Table 6, below, where +++indicates over 600 colonies detected; ++ indicates 400-600 colonies detected; +indicates 1-399 colonies detected; and – indicates no colonies detected at the corresponding chloramphenicol concentration. "sdAb2", "sdAb6", "sdAb20", and "sdAb26" are sdAb candidates that bind BAP42 oligomers.

their ability to inhibit aggregation of the peptide to fibrillar forms. This assay was performed using the thioflavin T (ThT), which, as discussed above, is a probe that recognizes rich "beta-sheet" secondary structures, the structure indeed characteristic of fibrillar BAP42. Accordingly, the greater aggregation inhibition by a candidate anti-oligomer sdAb, the less fibrils formed, and thus the smaller the signal emitted by ThT during the assay. Other selected anti-oligomer sdAbs show similar aggregation inhibition.

Figure 15:
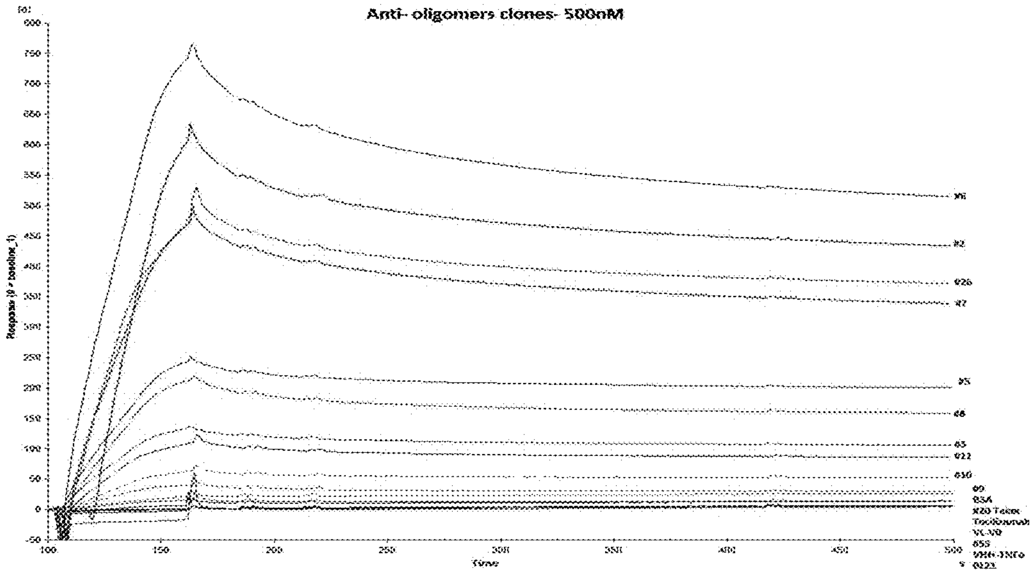
FIG. 15 shows BIAcore analysis and binding profiles of exemplary antibody molecules to the oligomeric form of BAP42.
Figure 16A:
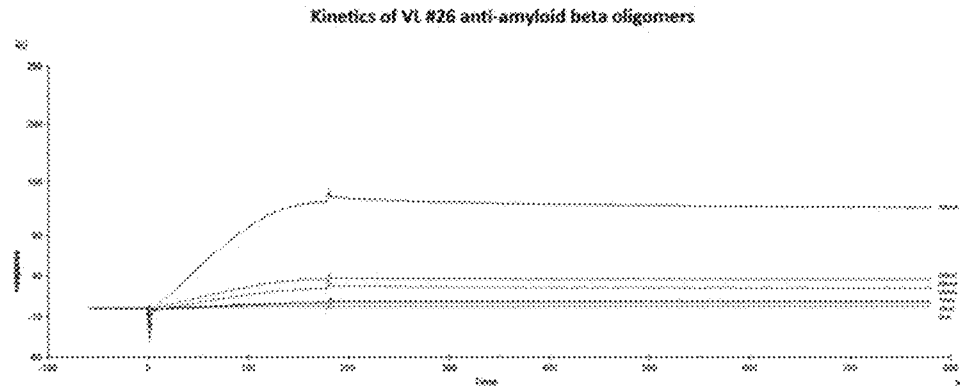
FIGS. 16A-16D show BIAcore kinetic studies of four exemplary antibody molecules (candidate anti-BAP42 oligomer antibodies), referred to as "VL#26" (FIG. 16A), "VL#20" (FIG. 16B), "VL#6" (FIG. 16C), and "VL#2" (FIG. 16D).
Figure 16B:
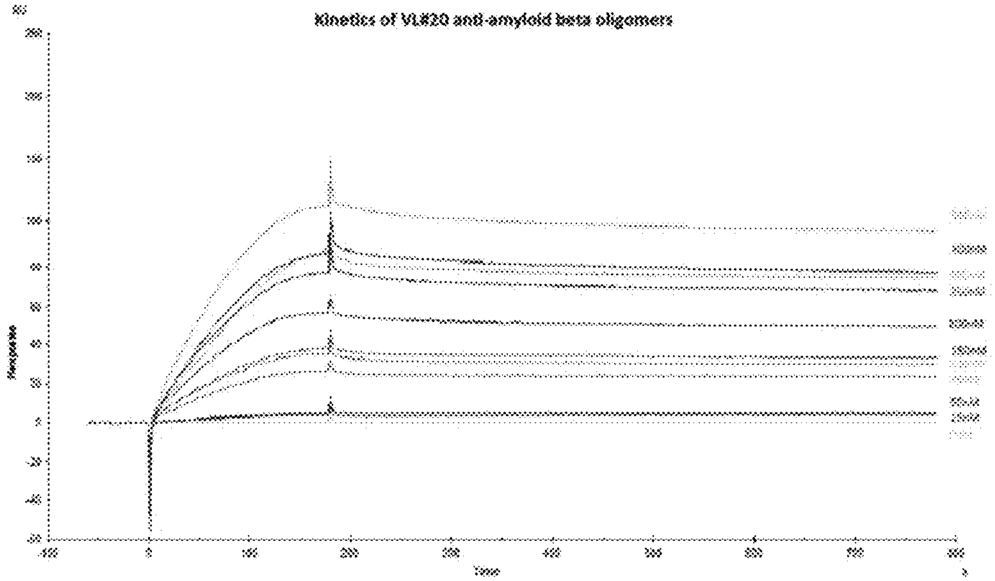
Figure 16C:
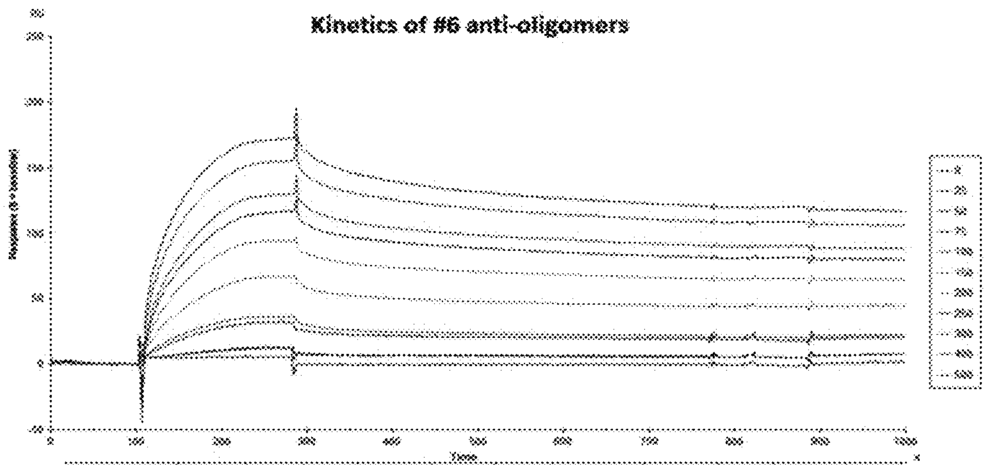
Figure 16D:
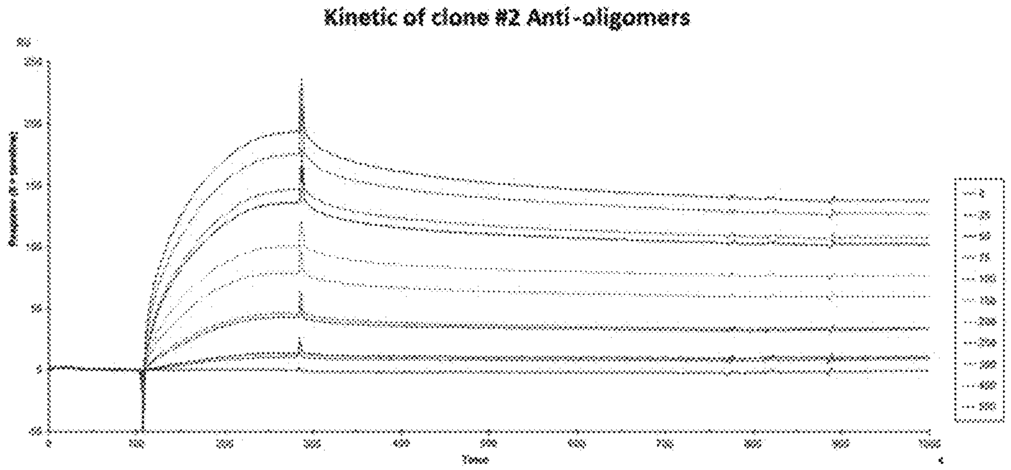

Anti-oligomer sdAbs where characterized further regarding their relative binding profile to BAP42 oligomers by BIAcore. Results are shown in FIG. 15.

Finally, from the antibodies analyzed by BIAcore, candidates showing best binding profiles to the oligomeric form of BAP42 (that is, "VL#26", "VL#20", "VL#6", and "VL#2") were selected for further kinetic studies in BIAcore and biodistribution studies. Results are showing in FIGS. 16A-16D, respectively (kinetic studies) and Tables 14-16, respectively (biodistribution studies), presented below.

Example 2—Development of BBB-Specific Delivery Peptides from a Viral Capsid Protein Delivery peptides were prepared based on a capsid protein (DEN2C). Segments of DEN2C have shown the ability to effect cell internalization of DNA cargo, with the expression of Green fluorescent protein (GFP) (Freire, et al. *FEBS* (2014) 281(1):191-215). The DEN2C protein was used in this Example to build a peptide library specific for the blood-brain barrier (BBB) in a six-stage process. Briefly, (a)

TABLE 6

| [chloramphenicol] mM | $10^0$ | | | | | | | $10^{-2}$ | | | | | | |
|---|---|---|---|---|---|---|---|---|---|---|---|---|---|---|
| | sdAb2 | sdAb6 | sdAb20 | sdAb26 | VL Vif (c+) | VH vif (c−) | pCFNI | sdAb2 | sdAb6 | sdAb20 | sdAb26 | VL Vif (c+) | VH vif (c−) | pCFNI |
| 0.03 | +++ | +++ | +++ | +++ | +++ | ++ | +++ | +++ | +++ | +++ | +++ | +++ | + | +++ |
| 0.06 | +++ | +++ | +++ | +++ | +++ | + | +++ | +++ | +++ | +++ | +++ | +++ | + | +++ |
| 0.12 | +++ | +++ | +++ | +++ | +++ | + | +++ | +++ | +++ | +++ | +++ | +++ | + | +++ |
| 0.25 | +++ | +++ | +++ | +++ | +++ | + | +++ | +++ | +++ | +++ | +++ | +++ | + | +++ |
| 0.31 | +++ | +++ | +++ | +++ | +++ | + | +++ | +++ | +++ | +++ | +++ | +++ | + | +++ |
| 0.62 | +++ | +++ | +++ | +++ | +++ | − | +++ | +++ | +++ | +++ | +++ | +++ | − | ++ |
| 1.24 | +++ | +++ | +++ | +++ | +++ | − | +++ | +++ | +++ | +++ | +++ | +++ | − | ++ |
| 1.86 | +++ | +++ | +++ | +++ | +++ | − | +++ | − | − | − | − | − | − | − |
| 2.48 | ++ | ++ | ++ | ++ | + | − | + | − | − | − | − | − | − | − |

v. Analysis of Selected sdAbs Against Non-Fibrillar BAP42

From the clones analyzed by ELISA, certain clones with high specificity for monomers and oligomers, but that do not recognize the fibrillar BAP42, were sequenced. Sequence information is provided in the Sequence Listing as SEQ ID NOs: 1-21. Following sequencing, homology amongst the candidates was evaluated, homology alignments performed, and homology trees constructed.

Ten antibodies were chosen to evaluate their recognition of the different BAP42 forms by Western blot. Results are shown in FIG. 13 and FIG. 14.

Figure 13:
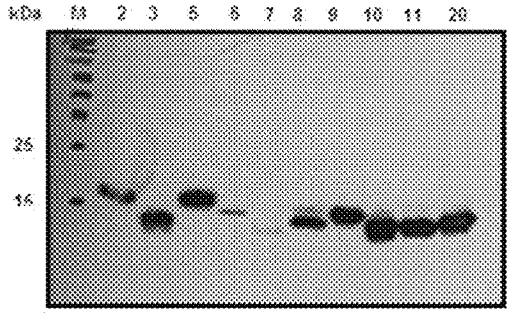
FIG. 13 shows the detection exemplary antibody molecules of the invention on Western blot.
Figure 14:
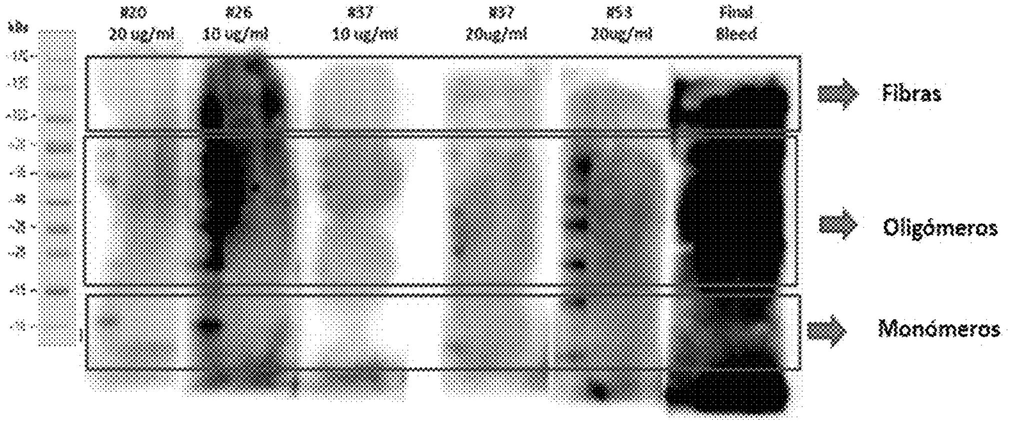
FIG. 14 shows recognition of mostly monomers and oligomers on Western blot analysis of different BAP42 isoforms in a PVDF membrane.

Specifically, FIG. 13 shows the detection of the 10 clones, purified and detected by Western blot, following purification and analysis of the 10 clones by ELISA against oligomeric BAP42. FIG. 14 shows recognition of mostly monomers and oligomers on Western blot analysis of different BAP42 isoforms in a PVDF membrane. Other selected anti-oligomer sdAbs show similar profiles in recognizing BAP42 oligomeric forms.

Once purified and verified in recognizing BAP42 oligomers, anti-oligomer antibodies were purified were tested for translocation capacity of the entire DEN2C protein was determined; (b) DEN2C peptides were produced and radiolabelled; then (c) tested in vitro for BBB-specific translocation and BBB cell internalization; as well as being (d) tested for toxicity with respect to BBB cells; (e) studied regarding their membrane potential effects and partition coefficients; and, finally, (f) tested in vivo for biodistribution and stability.

a. Determination of DEN2C Translocation Capacity in an In Vitro BBB Model

First, the entire protein sequence encoded by the DEN2C gene was exposed on the surface of phage and used to test interaction with a BBB-model.

Pphagemid DNA containing the gene of interest (DEN2C-pIII fusion phagemid) was introduced into *E. coli* SS320 cells, and the genes that encode the peptide were expressed in the periplasm of the cell. The envelope protein and genes important for forming M13 phage were provided by helper phage deficient in packaging signals. Co-infection of the host bacterium with the phagemid and helper phage produced hybrid virions (phage-DEN2 or DEN-phage), exposing the pIII-DEN2 fusions.

An in vitro BBB model was prepared using BECs growing in a transwell system. Specifically, the transwell system was composed of bEnd3 cells on a microporous membrane, forming an in vitro endothelial barrier between the upper compartment (apex) and lower compartment (base) of a "tissue culture insert". Then phage-DEN2 were incubated with the bEnd3 cells. That is, prepared phages were added to the upper compartment (apex) and incubated for 30 minutes. The experiment was repeated using samples of helper phage, phage fused a capsid protein (DEN-phage), and a positive control that crosses the BBB (+phage). Transmigration ability of DEN-phage was determined, based on comparing phage titer in the apex and base, on either side of the model-BBB, relative to the total initial phage (stock), for the samples of helper phage, DEN-phage, and the positive control. Results are shown in FIG. 17.

Figure 17:
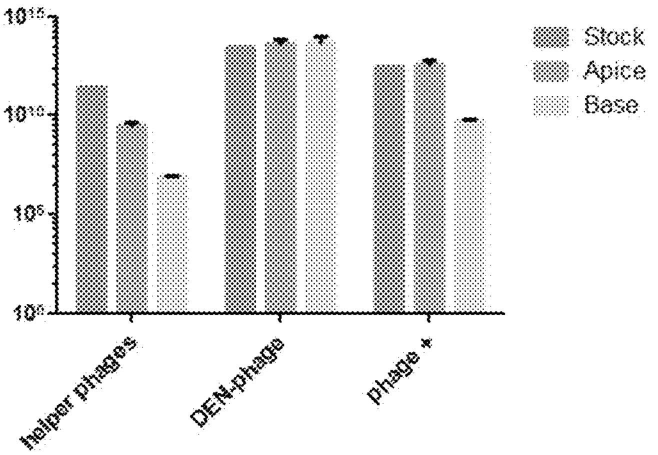
FIG. 17 shows transmigration of phage in fusion with peptides (DEN-phage) based on comparing phage titer in the apex and base, on either side of an in vitro BBB model, relative to the total initial phage (stock), for samples of helper phage, DEN-phage, and a positive control that crosses the BBB (+phage).

As FIG. 17 demonstrates, the DEN2C gene enhances translocation ability of the phage compared to the positive control. The results showed that equilibrium was achieved between the apex and the base, across the model BBB, where both apex and base had the same phage titer of $10^{12}$. These results surprisingly demonstrate that the DEN-phage moved freely through the endothelial barrier. Phage with capacity to translocate the barrier were collected from the base and re-amplified.

Tests were carried out to ensure the integrity of the model barrier. The integrity of the barrier may be tested in various ways, for example, using fluorescent molecules of different molecular masses. Specifically, endothelial barrier integrity was tested using a fluorescent molecule with 40 kDa dextran (FD40) in the in vitro BBB system used. Fluorescence was assayed in the base, after applying FD40 to the apex, either using a cell-free control (Blank), using the BBB model with bEnd3 cells (Cells), and using the BBB model after incubation with phages (phages). Results are shown in FIG. 18.

Figure 18:
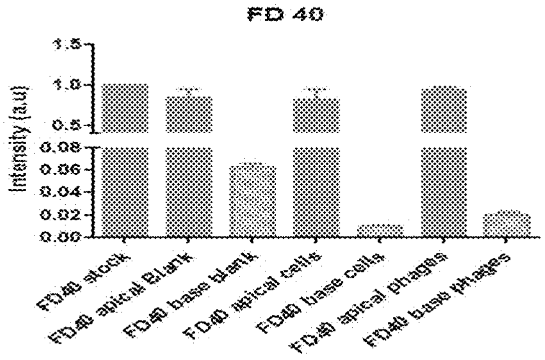
FIG. 18 shows endothelial barrier integrity of an in vitro BBB model, testing with a 40 kDa dextran fluorescent molecule (FD40) using a cell-free control (Blank), the BBB model with bEnd3 cells (Cells), and using the BBB model after incubation with phages (phages).
Figures 19A, 19B, 19C, 19D, 19E, 19F:
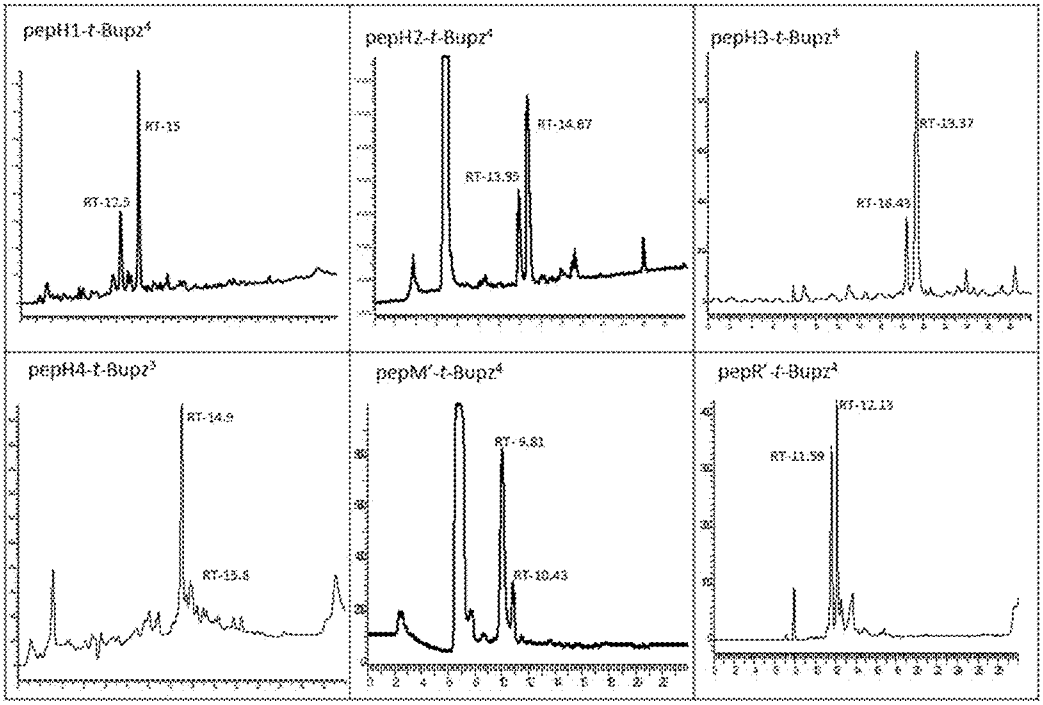
FIGS. 19A-19F show HPLC results for different DEN2C peptides.
Figures 20A, 20B, 20C, 20D, 20E, 20F:
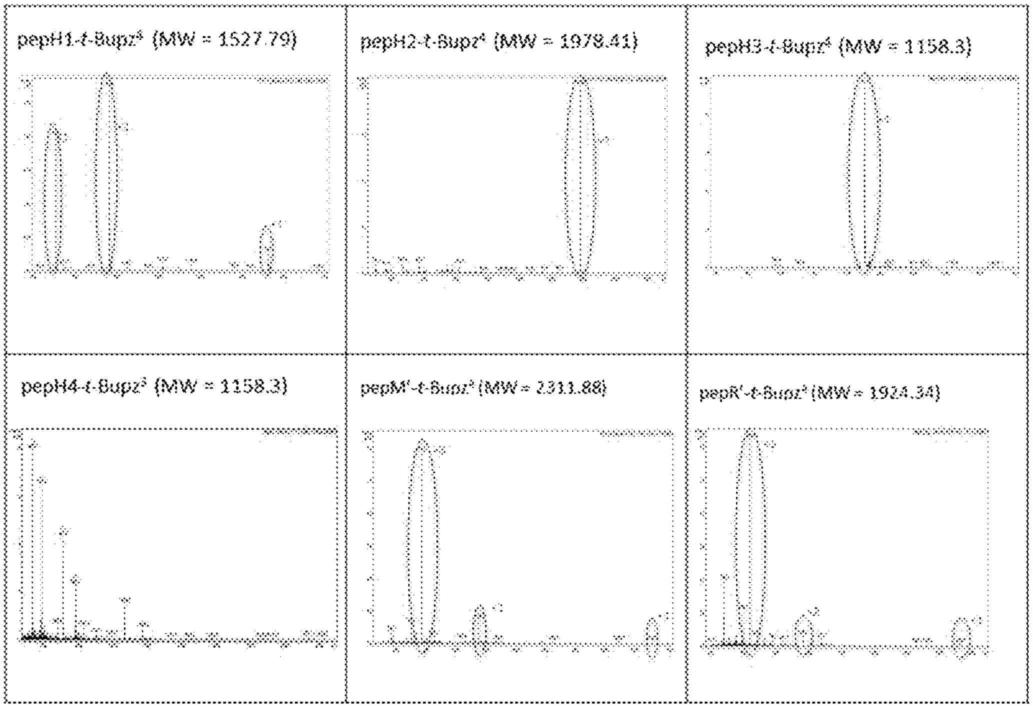
FIGS. 20A-20F show MS results for different DEN2C peptides.
Figures 21A, 21B, 21C, 21D, 21E, 21F:
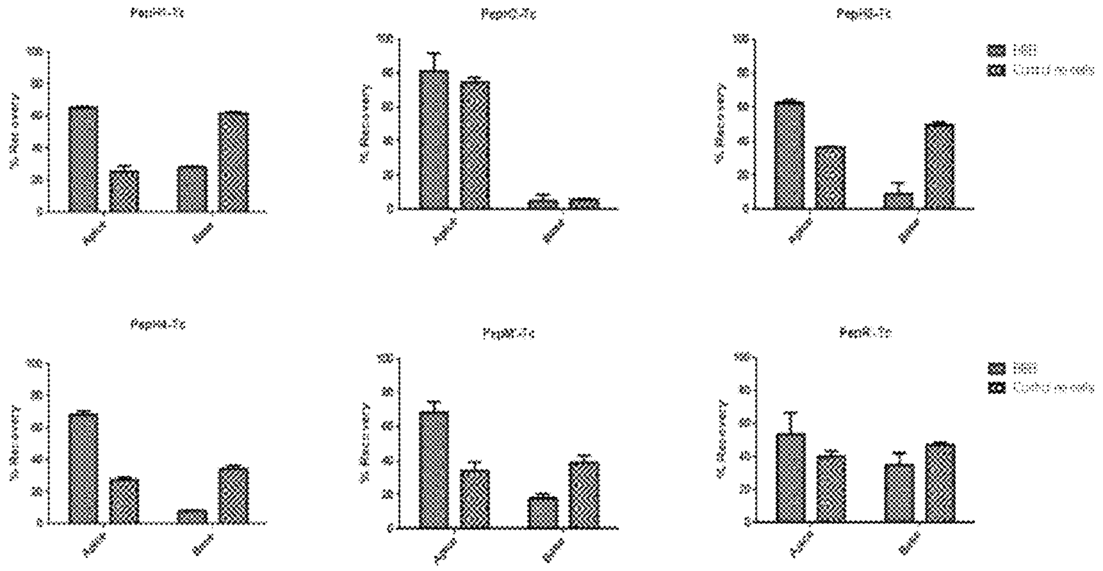
FIGS. 21A-21F show % $^{99m}$Tc-radiopeptide recovered in the apex and base of a transwell system, indicating transmigration of different DEN2C peptides after 5 hours of incubation with tissue culture inserts of bEnd3 cells (BBB model) and with no cells (control).
Figures 22A, 22B, 22C, 22D, 22E, 22F:
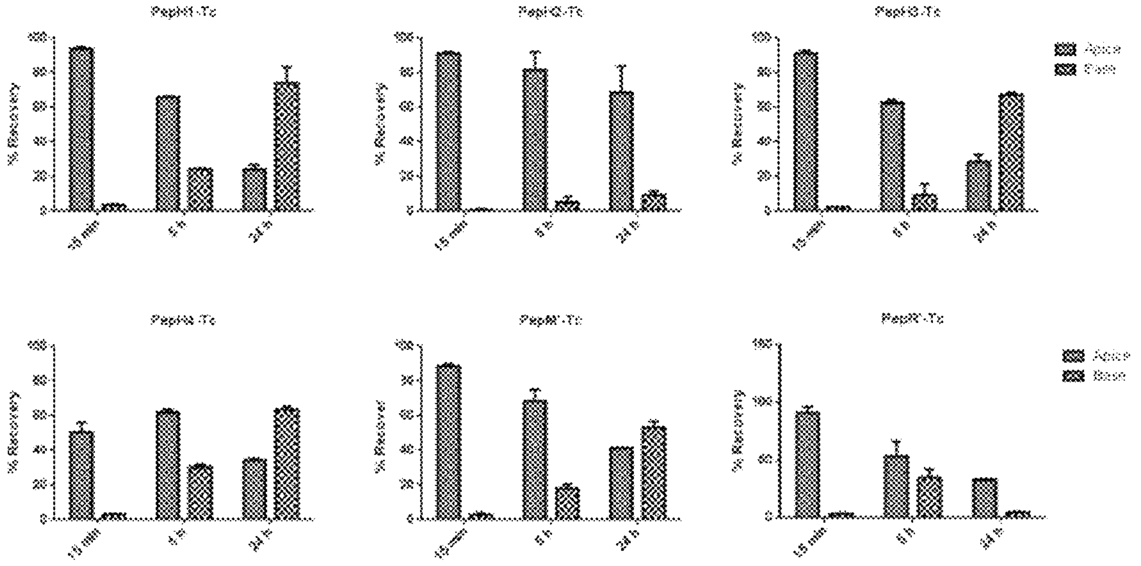
FIGS. 22A-22F show % $^{99m}$Tc-radiopeptide recovered in the apex and base of a transwell system, indicating transmigration of different DEN2C peptides after 15 minutes, 5 hours, and 24 hours incubation in tissue culture inserts with bEnd3 cells (BBB).
Figures 23A, 23B, 23C, 23D, 23E:
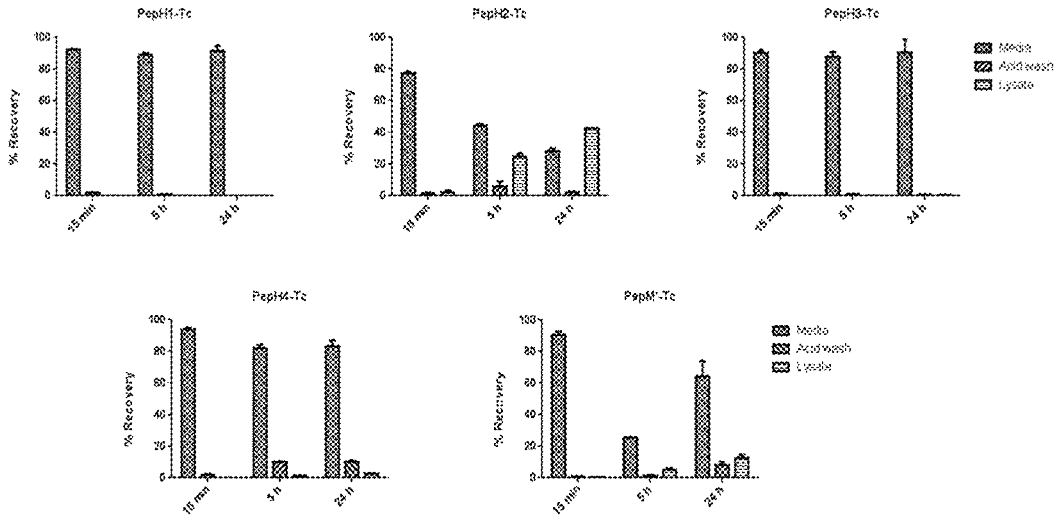
FIGS. 23A-23E show internalization capacity of different DEN2C peptides in BBB cells, after 15 minutes, 5 hours, and 24 hours of incubation.
Figures 24A, 24B, 24C, 24D, 24E:
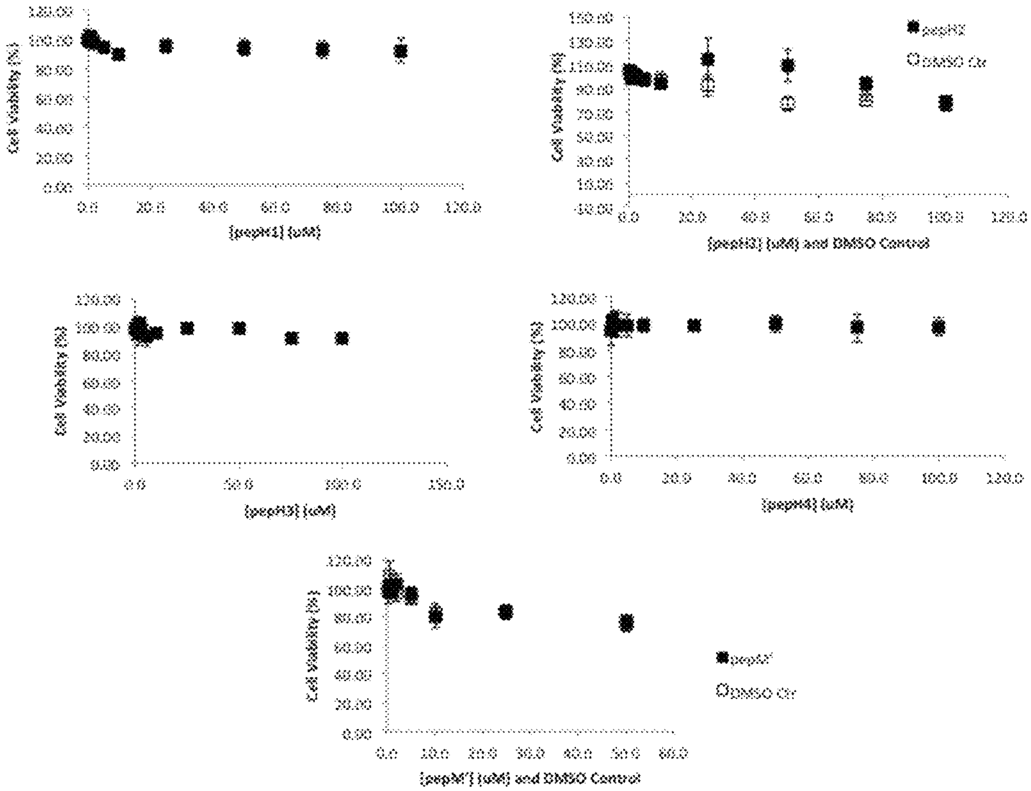
FIGS. 24A-24E shows lack of toxicity of different concentrations of selected DEN2C peptides on BBB cells.

As FIG. 18 shows, there was greater retention of the molecule with a cell barrier (less than 2% traversal by FD40) compared to when there was no barrier (about 8% FD40 at the base). Further, the integrity of the barrier did not seem to be affected by incubation with phages (still about 2% traversal of FD40 with phage present).

b. Production of DEN2C Peptides and Radiolabelling

Small peptides derived from the DEN2C domain of the protein, having about 5 to about 25 amino acids, were synthesized based on Fmoc chemistry on solid phase consisting of repeated cycles of coupling-wash, wash, and deprotection.

These peptides (according to SEQ ID NOs: 22-27 and 127) then were conjugated with a chelate or marked with a radioactive isotope, technetium or gallium. The compounds then were interacted with bEnd3 cells, for analysis of both the peptides' translocation capacity in a BBB in vitro model and their capability for cellular internalization. Two different tags were used in these analyses, to allow confirmation of results.

More specifically, the conjugation involved the following steps: swelling the resin; deprotection of terminal amino groups; conjugation reaction using activating agents and a base; and at the end of cleavage, obtaining a peptide-chelate product. The chelates used were pyrazol derivatives such as t-BuPz4 (Morais, et al. *J Med Chem* (2013) 56(5):1961-73), facilitating labeling with technetium; and NODA-GA (tBu) 3 (4-(4,7-bis (2-tert-butoxy)-2-oxoethyl)-1,4,7-triazacyclononan-1-yl)-5-(tert-butoxy) 5-oxopentanoic acid), which facilitates marking with gallium.

HPLC (High-performance liquid chromatography) was carried out to purify the peptide-chelates and purification was confirmed by mass spectroscopy (MS). Results are shown in FIGS. 19A-19F (HPLC results obtained for different peptides) and FIGS. 20A-20F (MS results for different peptides, where MW of t-BuPz4 326.6 $gmol^{-1}$). HPLC results showed two major species that correspond to the peptide alone (shorter retention time) and the peptide in conjugation with the chelate (longer retention time). MS results confirm the purification of peptide-chelate species (having a higher MW than the peptide alone). Similarly, conjugates were analyzed with NODA-GA (tBu) 3 (data not shown). Finally the peptides were radiolabelled, at a final concentration of $8\times10^{-5}$ M.

The features of the original and conjugated peptides are summarized in Table 7, below. Table 7 lists each peptide's name, isoelectric point (PI), charge (number of positive residues), calculated mass (in Da), and ion found; as well as the name, calculated mass, and found ion for the corresponding conjugate; and also retention times in HPLC and the partition coefficient (log Po/w). These values allowed the determination of the hydrophilic nature of peptides, where pepH1 and pepH4 were identified as the most hydrophilic peptides.

TABLE 7

| Peptide | PI | Charge | Calcd exact mass (Da) | Found [ion] | Peptide conjugates | Calcd exact mass (Da) | Found [ion] | $t_R$ (min) Peptide conjugates | $t_R$ (min) radiopeptides | log Po/w of radiopeptides |
|---|---|---|---|---|---|---|---|---|---|---|
| PepH1 | 11 | 2 | 1219.4 | 1220.4 $[M+H]^+$ | $Pz^1$-pepH1 | 1527.79 | 1527.10 $[M+H]^+$ | $12.1^a$ | $^{99m}Tc(CO)3$-$Pz^1$-pepH1: $16.1^a$ | −1.76 ± 0.11 |
| | | | | | NODAGA-pepH1 | 1576.60 | 789.10 $[M+2H]^{2+}$ | $13.6^b$ | $^{67}Ga$-NODAGA-pepH1: $13.8^b$ | −2.16 ± 0.04 |
| PepH2 | 11 | 2 | 1670.1 | 1671.1 $[M+H]^+$ | $Pz^1$-pepH2 | 1978.41 | 1978.30 $[M+H]^+$ | $20.2^a$ | $^{99m}Tc(CO)3$-$Pz^1$-pepH2: $22.4^a$ | 0.65 ± 0.13 |
| | | | | | NODAGA-pepH2 | 2027.16 | 2027.80 $[M+H]^+$ | $23.5^b$ | $^{67}Ga$-NODAGA-pepH2: $23.7^b$ | 0.35 ± 0.14 |

TABLE 7-continued

| Peptide | PI | Charge | Calcd exact mass (Da) | Found [ion] | Peptide conjugates | Calcd exact mass (Da) | Found [ion] | $t_R$ (min) Peptide conjugates | $t_R$ (min) radiopeptides | log Po/w of radiopeptides |
|---|---|---|---|---|---|---|---|---|---|---|
| PepH3 | 11 | 2 | 843 | 844 $[M + H]^+$ | $Pz^1$-pepH3 | 1151.30 | 1151.80 $[M + H]^+$ | 13.5[a] | $^{99m}$Tc(CO)3-$Pz^1$-pepH3: 15.9[a] | 0.11 ± 0.06 |
| | | | | | NODAGA-pepH3 | 1200.18 | 1200.00 $[M + H]^+$ | 13.4[b] | $^{67}$Ga-NODAGA-pepH3: 13.7[b] | 1.21 ± 0.09 |
| PepH4 | 11.7 | 6 | 2671.2 | 1336 $[M + 2H]^{2+}$ | $Pz^2$-pepH4 | 2934.52 | 735.40 $[M + H]^+$ | 10.6[a] | $^{99m}$Tc(CO)3-$Pz^1$-pepH4: 12.8[a] | −1.84 ± 0.31 |
| | | | | | NODAGA-pepH4 | 3027.42 | 1010.14 $[M + 3H]^{3+}$ | 18.2[b] | $^{67}$Ga-NODAGA-pepH4: 18.4[b] | −0.80 ± 0.13 |
| PepM' | 12.0 | 3 | 2313.2 | 1156 $[M + 2H]^{2+}$ | $Pz^2$-pepM' | 2576.51 | 1311.3 $[M + 2H]^{2+}$ | 10.0[a] | $^{99m}$Tc(CO)3-$Pz^1$-pepM': 18.0[a] | −0.21 ± 0.04 |
| | | | | | NODAGA-pepM' | 2669.04 | 1335.7 $[M + 2H]^2$ | 15.8[b] | $^{67}$Ga-NODAGA-pepM': 16.0[b] | −0.10 ± 0.18 |

c. In Vitro Testing of BBB-Specific Translocation and Cell Internalization of DEN2C Peptides Using the same in vitro model of the BBB described above, peptides labelled with technetium and gallium were tested for the ability to cross endothelial barrier. For each peptide, bEnd3 cells cultured on "tissue culture inserts" were incubated with 5 μCimL$^{-1}$-labelled peptide for different incubation times: 15 min, 5 h and 24 h. As a control, the model without cells was used (Control no cells) or (Filters) and compared to models with cells (BBB) or (Cells). Results for the 5 hour-incubation are shown in FIGS. 21A-21F.

FIGS. 21A-21F show the percent activity of the radioisotope technetium-labelled peptides at the apex and base after 5 hours of incubation with the in vitro model described above, using the BBB-model or no cells (as a control); and values were obtained from two independent assays. Radioisotope activity showed that transmigration after 5 h of incubation using the technetium-labelled peptides was different in the presence of the barrier than without it, further confirming that cells in fact formed a barrier which interfered with the free passage of the peptide. Moreover, the results indicated promising candidates. Specifically, for each of pepH1 and pepH3, there was an overpass of 50% in the control, compared with only 20% in the presence of a cell barrier. The translocation of pepH2 was not observed in either the control nor in the BBB model. For PepR', the passage was similar in both the control and the model BBB.

Results for the incubations of 15 minutes, 5 hours, and 24 hours are shown together in FIGS. 22A-22F. That is, FIGS. 22A-22F show the percent activity of the radioisotope technetium-labelled peptides at the apex and base after 15 minutes, 5 hours, and 24 hours of incubation with the in vitro model described above, using the BBB-model or no cells (as a control); and values were obtained from two independent assays. Differences again were observed, confirming the integrity of the barrier, as well as identifying peptides that crossed the barrier. Specifically, pepH2 showed limited translocation even after 24 h, with only 9% of the peptide crossing the barrier, confirming, as noted above, that a barrier with high barrier capacity formed. Nonetheless, pepH1 and pepH3 surprisingly showed effective translocation across this barrier, that is, each showing about 70% radioactivity at the base after 24 hours. PepH4 and pepM also exhibit good capacity for translocation and transmigration (showing about 60% and 50%, respectively). PepR' was more limited in crossing the barrier; it strongly interacted with the surface of the inserts and was difficult to recover. PepR' thus was excluded from further tests.

In addition to testing models of BBB, an uptake test was performed to determine the internalizing ability of the candidate peptides. BEnd3 cells were cultured in 24 well plates. At each time point, the medium containing the peptide, which had not interacted with the cells, was collected. In the next step, the cells were washed with an acidic buffer that releases peptides more strongly bound to the cell membrane (sample acid wash). Finally, the cells were lysed to release internalized peptides and to quantify the activity inside the cells. Results are showing in FIGS. 23A-23E.

FIGS. 23A-23E show percent activity of the radioisotope technetium-labelled peptides in the media, wash buffer (acid wash) and lysate, after 15 minutes, 5 hours, and 24 hours of incubation with bEnd3 cells; and values were obtained from two independent assays. The results showed that peptides with good ability to translocate the BBB model also had low interaction with the cells. Specifically, pepH1, pepH3, pepH4 mainly remained in the incubation medium. PepH2 was observed to highly interact with cells and become internalized, showing over 40% radioactivity in the lysate. PepM', as well as showing high transmigration (about 50%), also appeared to become internalized and accumulated within the cells (about 13% of radioactivity in the lysate).

These promising results surprisingly demonstrate that pepH1 and pepH3 provide BBB-specific delivery peptides. Table 8 provides sequence information, as follows:

TABLE 8

| | |
|---|---|
| PepH1 | VQQLTKRFSL (SEQ ID NO: 22) |
| PepH2 | KLFMALVAFLRFLT (SEQ ID NO: 23) |
| PepH3 | AGILKRW (SEQ ID NO: 24) |
| PepH4 | KSKAINVLRGFRKEIGRMLNILN (SEQ ID NO: 25) |
| PepM' | LVAFLRFLTIPPTAGILKRW (SEQ ID NO: 26) |
| PepR' | KEIGRMLNILNRRRR (SEQ ID NO: 27) |

Table 9 summarizes results regarding uptake (internalization) and cellular interaction, as well as transmigration across an in vitro model for BBB, for peptides labelled with technetium and gallium, after 15 minutes, 5 hours, and 24-hours of incubation, based on percent recovery of radiopeptide. The Table lists the peptides, providing each peptide's name, % BBB transmigration, % cellular interaction, and % internalized, each after 25, minutes, 5 hours, and 24 hours of incubation.

TABLE 9

| Percentage of recovered dose in the base | | | | | | | |
|---|---|---|---|---|---|---|---|
| | Time | BBB transmigration | | Cellular interaction | | Internalization | |
| Peptide | (hours) | 99mTc | $GaCl_3$ | 99mTc | $GaCl_3$ | 99mTc | $GaCl_3$ |
| | 0.25 | 3.75 ± 0.5 | 1.13 ± 0.2 | 0.63 ± 0.1 | 0.25 ± 0.0 | 0.16 ± 0.0 | 0.00 ± 0.0 |
| PepH1 | 5 | 24.3 ± 0.4 | 21.56 ± 0.4 | 0.30 ± 0.0 | 0.80 ± 0.3 | 0.10 ± 0.0 | 0.10 ± 0.0 |
| | 24 | 73.83 ± 9.4 | 71.47 ± 3.7 | 0.38 ± 0.1 | 0.62 ± 0.0 | 0.12 ± 0.0 | 0.16 ± 0.0 |
| | 0.25 | 0.79 ± 0.7 | 0.33 ± 0.1 | 1.60 ± 0.3 | 0.77 ± 0.1 | 2.15 ± 1.2 | 0.84 ± 0.1 |
| PepH2 | 5 | 5.21 ± 3.3 | 4.06 ± 0.3 | 5.95 ± 3.0 | 1.48 ± 0.1 | 24.8 ± 2.0 | 6.97 ± 0.3 |
| | 24 | 9.32 ± 2.5 | 13.51 ± 0.7 | 2.20 ± 0.4 | 1.16 ± 0.1 | 42.7 ± 0.0 | 9.24 ± 1.2 |
| | 0.25 | 2.70 ± 0.0 | 1.87 ± 0.3 | 1.50 ± 0.1 | 0.26 ± 0.0 | 0.15 ± 0.1 | 0.03 ± 0.0 |
| PepH3 | 5 | 9.16 ± 6.5 | 26.47 ± 0.4 | 1.15 ± 0.1 | 0.73 ± 0.0 | 0.15 ± 0.1 | 0.12 ± 0.0 |
| | 24 | 67.23 ± 1.2 | 72.63 ± 0.7 | 0.60 ± 0.1 | 0.60 ± 0.1 | 0.35 ± 0.2 | 0.30 ± 0.1 |
| | 0.25 | 3.30 ± 0.5 | 0.93 ± 0.1 | 2.06 ± 0.3 | 4.06 ± 0.2 | 0.17 ± 0.0 | 0.26 ± 0.0 |
| PepH4 | 5 | 30.08 ± 1.6 | 16.60 ± 1.1 | 10.10 ± 0.1 | 3.00 ± 0.1 | 1.53 ± 0.0 | 0.78 ± 0.0 |
| | 24 | 63.45 ± 1.9 | 60.79 ± 2.6 | 10.23 ± 0.8 | 3.82 ± 0.1 | 2.83 ± 0.2 | 1.55 ± 0.1 |
| PepHM' | 24 | 53.47 ± 3.1 | 47.31 ± 1.2 | 8.32 ± 1.9 | 2.23 ± 0.1 | 12.81 ± 2.0 | 3.68 ± 0.0 |

As Table 9 shows, the results for transmigration were reproducible for both types of markings. PepH1 and pepH3 both showed high (about 70%) transmigration and little interaction with the cells, providing BBB-specific delivery peptides. In contrast, pepH2 seemed to strongly interact with the cells and showed low translocation; while pepH4 and pepM appeared to interact with the cells, as well as having transmigration ability. In sum, the BBB in vitro assay demonstrated high translocation of pepH1 and pepH3 (>70% at 24 h) and low cellular interaction/accumulation. PepH2, however, presented low BBB translocation and high cellular interaction and internalization (>40%). Moreover, the results demonstrated that pepH1 and pepH3 combine higher solubility in aqueous medium with improved translocation across the BBB, as well as low entrapment in BECs.

d. Toxicity: Assaying Cell Viability and BBB Integrity in the Presence of PepH1 and PepH3

To test possible toxicity of selected peptides to BBB cells, $5\times10^4$ bEnd3 cells were cultured in 96-well plates, at 100 μL/well, and incubated for 24 hours. The peptides then were added at concentrations of 0.1-100 μM, with the exception of pepM' (which was added at concentrations of 0.1-50 μM). As a control providing 100% of viability, a well with serum-free media was included.

After 24 hours of incubation, a MTT assay was performed, which is a colorimetric assay for assessing cell metabolic activity. A MTT solution at 5 mg/mL in PBS was added to each well and incubated for 2 hours. After this period, the solution was removed and DMSO added to solubilize violet crystals formed. Absorbance was measured at 540 nm. The viability percentage $[\text{Absorbance}_{\textit{peptide-treated cells}}/\text{Absorbance}_{\textit{untreated-cells}})*100]$ was calculated and IC50 values were calculated from three independent assays. Results are shown in FIGS. 24A-24E.

As FIGS. 24A-24E show, the selected peptides have no effect on cell viability, specifically, there was no observable nor measurable effect using the assay described. Whereas a small decrease in viability was observed for each of pepH2 and pepM', this in fact was due to the DMSO concentration used to dilute the peptide (a conclusion arrived at by comparing results to those obtained with the DMSO control).

In addition to determining cell viability and peptide toxicity, an assay was performed to confirm barrier integrity in the presence of the selected peptides. Fluorescent dextrans FD4 and FD40, (having molecular weights of 4 kDa and 40 kDa, respectively) that do not cross the BBB were used, similarly as described above. The fluorescein molecule (FITC), having a molecular weight of 326 Da, was used as a control (based on the literature, molecules with molecular weight less than 500 Da may have transmigration capacity).

bEnd3 cells were cultured, as described above, in "tissue culture inserts" and incubated with the various peptides, each at a concentrations of approximately 0.1 μM and 1 μM, for 24 hours. That is, using radiolabelled peptides, cells were incubated with 5 $\mu\text{CimL}^{-1}$ (approximately 0.1 μM) for a period of 24 h; as well as at a concentration 100 times greater. PepH2 and PepM' needed DMSO for solubilization; the higher concentration of Peptide/DMSO resulted in higher error and more cell death. For concentration below 40 μM, there was no cell death. Values were obtained from two independent assays. Results are shown in FIGS. 25A-25C.

Figures 25A, 25B, 25C:
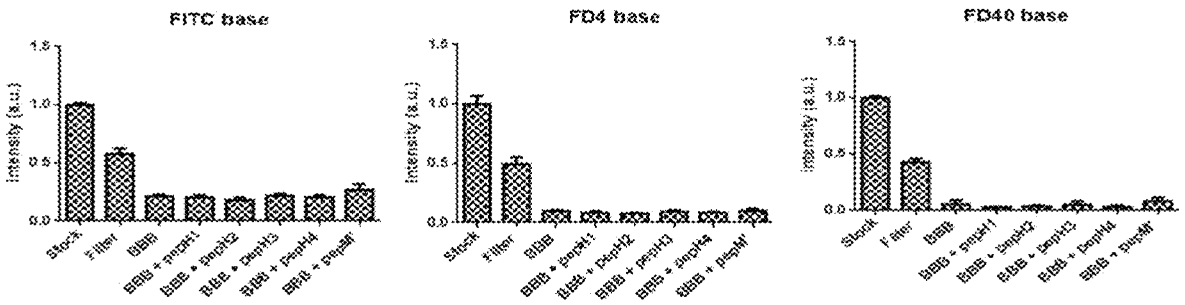
FIGS. 25A-25C show transmigration capacity of fluorescent molecules (Stocks) across filters without BBB cells (Filter), across the bEnd3 barrier (BBB), and across the bEnd3 barrier pre-incubated with the different peptides.

FIGS. 25A-25C show transmigration capacity of fluorescent molecules (Stocks) across filters without BBB cells (Control), across the bEnd3 barrier, and across the bEnd3 barrier pre-incubated with the different peptides. Each of the fluorescent molecules showed greater translocation in the control (Filter) experiments, than in experiments using cells (BBB), demonstrating a functional in vitro BBB model assay. Comparing results from the BBB experiment, with the BBB-plus-peptides experiment, showed that transmigration capacity is lower for higher molecular weight molecules, as would be expected.

Critically, clearance of the fluorescent probes (FITC, FD4, and FD40) from the apical compartment in the presence of the different peptides was similar to the control, which demonstrates the absence of fenestration in the cell barrier and paracelular leakage. Moreover, the cell viability assays showed that the percentage of viable cells was above 90%, even at 100 μM of peptides. Accordingly, results from the viability and barrier integrity tests demonstrated that the selected peptides were surprisingly not toxic.

e. Effects on Membrane Potential of Peptides PepHI and PepH3 and $K_p$ for PepH3

The peptides pepH1 and pepH3 were studied for their interaction with membrane models, specifically with 100 nm unilaminar vesicles ("LUVs"), and pepH2 was included as a negative control regarding transmigration capacity. The vesicles were made with different lipidic compositions, having different amounts of lipid membrane components, such as POPC, POPS, POPG, and cholesterol (Chol). POPC is a lipid with fluidic properties similar to those found in biological membranes. Cholesterol in the presence of POPC confers rigidity to the fluidic membranes, allowing formation of "lipidic rafts-like platforms" known to be present in the bilayer of eukaryotic membranes. POPS and POPG are negatively-charged lipids, present in eukaryotic and bacterial cells, respectively. As noted above, whereas the majority of eukaryotic cells have negatively charged lipids in the inner parts of their membranes, endothelial cells from the BBB have higher negatively-charged surfaces compared to cells from other endothelia. This negative charge is due not only to the negatively-charged lipids, but also to higher levels of glycosylation. Either way, the negative charges of POPS and POPG provide models that mimic the negatively-charged BBB, allowing analysis of their electrostatics interactions with selected peptides.

Different lipidic compositions were tested: POPC; POPC:POPS (4:1); POPC:POPG (4:1); POPC:Chol (2:1); POPC:POPS (3:2); and POPC:POPS (1:4). Results are shown in FIGS. 26A-26C.

Figure 26A:
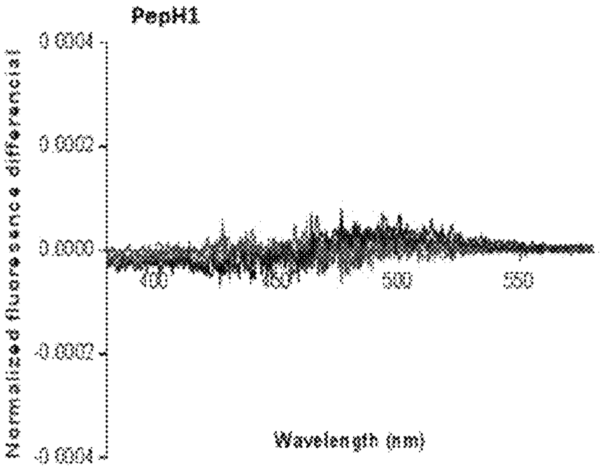
FIGS. 26A-26C show interaction and disturbances in bipolar potential of selected DEN2C peptides with membrane models (LUVs) of di-8-ANEPPS-labelled lipid compositions: POPC; POPC:POPS (4:1); POPC:POPS (3:2); POPC:POPS (1:4); POPC:POPG (4:1); and POPC:Chol (2:1).
Figure 26B:
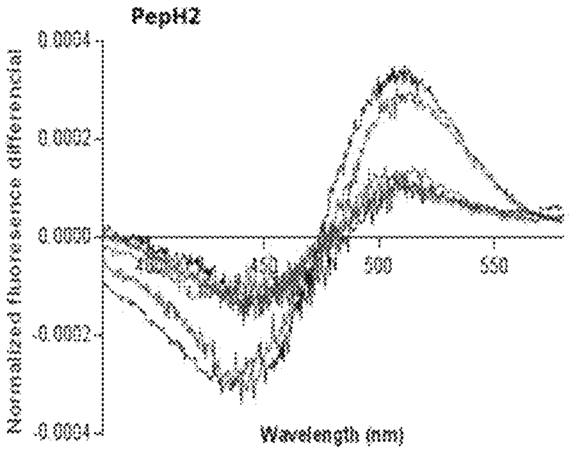
Figure 26C:
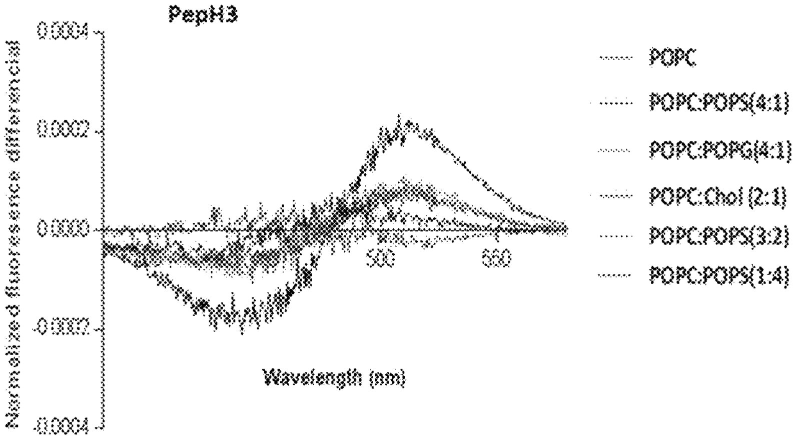

FIGS. 26A-26C show the results obtained in the assay using a probe, di-8ANEPPS, to evaluate disturbances in the bipolar potential of the membrane. PepH1 showed no alteration in the differential spectrum, presenting no interaction in the different membrane models tested. PepH3 showed alterations in the spectrum, indicating interactions with the membrane, especially with the negatively-charged membranes, such as POPC:POPS (1:4). Finally pepH2 showed high interaction with the different membrane models tested. These results correlated well with the results using the BBB model, for which pepH2 showed a high internalization percentage and a higher cellular interaction compared with pepH1 and pepH3.

For the pepH3, the "partition coefficient" or "affinity constant" also was determined, since this peptide intrinsically presents a tryptophan and, thus, successful administrations of the lipid compositions allowed determination of pepH3's affinity constant. Results are shown in FIG. 27 and Table 10.

Figure 27:
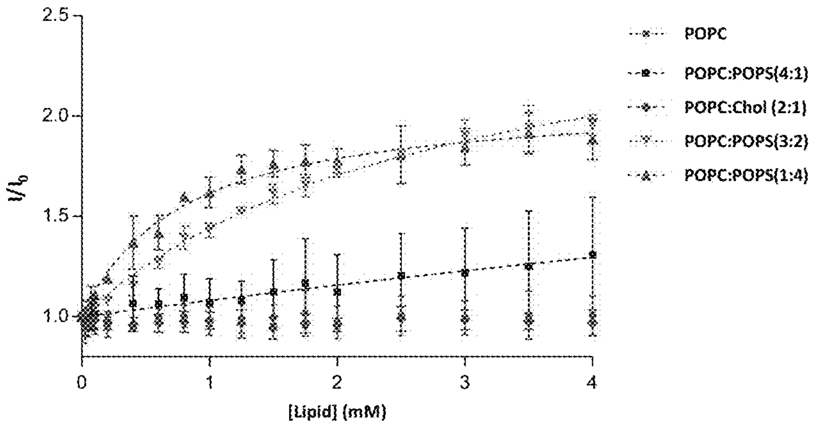
FIG. 27 shows determination of $K_p$ constant for the DEN2C peptide pepH3 through intrinsic fluorescence of trp.
Figures 28A, 28B, 28C, 28D:
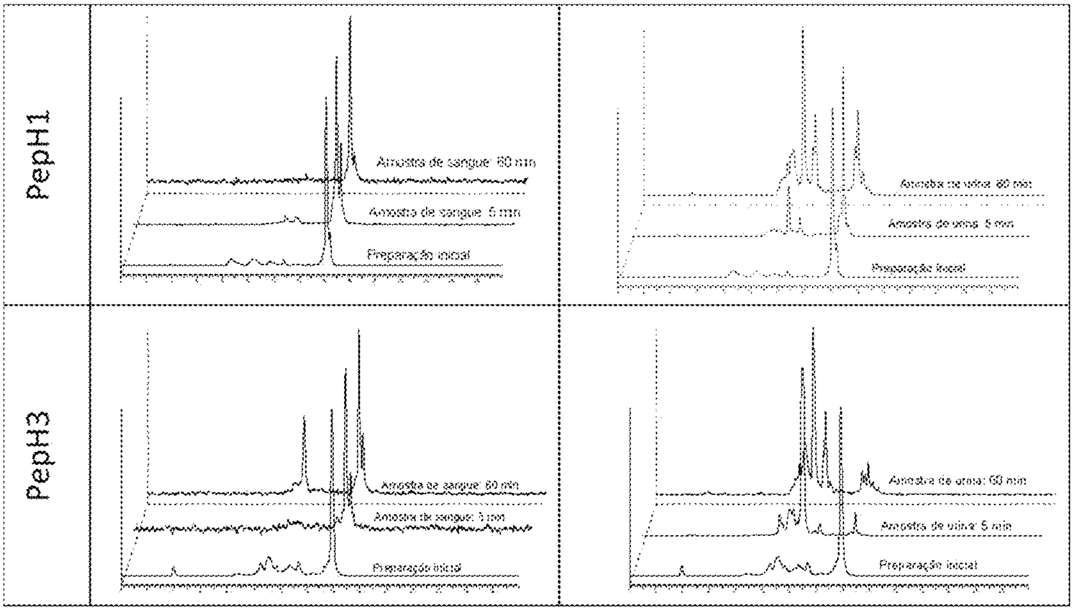
FIGS. 28A-28D show pepH1 stability in blood (FIG. 28A) and urine (FIG. 28B), and pepH3 stability blood (FIG. 28C) and urine (FIG. 28D), before and 5 and 60 minutes after injection into mice, using HPLC analysis.

As FIG. 27 and Table 10 show, this assay confirmed higher interaction of pepH3 with membrane models rich in POPS, since the affinity constant for POPC:POPS (1:4) is 5 times higher ($K_p$=1,558) than that for other lipid compositions studied (compare, e.g., POPC:POPS (4:1) with a $K_p$=324). PepH2 and pepH3 are the most hydrophobic peptides (Po/w). In addition, pepH2 interacts with various lipid compositions of membrane models, while pepH3 only interacts with membranes rich in PS (a negatively charged phospholipid). The fluorescent spectra obtained verified that pepH1 does not interact with the lipidic membranes studied and showed no alteration in the dipole potential for different membrane models; while pepH2 shows higher interaction with all membrane models; and pepH3 shows higher interactions for lipidic models rich in negative charges, such as PS.

TABLE 10

| Lipidic Membrane | $K_p$ ± SD |
|---|---|
| POPC | — |
| POPC:POPS (4:1) | 342 ± 102 |
| POPC:Chol (2:1) | — |
| POPC:POPS (3:2) | 455 ± 46 |
| POPC:POPS (1:4) | 1,558 ± 216 |

These studies also facilitated understanding of the mechanism of transmigration for these peptides, e.g., where specific markers for different cellular compartments or cell inhibitors also are used.

f. In Vivo Testing for Biodistribution and Stability of Peptides PepHI and PepH3

To evaluate the capacity to cross the BBB in vivo, the selected peptides, pepH1 and pepH3, were analyzed for biodistribution in CD1 mice. The peptides were labelled with technetium at a final concentration of $8.5\times10^{-5}$ M and diluted in PBS. CD1 mice were injected (iv injection, tail vein). The mice were sacrificed by cervical dislocation after 5 and 60 minutes of incubation. The tissues of interest were dissected and washed to remove excess blood, weighed, and measured for radioactivity. Technetium radioactivity of the different peptides was measured for different organs.

Initial results are presented in Table 11, where "% I.A. refers to the "% injected activity", that is, the amount of radioactivity measured in a given organ compared to the total originally injected.

TABLE 11

| | $^{99m}$Tc-PepH1 (% I.A./g) | | $^{99m}$Tc-PepH3 (% I.A./g) | |
|---|---|---|---|---|
| Organ | 5 min (n =3) | 1 hour (n =2) | 5 min (n =3) | 1 hour (n =2) |
| Blood | 3.1 ± 0.5 | 1.0 ± 0.2 | 4.7 ± 0.6 | 1.2 ± 0.4 |
| Liver | 7.0 ± 1.1 | 2.4 ± 1.0 | 7.6 ± 0.1 | 2.3 ± 0.2 |
| Intestine | 3.8 ± 2.3 | 13.0 ± 2.0 | 3.0 ± 0.3 | 7.4 ± 0.4 |
| Spleen | 0.7 ± 0.2 | 0.22 ± 0.01 | 1.5 ± 0.2 | 0.81 ± 0.01 |
| Heart | 1.1 ± 0.4 | 0.39 ± 0.02 | 1.5 ± 0.5 | 0.35 ± 0.01 |
| Lung | 2.6 ± 0.5 | 1.4 ± 0.3 | 3.7 ± 0.2 | 1.0 ± 0.2 |
| Kidney | 14.6 ± 8.2 | 1.6 ± 0.3 | 11.9 ± 3.8 | 0.4 ± 2.0 |
| Muscle | 0.6 ± 0.2 | 0.2 ± 0.0 | 1.0 ± 0.2 | 0.3 ± 0.1 |
| Bone | 0.6 ± 0.2 | 0.16 ± 0.01 | 1.2 ± 0.1 | 0.26 ± 0.05 |
| Stomach | 0.7 ± 0.4 | 0.31 ± 0.08 | 0.17 ± 0.02 | 0.4 ± 0.2 |
| Pancreas | 0.8 ± 0.2 | 0.41 ± 0.01 | 1.1 ± 0.1 | 0.5 ± 0.2 |
| Brain | 0.11 ± 0.02 | 0.03 ± 0.00 | 0.15 ± 0.02 | 0.04 ± 0.01 |
| Excretion (% I.A.) | 17.1 ± 7.9 | 32.7 ±0.2 | 19.6 ± 0.3 | 10.5 ± 8.6 |

As Table 11 shows, when mice were injected with 10 μg of pepH1 and pepH3, the radioactivity in the brain was determined to be 0.11-0.15%. Considering accumulation in organs of excretion, such as the kidney and liver, it was observed that after 60 minutes, much of the peptides had been excreted. The percentage collected in the brain was about 0.15% for the doses tested, providing a surprisingly good translocation percentage for the selected peptides (compare Rosler et al. *Neuropharmacology* (2011) 61:1413-1418; and Yu et al. *Sci Transl Med* (2011) 84(3):84ra44)).

The biodistribution studies were repeated, using higher doses of each peptide, specifically, a one hundred fold increase, as well as using PepH2 as a negative control, and allowing incubation for 2 minutes and 60 minutes. Tissue biodistribution profile in percentage of injected radiopeptide activity per gram of tissue/organ was measured and results are presented in Table 12.

TABLE 12

| Organ | $^{99m}$Tc-PepH1 (140 μg/mouse) (% I.A./g) | | $^{99m}$Tc-PepH2 (80 μg/mouse) (% I.A./g) | | $^{99m}$Tc-PepH3 (140 μg/mouse) (% I.A./g) | |
|---|---|---|---|---|---|---|
| | 2 min | 1 hour | 2 min | 1 hour | 2 min | 1 hour |
| Blood | 3.1 ± 0.5 | 1.0 ± 0.2 | 8.9 ± 0.6 | 3.8 ± 0.2 | 8.6 ± 0.9 | 0.43 ± 0.04 |
| Liver | 7.0 ± 1.1 | 2.4 ± 1.0 | 16.7 ± 1.1 | 21.7 ± 0.9 | 18.8 ± 6.1 | 2.3 ± 0.2 |
| Intestine | 3.8 ± 2.3 | 13.0 ± 2.0 | 0.5 ± 0.1 | 1.64 ± 0.07 | 1.4 ± 0.2 | 23.0 ± 7.9 |
| Spleen | 0.7 ± 0.2 | 0.22 ± 0.01 | 13.6 ± 0.3 | 10.6 ± 0.4 | 1.6 ± 0.4 | 0.81 ± 0.01 |
| Heart | 1.1 ± 0.4 | 0.39 ± 0.02 | 3.45 ± 0.02 | 1.2 ± 0.2 | 2.2 ± 0.3 | 0.14 ± 0.01 |
| Lung | 2.6 ± 0.5 | 1.4 ± 0.3 | 126 ± 20 | 51.4 ± 4.4 | 4.48 ± 0.01 | 0.31 ± 0.03 |
| Kidney | 14.6 ± 8.2 | 1.6 ± 0.3 | 5.0 ± 1.5 | 3.3 ± 0.8 | 23.1 ± 3.4 | 3.5 ± 0.7 |
| Muscle | 0.6 ± 0.2 | 0.2 ± 0.0 | 0.61 ± 0.09 | 0.43 ± 0.03 | 1.4 ± 0.2 | 0.2 ± 0.1 |
| Bone | 0.6 ± 0.2 | 0.16 ± 0.01 | 1.6 ± 0.1 | 1.4 ± 0.1 | 1.89 ± 0.04 | 0.19 ± 0.01 |
| Stomach | 0.7 ± 0.4 | 0.31 ± 0.08 | 2.0 ± 0.6 | 9.4 ± 0.2 | 1.1 ± 0.2 | 5.2 ± 0.7 |
| Brain | 0.11 ± 0.02 | 0.03 ± 0.00 | 0.37 ± 0.04 | 0.2 ± 0.1 | 0.31 ± 0.07 | 0.03 ± 0.01 |
| Excretion (% I.A.) | 17.1 ± 7.9 | 32.7 ± 0.2 | — | 12.7 ± 4.2 | — | 36.0 ± 11.2 |

The 140 μg of peptide corresponds to molar amounts as follows: or pepH1, 140 μg equals 1.15 mM; for pepH2, 140 μg equals 0.84 mM; for pepH3, 140 μg equals 1.67 mM; and for pepH4, 140 μg equals 0.524 mM. As Table 12 shows, upon increasing the dose to 140 μg for peptides pepH1 and pepH3, and to 80 μg for pepH2, radioactivity due to pepH3 in the brain doubled (0.31%); while there was no increase in % radioactivity due to pepH1. For these peptides (pepH1 and pepH3), radioactivity accumulated in the excretion organs, e.g., the kidneys and liver, but was observed to decrease considerably by 60 min, indicating that the majority of these peptides were excreted by that time.

PepH2 accumulated in other organs besides those for excretion, such as in the lungs, as well as showing increasing accumulation in the liver after 60 min. Regarding radioactivity levels in the brain, pepH2 and pepH3 both showed 0.37%; while pepH2 showed 0.2%, after 60 minutes. Further, less pepH2 was excreted after 60 min (12.7%) compared with pepH1 and pepH3 (32.7% and 36%, respectively), as expected due to pepH2 being highly hydrophobic, as noted above.

In sum, pepH1, pepH2 and pepH3 demonstrated rapid brain uptake (after 2 min). For pepH1 and pepH3, brain uptake was followed by rapid brain washout, concomitant with fast elimination of the total radioactivity from most organs. Radiopeptides were rapidly cleared from the blood, liver, kidney, and highly irrigated organs, accumulating in the intestine. At 1 h, an important fraction of injected activity was excreted (>30%). In particular, pepH2 was taken up by the brain but brain washout was slower. Accumulation in liver, spleen, and lungs was also observed. These results were consistent with the high hydrophobicity of pepH2. Without being bound by theory, the data was consistent with an AMT mechanism of BBB translocation.

Finally, stability of the peptides was determined. Urine and blood were taken from the animals after death, filtered, and analyzed by RT-HPLC. HPLC analysis was conducted to assess the stability of pepH1 and pepH3 peptides in blood and urine, 5 and 60 minutes post-administration, compared to the respective original preparations. Results are shown in FIGS. 28A-28D.

FIGS. 28A-28D show the profile of pepH1 and pepH3 each in its original preparation, prior to injection into the animals, and then after 5 and 60 minutes following injection in the blood and urine. The results evidenced that the peptides were surprisingly stable in the blood and urine, although new species, with shorter retention times, did appear in the urine after 60 minutes.

In sum, in vitro and in vivo results show that selected DEN2C peptides cross the BBB efficiently. In particular, as noted above, the results surprisingly demonstrated that pepH3 penetrated the brain and returned to blood circulation to be excreted. Accordingly, pepH3 was identified as an exemplary delivery peptide, showing delivery to the brain greater than or comparable with other molecules described in the literature (Muruganandam, et al. (2002) FASEB J, 16(2): 240-241; and Abulrob, et al. (2005) *J Neurochem* 95(4):1201-1214), along with the surprising advantage of being able to enter and leave the brain, as well as not accumulating in other organs besides the excretory organs. Indeed, the percentage of pepH3 in the brain was comparable to the very few known "high performance" BBB-translocator peptides. For example, percentages of brain uptake of other radiolabelled peptides, such as TAT, penetratin, synB1, and others range from only 0.2-0.9% ID/g of tissue (Sarko, et al., *Mol Pharm* (2010) 7(6):2224-2231). PepH3 was selected for linkage to exemplary anti-BAP42 oligomer sdAb, described above.

Example 3—Constructs of Anti-Non-Fibrillar BAP42 sdAbs and BBB-Specific Delivery Peptides Constructs were prepared by conjugating a delivery peptide of interest with a selected sdAb specific for BAP42 oligomers, to provide therapeutics for treating Alzheimer's and related disorders with increased bioavailability. The process involved the following five stages: (a) test cloning delivery peptides with test sdAbs; and (b) determining their expression; followed by (c) preparing antibody-peptide constructs; (d) determining their ability to hinder BAP42 aggregation; and then (e) analyzing their in vivo biodistribution and BBB-passage.

a. Test Cloning of Selected Delivery Peptides with Test sdAbs

Test cloning was conducted to select promising fusion constructs, in terms of stability (e.g., good expression levels and solubility when expressed), as well as good activity (e.g., promoting BBB-specific passage with low toxicity). Specifically, test clonings of pepH1, pepH2, pepH3, and pepM' were performed, where each peptide was fused to an irrelevant antibody to mimic the final antibody-peptide construct.

PepH2 was used as a negative control for transmigration. The irrelevant antibody used is a sdAb that is very stable and helps mimic the final antibody-peptide product. Conjugation was carried out in various formats, including as a bispecific antibody with the delivery peptide at the N-terminal, C-Terminal or both. PepH1, pepH2, pepH3, or pepM' ("pepDEN") was attached to either the N- or C-terminus of the test sdAb, using a linker, and including a Histidine tag, HA, and an SfiI site.

b. Expression of Test Antibody-Peptide Constructs

The antibody-peptide constructs were amplified by PCR and then purified, followed by insertion into expression vectors, namely the expression vectors T7 and pET21, and the chimeras confirmed by sequencing. The chimeras then were used to transform bacterial cells, specifically, the bacterial strain BL21. Transformation in BL21 produced several colonies. The colonies that were "screened" by PCR to identify clones of interest. Identified clones of interest were expressed using IPTG or an auto-induction media.

Results of a comassie gel demonstrated that sdAb-pepH was expressed at higher levels and as a more soluble product, compared with the other peptide constructs, as well as showing especially high expression from constructs with the peptide at the C-terminal end of the sdAb.

These results, together with the results from biodistribution and stability/expression analyses, confirm the utility of pepH3 as a delivery peptide, e.g., for use in delivering anti-oligomer BAP42 sdAbs to the brain. The pepH3 next was conjugated to an anti-oligomer BAP42 sdAb of the present invention, as described below.

c. Preparation of Antibody-Peptide Constructs

Different antibody molecules and antibody-peptide constructs were cloned, as summarized in Table 13 below.

TABLE 13

| Antibody Molecules or Constructs | Name | SEQ ID NOs |
|---|---|---|
| anti-BAP42 sdAb | #2 | SEQ ID NO: 1 |
| | #20 | SEQ ID NO: 2 |
| | #6in | SEQ ID NO: 3 |
| | #27in | SEQ ID NO: 4 |
| anti-BAP42 sdAb-pepH3 | #2-Pep3+ | SEQ ID NO: 28 |
| | #20-Pep3+ | SEQ ID NO: 32 |
| | #6-Pep3+ | SEQ ID NO: 36 |
| | #27-Pep3+ | SEQ ID NO: 40 |
| positive control for BBB transmigration | FC5 | SEQ ID NO: 112 |
| positive control for BAP binding | Abx | SEQ ID NO: 117 |
| Irrelevant sdAb | PMP6A6 | SEQ ID NO: 122 |
| Irrelevant-pepH3 | PMP6A6-PepH3 | SEQ ID NO: 123 |

As Table 13 shows, additional constructs were used along with pepH3 that show transmigration ability of BBB. As a positive control for BBB transmigration, an FC5 antibody was cloned; as a positive control for binding to BAP, an antibody against BAP ("Abx") was cloned; and as a negative control, an irrelevant antibody ("PMP6A6") also was cloned. FC5 is a sdAb described in the literature, which was developed by phage display against endothelial cells of the human brain and can bind receptors on the BBB, specifically the glycosylated luminal BEC protein (Cdc50A) (see, Muruganandam, et al. (2002) FASEB J, 16(2): 240-241; and Abulrob, et al. (2005) *J Neurochem* 95(4):1201-1214). Abx is a nanobody against BAP polypeptides (see, U.S. 20080107601 to Lauwereys, et al.). PMP6A6 also is a nanobody, one that binds to serum albumin (see, U.S. 2014/0228546 to Dombrecht, et al.).

Depending on the antibody gene, final constructs were cloned into either pET21a, pET28a, or in pT7 vectors. After cloning, these constructs were sequenced and expressed for further characterization.

d. Effect of Antibody-Peptide Constructs in Hindering BAP42 Aggregation

Once produced and purified, immunospecificities of the constructs were also measured and confirmed to be similar to those of the corresponding sdAb without the fused peptide.

Anti-oligomers also were tested for their ability to inhibit aggregation of BAP42. This assay was performed using Thioflavin T (ThT), which, as described above, recognizes beta-sheet rich structures, characteristic of fibrillar form of BAP42, so that the ability of sdAbs to inhibit aggregation can be assessed. Specifically, the more aggregation is inhibited, the smaller the signal emitted by ThT. Two proportions were tested, namely, 1:5 (one molecule for sdAb for every 5 BAP42 molecules) and 1:20 (one molecule for sdAb for every 20 BAP42 molecules). Results are shown in FIGS. 29A-29B.

Figure 29A:
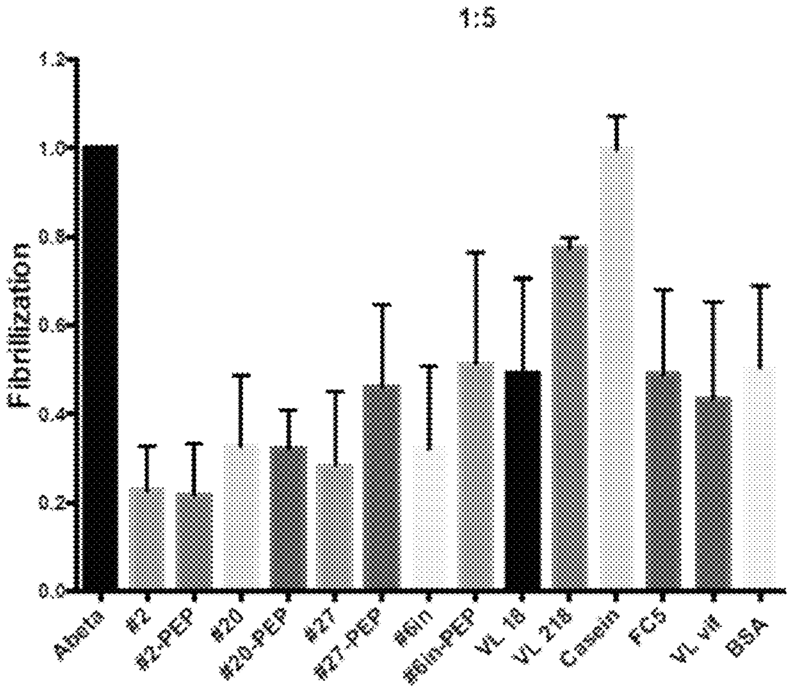
FIGS. 29A-29B show inhibition of BAP42 aggregation using antibody molecules and antibody-peptide constructs of the invention at two proportions: 1:5 (one molecule for sdAb for every 5 BAP42 molecules) (FIG. 29A) and 1:20 (one molecule for sdAb for every 20 BAP42 molecules) (FIG. 29B).
Figure 29B:
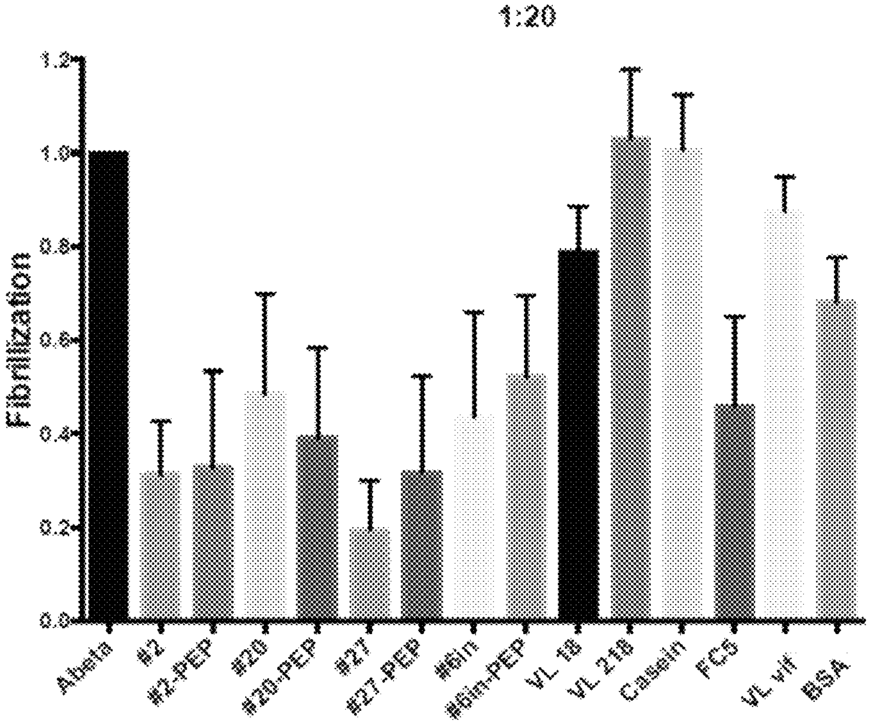

FIGS. 29A-29B show that sdAbs of the invention, with and without fused peptide, indeed prevented fibrillization; whereas antibodies that are not specific for BAP42 (e.g., FC5 and other unrelated single light chain variable domain antibodies, VL18 and VL218) do not inhibit fibrillization, or even may promote fibrillization.

e. Biodistribution and BBB-Passage of Antibody-Peptide Constructs

The different antibody-peptide constructs were used in biodistribution assays, and results compared with the biodistribution of the respective DEN2C peptides (pepH1, pepH2, pepH3, and pepM', chemically synthesized). Selected antibody molecules (sdAbs) were those that showed strong binding to BAP42, as well as effectively inhibiting aggregation of BAP oligomers in vitro. After expression and purification, the sdAbs and sdAb-peptide constructs were conjugated to technetium ($^{99}$Tc) and a biodistribution assay was performed, as previously described. The results are shown in Tables 14-16, below.

Tables 14-16 show the biodistribution of different anti-BAP42 sdAbs and constructs thereof with different peptides ("pepH3"). Table 14 shows biodistribution results for chimera of "#2" and "#2-pepH3"; Table 15 shows distribution results for "#20" and "#20-pepH3"; and Table 16 shows distribution results for "#27in" and "#27in-pepH3".

TABLE 14

| | #2-$^{99m}$Tc (% I.A./g) | | #2-pepH3-$^{99m}$Tc (% I.A./g) | |
|---|---|---|---|---|
| Organ | 2 min (n = 3) | 1 h (n = 3) | 2 min (n = 3) | 1 h (n = 3) |
| Blood | 15.2 ± 5.0 | 1.5 ± 0.3 | 18.6 ± 0.5 | 4.0 ± 1.9 |
| Liver | 10.3 ± 1.2 | 12.9 ± 0.8 | 9.7 ± 0.5 | 8.0 ± 1.4 |
| Intestine | 2.0 ± 0.3 | 1.5 ± 0.2 | 2.0 ± 0.2 | 1.6 ± 0.3 |
| Spleen | 3.9 ± 0.6 | 4.6 ± 0.3 | 3.2 ± 0.5 | 2.9 ± 0.6 |
| Heart | 4.0 ± 0.9 | 0.93 ± 0.03 | 3.6 ± 0.5 | 2.0 ± 0.1 |
| Lung | 6.5 ± 0.5 | 1.51 ± 0.08 | 15.7 ± 3.5 | 4.3 ± 0.8 |
| Kidney | 33.1 ± 6.6 | 77.2 ± 8.7 | 40.8 ± 4.4 | 68.7 ± 3.6 |
| Muscle | 1.0 ± 0.2 | 0.55 ± 0.03 | 0.9 ± 0.2 | 0.7 ± 0.2 |
| Bone | 1.7 ± 0.4 | 1.42 ± 0.06 | 1.9 ± 0.2 | 1.3 ± 0.2 |
| Stomach | 0.3 ± 0.2 | 0.2 ± 0.1 | 1.1 ± 0.5 | 0.8 ± 0.2 |
| Brain | 0.55 ± 0.13 | 0.09 ± 0.01 | 1.5 ± 0.5 | 0.2 ± 0.1 |
| Excretion (% I.A.) | — | 5.9 ± 1.3 | — | 13.1 ± 1.2 |

TABLE 15

| | #20-$^{99m}$Tc (% I.A./g) | | #20-pepH3-$^{99m}$Tc (% I.A./g) | |
|---|---|---|---|---|
| Organ | 2 min (n = 3) | 1 h (n = 3) | 2 min (n = 3) | 1 h (n = 3) |
| Blood | 10.3 ± 1.2 | 3.7 ± 0.3 | 17.8 ± 1.4 | 0.7 ± 0.1 |
| Liver | 13.9 ± 1.8 | 11.8 ± 0.5 | 17.2 ± 0.7 | 24.8 ± 7.8 |
| Intestine | 1.4 ± 0.3 | 1.0 ± 0.3 | 1.01 ± 0.06 | 1.0 ± 0.2 |
| Spleen | 6.2 ± 0.9 | 4.5 ± 1.0 | 4.4 ± 0.1 | 8.4 ± 0.7 |
| Heart | 1.8 ± 1.2 | 1.24 ± 0.04 | 3.3 ± 0.2 | 0.7 ± 0.3 |
| Lung | 13.0 ± 3.8 | 2.4 ± 0.1 | 9.4 ± 2.1 | 1.0 ± 0.3 |
| Kidney | 23.8 ± 4.0 | 55.3 ± 4.4 | 24.5 ± 1.8 | 56.7 ± 12.4 |
| Muscle | 0.54 ± 0.07 | 0.6 ± 0.2 | 0.46 ± 0.03 | 0.4 ± 0.1 |
| Bone | 1.5 ± 0.4 | 0.9 ± 0.1 | 1.6 ± 0.2 | 2.0 ± 0.7 |
| Stomach | 1.0 ± 0.3 | 0.32 ± 0.04 | 0.89 ± 0.07 | 0.7 ± 0.1 |
| Brain | 0.57 ± 0.12 | 0.10 ± 0.02 | 0.67 ± 0.18 | 0.04 ± 0.01 |
| Excretion (% I.A.) | — | 3.0 ± 0.8 | — | 6.6 ± 0.4 |

TABLE 16

| | #27in-$^{99m}$Tc (% I.A./g) | | #27in-pepH3-$^{99m}$Tc (% I.A./g) | |
|---|---|---|---|---|
| Organ | 2 min (n = 2) | 1 h (n = 2) | 2 min (n = 3) | 1 h (n = 3) |
| Blood | 3.3 ± 0.7 | 1.3 ± 0.4 | 15.8 ± 3.2 | 1.7 ± 0.1 |
| Liver | 11.4 ± 0.6 | 20.5 ± 7.1 | 20.2 ± 4.0 | 22.7 ± 3.0 |
| Intestine | 2.1 ± 0.3 | 2.3 ± 0.4 | 1.2 ± 0.2 | 0.91 ± 0.05 |
| Spleen | 3.4 ± 0.2 | 10.5 ± 2.5 | 7.6 ± 2.7 | 7.6 ± 5. |
| Heart | 3.8 ± 1.0 | 1.4 ± 0.2 | 6.5 ± 1.4 | 1.3 ± 0.2 |
| Lung | 150.6 ± 0.9 | 69.6 ± 23.1 | 20.4 ± 10.5 | 4.8 ± 1.8 |
| Kidney | 12.6 ± 3.5 | 7.3 ± 0.5 | 21.2 ± 9.0 | 41.9 ± 5.8 |
| Muscle | 0.55 ± 0.02 | 0.36 ± 0.02 | 0.9 ± 0.1 | 0.5 ± 0.1 |
| Bone | 1.0 ± 0.2 | 0.7 ± 0.2 | 2.5 ± 0.3 | 1.6 ± 0.3 |
| Stomach | 1.1 ± 0.4 | 0.9 ± 0.3 | 1.8 ± 1.2 | 1.1 ± 0.2 |
| Brain | 0.16 ± 0.09 | 0.04 ± 0.01 | 0.9 ± 0.6 | 0.08 ± 0.01 |
| Excretion (% I.A.) | — | 5.5 ± 0.8 | — | 8.7 ± 0.4 |

The results show surprisingly improved biodistribution profiles of exemplary constructs. Table 14, for example, shows that linking "#2" sdAb to the delivery peptide increased its presence in the brain, within 2 minutes, by a factor of about 3, and only slowed washout from the brain, after an hour, by a factor of about 2. That is, about three times as much reached the brain, in 2 minutes, while only about twice as much remained, after an hour. Even more surprisingly, Table 16 shows that linking "#27in" sdAb to the delivery peptide increased its presence in the brain, within 2 minutes, by a factor of about 6, and only slowed washout from the brain, after an hour, by a factor of about 2. That is, about six times as much reached the brain, in 2 minutes, while only about twice as much remained, after an hour. Selected antibodies were used in preliminary studies in transgenic animal models for Alzheimer's disease, for confirming in vivo efficacy, as described in the Example below.

Example 4—Pre-Clinical Efficacy of Candidate Compounds

In vivo testing in 5xFAD transgenic mice was conducted, using selected anti-BAP42 sdAbs, with and without conjugation to selected BBB-specific delivery peptides. Results were assessed using in vivo imaging and observing the effects on beta-amyloid plaques in the brains of the animals. Specifically, animals are injected with the following three formulations, identified as follows:

Compound "A", which corresponds to a formulation comprising "sdAb#2";

Compound "B", which corresponds to a formulation comprising "sdAb#2-pep"; and

Compound "C", which corresponds to the vehicle without an active agent.

Each compound was administered by ip injection to the test animals, 3× weekly, ever Monday, Wednesday, and Friday, using 375 μg of active agent per administration. Immunohistochemistry and imaging followed sacrifice of the animals. Specifically, animals are sacrificed and the hippocampus and cortex regions of the brain sectioned and stained with Thiazin Red, a compound which indicates the presence of plaques. Results are shown in FIGS. 30A-30B, Table 17, and FIGS. 31A-31D.

Figure 30A:
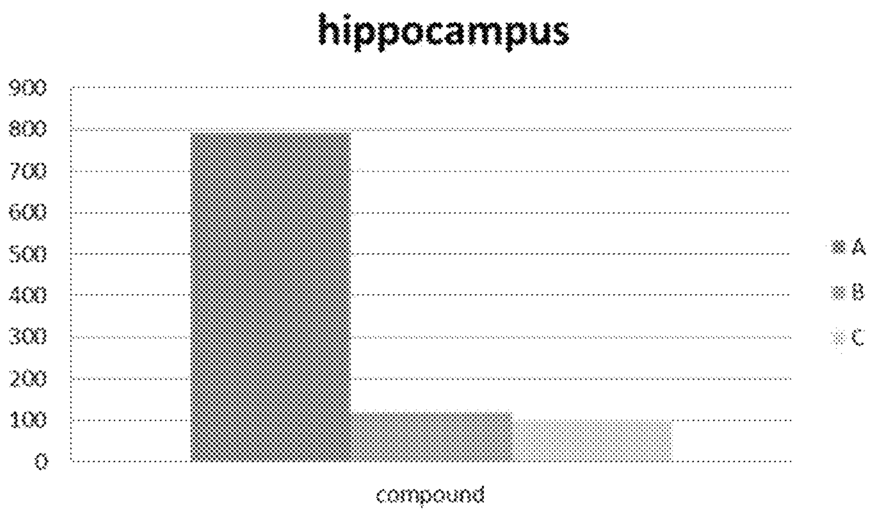
FIGS. 30A-30B show results of thiazine red staining in the hippocampus (FIG. 30A) or cortex (FIG. 30B) of 5xFAD transgenic mice treated with an exemplary antibody molecule "A" or exemplary antibody-peptide construct "B" of the invention, or with a control "C".
Figure 30B:
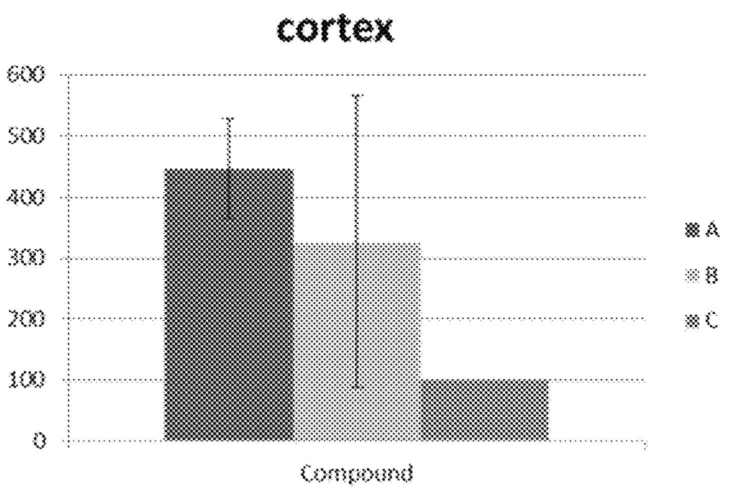
Figure 31A:
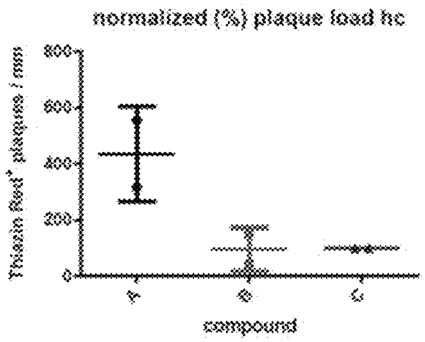
FIGS. 31A-31D show results of thiazine red staining, indicating normalized plaque load/mm (FIG. 31A) and plaques/mm (FIG. 31B) in the hippocampus; and normalized plaque load/mm (FIG. 31C) and plaques/mm (FIG. 31D) in the cortex of 5xFAD transgenic mice treated with an exemplary antibody molecule "A" or exemplary antibody-peptide construct "B" of the invention, or with a control "C".
Figure 31B:
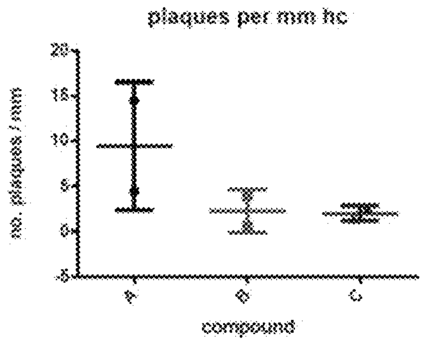
Figure 31C:
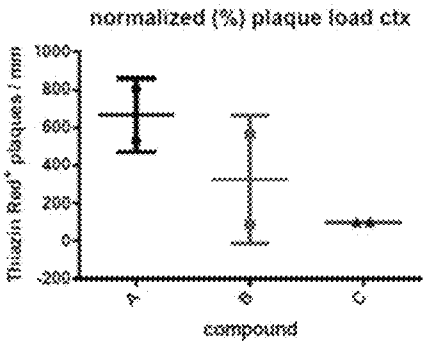
Figure 31D:
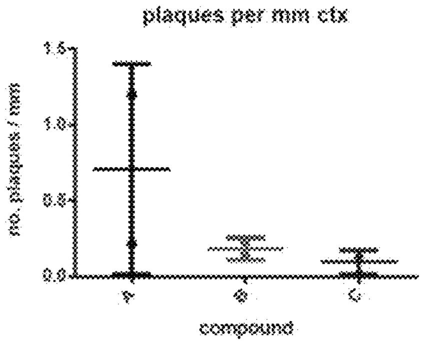

FIGS. 30A-30B show results from 5xFAD transgenic mice treated with candidates "A", "B", and "C", as identified above, after staining with thiazin red in the hippocampus (FIG. 30A) and in the cortex (FIG. 30B). Measurements were normalized to compound C (100%), used as a control. Compounds A and B effectively indicated plaque number compared to the control, and this is especially so for Compound B, corresponding to the antibody-peptide construct "sdAb#2-pep". Table 17 provides absolute and relative numbers of plaques identified by thiazin red. FIGS. 31A-31D further demonstrate these results, showing normalized plaque load (FIG. 31A) and plaques per mm (FIG. 31B) in the hippocampus; and normalized plaque load (FIG. 31C) and plaques per mm (FIG. 31D) in the cortex.

TABLE 17

| normalized cortex | | | plaques per mm | | |
|---|---|---|---|---|---|
| A | B | C | A | B | C |
| 803.2236 | 87.84731 | 100 | 1.198774 | 0.131108 | 0.1492453 |
| 528.5502 | 564.8345 | 100 | 0.2171391 | 0.2320454 | 0.04108201 |
| **normalized hc** | | | **plaques per mm** | | |
| A | B | C | A | B | C |
| 554.4905 | 150.4523 | 100 | 14.46397 | 3.92457 | 2.608514 |
| 315.0766 | 42.34347 | 100 | 4.478287 | 0.6018416 | 1.421333 |

Additional antibody molecules and antibody-peptide constructs used in the Examples are summarized in Table 18, Table 19, and Table 20 below.

TABLE 18

| Antibody Molecules | Name | SEQ ID NOs |
|---|---|---|
| anti-BAP42 sdAb | #1 | SEQ ID NO: 5 |
| | #3 | SEQ ID NO: 6 |
| | #4 | SEQ ID NO: 7 |
| | #5 | SEQ ID NO: 8 |
| | #6 | SEQ ID NO: 9 |
| | #7 | SEQ ID NO: 10 |
| | #8 | SEQ ID NO: 11 |
| | #9 | SEQ ID NO: 12 |
| | #10 | SEQ ID NO: 13 |
| | #11 | SEQ ID NO: 14 |
| | #14 | SEQ ID NO: 15 |
| | #17 | SEQ ID NO: 16 |
| | #19 | SEQ ID NO: 17 |
| | #26 | SEQ ID NO: 18 |
| | #29 | SEQ ID NO: 19 |
| | #37 | SEQ ID NO: 20 |
| | #53 | SEQ ID NO: 21 |

TABLE 19

| Antibody-Peptide Constructs | Name | SEQ ID NOs |
|---|---|---|
| anti-BAP42 sdAb-pep constructs | #2-PepH1 | SEQ ID NO: 29 |
| | #2-PepH2 | SEQ ID NO: 30 |
| | #2-PepH4 | SEQ ID NO: 31 |
| | #20-PepH1 | SEQ ID NO: 33 |
| | #20-PepH2 | SEQ ID NO: 34 |
| | #20-PepH4 | SEQ ID NO: 35 |
| | #6in-PepH1 | SEQ ID NO: 37 |
| | #6in-PepH2 | SEQ ID NO: 38 |
| | #6in-PepH4 | SEQ ID NO: 39 |
| | #27in-PepH1 | SEQ ID NO: 41 |
| | #27in-PepH2 | SEQ ID NO: 42 |
| | #27in-PepH4 | SEQ ID NO: 43 |
| | #1-PepH3 | SEQ ID NO: 44 |
| | #1-PepH1 | SEQ ID NO: 45 |
| | #1-PepH2 | SEQ ID NO: 46 |
| | #1-PepH4 | SEQ ID NO: 47 |
| | #3-PepH3 | SEQ ID NO: 48 |
| | #3-PepH1 | SEQ ID NO: 49 |
| | #3-PepH2 | SEQ ID NO: 50 |
| | #3-PepH4 | SEQ ID NO: 51 |
| | #4-PepH3 | SEQ ID NO: 52 |
| | #4-PepH1 | SEQ ID NO: 53 |
| | #4-PepH2 | SEQ ID NO: 54 |
| | #4-PepH4 | SEQ ID NO: 55 |
| | #5-PepH3 | SEQ ID NO: 56 |
| | #5-PepH1 | SEQ ID NO: 57 |
| | #5-PepH2 | SEQ ID NO: 58 |
| | #5-PepH4 | SEQ ID NO: 59 |
| | #6-PepH3 | SEQ ID NO: 60 |
| | #6-PepH1 | SEQ ID NO: 61 |
| | #6-PepH2 | SEQ ID NO: 62 |
| | #6-PepH4 | SEQ ID NO: 63 |
| | #7-PepH3 | SEQ ID NO: 64 |
| | #7-PepH1 | SEQ ID NO: 65 |
| | #7-PepH2 | SEQ ID NO: 66 |
| | #7-PepH4 | SEQ ID NO: 67 |
| | #8-PepH3 | SEQ ID NO: 68 |
| | #8-PepH1 | SEQ ID NO: 69 |
| | #8-PepH2 | SEQ ID NO: 70 |
| | #8-PepH4 | SEQ ID NO: 71 |
| | #9-PepH3 | SEQ ID NO: 72 |
| | #9-PepH1 | SEQ ID NO: 73 |
| | #9-PepH2 | SEQ ID NO: 74 |
| | #9-PepH4 | SEQ ID NO: 75 |
| | #10-PepH3 | SEQ ID NO: 76 |
| | #10-PepH1 | SEQ ID NO: 77 |
| | #10-PepH2 | SEQ ID NO: 78 |
| | #10-PepH4 | SEQ ID NO: 79 |
| | #11-PepH3 | SEQ ID NO: 80 |
| | #11-PepH1 | SEQ ID NO: 81 |
| | #11-PepH2 | SEQ ID NO: 82 |
| | #11-PepH4 | SEQ ID NO: 83 |
| | #14-PepH3 | SEQ ID NO: 84 |
| | #14-PepH1 | SEQ ID NO: 85 |
| | #14-PepH2 | SEQ ID NO: 86 |
| | #14-PepH4 | SEQ ID NO: 87 |
| | #17-PepH3 | SEQ ID NO: 88 |
| | #17-PepH1 | SEQ ID NO: 89 |
| | #17-PepH2 | SEQ ID NO: 90 |
| | #17-PepH4 | SEQ ID NO: 91 |
| | #19-PepH3 | SEQ ID NO: 92 |
| | #19-PepH1 | SEQ ID NO: 93 |
| | #19-PepH2 | SEQ ID NO: 94 |
| | #19-PepH4 | SEQ ID NO: 95 |
| | #26-PepH3 | SEQ ID NO: 96 |
| | #26-PepH1 | SEQ ID NO: 97 |
| | #26-PepH2 | SEQ ID NO: 98 |
| | #26-PepH4 | SEQ ID NO: 99 |
| | #29-PepH3 | SEQ ID NO: 100 |
| | #29-PepH1 | SEQ ID NO: 101 |
| | #29-PepH2 | SEQ ID NO: 102 |
| | #29-PepH4 | SEQ ID NO: 103 |
| | #37-PepH3 | SEQ ID NO: 104 |
| | #37-PepH1 | SEQ ID NO: 105 |
| | #37-PepH2 | SEQ ID NO: 106 |
| | #37-PepH4 | SEQ ID NO: 107 |
| | #53-PepH3 | SEQ ID NO: 108 |
| | #53-PepH1 | SEQ ID NO: 109 |
| | #53-PepH2 | SEQ ID NO: 110 |
| | #53-PepH4 | SEQ ID NO: 111 |

TABLE 20

| Antibody Molecule or Constructs | Name | SEQ ID NOs |
|---|---|---|
| Controls | #FC5 | SEQ ID NO: 112 |
| | # FC5-PepH3 | SEQ ID NO: 113 |
| | # FC5-PepH1 | SEQ ID NO: 114 |
| | # FC5-PepH2 | SEQ ID NO: 115 |
| | # FC5-PepH4 | SEQ ID NO: 116 |
| | #Abx | SEQ ID NO: 117 |
| | # Abx -PepH3 | SEQ ID NO: 118 |
| | # Abx -PepH1 | SEQ ID NO: 119 |
| | # Abx -PepH2 | SEQ ID NO: 120 |
| | # Abx -PepH4 | SEQ ID NO: 121 |
| | #PMP6A6 | SEQ ID NO: 122 |
| | # PMP6A6-PepH3 | SEQ ID NO: 123 |
| | # PMP6A6-PepH1 | SEQ ID NO: 124 |
| | # PMP6A6-PepH2 | SEQ ID NO: 125 |
| | # PMP6A6-PepH4 | SEQ ID NO: 126 |

Example 5—Diagnostic Use of Candidate Compounds as Biomarkers Predictive for AD The following examples demonstrate use of anti-BAP42 sdAbs of the invention, with and without conjugation to BBB-specific delivery peptides, in (a) in vitro and (b) in vivo diagnosis.

a. In Vitro Diagnosis of AD using Cerebrospinal Fluid of AD Patients

To diagnose AD, samples of cerebrospinal fluid were collected from patients in different stages of Alzheimer's disease, according to the ethical procedures. Specifically, the CSF samples were obtained from patients with cognitive complaints, memory problems, properly identified dementia at the Hospital Santa Maria, Lisbon. Patients were subjected to standard protocol for evaluating medical history, as well as neurological examination, laboratory tests, and brain imaging (CT scan or MRI scan), and also neurophysiological evaluation with the battery of Lisbon for Evaluation of Dementia (BLAD). The inclusion of a patient in the MCI (mild cognitive impairment) group was based on the criteria of the European Consortium on Alzheimer's disease (EADC) and the American Psychiatric Association (DSM-IV-TR, 2000).

Control samples also were collected. Sample collection was made in accordance with standard procedures of the Department of Neurology of the Hospital de Santa Maria. This study was approved by the Ethics Committee of the Hospital de Santa Maria and patients gave their informed consent.

CSF samples from at least 86 patients were collected, where the patients were 62.2±9.0 years (45 were men and 43 were women; 41 were diagnosed as having MCI; 45 were diagnosed with dementia (most of which associated with Alzheimer's disease).

The samples collected are exposed to anti-BAP42 sdAbs (sdAbs) of the invention or to constructs of the sdAbs with BBB-specific delivery peptides (sdAb-peps) of the invention, in particular, constructs presented in Table 13, above. Specifically, the sdAbs and/or sdAb-peps are immobilized on a CMS chip; different CSF samples are contacted with the chip, and binding detected using BIAcore. When connected, registered signal identifies the corresponding sdAb or sdAb-pep as a biomarker for AD, as well as quantifying the amount of BAP42 oligomers/monomers present. Certain sdAbs and sdAb-peps that recognize and immunospecifically bind BAP42 oligomers in these different CSF samples also show a correlation between recognition and the stage of Alzheimer's, proving biomarkers for specific stages of AD, in particular, in early clinical diagnosis, identifying early stages of Alzheimer's and/or stages associated with mild cognitive impairment.

b. In Vivo Imaging Using Labelled sdAbs and Constructs Thereof with BBB-Specific Peptides Selected sdAbs and sdAb-peps are marked with $^{99}$Tc/$^{67}$Ga for imaging. For this, sdAb/sdAbs-pep are selected that recognize BAP42 in vitro and can translocate the BBB, while not demonstrating disaggregation of beta-amyloid plaques that have formed. For imaging purposes, sdAbs are selected that bind BAP42 oligomers in order to provide an image indicating the presence of the oligomers in the brain, but without necessarily causing disaggregation. Such sdAb/sdAbs-pep provide biomarkers for in vivo diagnosis by imaging of "senile plaques" characteristic of AD.

Specifically, sdAb #2-pep was labelled with $^{99}$Tc, as described above. Two healthy mice were injected with the labelled construct and sacrificed, 2 minutes or 60 minutes after injection, and SPECT (Single-Photon Emission Computed Tomography) was performed on the animal. Results are shown in FIGS. 32A-32B.

Figures 32A, 32B:
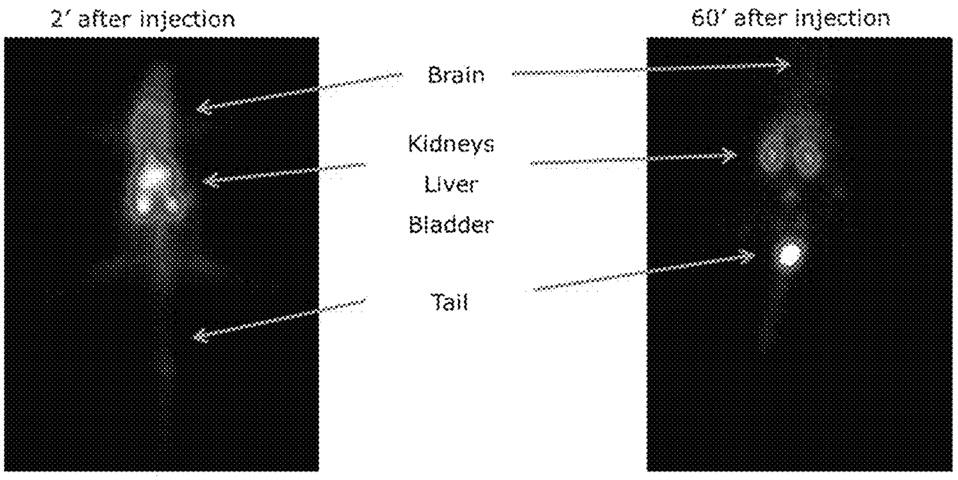
FIGS. 32A-32B shows SPECT image of a $^{99}$Tc-labelled sdAb-pep construct in mice at 2 and 60 minutes after injection, respectively.

As FIG. 32A shows, after two minutes, a signal was detected in the brain and in organs like the bladder and kidneys. As FIG. 32B shows, after 60 minutes, signal from the brain was no longer observed, but the signal at the kidney persists. These results evidence that the sdAb construct indeed reached the brain of the animal, and was thereafter removed from the brain. The signal detected in the tail, in the image corresponding to 60 minutes after injection, was normal and represented the site of injection in the old mice used.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled

We claim:

1. A fusion protein comprising a peptide with the amino acid sequence of SEQ ID NO: 22 or 24 and at least one cargo molecule, wherein the cargo molecule is selected from the group consisting of a polypeptide, an antibody, and an antibody fragment; wherein the fusion protein facilitates delivery of the cargo molecule across a blood brain barrier, wherein the peptide is heterologous to the cargo molecule.

2. The fusion protein of claim 1, wherein the cargo molecule is the antibody or the antibody fragment.

3. The fusion protein of claim 2, wherein the antibody or antibody fragment is selected from the group consisting of a monoclonal antibody, a polyclonal antibody, a multispecific antibody, a bispecific Fv (sdFv), a humanized antibody, a single chain Fv (scFv), a single chain antibody, a single domain antibody, a rabbit antibody, an anti-idiotypic (anti-Id) antibody, a diabody, a minibody, an intrabody, a nanobody, an Fab fragment, and an F(ab') fragment.

4. The fusion protein of claim 3 comprising instant SEQ ID NO: 28, 29, 32, 33, 36, 37, 38, and 40, 41, 45, 48, 49, 52, 53, 56, 57, 60, 61, 64, 65, 68, 69, 72, 73, 76, 77, 80, 81, 84, 85, 88, 89, 92, 93, 96, 97, 100, 101, 104, 105, 108, or 109.

5. A method of delivering a cargo molecule across the blood brain barrier of a subject, comprising administering the fusion protein of claim 1 to a subject in need thereof.

6. A nucleotide sequence encoding the fusion protein according to claim 1.

7. A vector comprising the nucleotide sequence of claim 6.

8. A host cell comprising the vector of claim 7.

9. The fusion protein of claim 1 further comprising an amino acid linker sequence.

* * * * *